US010154901B2

(12) United States Patent
Straubinger et al.

(10) Patent No.: US 10,154,901 B2
(45) Date of Patent: Dec. 18, 2018

(54) STENT FOR THE POSITIONING AND ANCHORING OF A VALVULAR PROSTHESIS IN AN IMPLANTATION SITE IN THE HEART OF A PATIENT

(71) Applicant: JenaValve Technology, Inc., Irvine, CA (US)

(72) Inventors: Helmut Straubinger, Aschheim (DE); Johannes Jung, Pforzheim-Huchenfeld (DE); Michael J. Girard, Lino Lakes, MN (US); Arnulf Mayer, Markt Schwaben (DE)

(73) Assignee: JenaValve Technology, Inc., Irvine, CA (US)

( * ) Notice: Subject to any disclaimer, the term of this patent is extended or adjusted under 35 U.S.C. 154(b) by 0 days.

(21) Appl. No.: 15/266,295

(22) Filed: Sep. 15, 2016

(65) Prior Publication Data

US 2017/0065410 A1    Mar. 9, 2017

Related U.S. Application Data

(63) Continuation of application No. 15/221,860, filed on Jul. 28, 2016, which is a continuation of application (Continued)

(51) Int. Cl.
*A61F 2/24* (2006.01)
*A61F 2/07* (2013.01)

(52) U.S. Cl.
CPC .............. *A61F 2/2418* (2013.01); *A61F 2/07* (2013.01); *A61F 2/2409* (2013.01);
(Continued)

(58) Field of Classification Search
CPC ..... A61F 2/2418; A61F 2/2415; A61F 2/2412
See application file for complete search history.

(56) References Cited

U.S. PATENT DOCUMENTS 4,922,905 A    5/1990  Strecker
5,002,566 A    3/1991  Carpentier et al.
(Continued)

FOREIGN PATENT DOCUMENTS

AU    2006308187 A1    5/2007
AU    2006310681 A1    5/2007
(Continued)

OTHER PUBLICATIONS

Aortenklappenbioprothese erfolgreich in der Entwicklung, May 16, 2003 (1 page).
(Continued)

*Primary Examiner* — Jason-Dennis Stewart
(74) *Attorney, Agent, or Firm* — Jones Robb, PLLC

(57) ABSTRACT

A device configured for implantation at a heart valve comprises an expandable stent. The stent comprises a first stent segment extending along a first length portion of the stent. The first stent segment is configured to be positioned and radially expanded against a vascular wall of a native aortic valve site. The first stent segment comprises a plurality of closed cell structures defining a circumference of the stent along the first length portion. The plurality of closed cell structures has a uniform density around the circumference. The stent also comprises a second stent segment disposed along a second length portion of the stent. The second stent segment comprises a plurality of interconnected strut members disposed around a circumference of the stent in alternating regions having a first strut density and a second strut density. The first strut density is higher than the second strut density.

16 Claims, 62 Drawing Sheets

Related U.S. Application Data

Figure 1A:
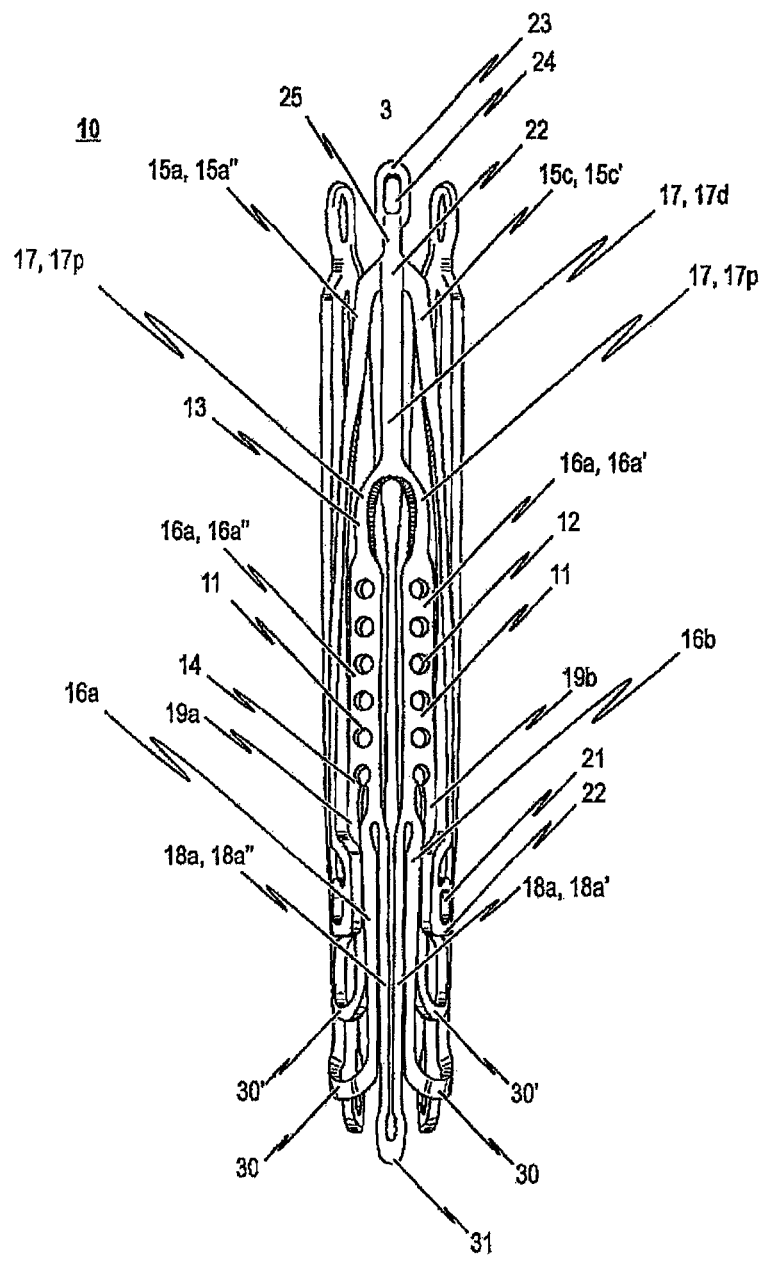

No. 14/312,180, filed on Jun. 23, 2014, now Pat. No. 9,439,759, which is a continuation of application No. 13/896,905, filed on May 17, 2013, now Pat. No. 8,790,395, which is a continuation of application No. 13/033,023, filed on Feb. 23, 2011, now Pat. No. 8,465,540, which is a continuation-in-part of application No. 12/713,058, filed on Feb. 25, 2010, now Pat. No. 8,398,704, which is a continuation-in-part of application No. 12/392,467, filed on Feb. 25, 2009, now Pat. No. 8,317,858, which is a continuation-in-part of application No. 12/285,544, filed on Oct. 8, 2008, now Pat. No. 9,168,130, which is a continuation-in-part of application No. 12/071,814, filed on Feb. 26, 2008, now Pat. No. 9,044,318.

(52) U.S. Cl.
CPC .... *A61F 2/2412* (2013.01); *A61F 2220/0058* (2013.01); *A61F 2220/0075* (2013.01); *A61F 2230/0023* (2013.01); *A61F 2230/0054* (2013.01)

(56) References Cited

U.S. PATENT DOCUMENTS

| | | |
|---|---|---|
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,469,868 A | 11/1995 | Reger |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenbilt et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 6,001,126 A | 12/1999 | Nguyen-Thien-Nhon |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 9/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 6/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,329,279 B2 | 2/2008 | Haug et al. |
| 7,381,218 B2 | 6/2008 | Schreck |
| 7,381,219 B2 | 6/2008 | Salahieh et al. |
| 7,393,360 B2 | 7/2008 | Spenser et al. |
| 7,399,315 B2 | 7/2008 | Lobbi |
| 7,405,259 B2 | 7/2008 | Frye et al. |
| 7,445,631 B2 | 11/2008 | Salahieh et al. |
| 7,452,371 B2 | 11/2008 | Pavcnik et al. |
| 7,473,275 B2 | 1/2009 | Marquez |
| 7,712,606 B2 | 5/2010 | Salahieh et al. |
| 7,748,389 B2 | 7/2010 | Salahieh et al. |
| 7,780,725 B2 | 8/2010 | Haug et al. |
| 7,824,442 B2 | 11/2010 | Salahieh et al. |
| 7,824,443 B2 | 11/2010 | Salahieh et al. |
| 7,867,274 B2 | 1/2011 | Hill et al. |
| 7,892,276 B2 | 2/2011 | Stocker et al. |
| 7,896,915 B2 | 3/2011 | Guyenot et al. |
| 7,914,575 B2 | 3/2011 | Guyenot et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |

(56) References Cited

U.S. PATENT DOCUMENTS

| | | |
|---|---|---|
| 7,967,853 B2 | 6/2011 | Eidenschink et al. |
| 7,988,724 B2 | 8/2011 | Salahieh et al. |
| 7,993,386 B2 | 8/2011 | Elliott |
| 8,002,824 B2 | 8/2011 | Jenson et al. |
| 8,012,198 B2 | 9/2011 | Hill et al. |
| 8,038,709 B2 | 10/2011 | Palasis et al. |
| 8,048,153 B2 | 11/2011 | Salahieh et al. |
| 8,052,749 B2 | 11/2011 | Salahieh et al. |
| 8,128,681 B2 | 3/2012 | Shoemaker et al. |
| 8,136,659 B2 | 3/2012 | Salahieh et al. |
| 8,137,394 B2 | 3/2012 | Stocker et al. |
| 8,182,528 B2 | 5/2012 | Salahieh et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,328,868 B2 | 12/2012 | Paul et al. |
| 8,343,213 B2 | 1/2013 | Salahieh et al. |
| 8,372,134 B2 | 2/2013 | Schlick et al. |
| 8,398,704 B2 | 3/2013 | Straubinger et al. |
| 8,414,641 B2 | 4/2013 | Stocker et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,512,399 B2 | 8/2013 | Lafontaine |
| 8,551,160 B2 | 10/2013 | Figulla et al. |
| 8,556,880 B2 | 10/2013 | Freyman et al. |
| 8,556,966 B2 | 10/2013 | Jenson |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,672,997 B2 | 3/2014 | Drasler et al. |
| 8,721,717 B2 | 5/2014 | Shoemaker et al. |
| 8,734,508 B2 | 5/2014 | Hastings et al. |
| 8,764,818 B2 | 7/2014 | Gregg |
| 8,778,020 B2 | 7/2014 | Gregg et al. |
| 8,808,364 B2 | 8/2014 | Palasis et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,851,286 B2 | 10/2014 | Chang et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,992,608 B2 | 3/2015 | Haug et al. |
| 8,998,976 B2 | 4/2015 | Gregg et al. |
| 9,005,273 B2 | 4/2015 | Salahieh et al. |
| 9,011,521 B2 | 4/2015 | Haug et al. |
| 9,028,542 B2 | 5/2015 | Hill et al. |
| 9,131,926 B2 | 9/2015 | Crisostomo et al. |
| 9,277,991 B2 | 3/2016 | Salahieh et al. |
| 9,277,993 B2 | 3/2016 | Gamarra et al. |
| 9,301,843 B2 | 4/2016 | Richardson et al. |
| 9,308,085 B2 | 4/2016 | Salahieh et al. |
| 9,320,599 B2 | 4/2016 | Salahieh et al. |
| 9,358,106 B2 | 6/2016 | Salahieh et al. |
| 9,358,110 B2 | 6/2016 | Paul et al. |
| 9,370,419 B2 | 6/2016 | Hill et al. |
| 9,370,421 B2 | 6/2016 | Crisostomo et al. |
| 9,387,076 B2 | 7/2016 | Paul et al. |
| 9,393,094 B2 | 7/2016 | Salahieh et al. |
| 9,393,113 B2 | 7/2016 | Salahieh et al. |
| 9,393,114 B2 | 7/2016 | Sutton et al. |
| 9,415,567 B2 | 8/2016 | Sogard et al. |
| 9,421,083 B2 | 8/2016 | Eidenschink et al. |
| 9,463,084 B2 | 10/2016 | Stinson |
| 9,474,598 B2 | 10/2016 | Gregg et al. |
| 9,474,609 B2 | 10/2016 | Haverkost et al. |
| 9,510,945 B2 | 12/2016 | Sutton et al. |
| 9,526,609 B2 | 12/2016 | Salahieh et al. |
| 9,554,924 B2 | 1/2017 | Schlick et al. |
| 2001/0011187 A1 | 8/2001 | Pavcnik et al. |
| 2001/0039450 A1 | 11/2001 | Pavcnik et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0193871 A1 | 12/2002 | Beyersdorf et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075776 A1 | 4/2005 | Cho |
| 2005/0075725 A1 | 5/2005 | Rowe |
| 2005/0096726 A1 | 5/2005 | Sequin et al. |
| 2005/0096735 A1 | 5/2005 | Hojeibane et al. |
| 2005/0098547 A1 | 5/2005 | Cali et al. |
| 2005/0113910 A1 | 5/2005 | Paniagua et al. |
| 2005/0096736 A1 | 6/2005 | Dsse et al. |
| 2005/0119728 A1 | 6/2005 | Sarac |
| 2005/0119736 A1 | 6/2005 | Zilla et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |

(56) References Cited

U.S. PATENT DOCUMENTS

| | | |
|---|---|---|
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0178740 A1 | 8/2006 | Stacchino et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271161 A1 | 11/2006 | Meyer et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0032856 A1 | 2/2007 | Limon |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Hans-Reiner et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0162107 A1 | 7/2007 | Haug et al. |
| 2007/0173932 A1 | 7/2007 | Cali et al. |
| 2007/0179592 A1 | 8/2007 | Schaeffer |
| 2007/0185565 A1 | 8/2007 | Scwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stoble |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 5/2008 | Pavcnik et al. |
| 2008/0102439 A1 | 5/2008 | Tian et al. |
| 2008/0125859 A1 | 5/2008 | Salahieh et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0255660 A1 | 6/2008 | Straubinger et al. |
| 2008/0200977 A1 | 8/2008 | Paul et al. |
| 2008/0215143 A1 | 9/2008 | Seguin |
| 2008/0234814 A1 | 9/2008 | Salahieh et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0216310 A1 | 8/2009 | Straubinger et al. |
| 2009/0216313 A1 | 8/2009 | Straubinger et al. |
| 2009/0222076 A1 | 9/2009 | Figulla et al. |
| 2009/0234443 A1 | 9/2009 | Ottma et al. |
| 2010/0174362 A1 | 7/2010 | Straubinger et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0292779 A1 | 11/2010 | Straubinger et al. |
| 2011/0004297 A1 | 1/2011 | Sogard et al. |
| 2011/0015616 A1 | 1/2011 | Straubinger et al. |
| 2011/0106244 A1 | 5/2011 | Ferrari et al. |
| 2011/0238159 A1 | 9/2011 | Guyenot et al. |
| 2011/0257735 A1 | 10/2011 | Salahieh et al. |
| 2011/0276129 A1 | 11/2011 | Salahieh et al. |
| 2011/0288626 A1 | 11/2011 | Straubinger et al. |
| 2011/0295363 A1 | 12/2011 | Girard et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0066419 A1 | 3/2013 | Gregg |
| 2013/0073037 A1 | 3/2013 | Gregg et al. |
| 2013/0079869 A1 | 3/2013 | Straubinger et al. |
| 2013/0089655 A1 | 4/2013 | Gregg |
| 2013/0090729 A1 | 4/2013 | Gregg et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0178930 A1 | 7/2013 | Straubinger et al. |
| 2013/0253635 A1 | 9/2013 | Straubinger et al. |
| 2013/0274865 A1 | 10/2013 | Haverkost et al. |
| 2013/0304199 A1 | 11/2013 | Sutton et al. |
| 2013/0345799 A1 | 12/2013 | Lafontaine |
| 2014/0083190 A1 | 3/2014 | Kaack et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0128969 A1 | 5/2014 | Hill et al. |
| 2014/0135912 A1 | 5/2014 | Salahieh et al. |
| 2014/0207229 A1 | 7/2014 | Shoemaker et al. |
| 2014/0243967 A1 | 8/2014 | Salahieh et al. |
| 2014/0379068 A1 | 12/2014 | Thielen et al. |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0127094 A1 | 5/2015 | Salahieh et al. |

(56) References Cited

U.S. PATENT DOCUMENTS

| | | |
|---|---|---|
| 2015/0142102 A1 | 5/2015 | Lafontaine et al. |
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0245909 A1 | 9/2015 | Salahieh et al. |
| 2015/0320557 A1 | 11/2015 | Sutton et al. |
| 2015/0335423 A1 | 11/2015 | Gregg et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0067040 A1 | 3/2016 | Agrawal et al. |
| 2016/0135951 A1 | 5/2016 | Salahieh et al. |
| 2016/0143731 A1 | 5/2016 | Backus et al. |
| 2016/0206423 A1 | 7/2016 | OConnor et al. |
| 2016/0213467 A1 | 7/2016 | Backus et al. |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0374793 A1 | 12/2016 | Lafontaine et al. |
| 2016/0376063 A1 | 12/2016 | Salahieh et al. |
| 2017/0007400 A1 | 1/2017 | Sogard et al. |
| 2017/0027693 A1 | 2/2017 | Paul et al. |

FOREIGN PATENT DOCUMENTS

| | | |
|---|---|---|
| CA | 2436258 A1 | 1/2005 |
| CA | 2595233 A1 | 7/2006 |
| CA | 2627555 A1 | 5/2007 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10121210 A1 | 11/2002 |
| DE | 19546692 C2 | 11/2002 |
| DE | 10301026 A1 | 2/2004 |
| DE | 10335948 B3 | 7/2004 |
| DE | 10302447 A1 | 2/2005 |
| DE | 10010074 B4 | 4/2005 |
| DE | 19857887 B4 | 5/2005 |
| DE | 10010073 B4 | 12/2005 |
| DE | 102005051849 | 5/2007 |
| DE | 102005052628 A1 | 5/2007 |
| DE | 202007005491 U1 | 7/2007 |
| EP | 0084395 A1 | 7/1983 |
| EP | 1519697 A1 | 8/1985 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0592410 B1 | 11/1995 |
| EP | 0729364 B1 | 9/1996 |
| EP | 0756498 B1 | 5/1997 |
| EP | 0778775 B1 | 6/1997 |
| EP | 0786970 A1 | 8/1997 |
| EP | 0871414 A1 | 10/1998 |
| EP | 0888142 A1 | 1/1999 |
| EP | 0928615 A1 | 7/1999 |
| EP | 0986348 B1 | 3/2000 |
| EP | 1041942 A1 | 10/2000 |
| EP | 1041942 B1 | 10/2000 |
| EP | 1041943 B1 | 10/2000 |
| EP | 1051204 A2 | 11/2000 |
| EP | 1089676 A2 | 4/2001 |
| EP | 1117446 B1 | 7/2001 |
| EP | 1158937 A1 | 12/2001 |
| EP | 1164976 A1 | 1/2002 |
| EP | 1171061 A1 | 1/2002 |
| EP | 1206179 B1 | 5/2002 |
| EP | 1235537 A1 | 9/2002 |
| EP | 1248655 A1 | 10/2002 |
| EP | 1251804 B1 | 10/2002 |
| EP | 1251805 A2 | 10/2002 |
| EP | 1257305 A1 | 11/2002 |
| EP | 1259193 A1 | 11/2002 |
| EP | 0971649 B1 | 12/2002 |
| EP | 1281357 A2 | 2/2003 |
| EP | 1281375 A2 | 2/2003 |
| EP | 1330213 A1 | 7/2003 |
| EP | 1017868 B1 | 9/2003 |
| EP | 1347785 A1 | 10/2003 |
| EP | 1354569 A1 | 10/2003 |
| EP | 1395208 A1 | 3/2004 |
| EP | 1401359 A2 | 3/2004 |
| EP | 1406561 A2 | 4/2004 |
| EP | 1408882 A1 | 4/2004 |
| EP | 1414295 A2 | 5/2004 |
| EP | 1435878 A1 | 7/2004 |
| EP | 1435879 A1 | 7/2004 |
| EP | 1441672 A1 | 8/2004 |
| EP | 1452153 A1 | 9/2004 |
| EP | 0987998 B1 | 10/2004 |
| EP | 1087727 | 11/2004 |
| EP | 1233731 | 12/2004 |
| EP | 1494616 A2 | 1/2005 |
| EP | 1499366 A1 | 1/2005 |
| EP | 1499366 B1 | 1/2005 |
| EP | 1253875 B1 | 4/2005 |
| EP | 1251803 B1 | 6/2005 |
| EP | 1539047 A2 | 6/2005 |
| EP | 1551274 A2 | 7/2005 |
| EP | 1560542 A1 | 8/2005 |
| EP | 1469797 B1 | 11/2005 |
| EP | 1603493 A2 | 12/2005 |
| EP | 1878407 A1 | 1/2006 |
| EP | 1663070 A2 | 6/2006 |
| EP | 1667614 A1 | 6/2006 |
| EP | 1690515 A1 | 8/2006 |
| EP | 1702247 A2 | 9/2006 |
| EP | 1734902 A1 | 12/2006 |
| EP | 1251805 B1 | 3/2007 |
| EP | 1255510 B1 | 3/2007 |
| EP | 1835948 A1 | 9/2007 |
| EP | 1112042 B1 | 11/2007 |
| EP | 1863545 A2 | 12/2007 |
| EP | 1886649 A2 | 2/2008 |
| EP | 1893132 A2 | 3/2008 |
| EP | 1900343 A2 | 3/2008 |
| EP | 1901681 A1 | 3/2008 |
| EP | 1259195 B1 | 10/2008 |
| EP | 1980220 A1 | 10/2008 |
| EP | 1994913 A2 | 11/2008 |
| EP | 2000115 A2 | 12/2008 |
| FR | 2828263 A1 | 2/2003 |
| GB | 2433700 A | 7/2007 |
| GB | 2440809 A | 2/2008 |
| JP | 2008539305 A | 11/2008 |
| WO | 9846165 | 10/1988 |
| WO | 9009102 | 8/1990 |
| WO | 9511055 A1 | 4/1995 |
| WO | 9524873 | 9/1995 |
| WO | 9528183 | 10/1995 |
| WO | 9613227 | 5/1996 |
| WO | 9732615 | 9/1997 |
| WO | 9843556 | 10/1998 |
| WO | 9937337 | 7/1999 |
| WO | 9966863 | 12/1999 |
| WO | 200015148 | 3/2000 |
| WO | 200018445 | 4/2000 |
| WO | 200025702 A1 | 5/2000 |
| WO | 200047139 A1 | 8/2000 |
| WO | 200053125 | 9/2000 |
| WO | 200062714 | 10/2000 |
| WO | 200110209 A1 | 2/2001 |
| WO | 01/36870 A1 | 5/2001 |
| WO | 2001135870 A1 | 5/2001 |
| WO | 200141679 A1 | 6/2001 |
| WO | 200151104 A1 | 7/2001 |
| WO | 200154625 A1 | 8/2001 |
| WO | 200158503 A1 | 8/2001 |

(56) References Cited

FOREIGN PATENT DOCUMENTS

| | | |
|---|---|---|
| WO | 200162189 A1 | 8/2001 |
| WO | 200164137 A1 | 9/2001 |
| WO | 2002136048 A1 | 5/2002 |
| WO | 2002058745 A1 | 8/2002 |
| WO | 2002100301 A1 | 12/2002 |
| WO | 2002102286 A1 | 12/2002 |
| WO | 2003007795 A2 | 1/2003 |
| WO | 20031003949 A2 | 1/2003 |
| WO | 2003009785 A1 | 2/2003 |
| WO | 2003013239 | 2/2003 |
| WO | 20031011195 A2 | 2/2003 |
| WO | 2003028592 A1 | 4/2003 |
| WO | 2003047468 A1 | 6/2003 |
| WO | 2003079928 A2 | 10/2003 |
| WO | 20031096935 A1 | 11/2003 |
| WO | 2004004597 A2 | 1/2004 |
| WO | 2004016201 A2 | 2/2004 |
| WO | 20040016200 A1 | 2/2004 |
| WO | 2004019825 A1 | 3/2004 |
| WO | 2004026117 A2 | 4/2004 |
| WO | 2004026173 A2 | 4/2004 |
| WO | 2004028399 A2 | 4/2004 |
| WO | 2007047945 A2 | 4/2004 |
| WO | 2004043301 A1 | 5/2004 |
| WO | 2004082527 A2 | 9/2004 |
| WO | 2004082528 A2 | 9/2004 |
| WO | 2004096100 A1 | 11/2004 |
| WO | 2005021063 A2 | 3/2005 |
| WO | 2005034812 A1 | 4/2005 |
| WO | 2005062980 A2 | 7/2005 |
| WO | 2005072654 A1 | 8/2005 |
| WO | 2006/066327 A1 | 6/2006 |
| WO | 2006066327 A1 | 6/2006 |
| WO | 2006076890 A1 | 7/2006 |
| WO | 2006102063 A2 | 9/2006 |
| WO | 2006108090 A2 | 10/2006 |
| WO | 2006124649 A2 | 11/2006 |
| WO | 2006127756 A2 | 11/2006 |
| WO | 2006127765 A1 | 11/2006 |
| WO | 2006132948 A1 | 12/2006 |
| WO | 2007047488 A2 | 4/2007 |
| WO | 2007048529 A1 | 5/2007 |
| WO | 2007051620 A1 | 5/2007 |
| WO | 2007059252 A1 | 5/2007 |
| WO | 2007071436 A2 | 6/2007 |
| WO | 2007098232 A2 | 8/2007 |
| WO | 2007120543 A1 | 10/2007 |
| WO | 2005/063980 A1 | 12/2007 |
| WO | 2008028569 A1 | 3/2008 |
| WO | 2008035337 A | 3/2008 |
| WO | 2008045949 | 4/2008 |
| WO | 2008070797 A2 | 6/2008 |
| WO | 2008079962 A1 | 7/2008 |
| WO | 2008101083 A2 | 8/2008 |
| WO | 2008125153 A1 | 10/2008 |
| WO | 2008138584 A1 | 11/2008 |
| WO | 20081150529 A | 12/2008 |
| WO | 2010086460 A9 | 8/2010 |

OTHER PUBLICATIONS

Screen shots from http:llwww.fraunhofer.de/presse/filme/2006/index.jsp, 2006 (2 pages).

Liang, Ma, et al., "Double-crowned valved stents for off-pump mitral valve replacement," Eur. J. Cardio-Thoracic Surgery, vol. 28, pp. 194-198 (2005) (5 pages).

Huber, Christoph H., et al. "Direct Access Valve Replacement (DAVR)—are we entering a new era in cardiac surgery?" Eur. J. Cardio-Thoracic Surgery, vol. 29, pp. 380-385 (2006) (6 pages).

English translation of DE 19 546 692 A1 (4 pages).

English translation of EP 1 469797 B1 (16 pages).

File history for German Patent DE 19 546692 filed Dec. 14, 1995 and patented Jul. 11, 2002 (111 pages).

Klein, Allan L. et al., "Age-related Prevalence of Valvular Regurgitation in Normal Subjects: A Comprehensive Color Flow Examination of 118 Volunteers," J. Am. Soc. Echocardiography, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," Thorac. Cardiov. Surg., vol. 56, pp. 328-336 (2008) (9 pages).

Gummert, J.F. et al., "Cardiac Surgery in Germany During 2006: A Report on Behalf of the German Society for Thoracic and Cardiovascular Surgery," Thorae. Cardiov. Surg., vol. 55, pp. 343-350 (2007) (8 pages).

English translation of Aortenklappenbioprothese erfolgreich in der Entwicklung, May 16, 2003 (2 pages).

Notice of Allowance in co-pending U.S. Appl. No. 15/221,860, dated Jan. 19, 2018.

Office Action in co-pending U.S. Appl. No. 15/221,860, dated Aug. 8, 2017.

STENT FOR THE POSITIONING AND ANCHORING OF A VALVULAR PROSTHESIS IN AN IMPLANTATION SITE IN THE HEART OF A PATIENT

This application is a continuation of U.S. patent application Ser. No. 15/221,860, filed Jul. 28, 2016, which is a continuation of U.S. patent application Ser. No. 14/312,180, filed Jun. 23, 2014, now U.S. Pat. No. 9,439,759, which is a continuation of U.S. patent application Ser. No. 13/896,905, filed May 17, 2013, now U.S. Pat. No. 8,790,395, which is a continuation of U.S. patent application Ser. No. 13/033,023, filed Feb. 23, 2011, now U.S. Pat. No. 8,465,540, which is a continuation-in-part application of U.S. patent application Ser. No. 12/713,058, filed Feb. 25, 2010, now U.S. Pat. No. 8,398,704, which is a continuation-in-part application of U.S. patent application Ser. No. 12/392,467, filed Feb. 25, 2009, now U.S. Pat. No. 8,317,858, which is a continuation-in-part application of U.S. patent application Ser. No. 12/285,544, filed Oct. 8, 2008, now U.S. Pat. No. 9,168,130, which is a continuation-in-part application of U.S. patent application Ser. No. 12/071,814, filed Feb. 26, 2008, now U.S. Pat. No. 9,044,318, each of which is incorporated herein by reference in its entirety.

DESCRIPTION

The present invention relates to a stent for the positioning and anchoring of an endoprosthesis in an implantation site in the heart of a patient. Specifically, the present invention relates to an expandable stent for an endoprosthesis used in the treatment of a stenosis (narrowing) of a cardiac valve and/or a cardiac valve insufficiency.

The present invention also relates to an endoprosthesis that includes a stent for positioning and anchoring of the prosthesis at the implantation site in the heart of a patient. Specifically, the present invention also relates to a collapsible and expandable prosthesis incorporating a stent that can be delivered to the implant site using a catheter for treatment of a stenosis (narrowing) of a cardiac valve and/or a cardiac valve insufficiency.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortic and mitral valves) are affected much more often than the right-sided part of the heart (pulmonary and tricuspid valves). The functional defect can result in narrowing (stenosis), inability to close (insufficiency) or a combination of the two (combined vitium). This invention relates to an endoprosthesis that includes an expandable stent capable of being implanted transluminally in a patient's body and enlarged radially after being introduced percutaneously for treating such a heart valve defect.

In the current treatment of severe narrowing of a cardiac valve and/or cardiac valve insufficiency, the narrowed or diseased cardiac valve is replaced with an endoprosthesis. Biological or mechanical valves models, which are typically surgically sewn into the cardiac valve bed through an opening in the chest after removal of the diseased cardiac valve, are used for this purpose. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stent can then be unfolded.

To this end, it is known that a stent may be comprised of, for example, a plurality of self-expanding longitudinal stent segments, the segments being articulated relative to one another. In order to anchor the stent securely in position in an appropriate blood vessel close to the heart, anchoring barbs are frequently used to engage with the vascular wall.

An expandable stent for the fastening and anchoring of an endoprosthesis is known from printed publication DE 10 010 074 A1, whereby the stent is essentially formed from wire-shaped, interconnected segments. DE 10 010 074 A1 proposes a stent for fastening and anchoring an endoprosthesis, the stent having different arched elements which assume the function of fastening and supporting the valvular prosthesis at the site of implantation. Specifically, three identically-configured positioning arches spaced 120° from one another respectively are used. These positioning arches are connected to one another by means of solid body articulations. In addition to the positioning arches, complementary curved retaining arches serve to anchor the endoprosthesis by pressing radially against the vascular wall following the unfolding of the stent.

However, there is a risk of inexact or incorrect implantation of an endoprosthesis using the solutions described above. Expressed in another way, there is a need for exact positioning and longitudinal alignment of an implanted endoprosthesis. In particular, it is only possible using great skill on the part of the attending surgeon or cardiologist—if at all—to position a stent sufficiently precisely, in both a lateral and longitudinal direction, to ensure that the associated endoprosthesis is located in the correct area of the patient's diseased heart valve.

Among other things, inexact implantation of a sub-optimally positioned endoprosthesis can lead to leakage or valvular insufficiency which results in considerable ventricular stress. For example, if an endoprosthesis is implanted too far above the plane of the native heart valve, this can lead to closure or blocking of the coronary artery ostia (inlet orifice of coronaries) and thus to fatal coronary ischemia and myocardial infarction.

Therefore, for the optimal treatment of a narrowed cardiac valve or a cardiac valve insufficiency, it is necessary to position a stent, to which a valvular prosthesis is affixed, as precisely as possible at the site of implantation of the cardiac valve to be treated.

An endoprosthesis for treating aortic valve insufficiency is known from printed publication DE 20 2007 005 491 U1. The endoprosthesis comprises a valvular prosthesis and a stent to position and anchor the endoprosthesis at the implantation site in the patient's heart. A stent having several (multiple, normally three, but two in case of bicuspid valve) positioning arches is employed in this endoprosthesis. In the implanted state of the stent, these positioning arches extend radially and serve to engage in the pockets of the native (diseased) cardiac valve to be treated. The valvular prosthesis affixed to the stent can then self-position into the plane of the cardiac valve. Retaining arches abut against the vascular wall of the aorta in the implanted state of the endoprosthesis, form a force-fit connection and are used to anchor the endoprosthesis.

While the positioning arches enable optimal positioning of the stent of this endoprosthesis at the site of implantation in the patient's heart, what cannot be ensured is that the valvular prosthesis attached to the lower end section of the stent is actually also positioned in the plane of the cardiac valve. In particular, substantial forces act on the endoprosthesis during the filling phase of the heart cycle (diastole), which can lead to the endoprosthesis displacing longitudinally relative the stent. Due to this longitudinal displacement of the implanted endoprosthesis, which occurs in the heart and blood vessels especially because of the peristaltic motion of the heart, the implanted endoprosthesis may no longer be able to provide a secure seal.

Moreover, there is the danger that, because of the longitudinal displacement of the valvular prosthesis relative to the stent occurring with the peristaltic motion, the threads or sutures used to fasten the valvular prosthesis to the stent may chafe against the stent. It can therefore not be excluded that the fastening threads may fray over the course of time and thus lose their fastening function. This would result in at least a partial separation of the valvular prosthesis from the stent, which in turn can lead to leakages, an inappropriate positioning or even complete detachment of the valvular prosthesis.

On the basis of the problems outlined above, certain embodiments of the present invention address the issue of providing a self-expandable endoprosthesis for treating a narrowed cardiac valve or a cardiac valve insufficiency which realizes optimum positioning accuracy and anchoring of an endoprosthesis to be implanted. In addition, the treatment of the narrowed cardiac valve or cardiac valve insufficiency should be by way of a simple procedure to enable routine treatment of narrowed cardiac valve or cardiac valve insufficiency without major stress to the patient.

In this regard and as it will be described later in detail, the invention provides an expandable stent for the positioning and anchoring of an endoprosthesis in an implantation site in the heart of a patient in the treatment of a narrowed cardiac valve or a cardiac valve insufficiency, wherein the stent comprises a plurality of positioning arches configured to be positioned within a plurality of pockets of the patient's native heart valve and positioned on a first side of a plurality of native heart valve leaflets, and a plurality of retaining arches configured to be positioned on a second side of the plurality of native heart valve leaflets opposite the first side.

As it will be described in detail later on, in some embodiments of the present invention, the expandable stent may further include at least one auxiliary arch interspaced between two adjacent retaining arches, wherein the at least one auxiliary arch includes a first arm connected at a first end thereof to a first retaining arch and a second arm connected at a first end thereof to a second retaining arch, and wherein the first and second arms of the at least one auxiliary arch each include respective second ends connected to one another at a joint that includes at least one fastening hole configured to receive a suture.

In addition or instead of the at least one auxiliary arch, the stent according to the present invention may further comprise at least one radial arch substantially circumferentially aligned with at least one of the plurality of positioning arches.

Otherwise, it is conceivable that the stent according to the present invention is further provided with a plurality of auxiliary arches, each of said plurality of auxiliary arches being interspaced between two adjacent retaining arches and including a first arm connected at a first end thereof to a first retaining arch and a second arm connected at a first end thereof to a second retaining arch.

Furthermore, the stent according to the present invention may also be provided with a plurality of extra arches, each of said plurality of extra arches being interspaced between a first retaining arch and an adjacent second retaining arch.

Preferably, the stent according to the present invention further comprises a plurality of leaflet guard arches, each interspaced between the two arms of one of the plurality of positioning arches.

A further task of certain embodiments of the present invention lies in specifying an endoprosthesis for the treatment of a stenosed cardiac valve or a cardiac valve insufficiency, whereby the endoprosthesis can be anchored securely at the site of implantation in the patent's heart. In addition, certain embodiments of the present invention also address the issue of substantially preventing displacement of an implanted endoprosthesis from its ideal site of implantation in spite of the forces acting on the endoprosthesis during the filling phase of the heart cycle.

The present invention is also directed to an endoprosthesis constituted by a stent as defined in the claims on the one hand and a valvular prosthesis affixed to the stent.

As described herein, stents may be radially expandable intravascular implants capable of being implanted transluminally and enlarged radially after being introduced percutaneously. The stents may be configured to be placed in a native diseased valve of a patient, such as a native stenotic aortic or pulmonary valve, using a minimally-invasive approach, such as a beating heart transapical procedure or a retrograde transaortic procedure. Although stents can be introduced into the body of the patient via any number of access points, a transvascular approach by femoral access or by transapical access for the aortic valve is preferred. However, this invention is not limited to these approaches.

A "native aortic valve" may be a tricuspid (with three leaflets) or congenitally bicuspid (with two leaflets).

An endoprosthesis may include an implant which (together with a stent to which the valvular prosthesis is affixed) functions as a check valve, opening to permit forward blood flow and closing to prevent retrograde flow. A valvular prosthesis may consists of at least two and preferably of three leaflets and a valve skirt on which the leaflets are connected.

From one aspect, an expandable stent of a collapsible and expandable prosthesis is proposed in accordance with certain embodiments of the present invention, the stent comprising at least one fastening portion by means of which a valvular prosthesis is connected to the stent. In addition, the stent comprises positioning arches and retaining arches. At least one positioning arch of the stent is connected with at least one retaining arch of the stent by a first connecting web. Additionally, the stent further comprises at least one auxiliary arch which interconnects the arms of respective retaining arches.

The at least one fastening portion extends along the longitudinal axis of the stent and comprises a plurality of fastening holes distributed in a longitudinal direction at discrete positions along the length of the at least one fastening portion. Thread or thin wire may be guided through each fastening hole to secure the valvular prosthesis to the stent. The advantage of this feature is that longitudinal displacement of the valvular relative to the stent is substantially minimized once implanted and so the prosthesis is not unduly disturbed or weakened as a result of the heart's peristaltic motion.

In addition to fastening holes, the fastening portion may include one or more notches to assist the seating and retaining of suture material. The notches also assist with even attachment of the prosthesis to the stent and, similarly to the fastening holes, minimize longitudinal displacement of the prosthesis.

Extending from and between a pair of fastening portions is a fastening arch, over which valve tissue is laid. In the expanded and implanted state of the stent and the valvular prosthesis affixed thereto, the fastening arch of the stent abuts against the vessel wall at least at the lower section of the stent in order to seal against leakage. Furthermore, with the fastening arch, the prosthesis tissue is separated and held away from positioning and retaining arches, thereby reducing the likelihood of these arches chaffing the tissue which, in turn may result in damage and weakening of the prosthesis. The fastening arch serves to anchor the lower edge of the valvular prosthesis and to tension the material so the prosthesis is effective as a valve. By having a fastening portion and fastening arches, the prosthesis is fully supported and anchored within the boundary of the stent. The combination of the two fastening mechanisms also provides a failsafe should one fastening mechanism fail. This is of particular relevance with suturing since a poorly sutured prosthesis will not be as effective as it should due to additional stresses and strains imparted to the prosthesis by the sutures. Thus, the arches allow fastening of the prosthesis in a manner that does not rely solely on suturing.

In an implanted configuration, the at least one positioning arches of the stent extends from the circumference of the stent in a generally radial direction. These positioning arches are designed to engage in the pockets of the native (diseased) cardiac valve that is being replaced which, in turn allows accurate positioning of the stent. Furthermore, on implantation, a positioning arch sits between the vascular wall and a leaflet of the native heart valve. The positioning arch then co-operates with a corresponding retaining arch resulting in clipping of the native leaflet between the two arches. In this way, the positioning and retaining arches together hold the stent in position and substantially eliminate axial rotation of the stent.

In a preferred embodiment (cf. the stent according to the eighteenth embodiment), the positioning arch may be shaped to have a substantially convex shape. In other words, the end of the arch that is positioned in the native valve leaflet may be curved towards the inside of the stent or towards the longitudinal axis of the stent. In this way, the shape of the each positioning arch provides an additional clipping force against the native valve leaflet.

The at least one retaining arch is connected to a positioning arch by a connecting web. The retaining arch extends radially in the implanted state of the stent such that the at least one retaining arch presses against the wall of the blood vessel in which the stent is deployed with a radially-acting tensioning force. In situ, the ends of each retaining arch also fits underneath the aortic valve annulus, providing further means for locating and anchoring the stent. In addition to the at least one retaining arch, certain embodiments of the invention provide for the stent to further comprise at least one auxiliary arch which interconnects the respective arms of the at least one retaining arch connected to the at least one positioning arch. As with the at least one retaining arch, the at least one auxiliary arch also protrudes radially in the expanded state of the stent such that the at least one auxiliary arch also presses against the wall of the blood vessel in which the stent is deployed with a radially-acting tensioning force.

The stent of a collapsible and expandable prosthesis may also include radial arches positioned between each positioning arch, with each radial arch extending upwards towards the upper end section of the stent. The radial arches provide additional means by which the stent may be retained within a catheter before and during implantation, and provide means by which the stent may be recaptured after implantation. The arches also add radial strength to the upper end section of the stent.

In the at least one fastening portion of the stent, by means of which the tissue component(s) of the overall prosthesis can be fastened to the stent, a plurality of fastening holes and optionally one or more notches is provided. These fastening holes and notches are longitudinally distributed at given positions on the fastening portion and guide at least one thread or thin wire to fasten the tissue component(s) of the valvular prosthesis to the stent, thereby enabling a precise positioning of the tissue component(s) of the overall prosthesis on the stent. Each individual fastening hole and notch provided in the at least one fastening portion thereby serves to guide a thread or thin wire with which the tissue component(s) of the valvular prosthesis is affixed or sewn to the fastening portion of the stent.

The means provided for fastening the tissue component(s) of the valvular prosthesis to the fastening portion of the stent (thread or thin wire) is guided by way of the fastening holes and notches so that a longitudinal displacement of the valvular prosthesis relative to the stent is substantially minimized. This also allows exact positioning of the valvular prosthesis relative the stent.

The secure and defined fixing of the tissue component(s) of the valvular prosthesis to the at least one fastening portion of the stent moreover effectively prevents the means used to fasten the tissue component(s) to the stent (threads or thin wires) from rubbing against the stent and thus degrading after a longer period of use.

In order to configure the plurality of fastening holes and any notches in the fastening portion, the at least one fastening portion is preferably configured as—in comparison to the respective arms of the positioning arch, retaining arch and auxiliary retaining arch—a widened segment. Thus, the fastening portion is a stent segment which comprises a relatively large amount of material, facilitating movement and position analysis when the stent is being implanted. For example, when fluoroscopy (cardiac catheterization=LHK) or ultrasound (trans-esophageal echocardiogram=TEE) is used to monitor the insertion procedure, the fastening portion of the stent is particularly distinguishable.

A preferred realization of the stent according to a particular embodiment the invention provides for a fastening portion to be configured within each arm of the stent's retaining arch.

In order to reinforce the respective retaining arches of the stent, the auxiliary arch as already mentioned above is provided. The auxiliary arch extends from the lower ends of the fastening portion and connects the respective arms of two neighboring retaining arches.

In manufacturing the stent used in the valvular prosthesis according to a particular embodiment of the invention, it is conceivable for the stent to exhibit a structure integrally cut from a portion of tube, in particular from a metal tube, which incorporates the positioning arches, retaining arches and auxiliary retaining arches as well as the at least one fastening portion with defined fastening holes and notches. It is also conceivable that the stent is cut out of a relatively large tube, i.e. a tube having a diameter which is larger compared with the diameter of the final stent in its collapsed configuration. For example, a tube having a diameter of approximately 10 mm may be used for cutting a specific stent pattern into this tube. Then the cut pattern will be different, as it will become necessary to crimp the stent to something smaller than what it was originally cut from. In particular, with this procedure it is possible to remove material during cutting and processing in a defined manner thereby enhancing the functionality of the final stent.

Specifically, it is conceivable to use a laser to cut the stent structure from a metal tube, whereby the structure is thereafter subject to an applicable shaping and thermal treatment process so that the stent can transform from a collapsed state during implantation into an expanded state at the site of implantation. This shaping and thermal treatment process is advantageously performed gradually in order to prevent damage to the stent structure.

Particularly preferred is for the stent to exhibit a structure integrally cut from a metal tube in which each positioning arch is allocated one retaining arch, and in which each upper end portion of the positioning arch towards the upper end of the stent is connected with the upper end portion of the associated retaining arch via a first connecting web. The at least one fastening portion, in which the plurality of fastening holes is provided, is thereby preferably configured within an arm of the retaining arch.

The stent preferably exhibits an integrally-formed structure which can transform from a first predefinable shape into a second predefinable shape, whereby the stent exhibits a first predefinable shape (collapsed shape) during insertion into the patient's body and a second predefinable shape (expanded shape) once implanted. Because of the stent's design, during the transition of the stent from the first predefinable shape into the second predefinable shape, the positioning arches, retaining arches and auxiliary arches are radially expanded as a function of the cross-sectional expansion of the stent. The stent's second shape is thereby preferably selected such that when the stent is expanded, the retaining arch and the auxiliary arch abut against the wall of the blood vessel in which the stent is deployed. In addition, the ends of the retaining arches are positioned beneath the native valve annulus, thereby providing additional anchoring of the stent.

To achieve a secure anchoring of the stent at the site of implantation, both the retaining and auxiliary arches should press against the wall of the vessel with a radial force, whereby this radial force can be set by subjecting the stent structure to a suitable shaping and thermal treatment process.

It is to be understood that the term "upper" refers to the stent when viewed in its implanted state. In other words, the term "upper" refers to the upper end section of the stent which, when implanted, is sited away from the heart. Similarly, use of the term "lower" refers to a proximal position on the stent which is located towards the ventricle side of the heart when the stent is viewed in its implanted position.

A preferred embodiment (cf. the eighteenth embodiment) of the stent according to the invention provides for the positioning arches and the associated retaining arches as well as auxiliary arches each to exhibit an essentially U-shaped, T-shaped or V-shaped structure which is closed toward the lower end of the stent. It is particularly preferred for each positioning arch to be cut from the material portion of a metal tube from which the essentially U-shaped, T-shaped or V-shaped structure of the associated retaining arch was taken. The respective auxiliary arches are preferably cut from a material portion of the metal tube situated between the essentially U-shaped, T-shaped or V-shaped retaining arch structures.

This preferred embodiment of the stent structure thus provides for the respective retaining and auxiliary arches of the stent to form the lower region of the endoprosthesis, whereby the positioning arches are configured symmetrically to the retaining arches although preferably disposed somewhat further toward the upper region of the endoprosthesis.

The respective upper ends of the positioning arches are connected to the respective upper ends of the associated retaining arches by means of a first connecting web in the upper region of the endoprosthesis. The fastening portions are configured in the respective arms of the retaining arch. In the expanded state of the stent, both the lower region with the fastening portions, as well as the connecting web disposed at the upper end of the stent between the respective positioning and retaining arches, spread out so that a radially-acting force is exerted on the blood vessel wall from both the lower region of the stent as well as the upper end of the stent, thereby enabling secure anchoring of the stent at the site of implantation.

In a preferred embodiment, the stent exhibits in its first shape (collapsed shape) an outer diameter of approximately 4 to 8 mm and a length of between 30 mm and 42 mm. More precisely, the stent may exhibit in its first shape (collapsed shape) an outer diameter of approximately 4.0 to 8.0 mm, preferably of approximately 5.0 mm, more preferably of approximately 6.0 mm, and a length of between 33.0 mm and 40.0 mm, preferably between 34.0 mm and 40.0 mm, and more preferably between 34.0 mm and 39.0 mm. This allows a prosthesis including the stent to be inserted easily into the patient's body, for example with a 21F delivery system, and to be used with an endoprosthesis having a diameter of between 19 mm and 28 mm. The aforementioned length specifications are the dimensions currently preferred, based on which the stent becomes suitable for the majority of patients to be treated.

In order to achieve a particularly secure anchoring of the implanted stent with the stretched valvular prosthesis affixed thereto, it is further conceivable for the stent to be subject to a shaping and thermal treatment process during its manufacture such that the finished stent exhibits a slightly concave configuration.

For example, the finished stent may exhibit a slightly concave configuration tapering toward its upper end section in its implanted and fully expanded state. When the stent together with a valvular prosthesis affixed thereto is in its implanted and fully expanded state, the largest diameter of the lower end section of the stent is positioned below the annulus and tries to assume a larger diameter than the upper end section of the stent even though the upper end section of the stent spreads out a little larger, thereby providing larger radial forces to anchor the stent and the valvular prosthesis affixed thereto in the implanted state. This enables a secure hold of the stent in the blood vessel without damaging the arterial wall. This configuration also provides secure anchoring that is able to withstand the peristaltic motion of the heart and the arterial wall and reliably seal the prosthesis against the arterial wall. It is of course also conceivable to design the concave configuration of the stent in its second shape to be of greater or lesser concavity.

Preferably, the stent diameter at the lower end section of the stent should be able to accommodate a range of annulus diameters around the target diameter. Within this range the forces applied due to the stiffness of the expanded and implanted stent to the vessel wall shall be adequate to prevent migration of the implanted stent, but not too great to cause annular rupture or AV node block. At the upper end section of the stent, it is desirable that the stent does not vary in diameter significantly to minimize the impact to the valve coaptation or opening performance even when the annulus diameter is not exactly at the target diameter.

It is preferable for the lower end area of the stent, when in its second shape, to exhibit a diameter of between 22 mm and 33 mm, preferably between 25 mm and 31 mm. It is conceivable for the stent to exhibit two or more differently dimensioned sizes whereby the optimal stent size can be selected depending upon specific patient. In addition, exact and patient-specific dimensions of the stent—starting from a given stent size—can be realized by appropriately curing the stent, in particular by a thermal treatment process.

In a particularly preferred realization, the stent comprises a valvular prosthesis, preferably a biological or pericardial valvular prosthesis, wherein the tissue component(s) of the valvular prosthesis is/are attached to the at least one fastening portion of the stent by means of a thread or the like.

A shape memory material is preferably used as the material for the stent, the material being designed such that the stent can transform from a temporary shape into a permanent shape under the influence of an external stimulus. The temporary shape is thereby the stent's first shape (i.e. the collapsed state of the stent), while the permanent shape is assumed in the stent's second shape (i.e. in the expanded state of the stent). In particular, use of a shape memory material such as Nitinol, i.e. an equiatomic alloy of nickel and titanium, allows for a particularly gentle implantation procedure when implanting the stent.

It is conceivable of course that other shape memory materials, for example shape-memory polymers, are used as the material for the stent. At least parts of the stent may be formed by using, for example, a polymer composite exhibiting a crystalline or semi-crystalline polymer network having crystalline switching segments. On the other hand, an amorphous polymer network having amorphous switching segments is also conceivable.

When manufacturing the stent preferably made from a shape memory material, the stent structure is preferably shaped after it has been cut from a tube. It is conceivable that the stent is cut out of a tube having a diameter which is larger compared with the diameter of the final stent in its collapsed configuration. Then, the laser-processed tube is crimped thereby achieving the diameter of the stent in its collapsed configuration. Once the desired shape has been formed, this shape is "fixed", this process being known as "programming". Programming may be effected by heating the stent structure, forming the stent into the desired shape and then cooling the stent. Programming may also be effected by forming and shaping the stent structure at lower temperature, this being known as "cold stretching." The permanent shape is thus saved, enabling the stent to be stored and implanted in a temporary, non-formed shape. If an external stimulus then acts on the stent structure, the shape memory effect is activated and the saved, permanent shape restored.

A particularly preferred embodiment provides for the external stimulus to be a definable switching temperature. It is thus conceivable that the stent material needs to be heated to a higher temperature than the switching temperature in order to activate the shape memory effect and thus regenerate the saved permanent shape of the stent. A specific switching temperature can be preset by the relevant selection of the chemical composition of the shape memory material.

It is particularly preferred to set the switching temperature to be in the range of between 10° C. and the patient's body temperature and preferably in the range of between 10° C. and room temperature. Doing so is of advantage, especially with regard to the medical device being used as an implant in a patient's body. Accordingly, all that needs to be ensured in this regard when implanting the stent is that the stent is warmed up to room temperature or the patient's body temperature (37° C.) at the site of implantation to activate the shape memory effect of the stent material.

The following will make reference to the included drawings in describing preferred embodiments of the stent according to the present invention in greater detail.

Figure 1B:
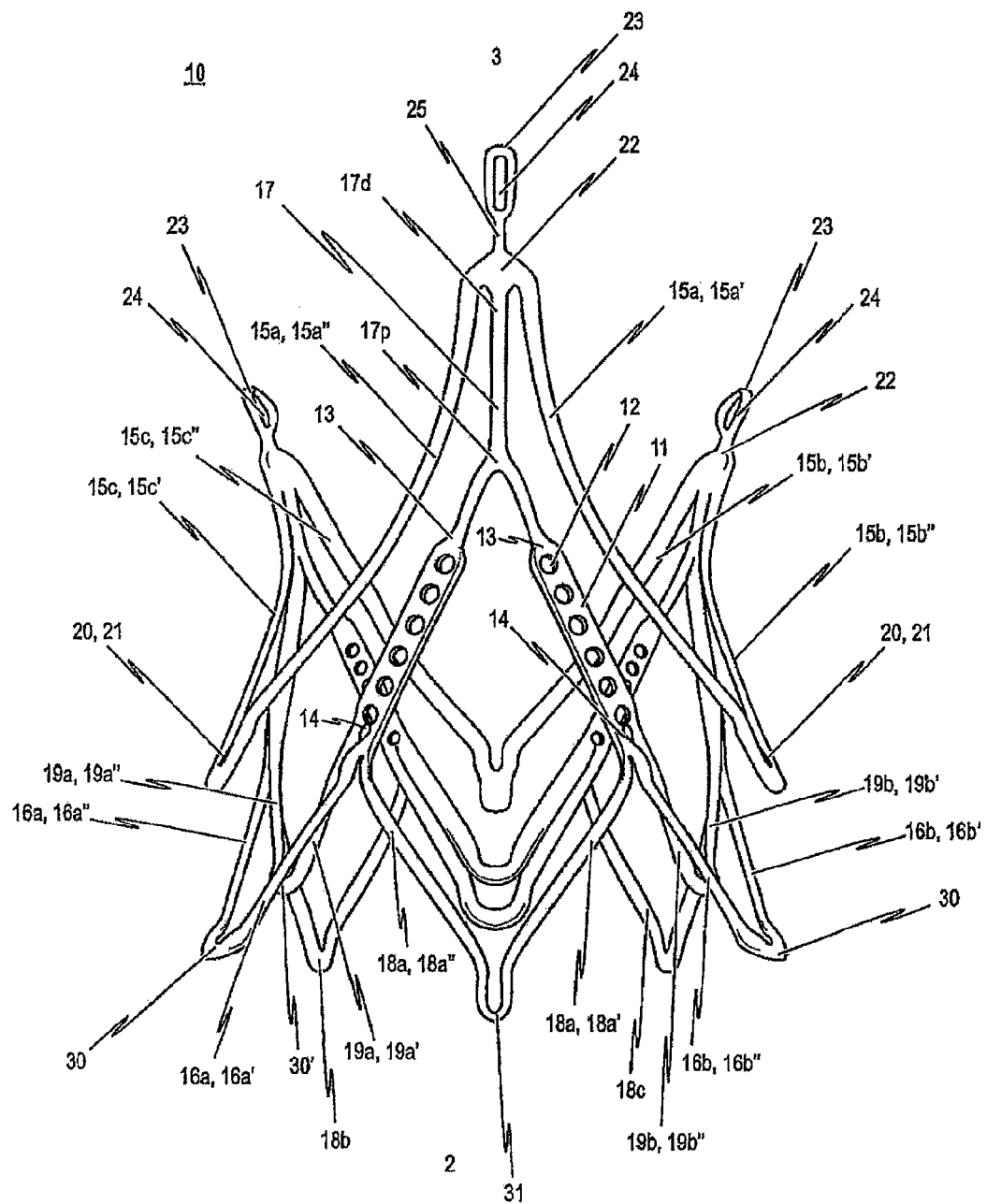
Figure 1C:
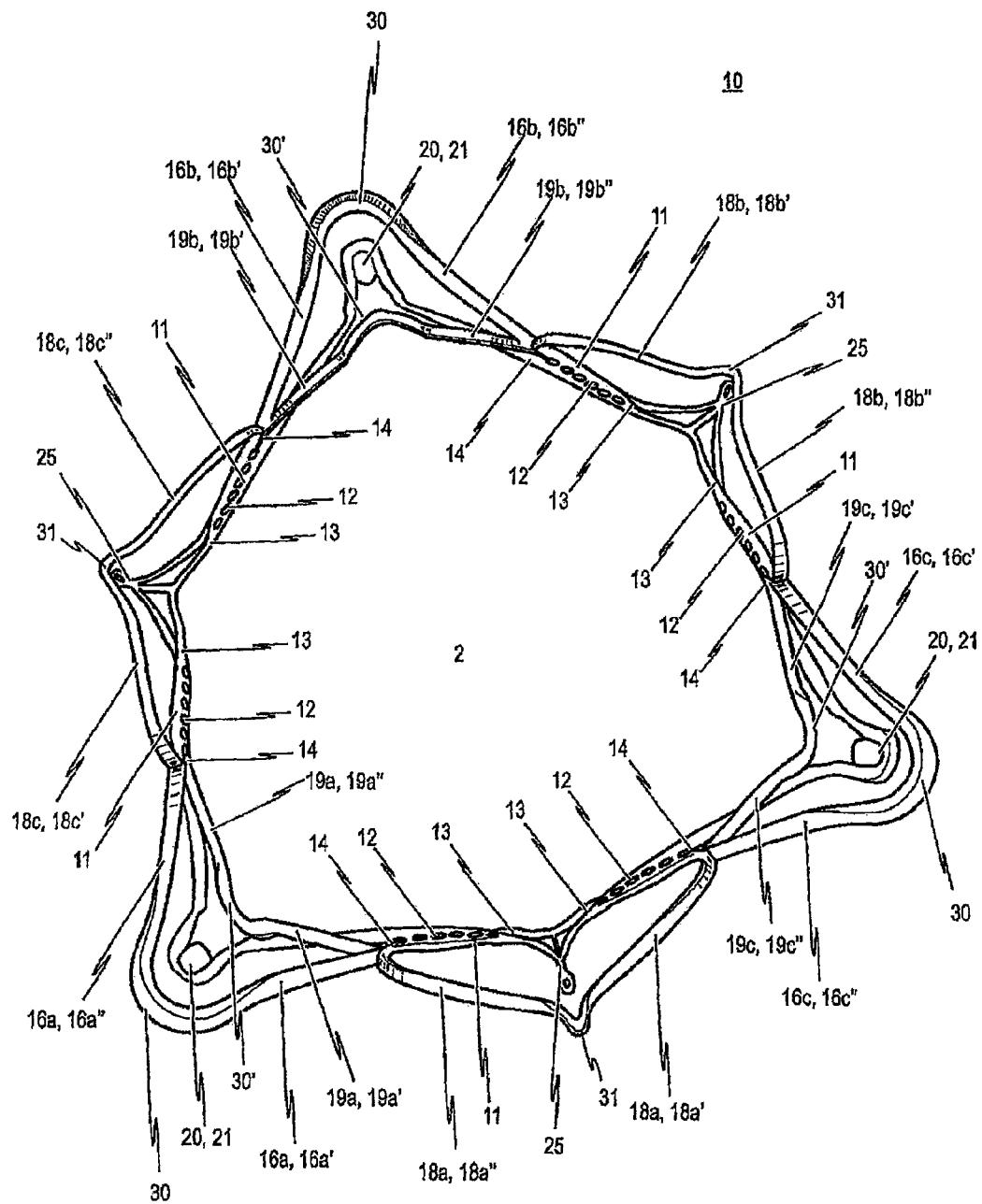
Figure 1D:
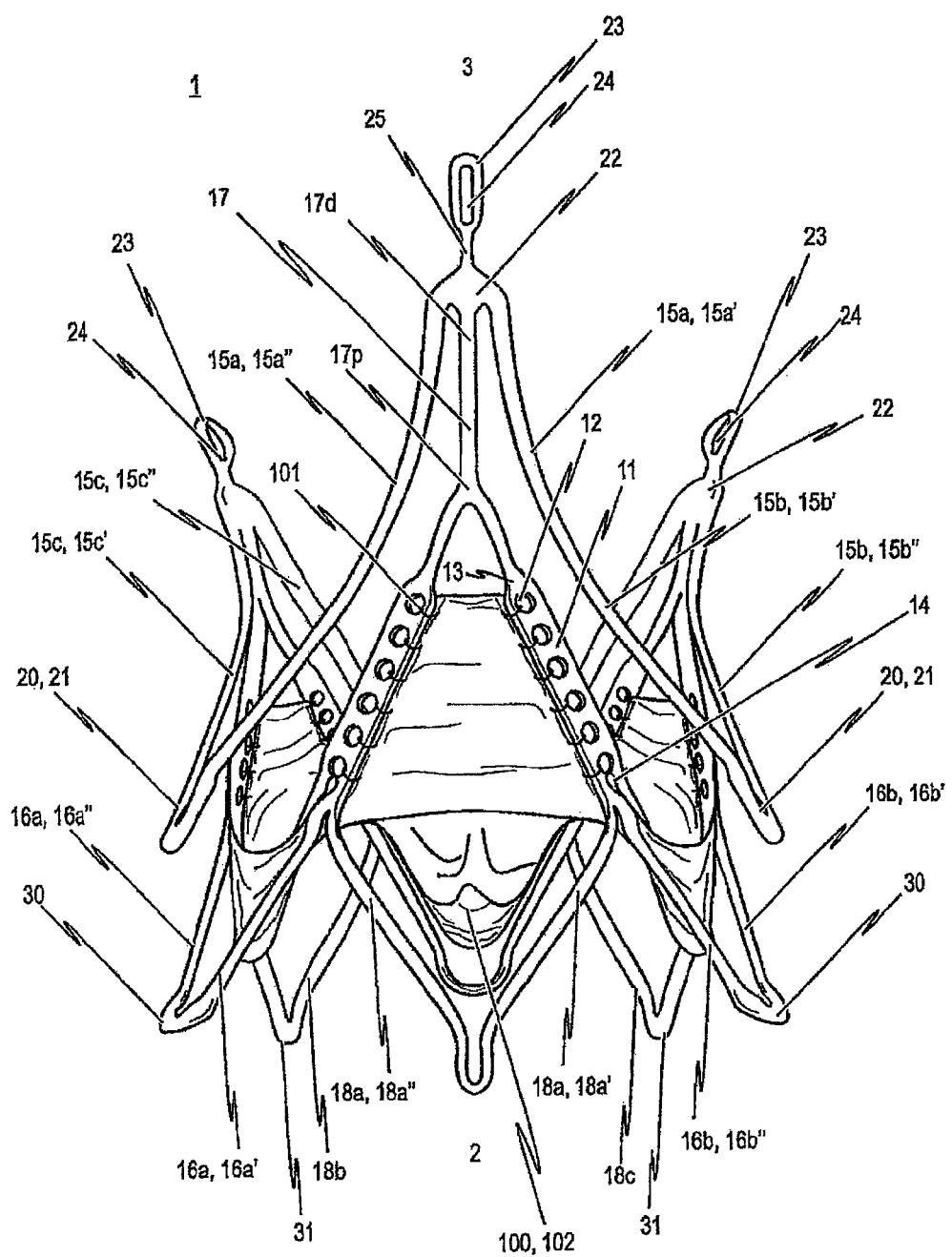
Figure 1E:
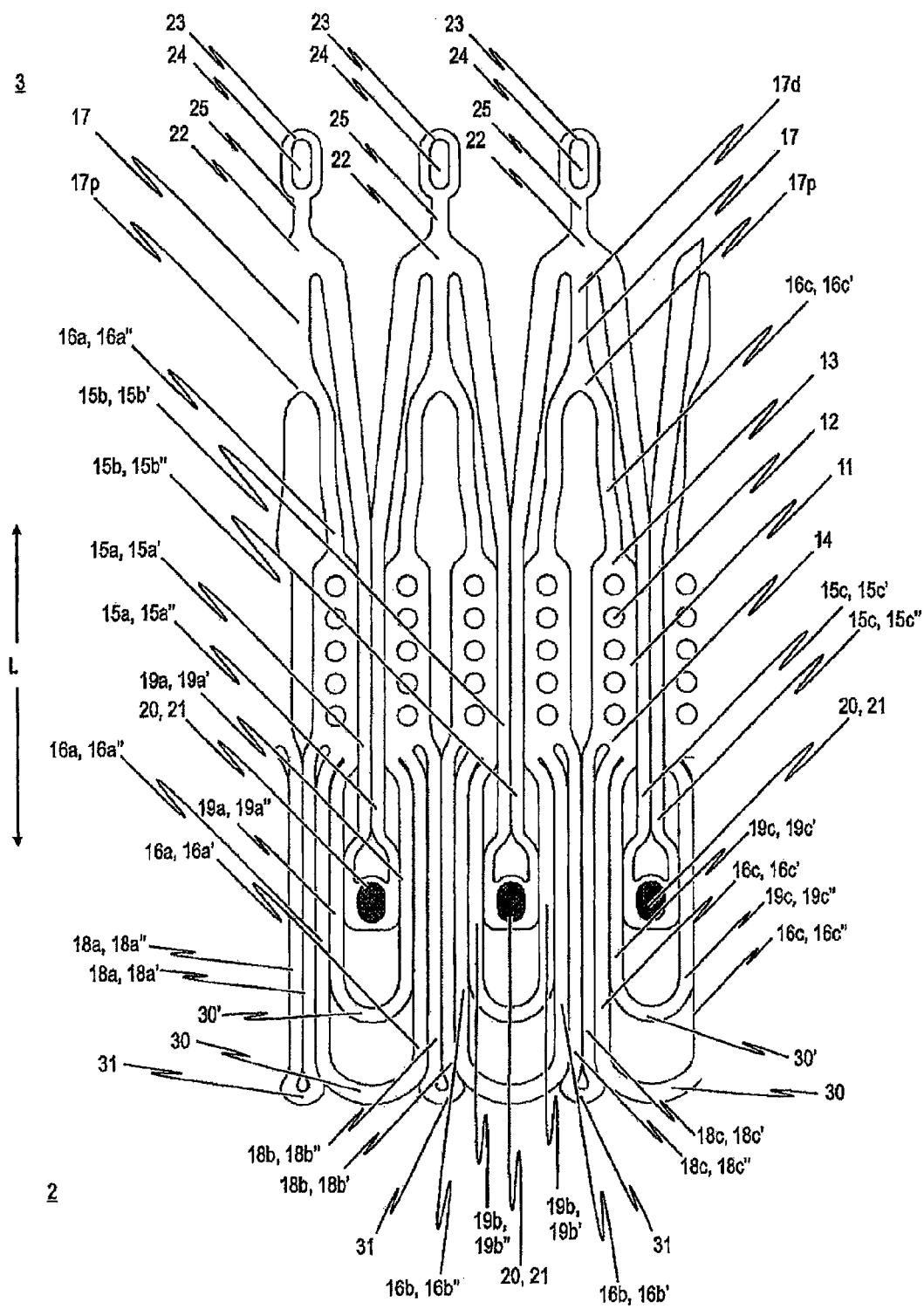
Figure 2A:
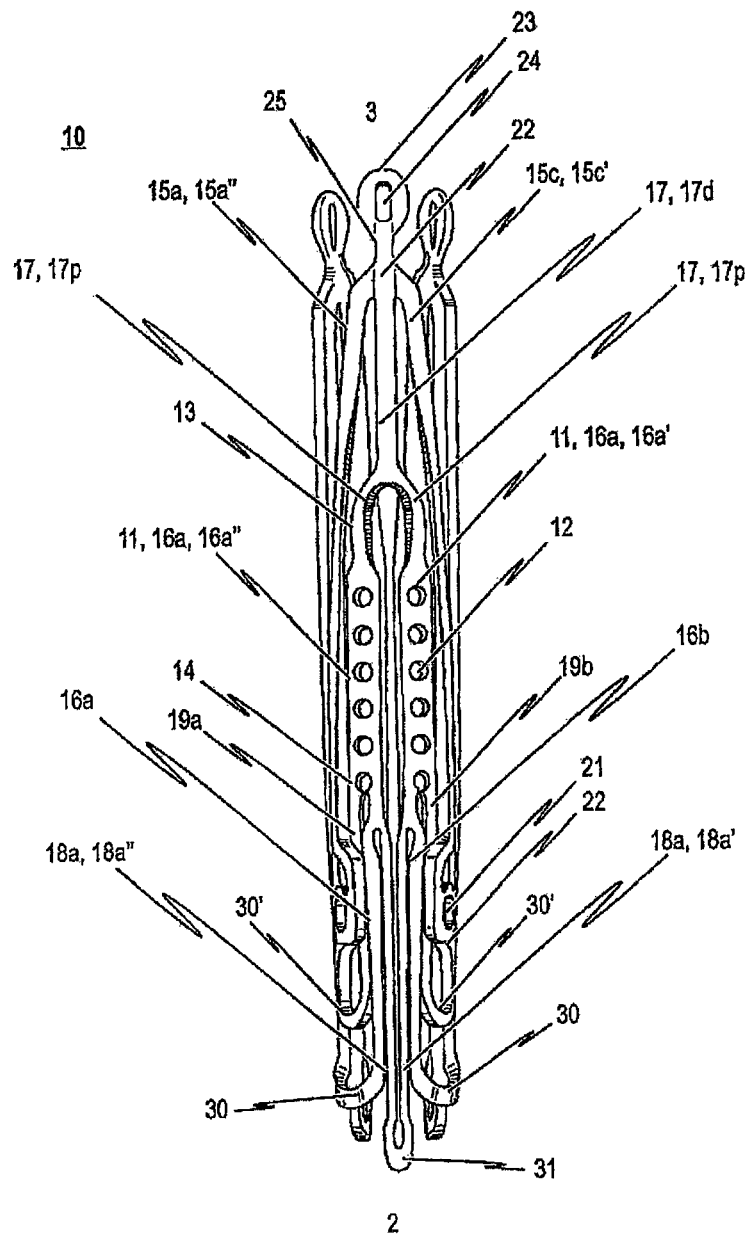
Figure 2B:
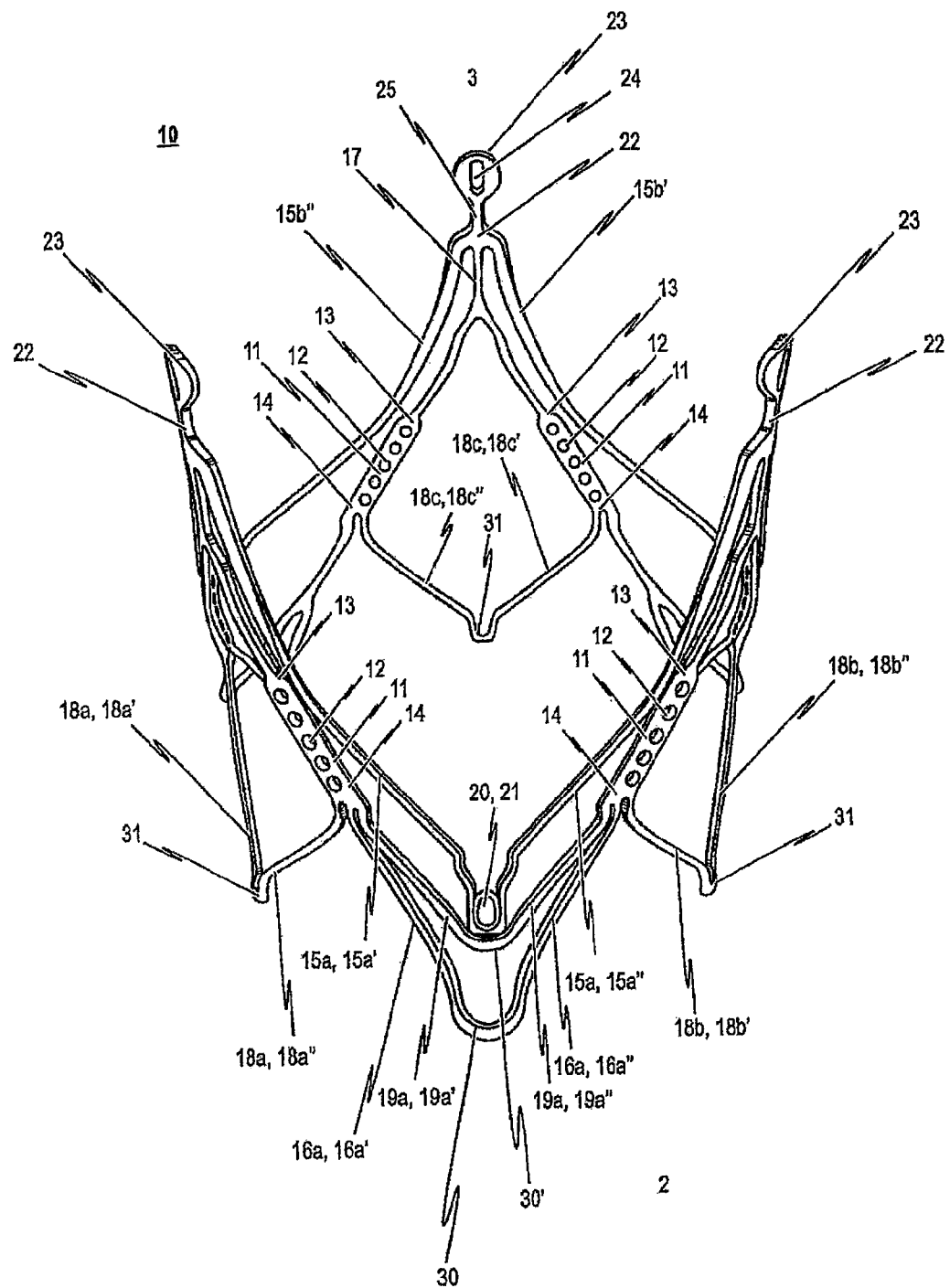
Figure 2C:
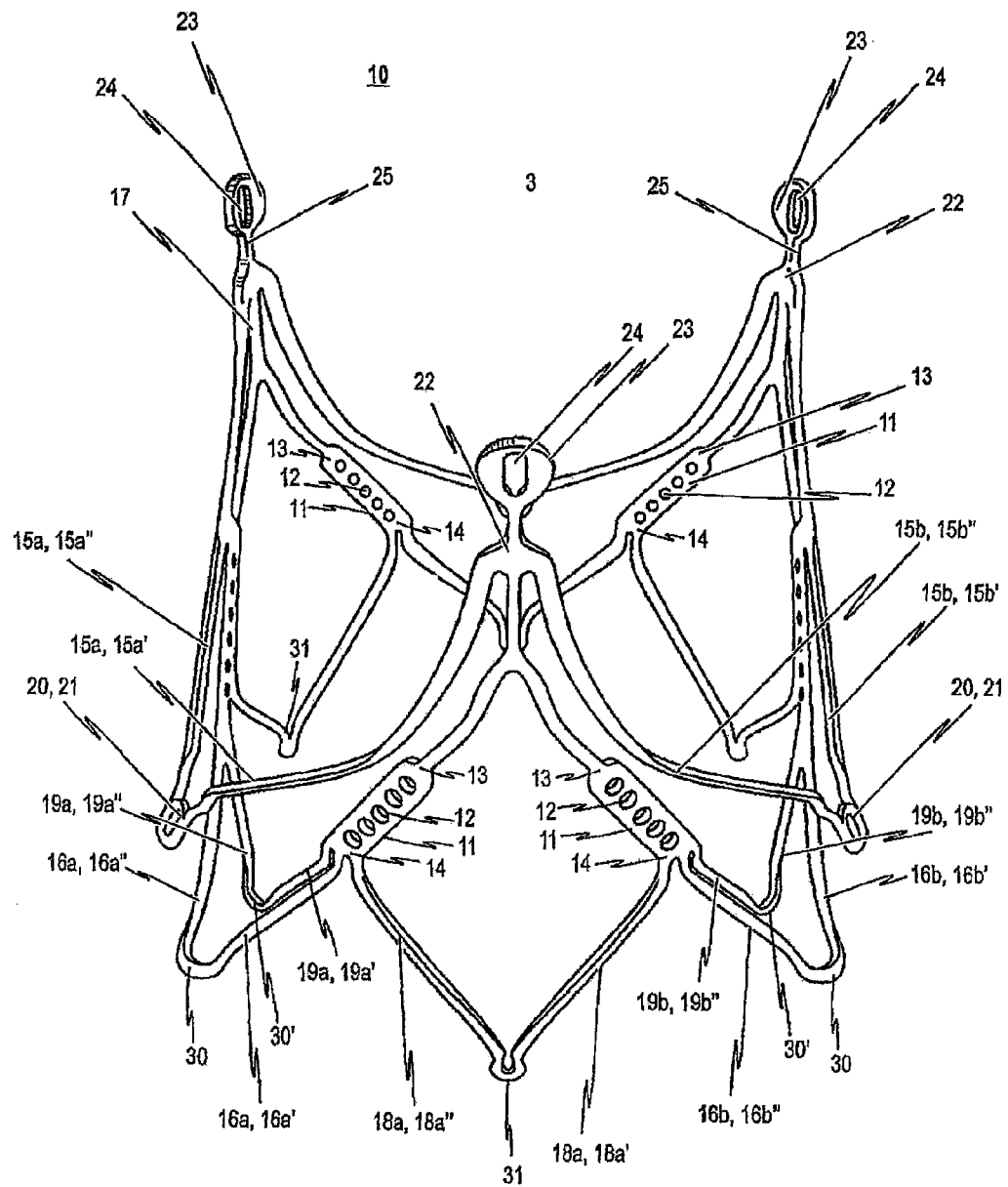
Figure 2D:
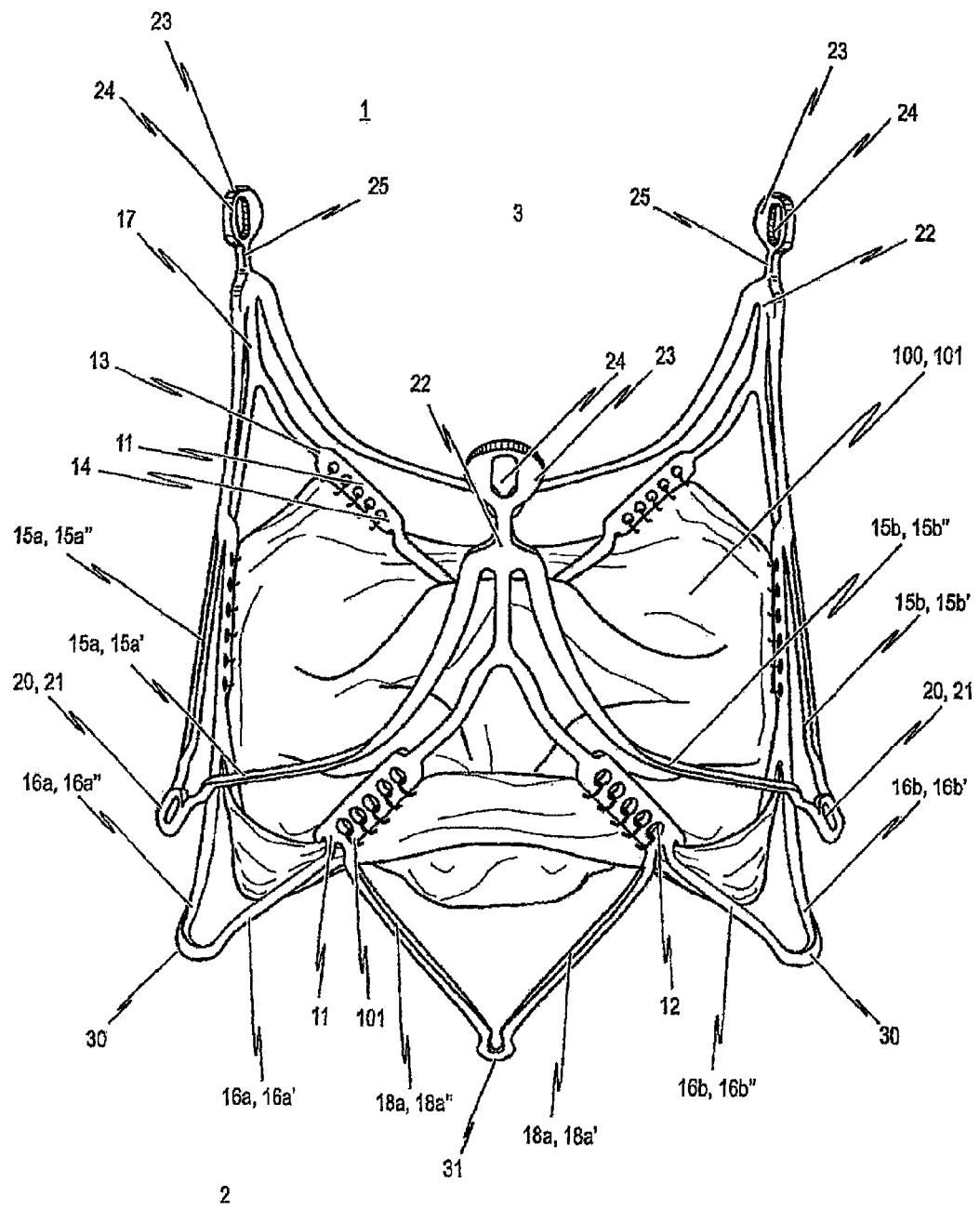
Figure 2E:
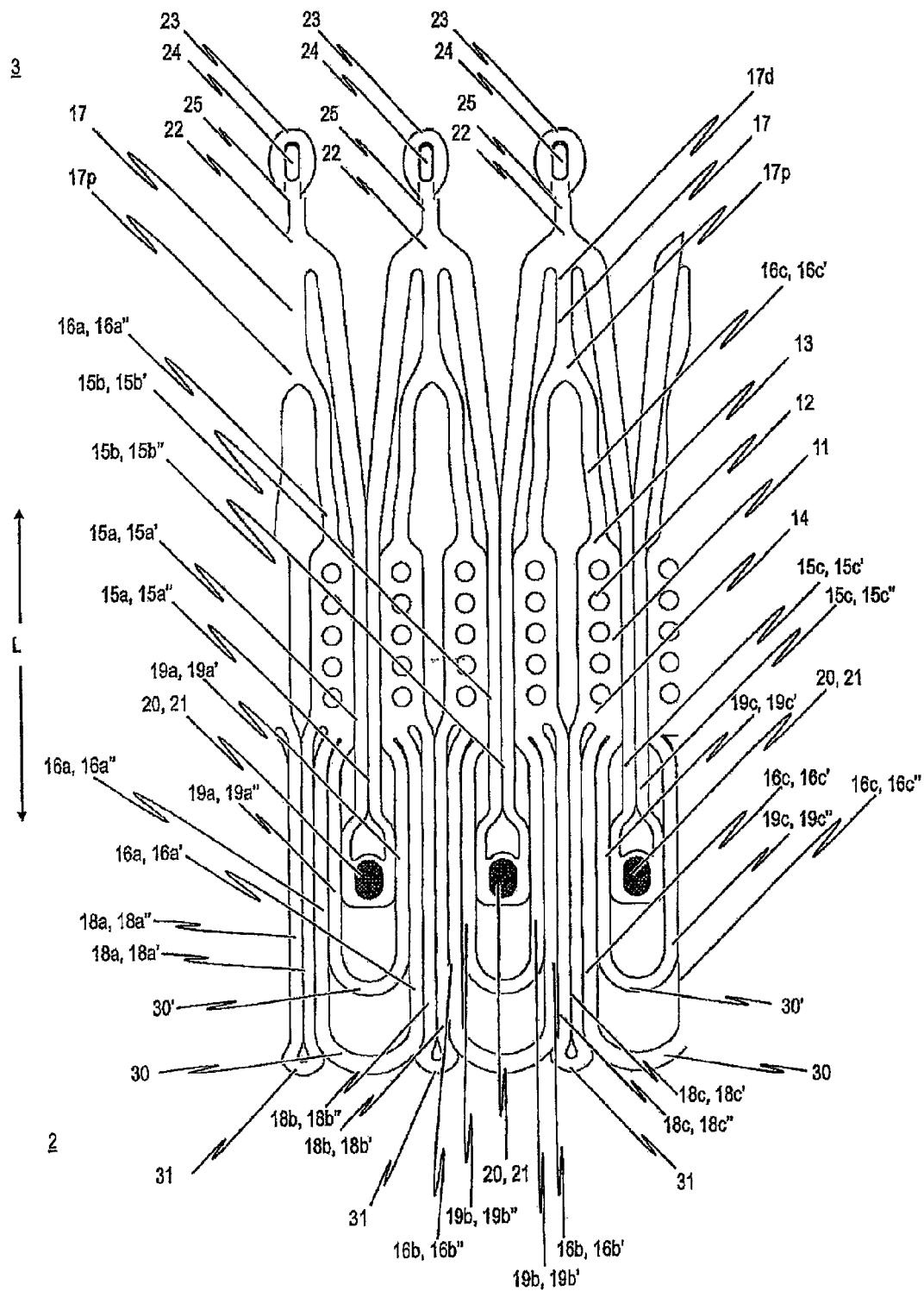
Figure 3:
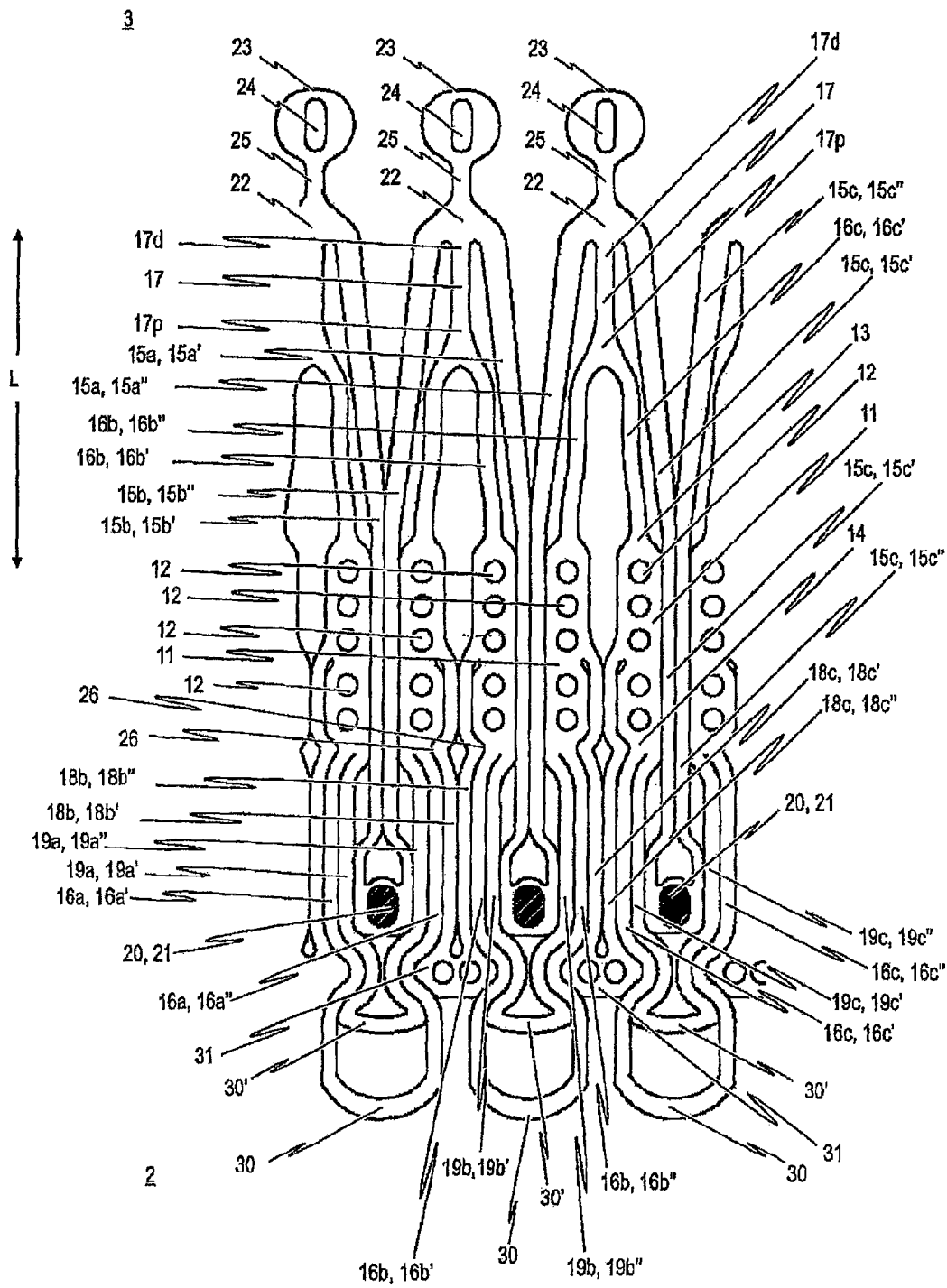
Figure 4:
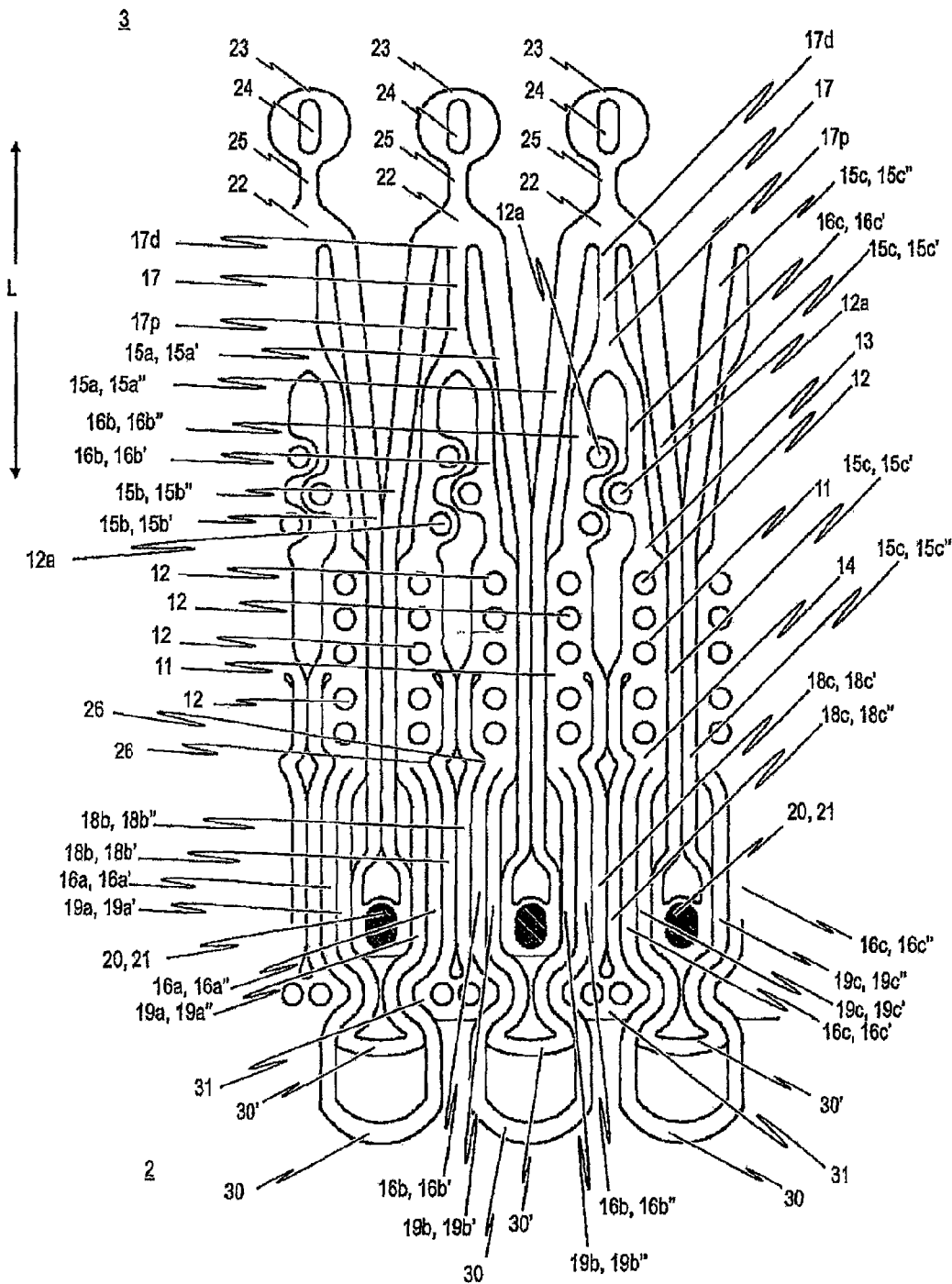
Figure 5A:
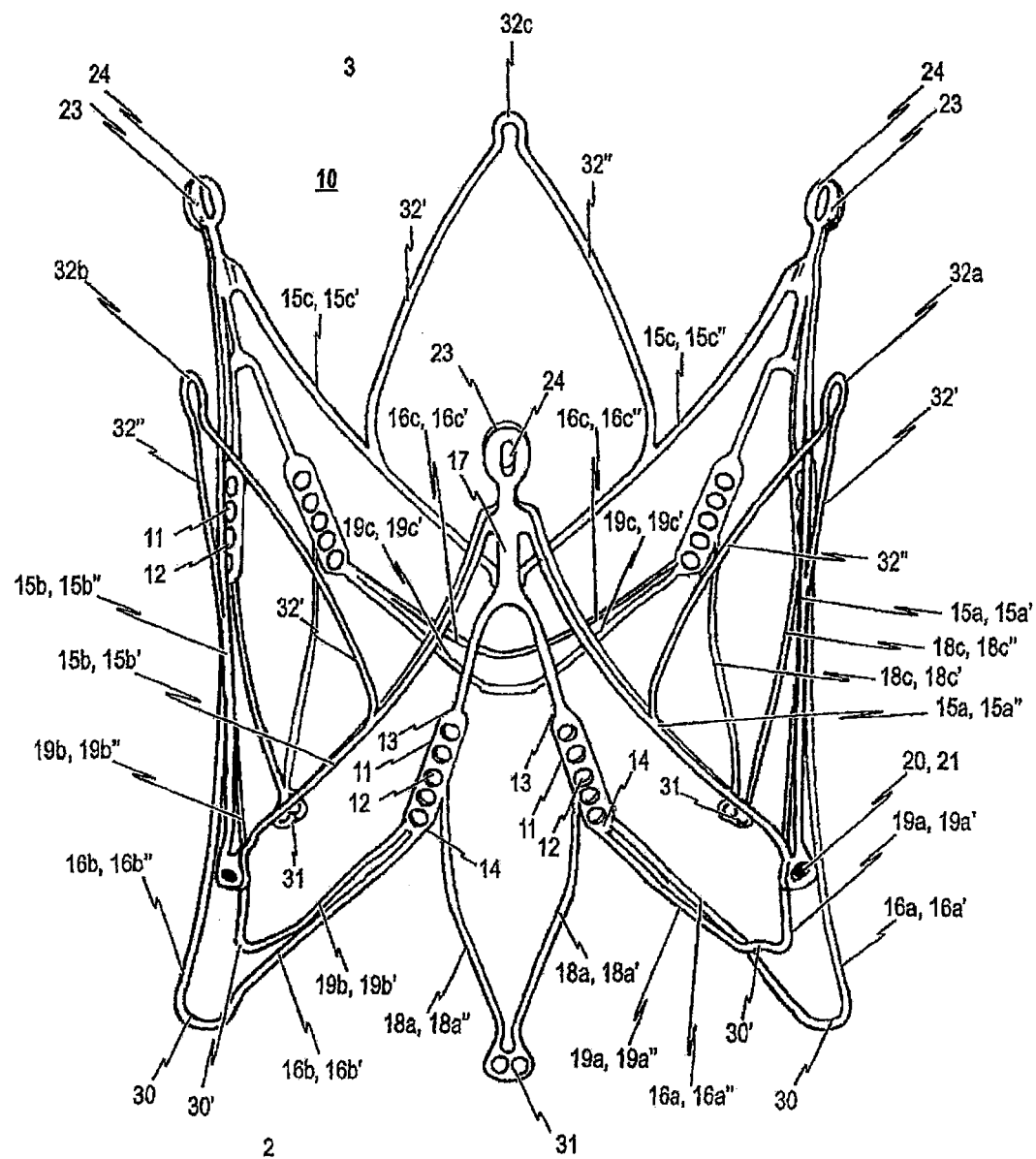
Figure 5B:
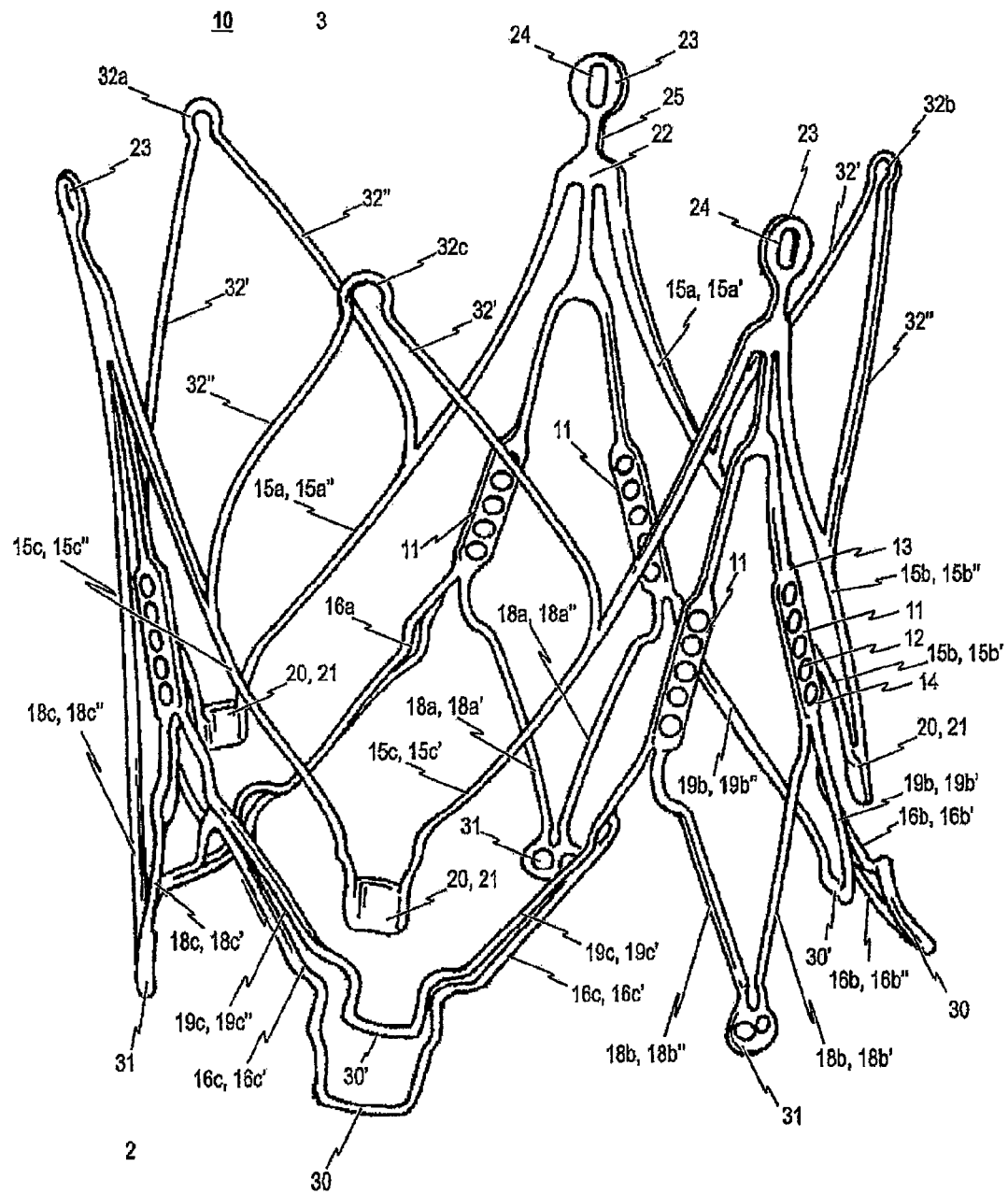
Figure 5C:
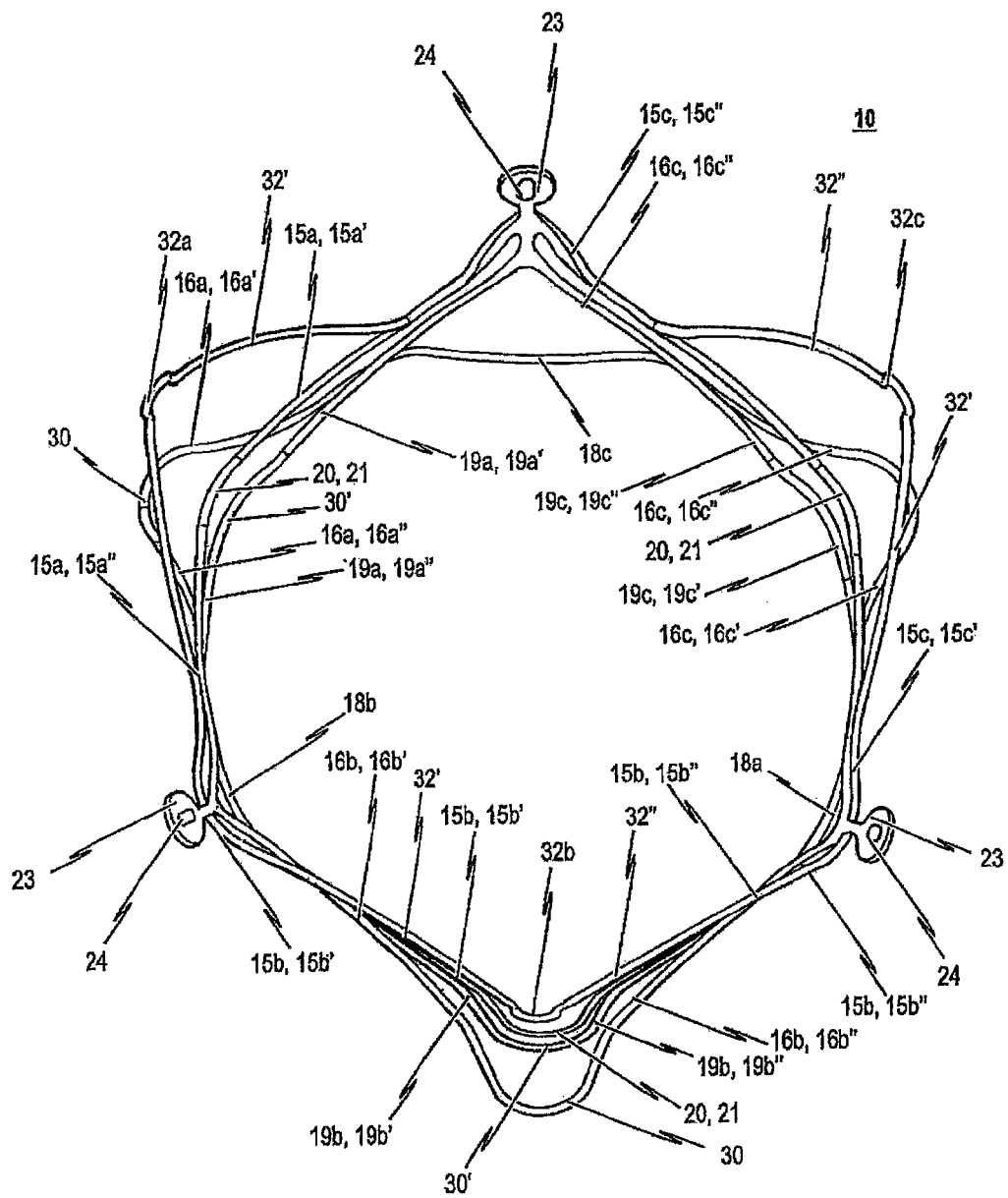
Figure 5D:
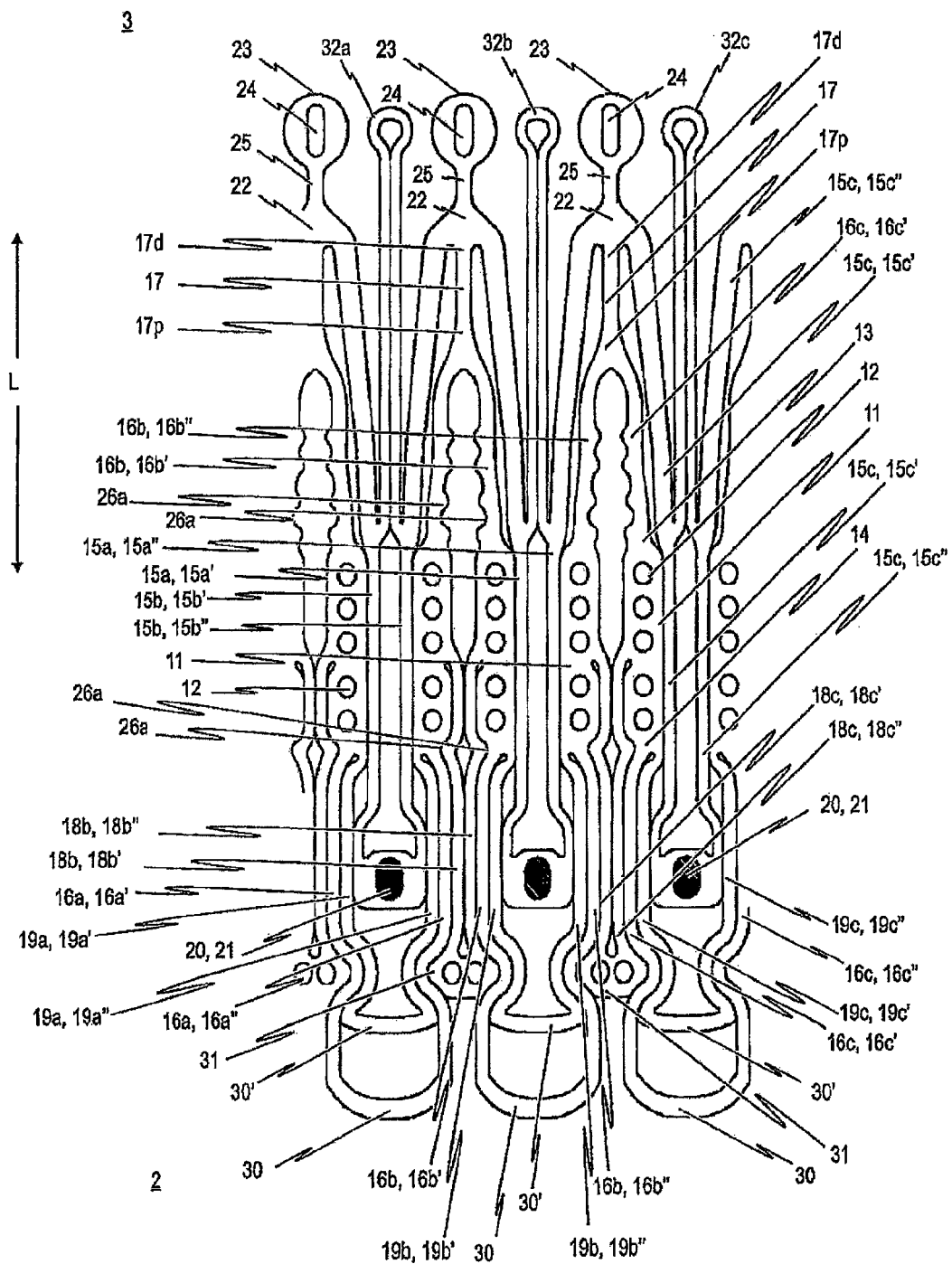
Figure 6A:
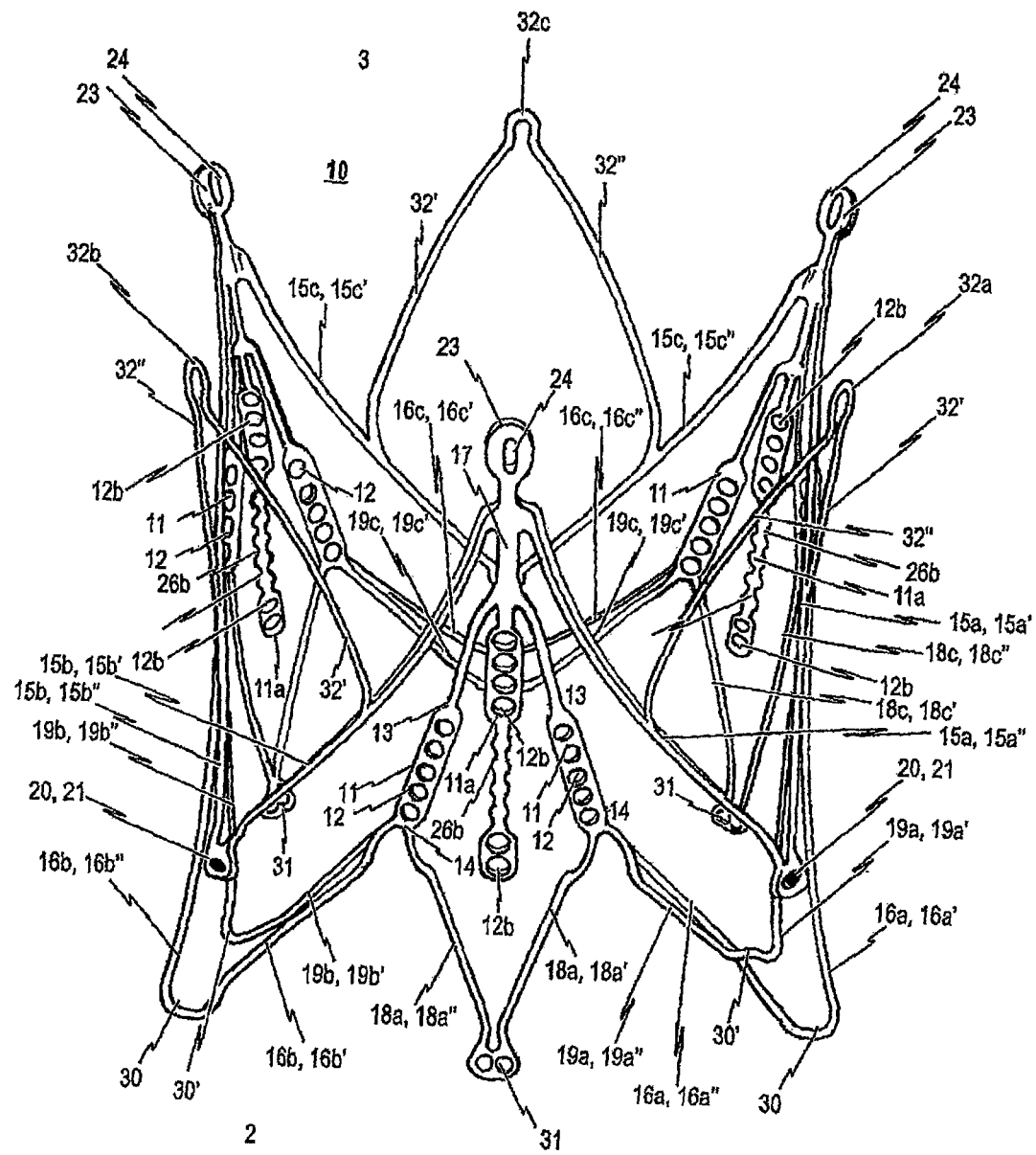
Figure 6B:
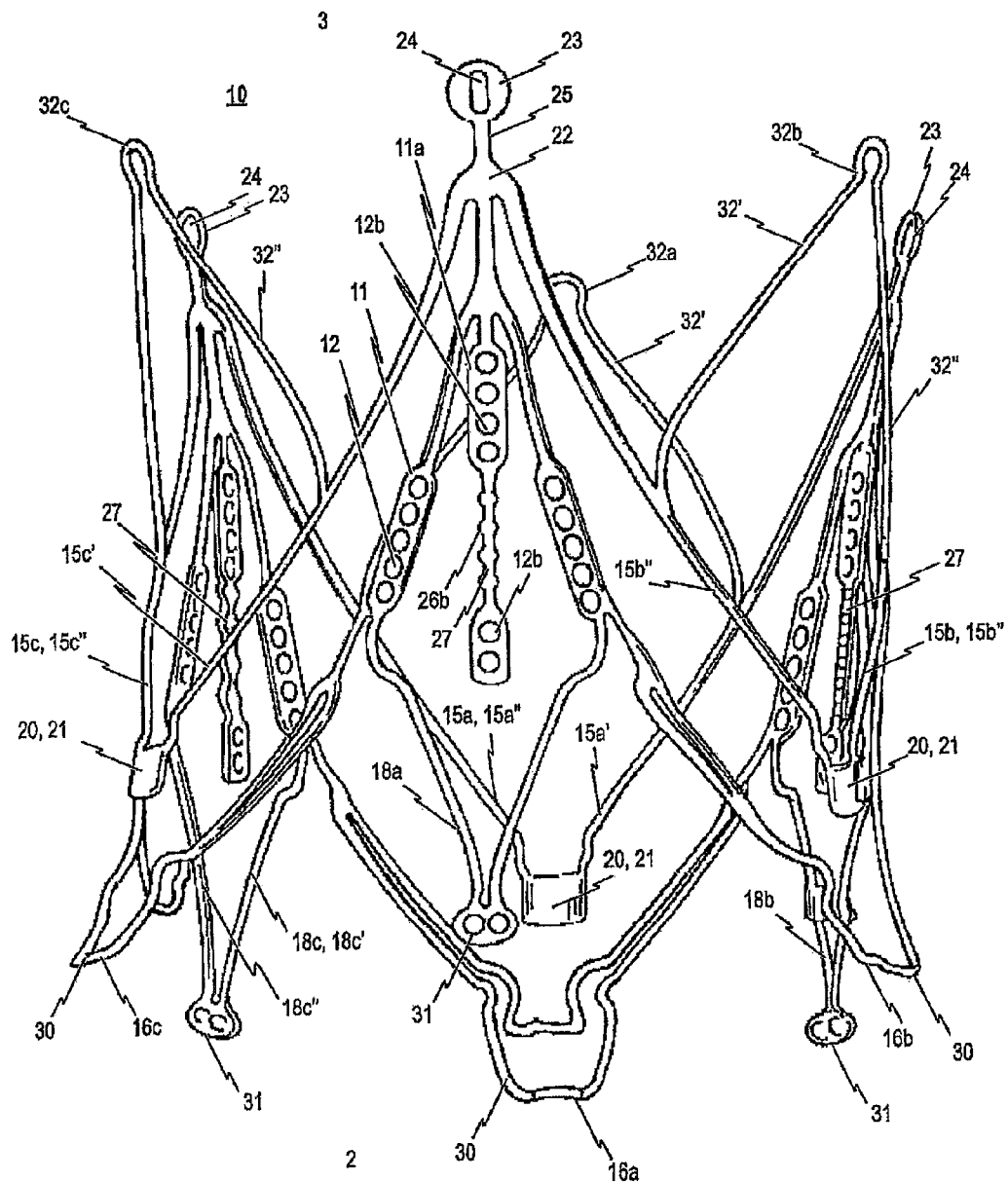
Figure 6C:
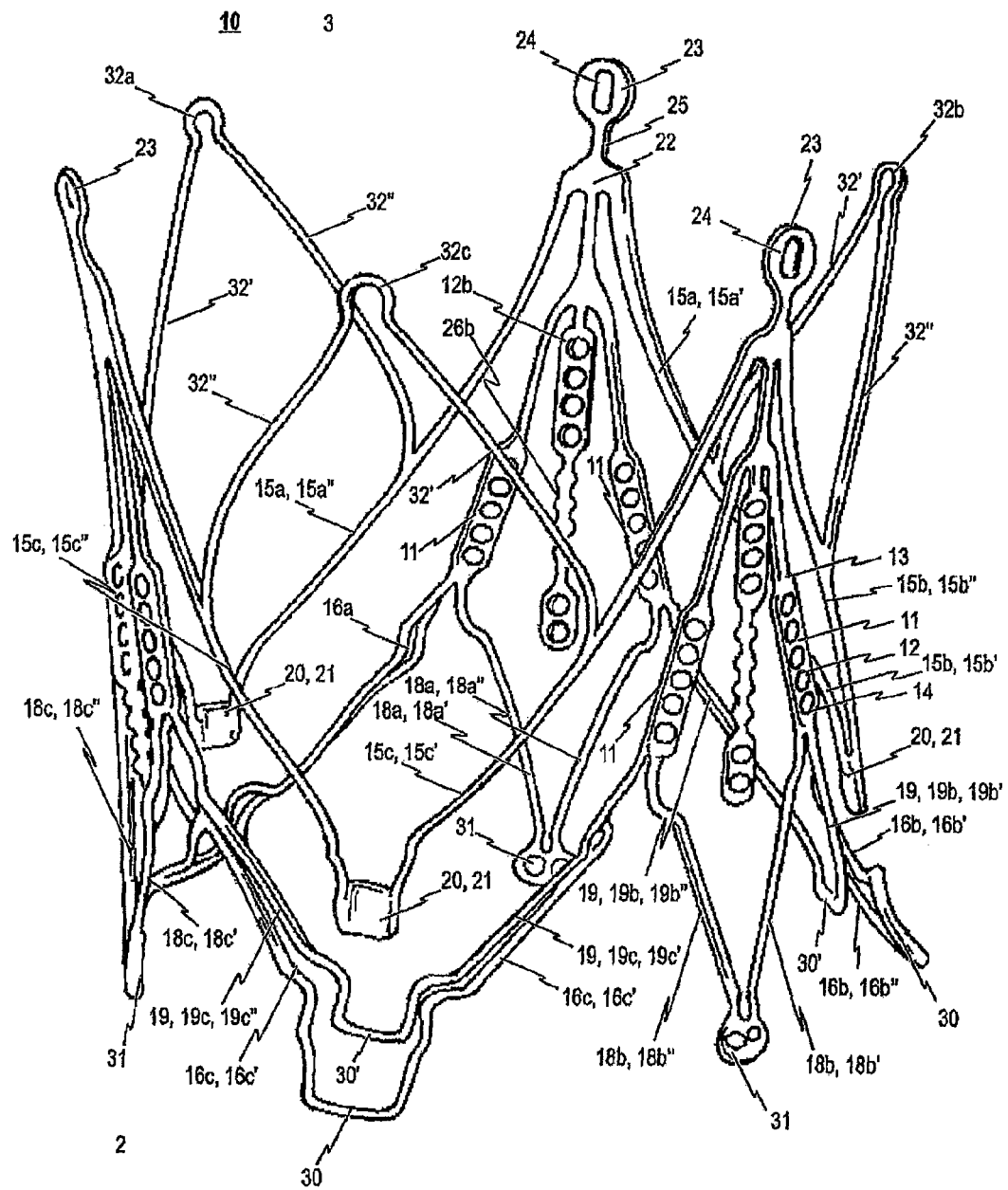
Figure 6D:
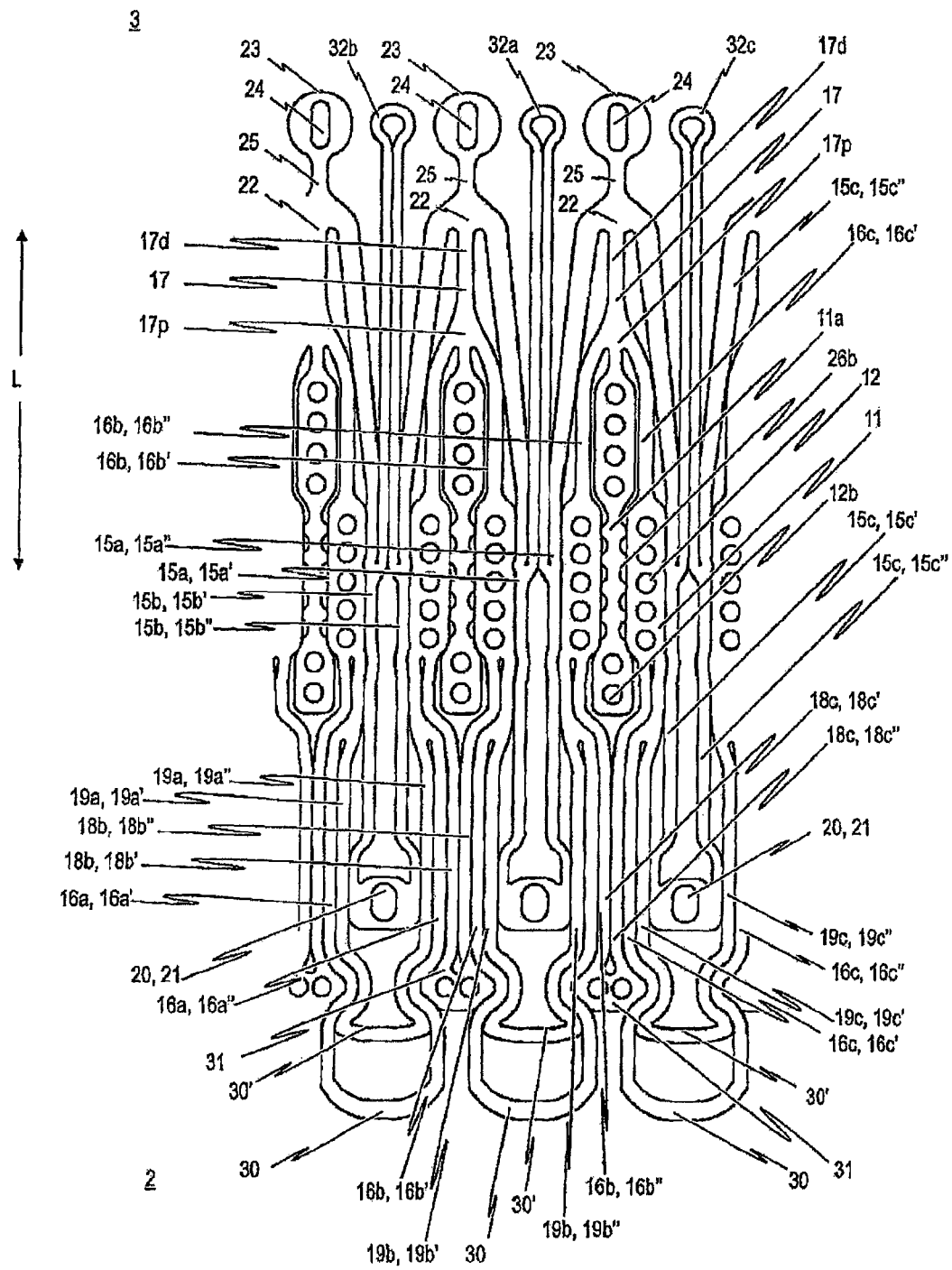
Figure 6E:
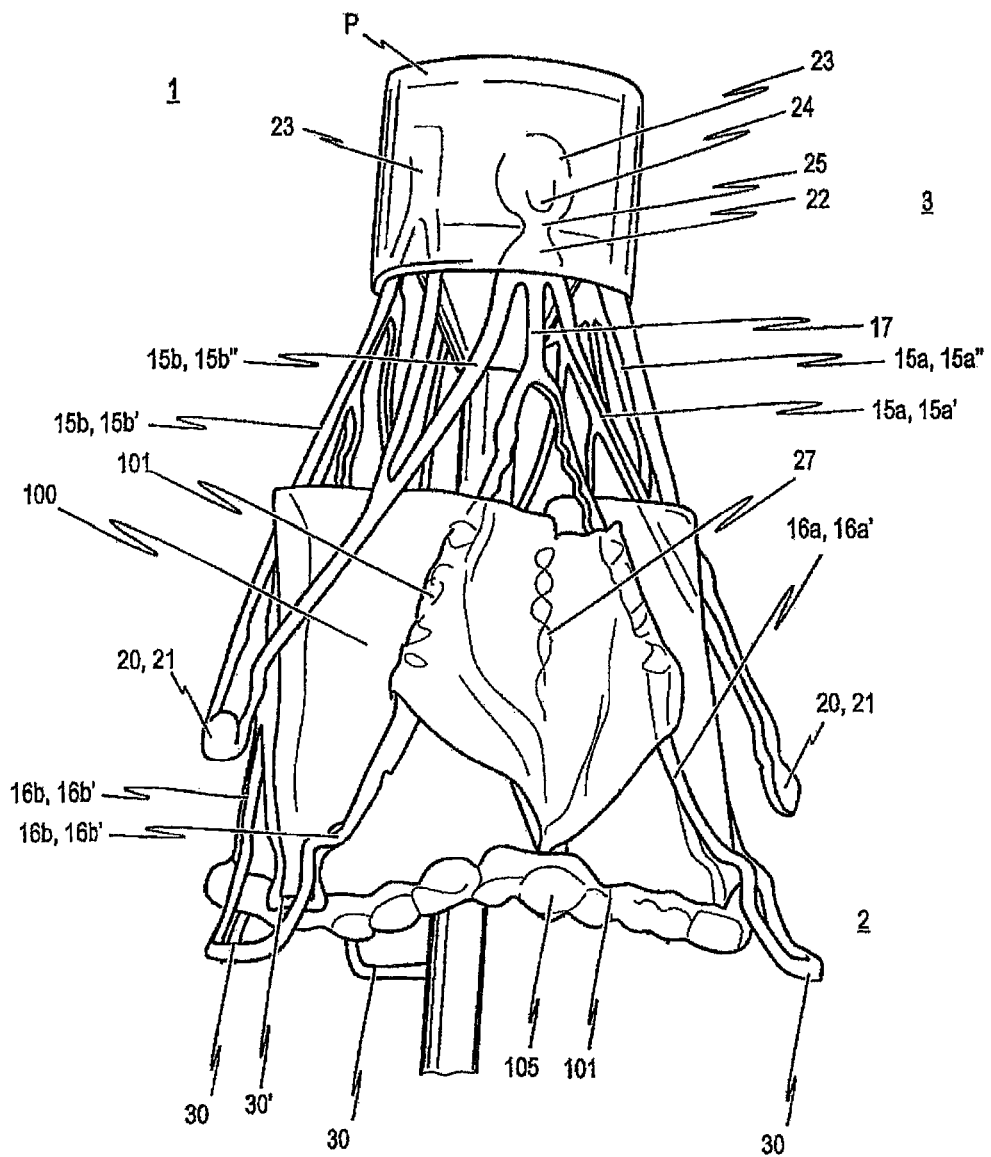
Figure 6F:
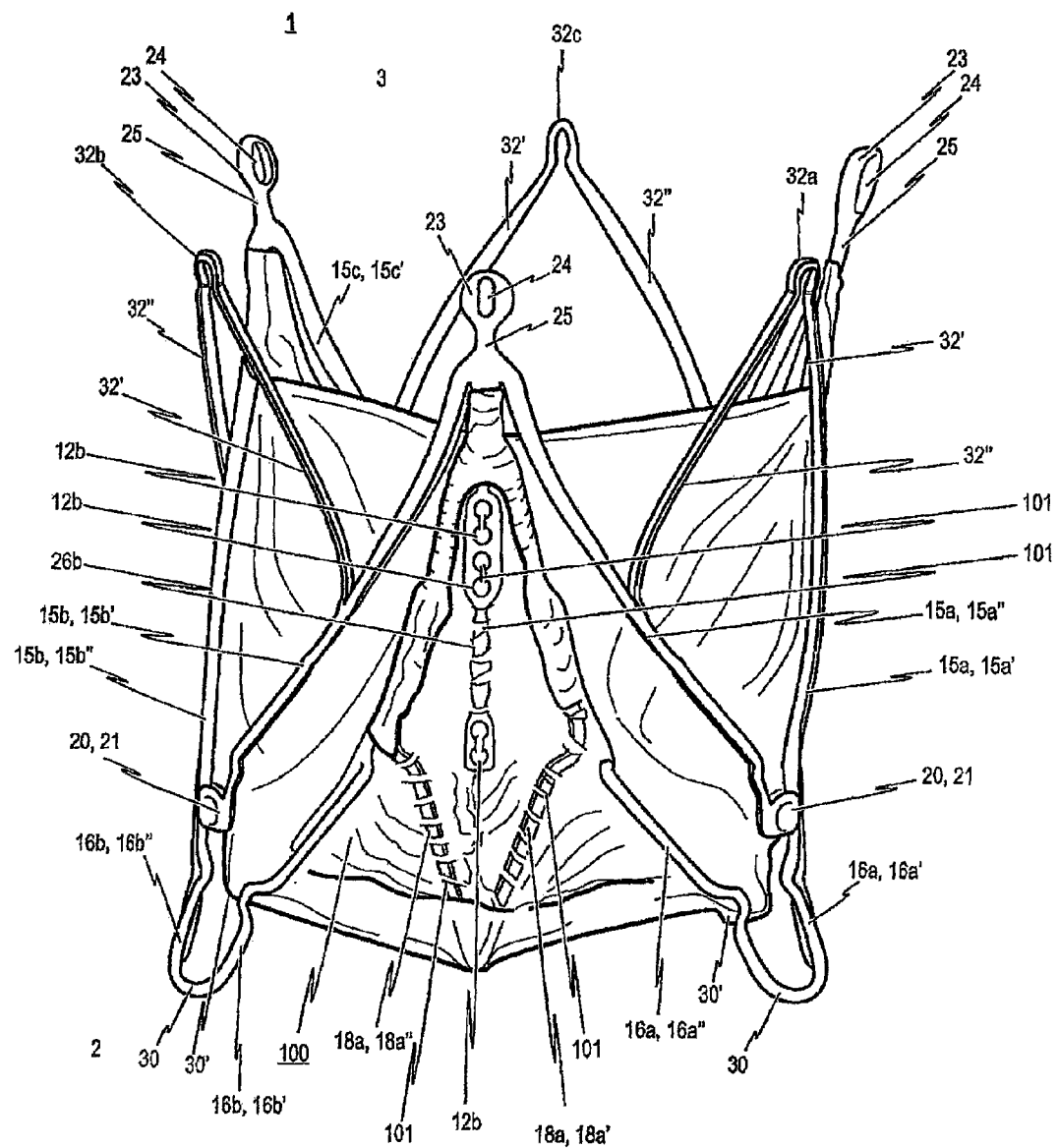
Figure 6G:
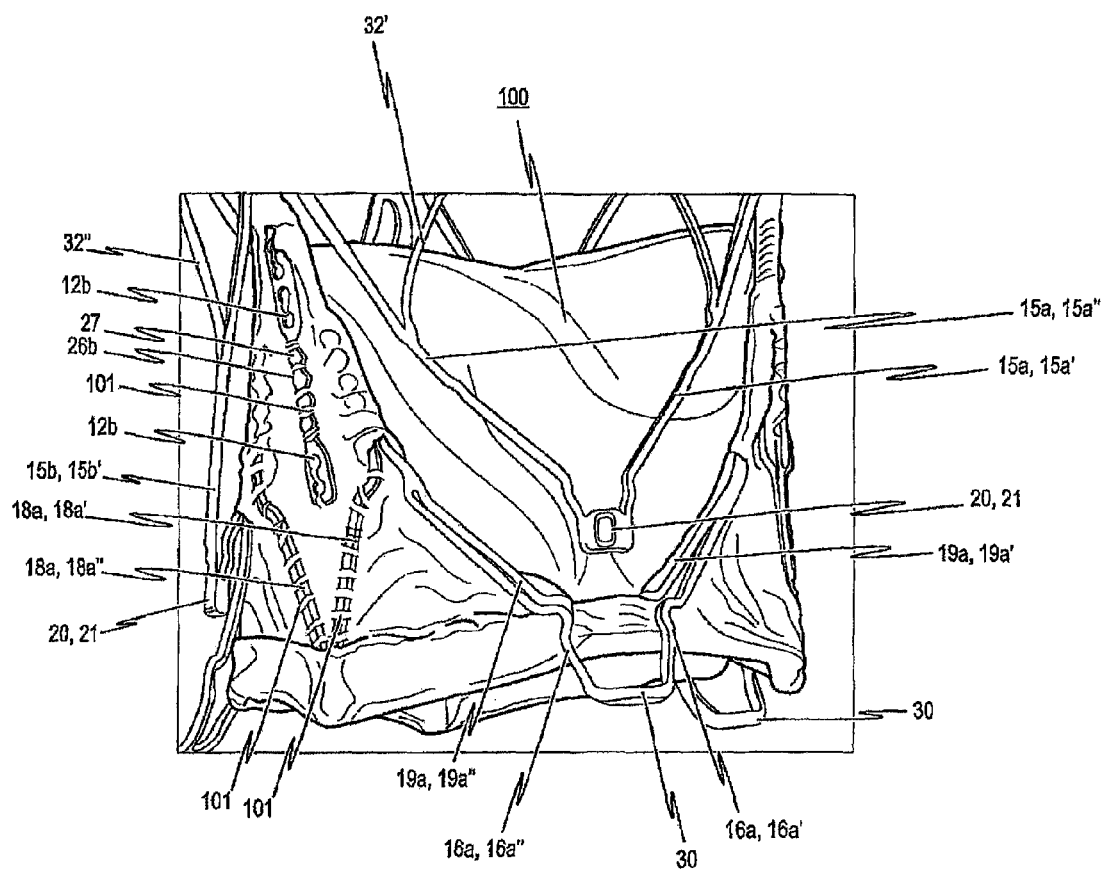
Figure 6H:
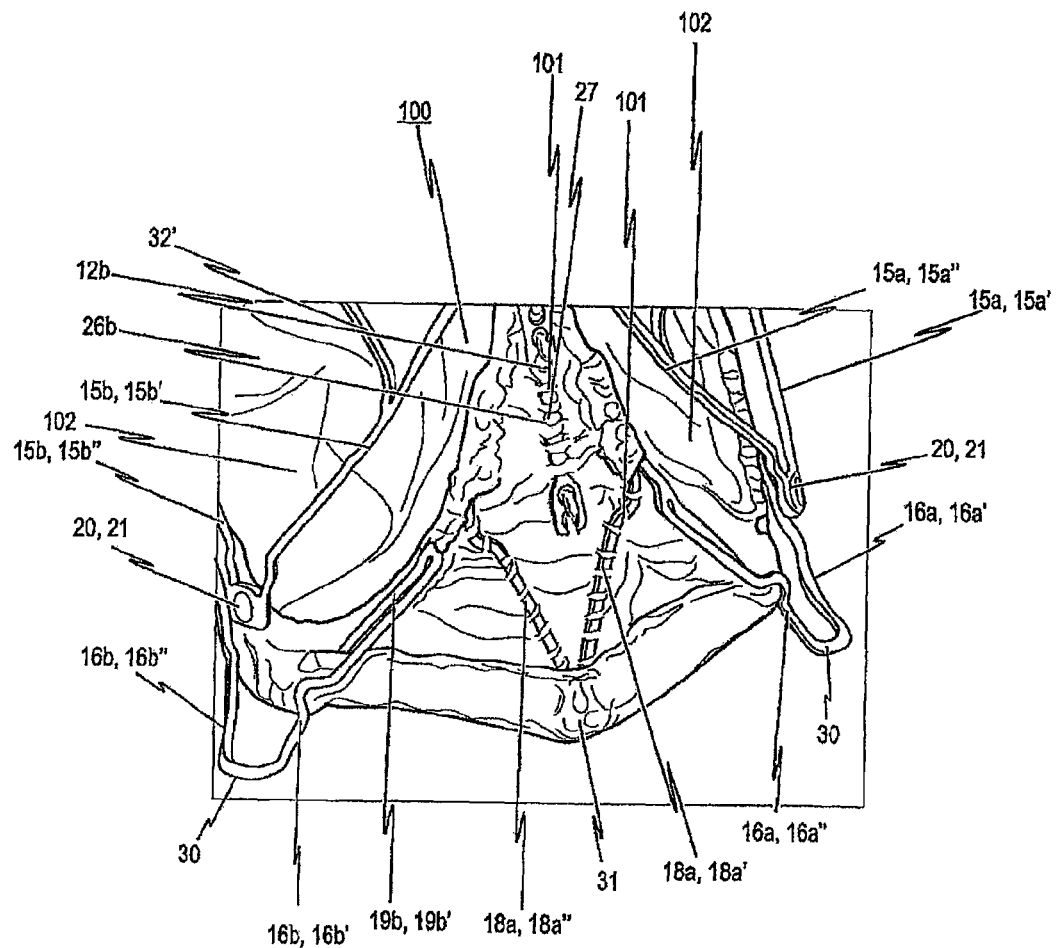
Figure 6I:
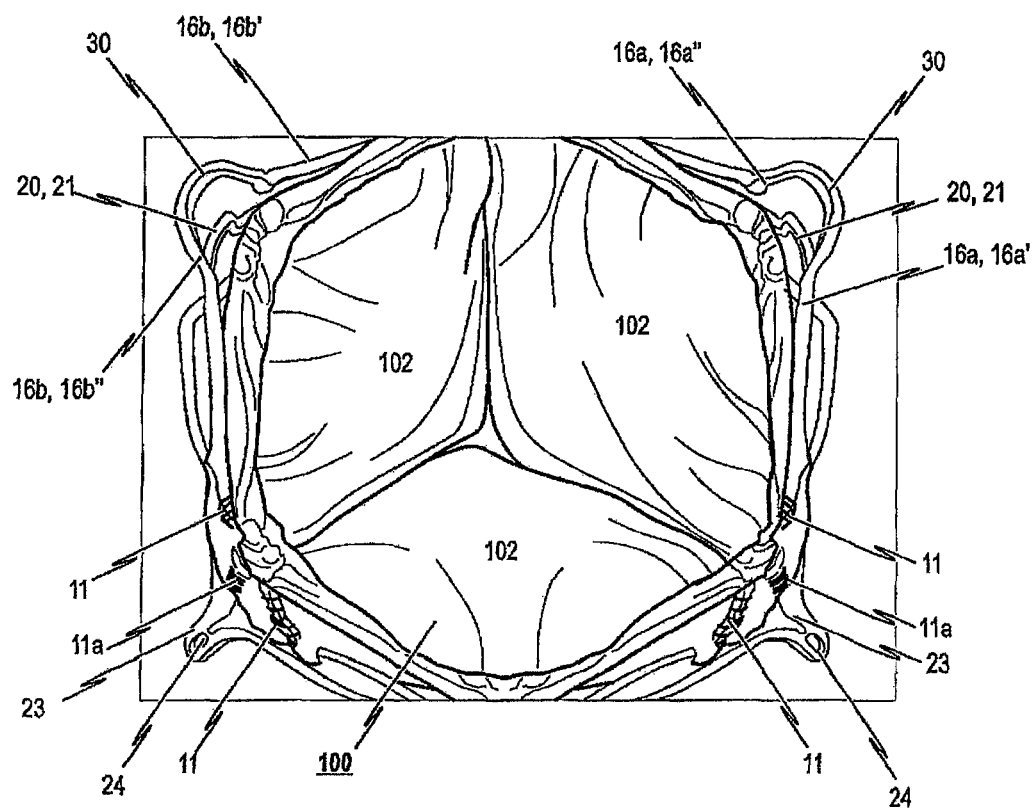
Figure 7A:
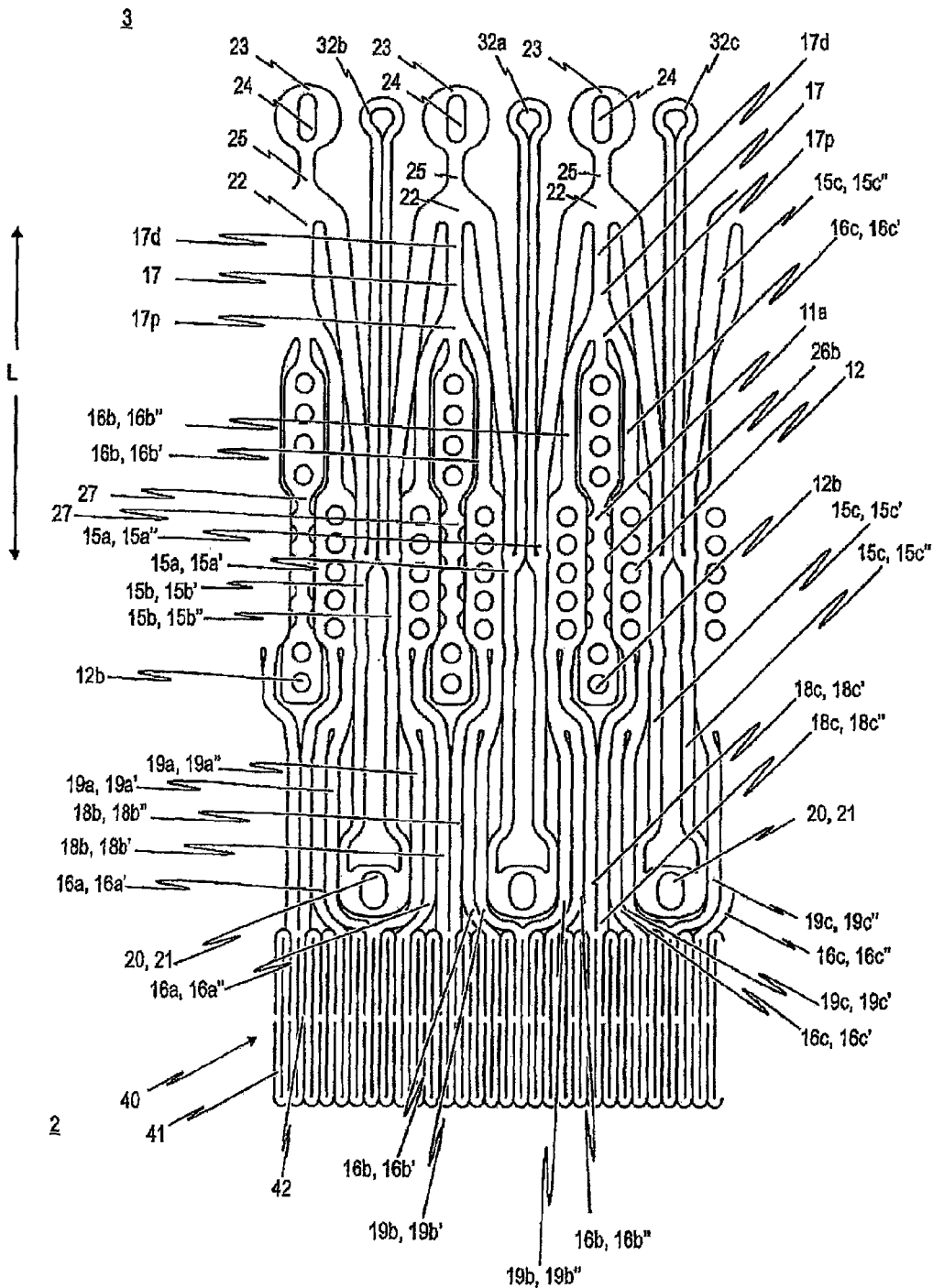
Figure 7B:
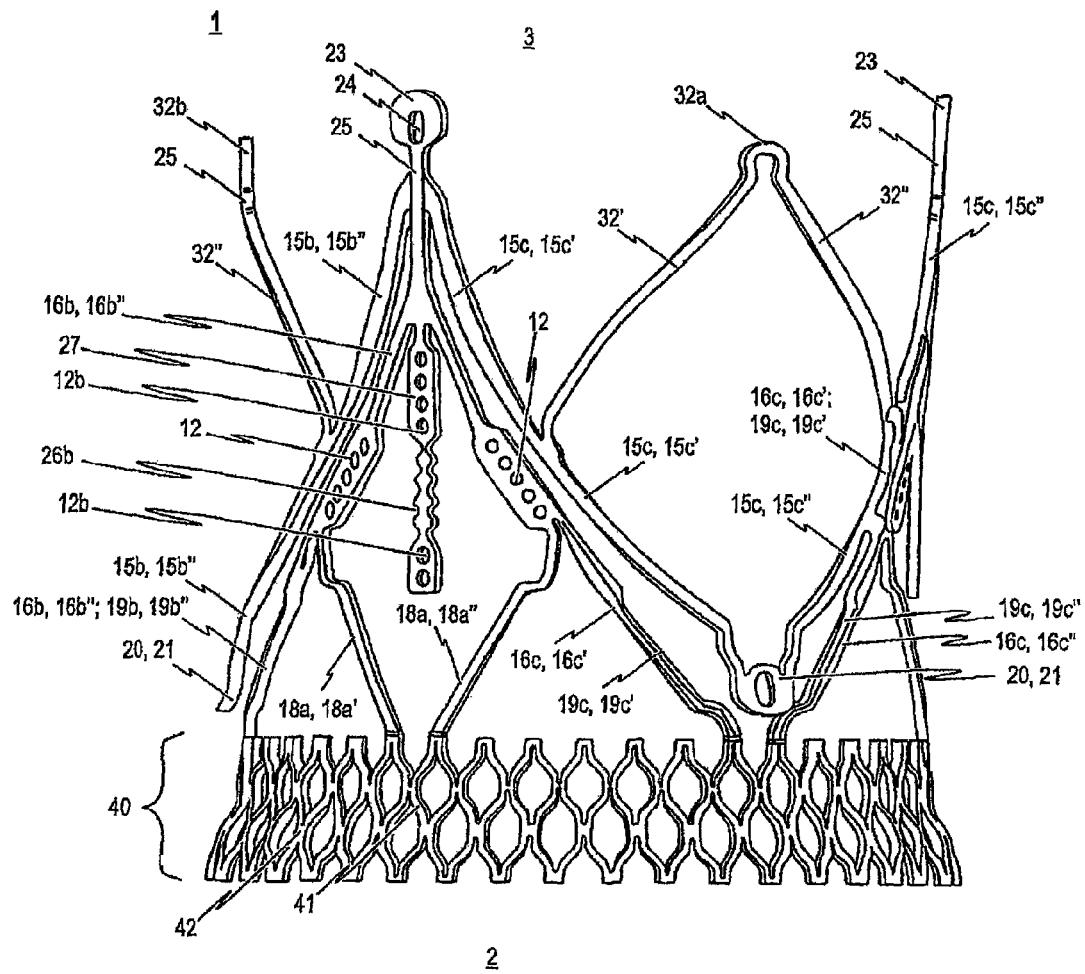
Figure 7C:
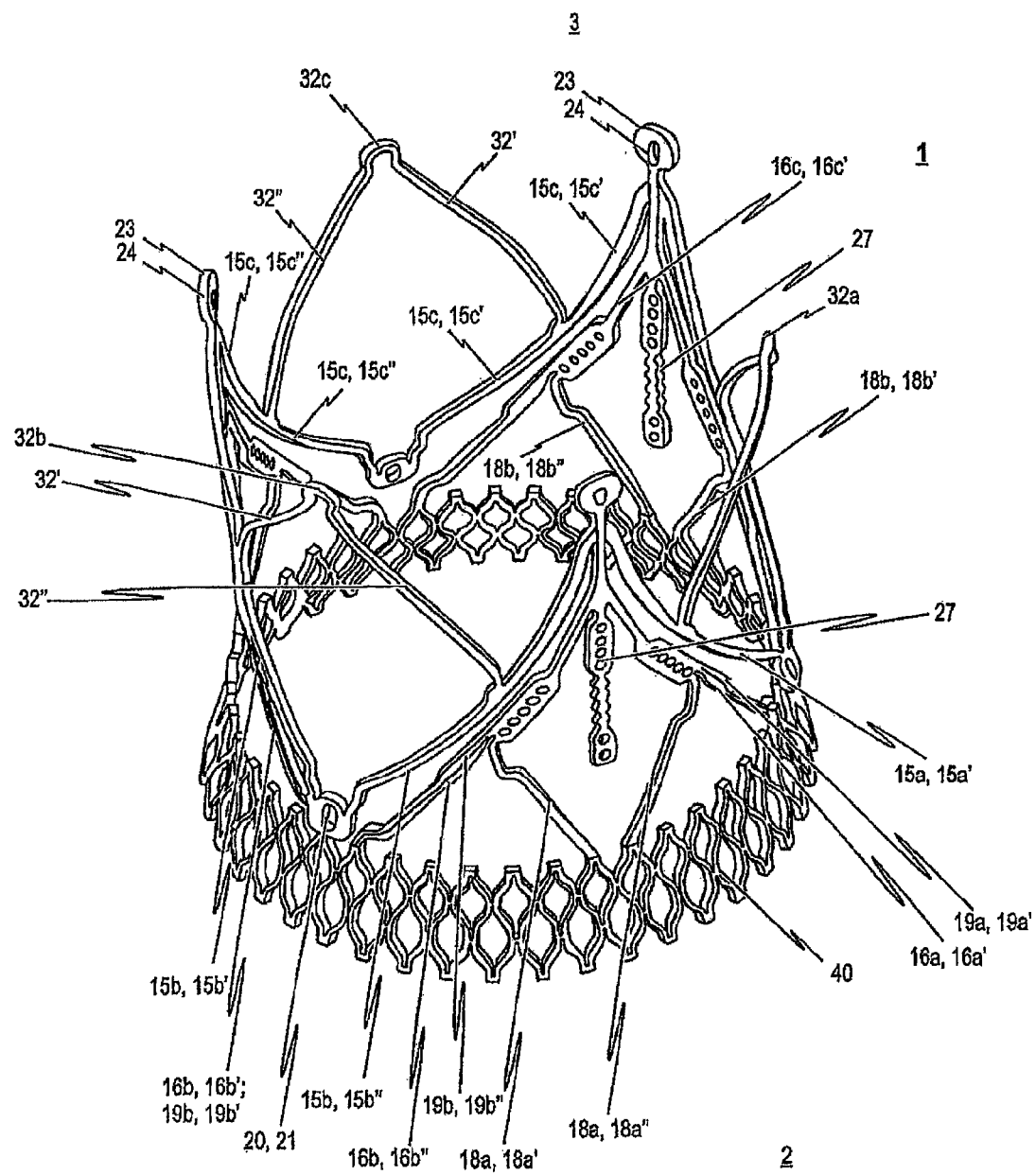
Figure 8A:
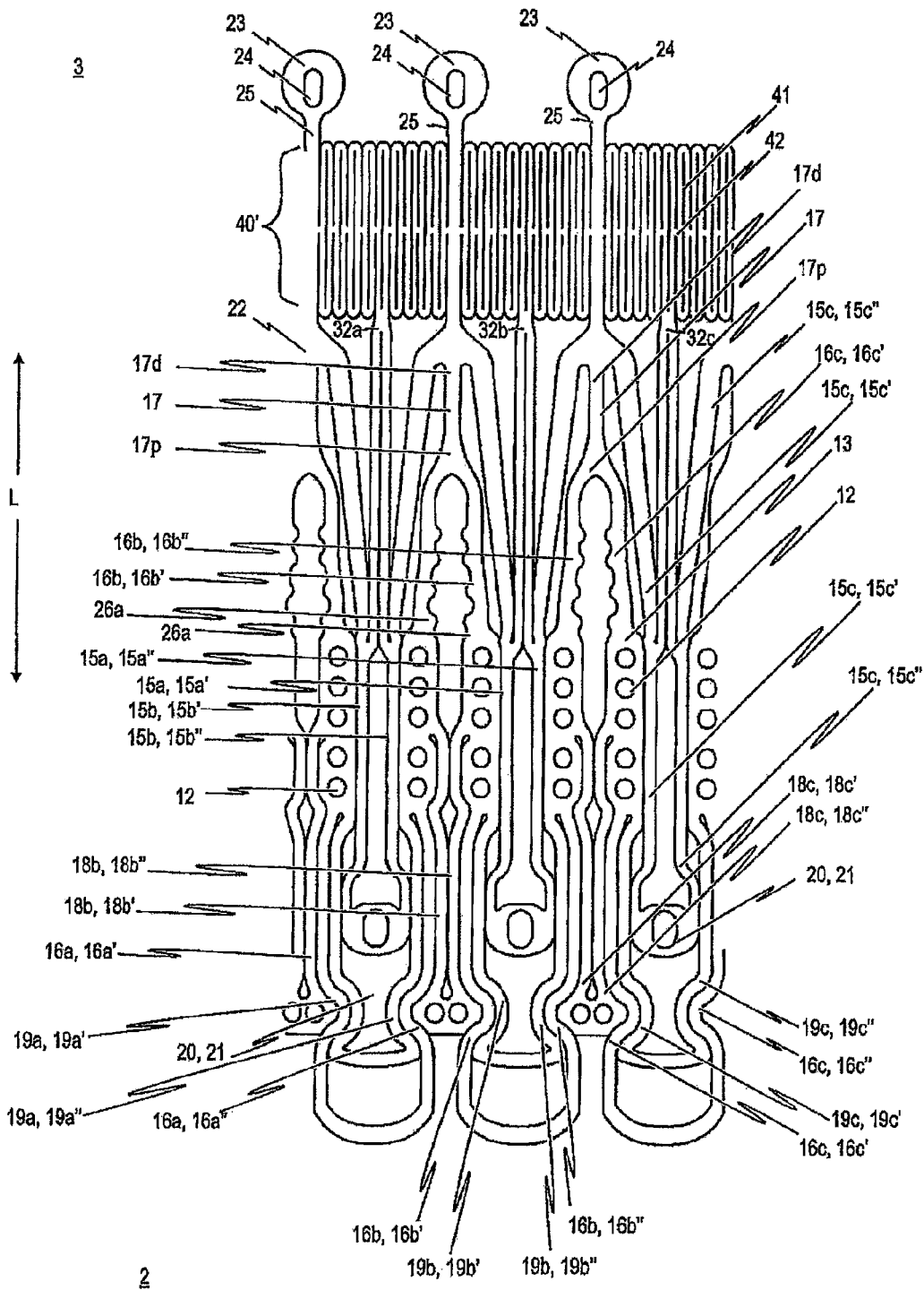
Figure 8B:
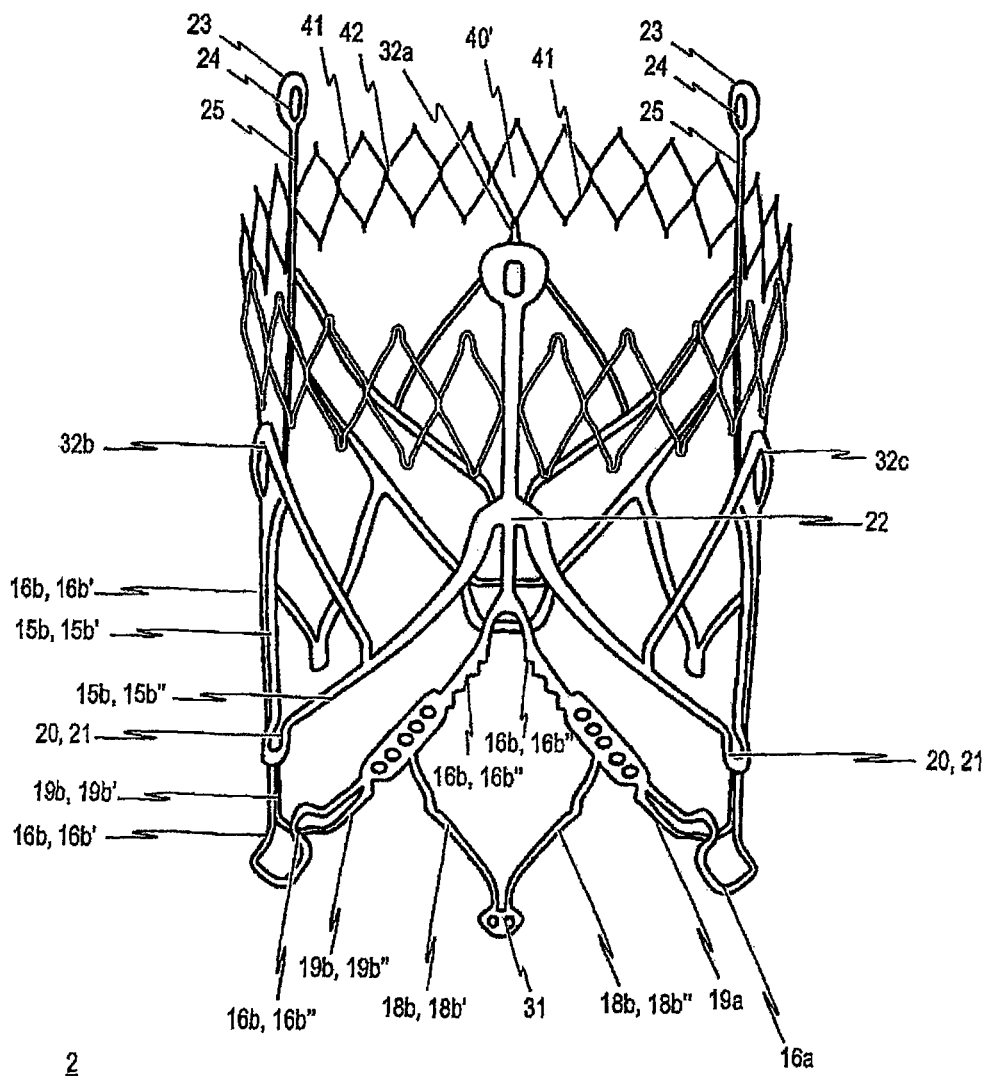
Figure 8C:
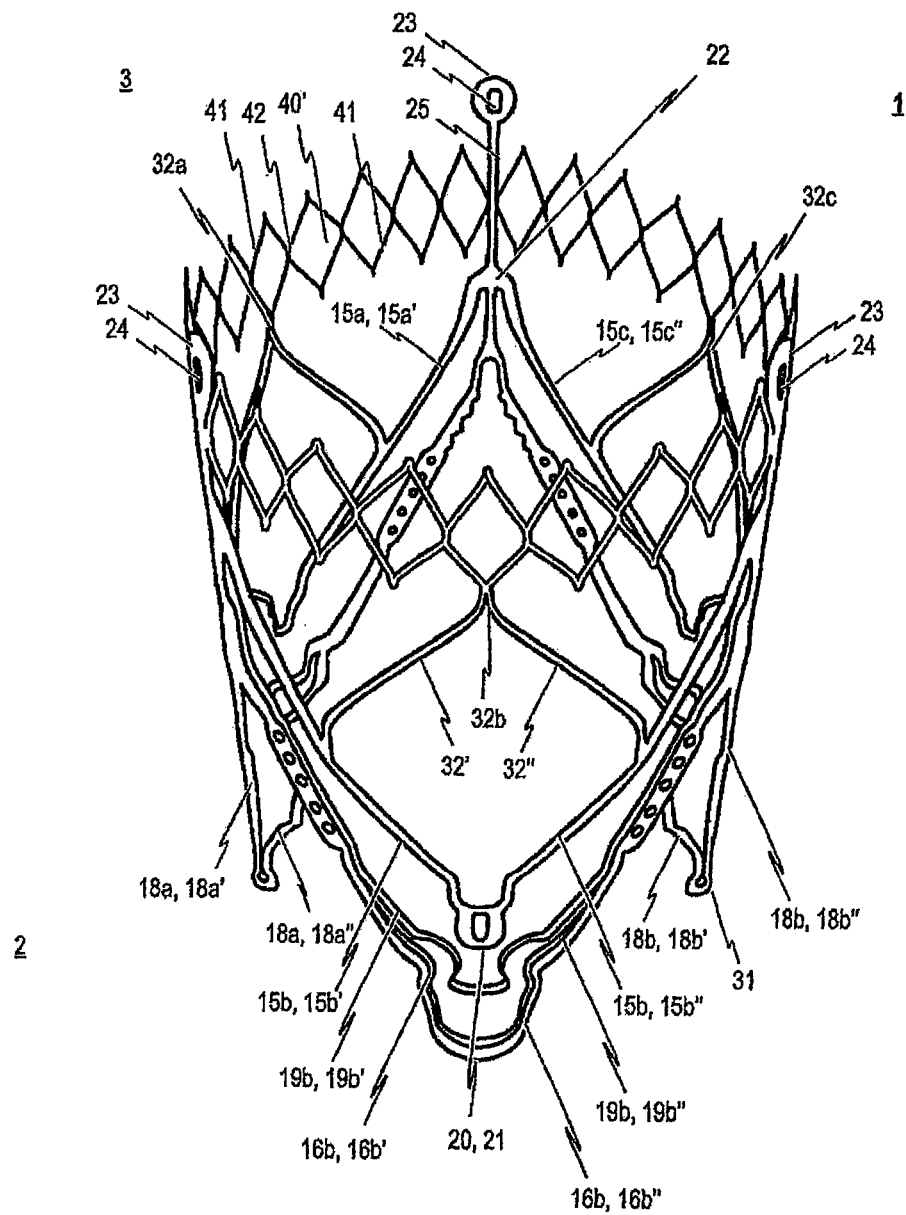
Figure 9A:
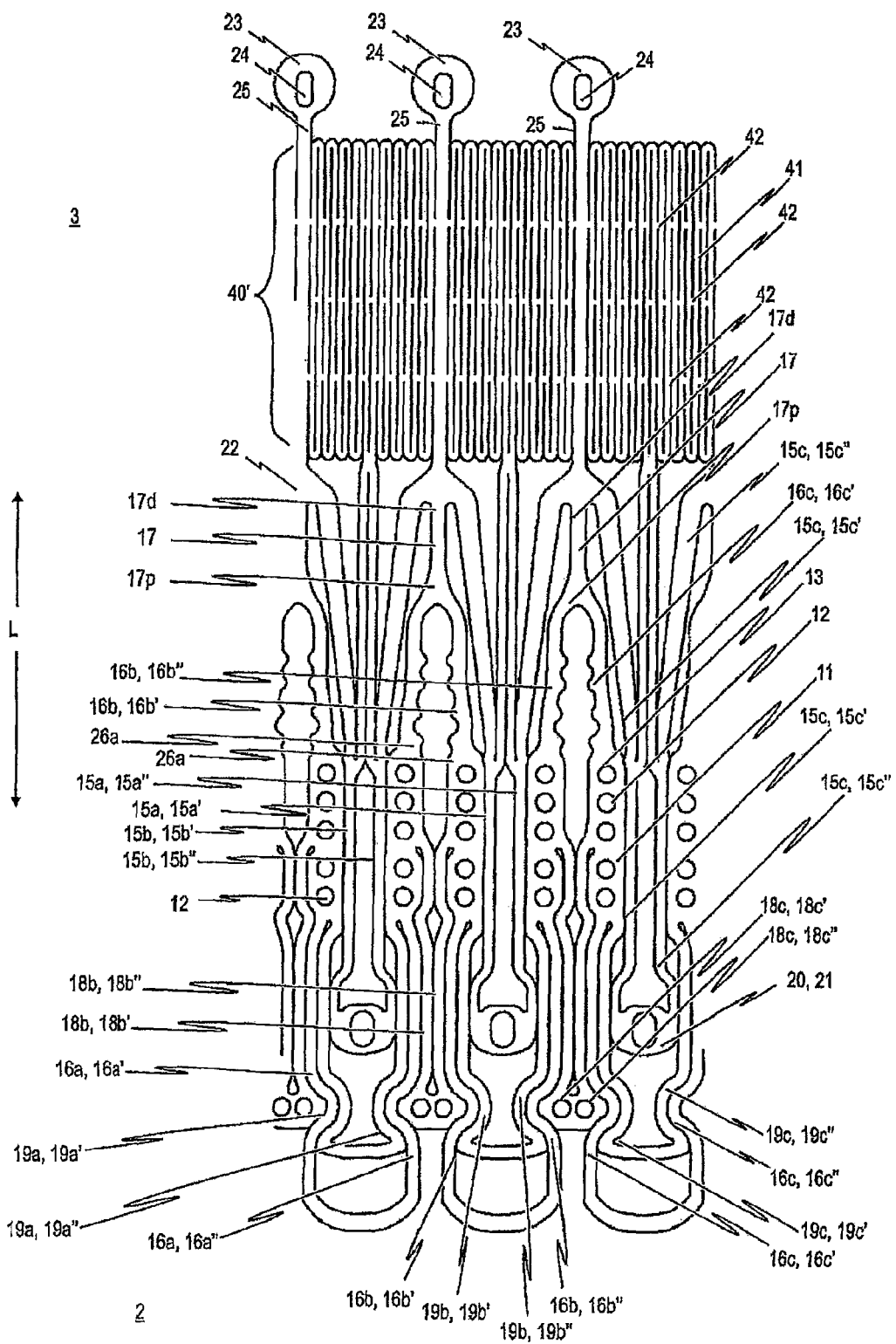
Figure 9B:
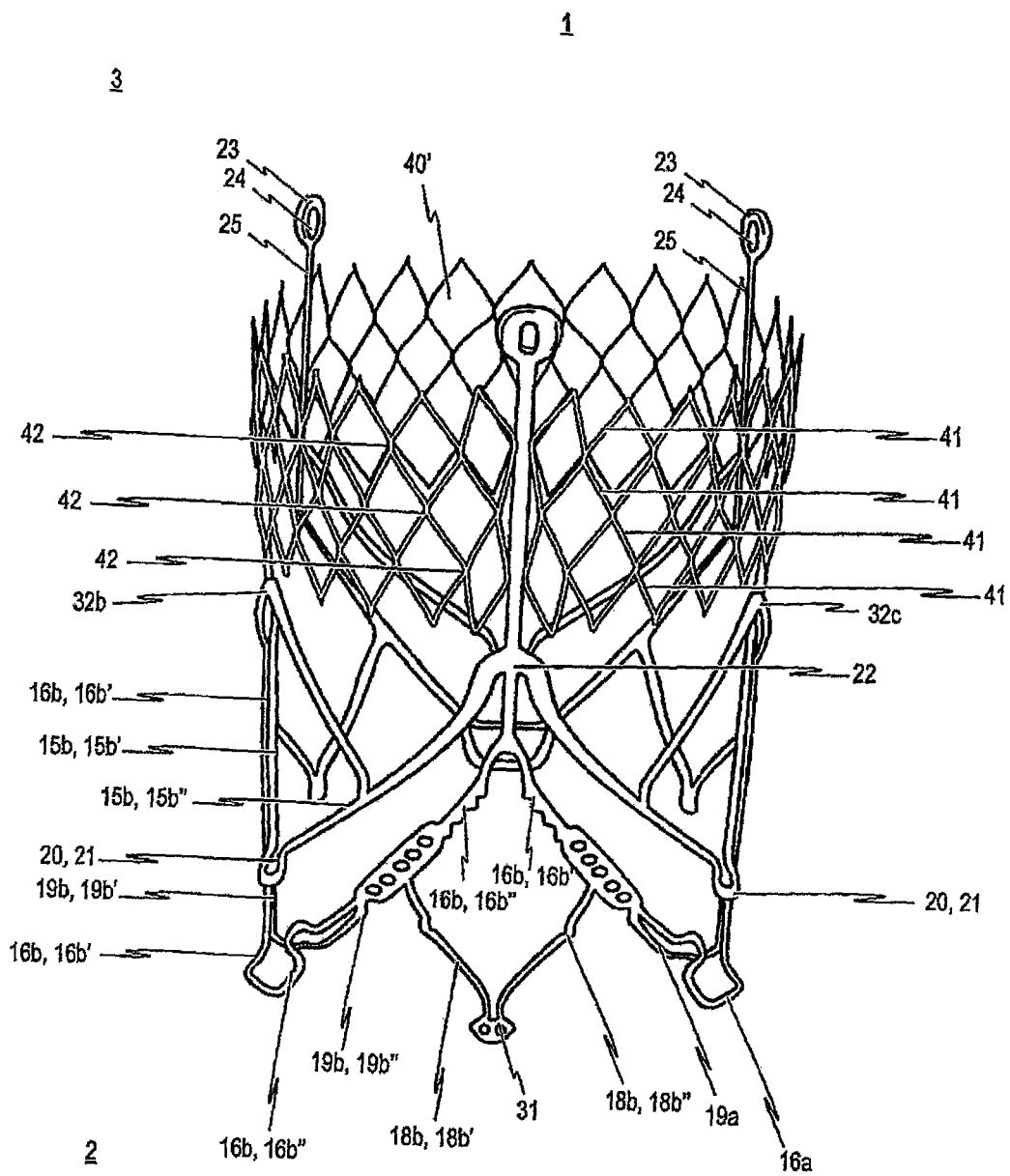
Figure 10:
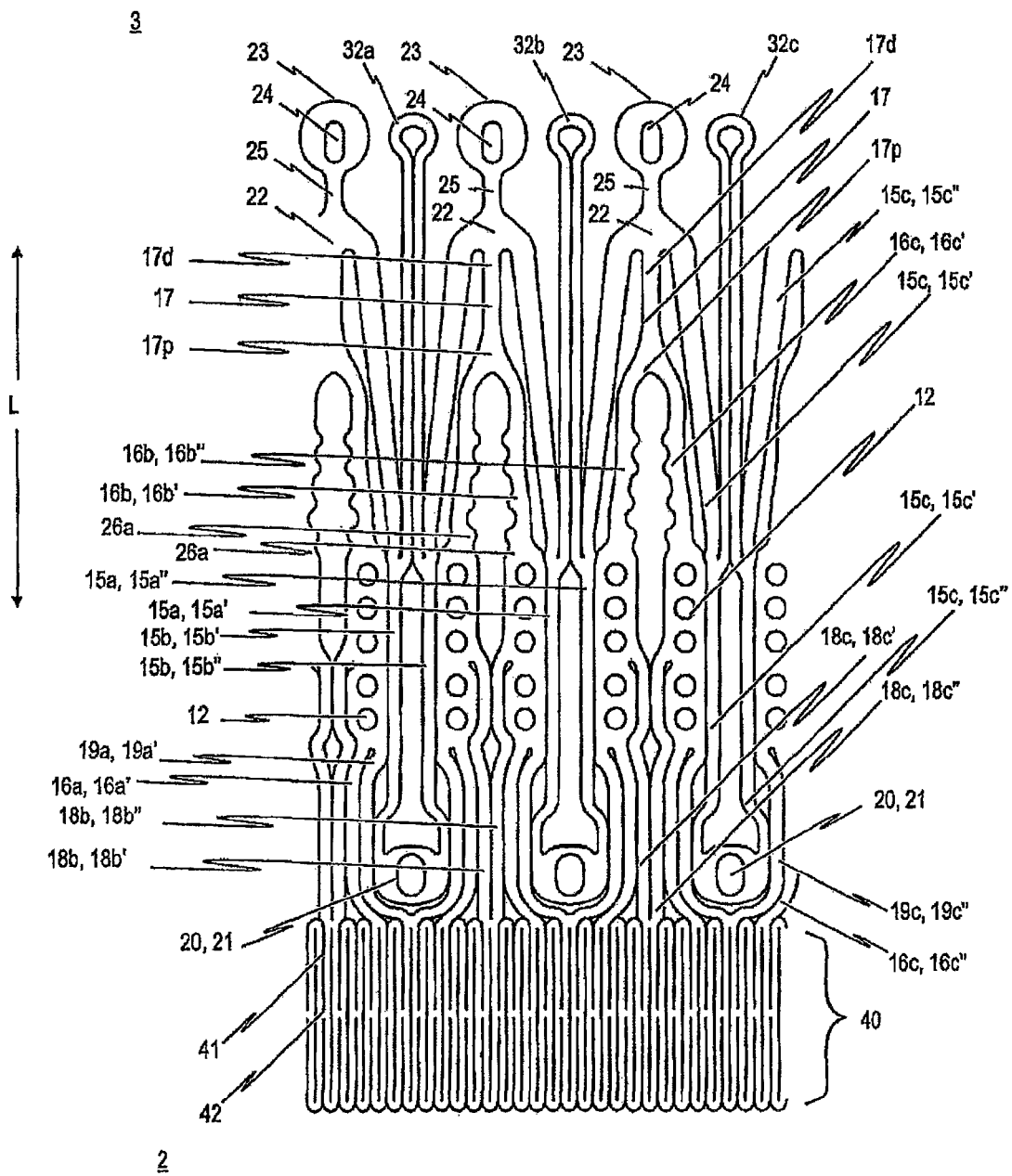
Figure 11:
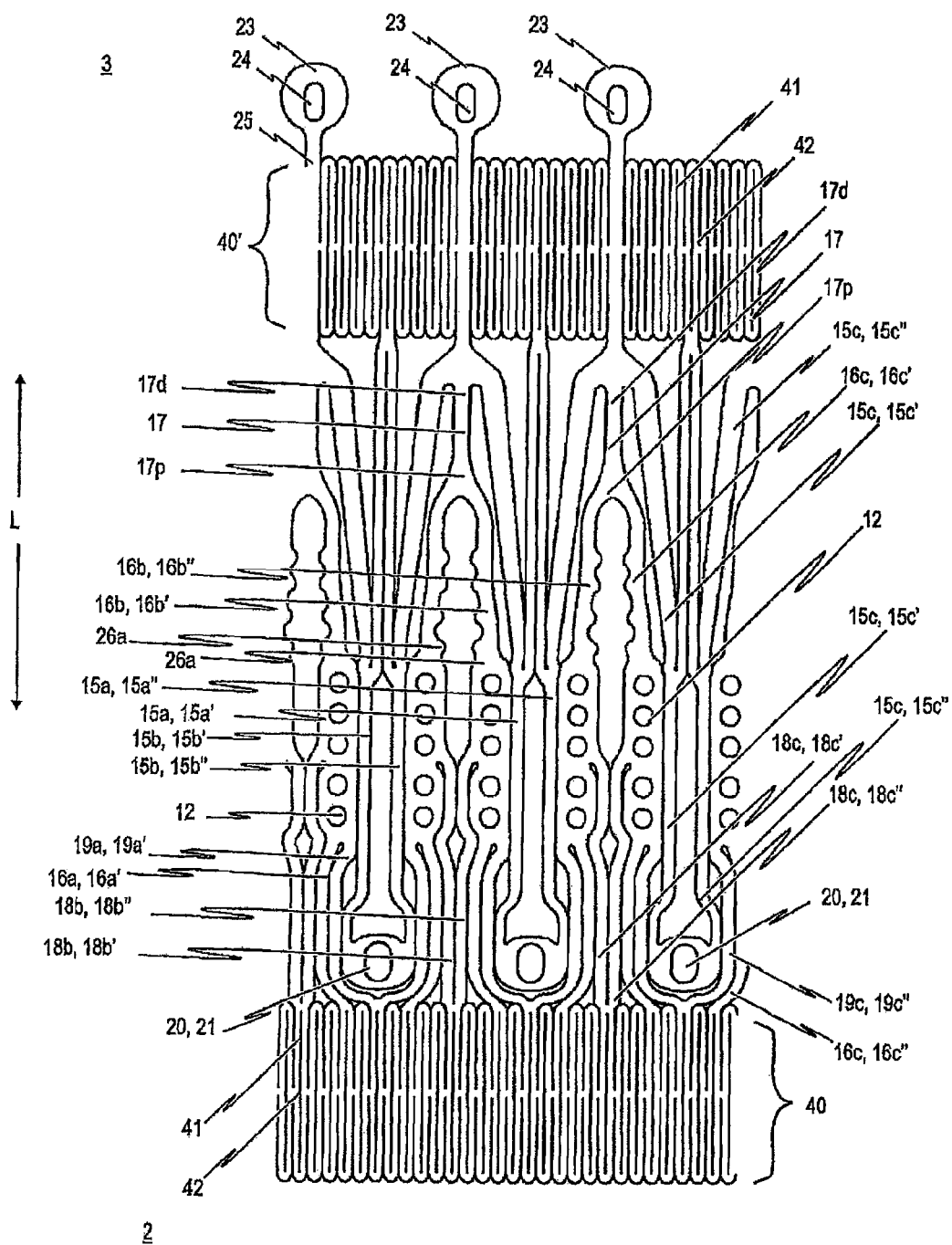
Figure 12:
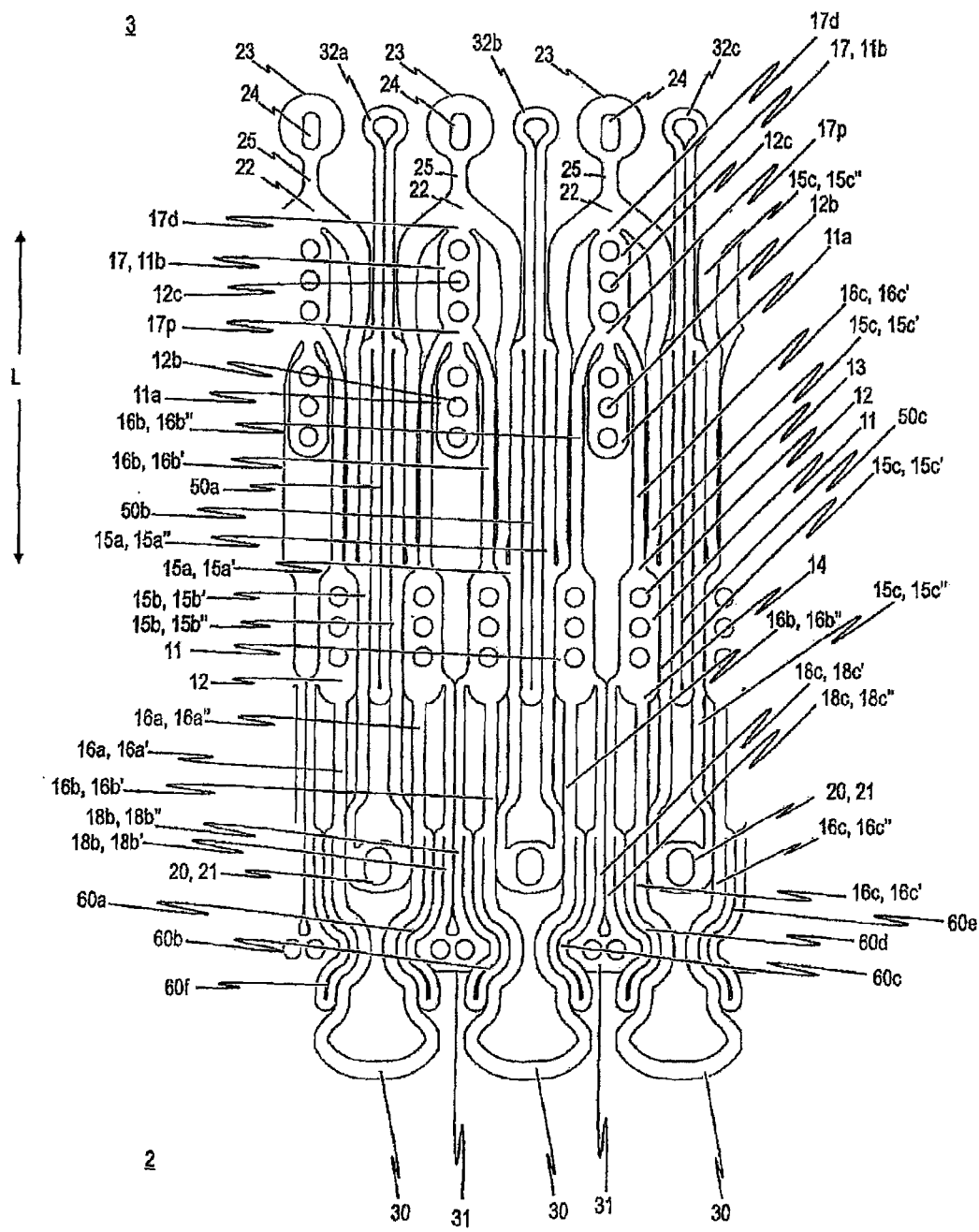
Figure 13A:
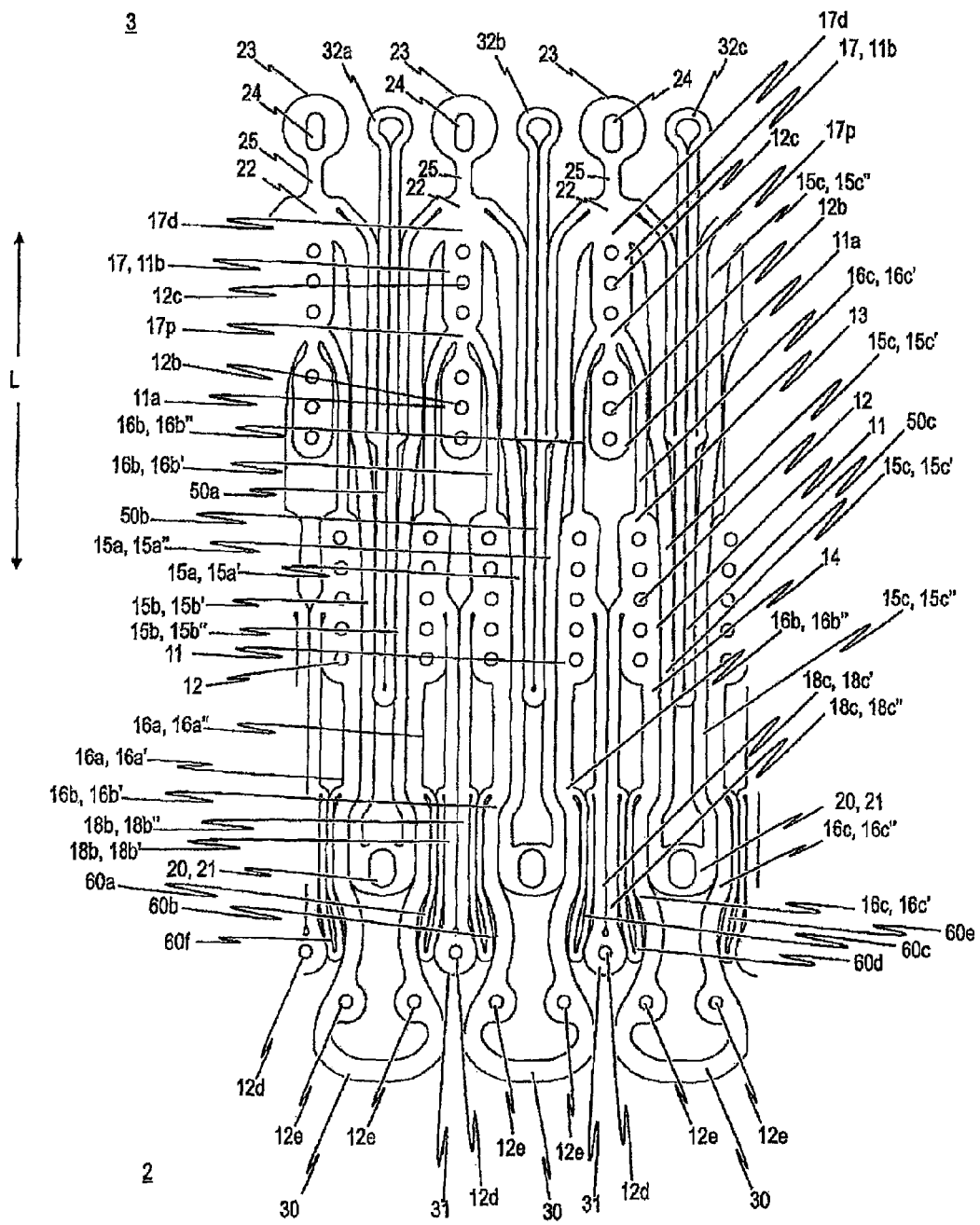
Figure 13B:
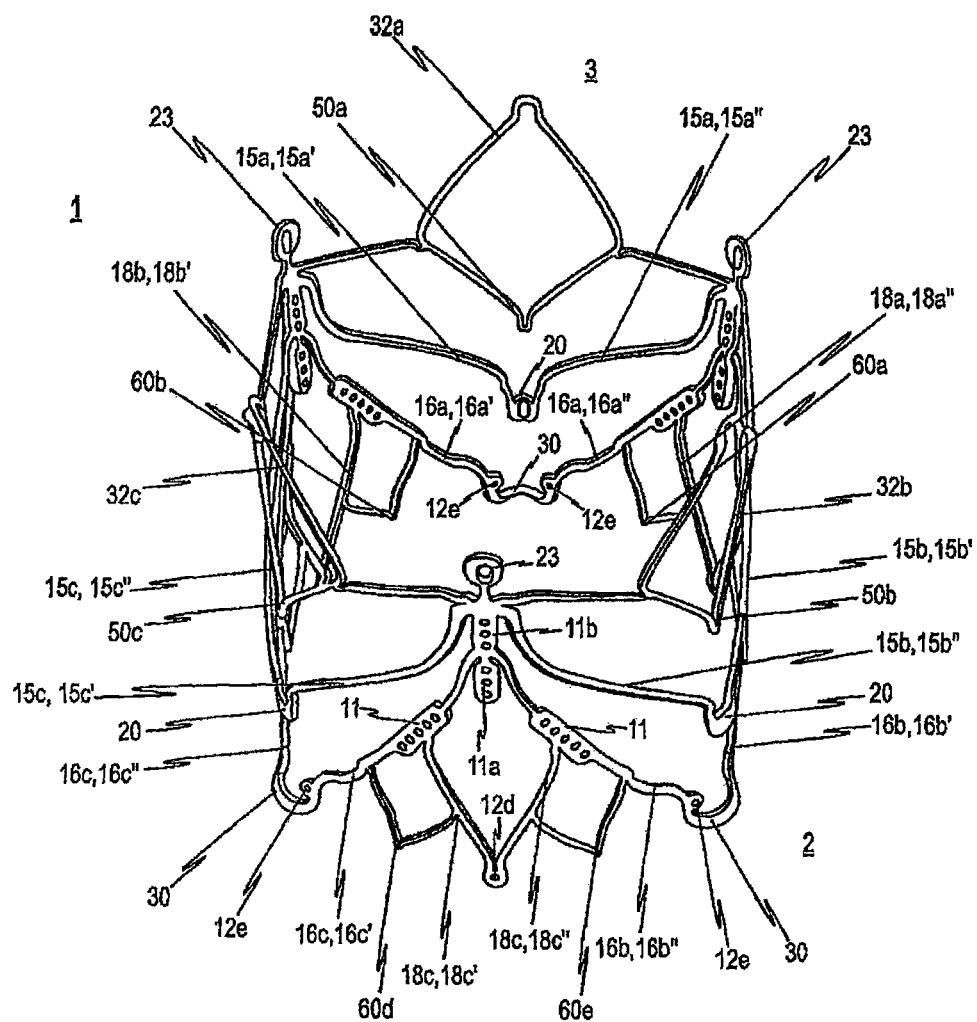
Figure 13C:
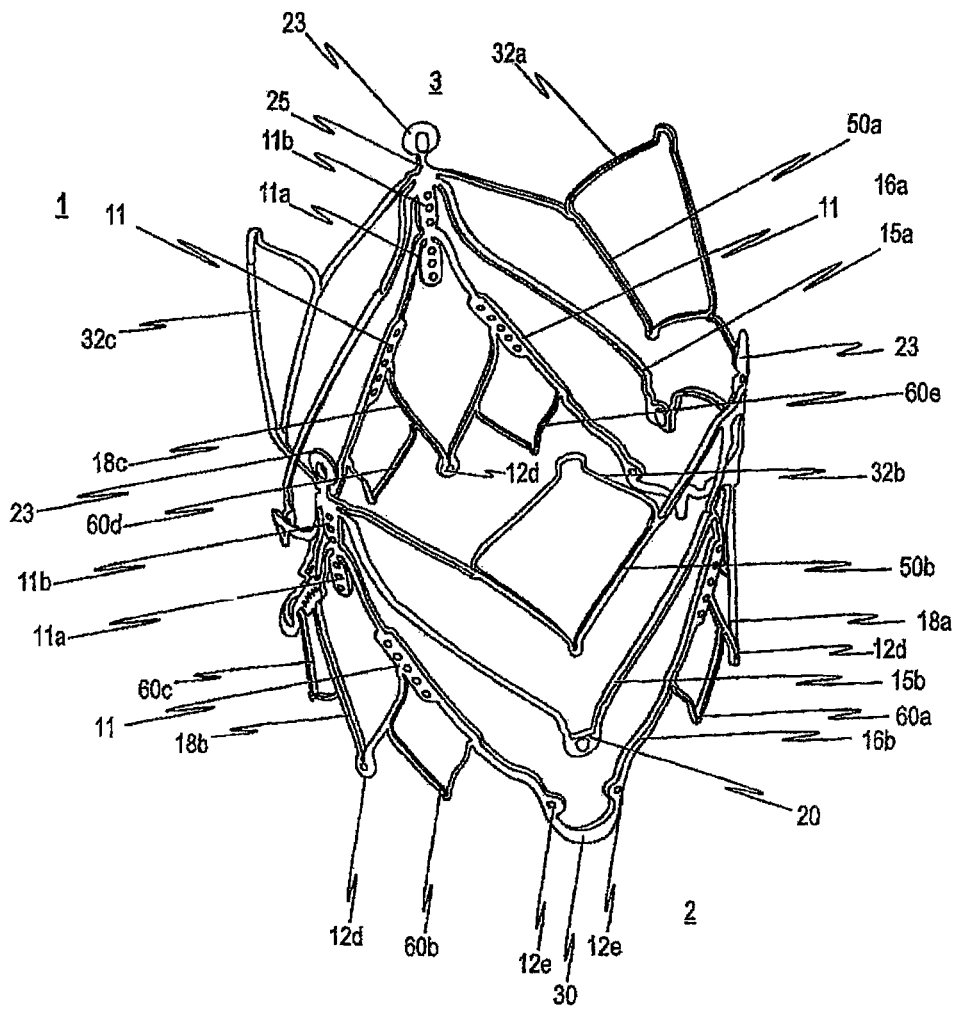
Figure 14A:
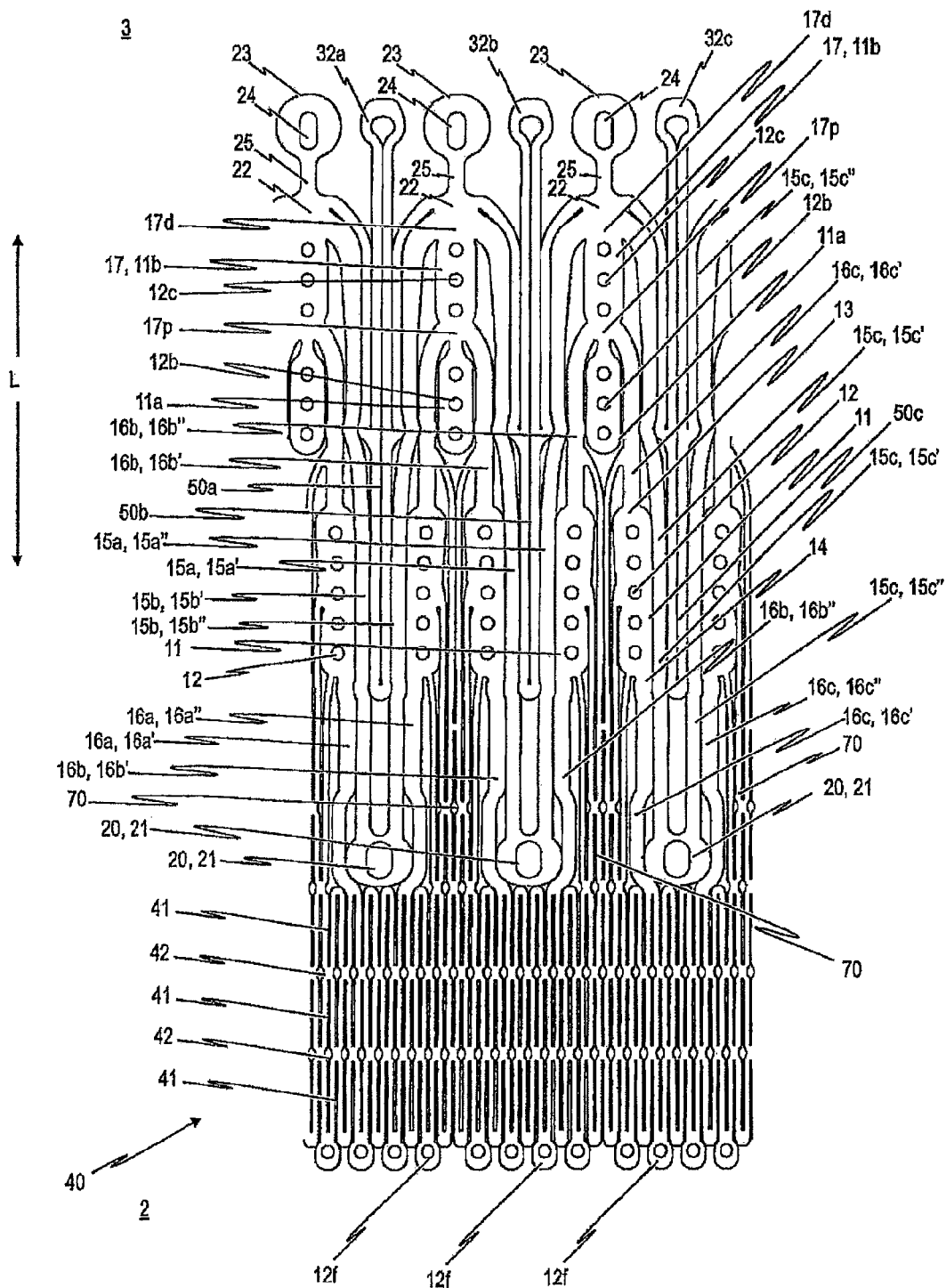
Figure 14B:
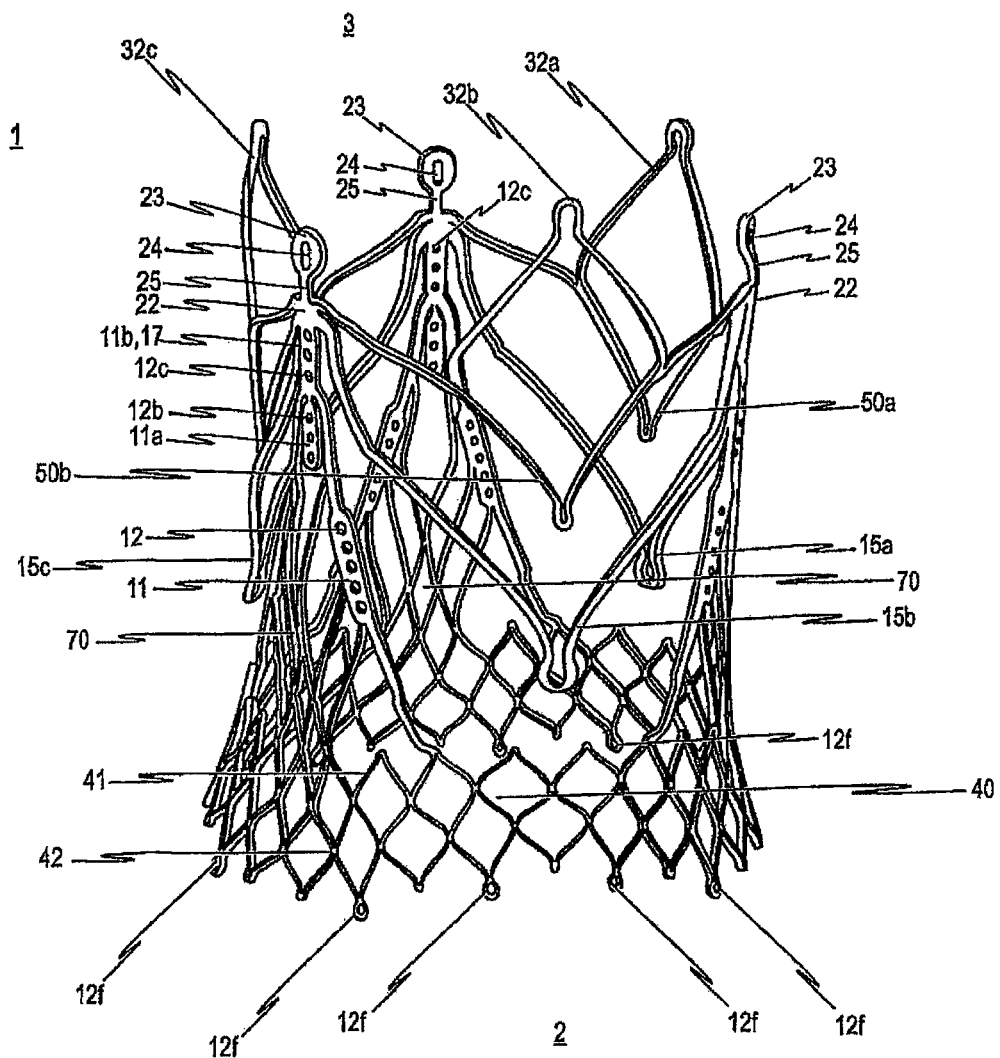
Figure 15:
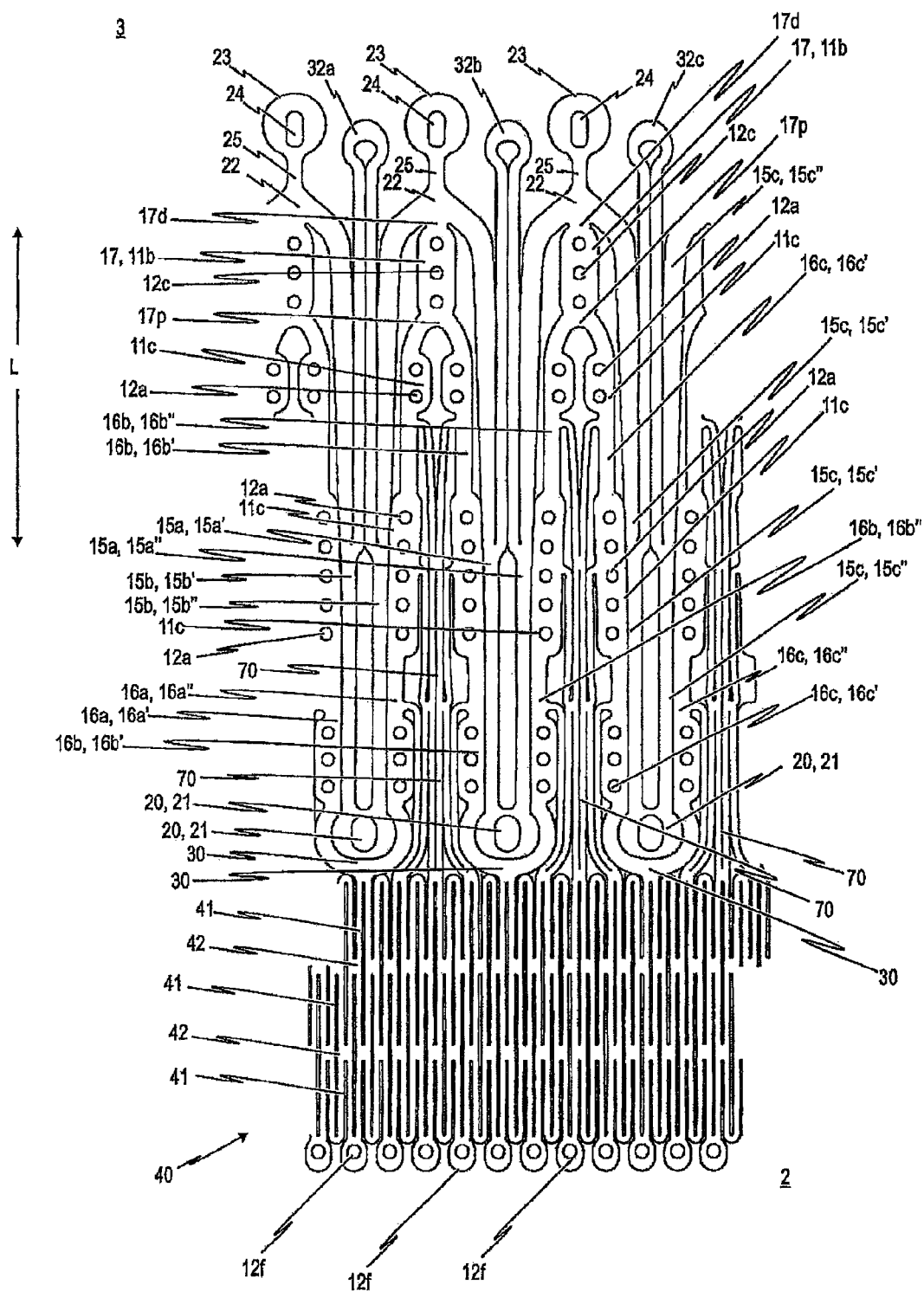
Figure 16A:
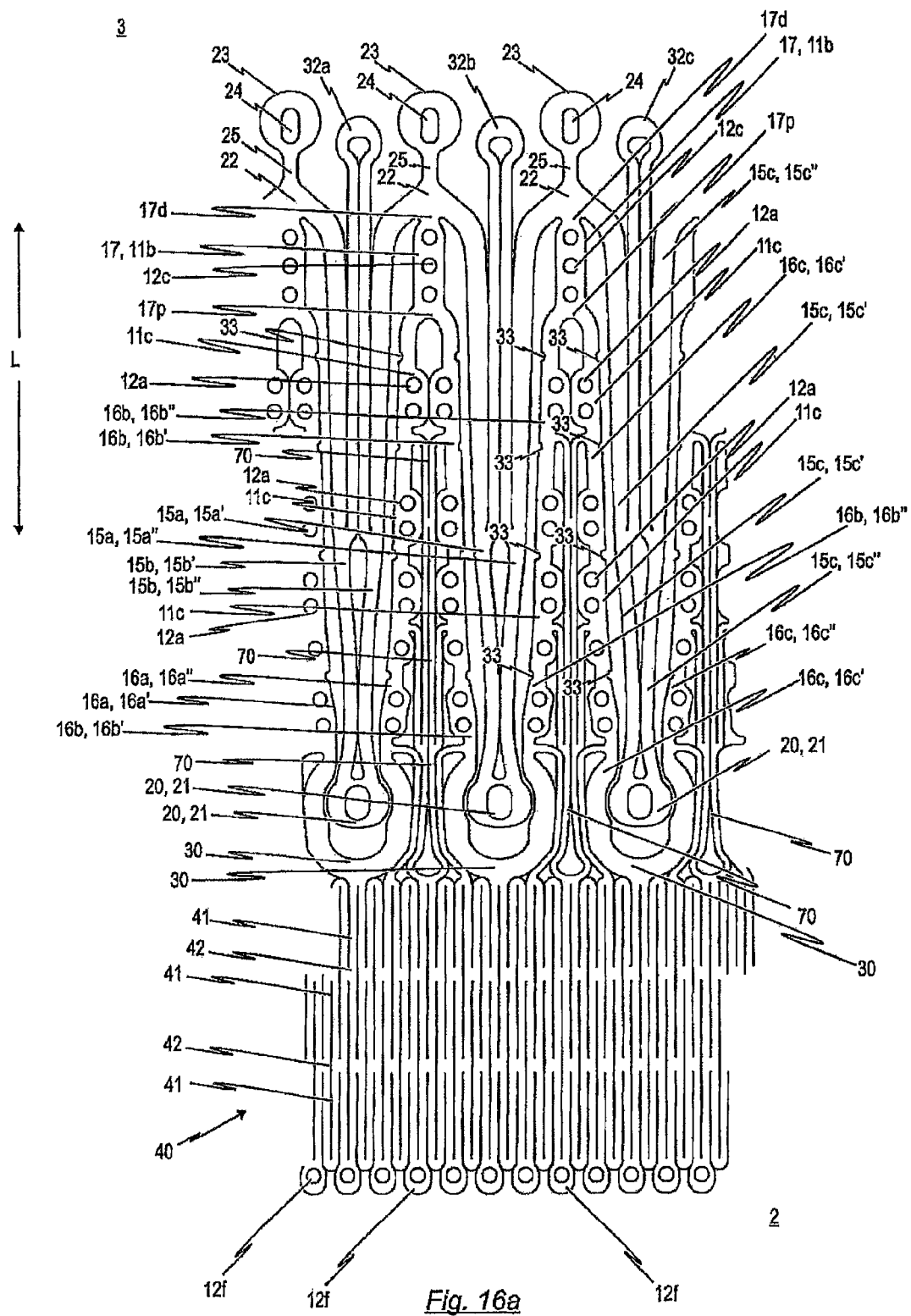
Figure 16B:
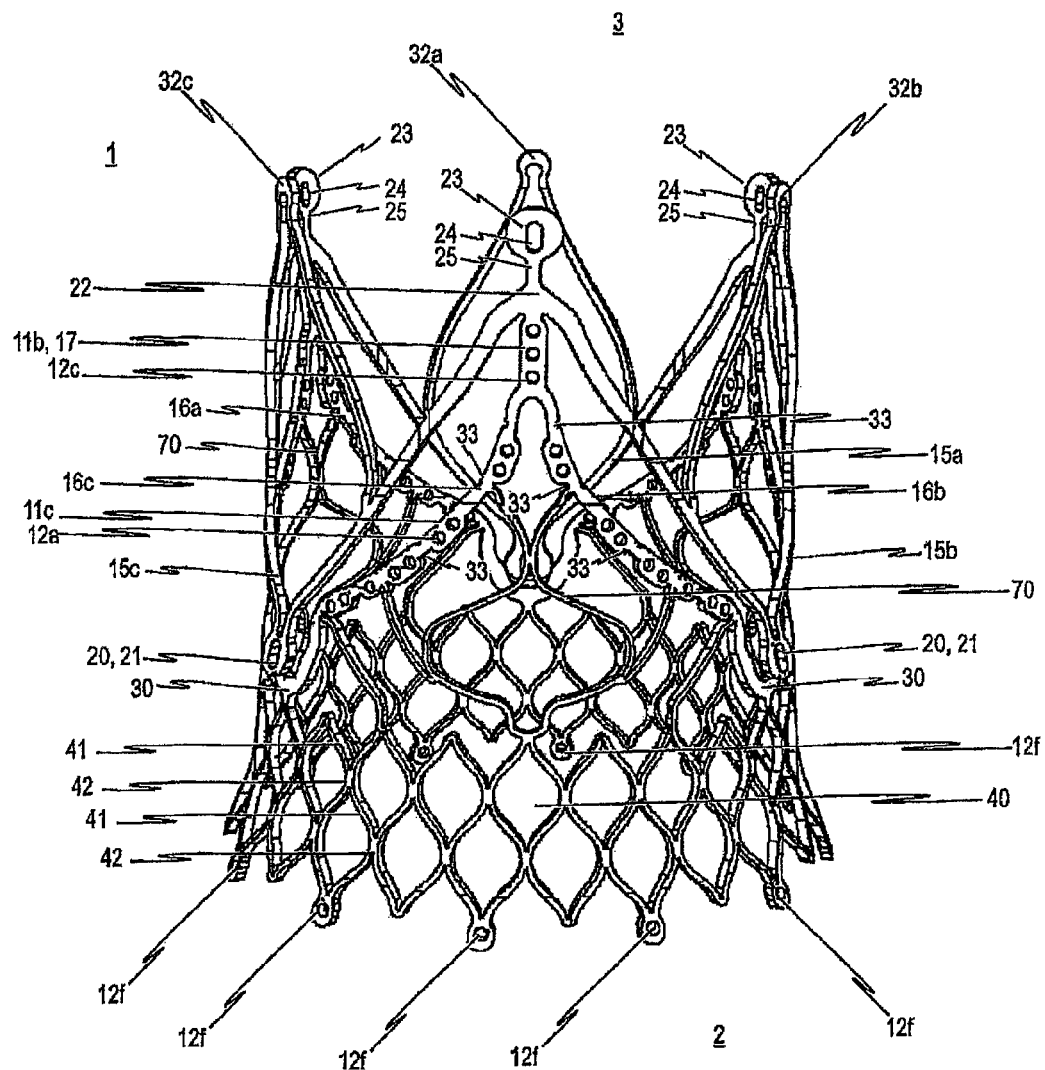
Figure 16C:
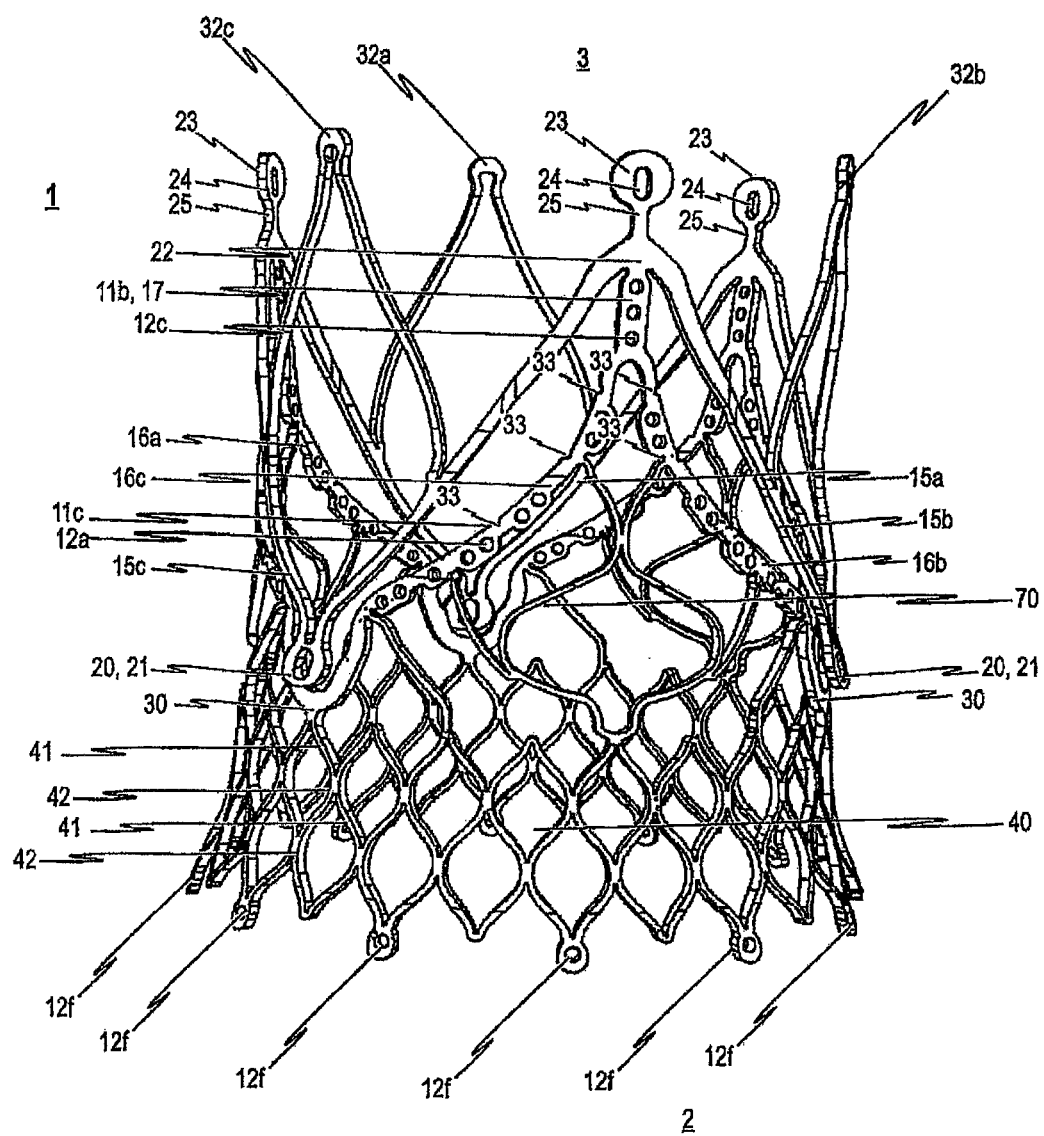
Figure 16D:
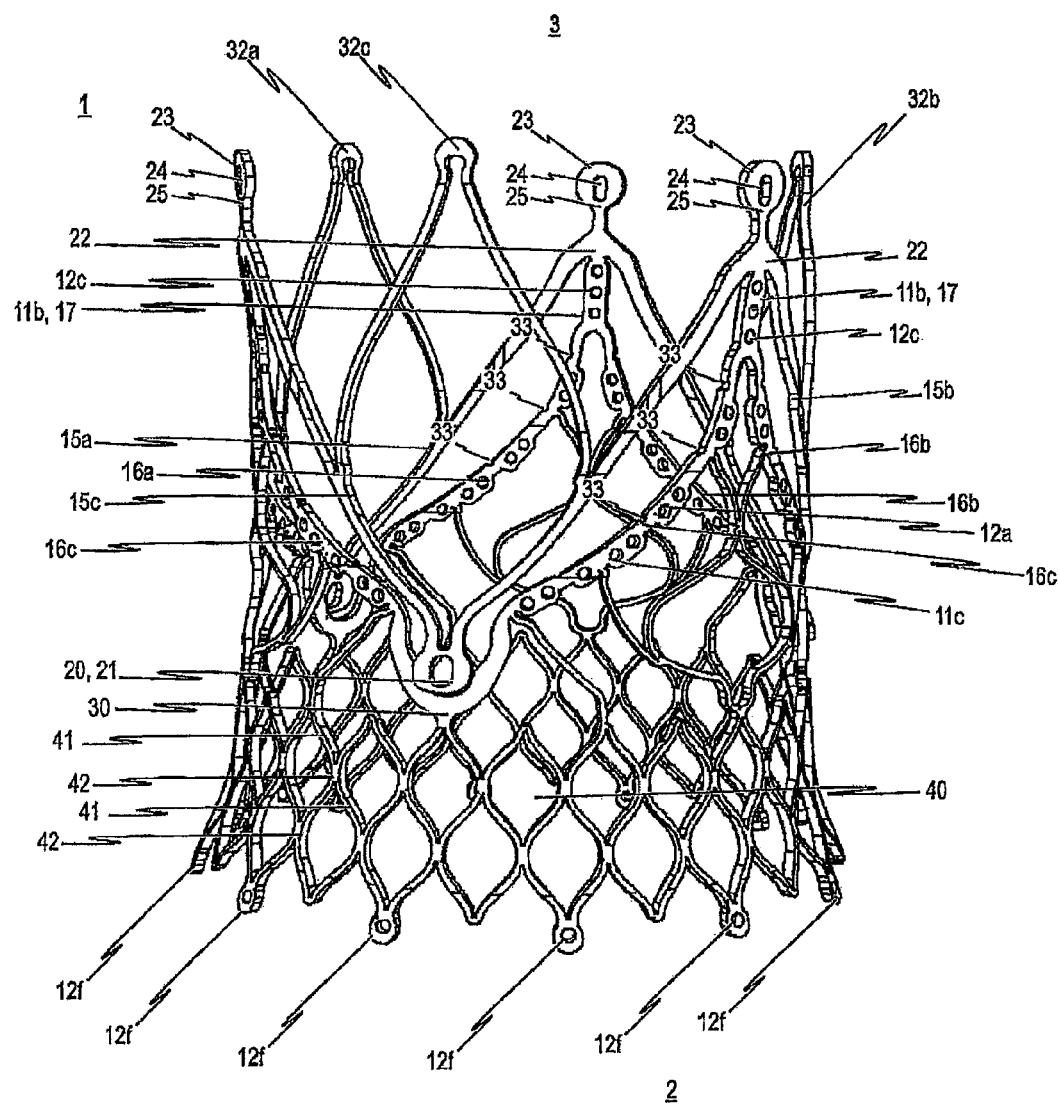
Figure 16E:
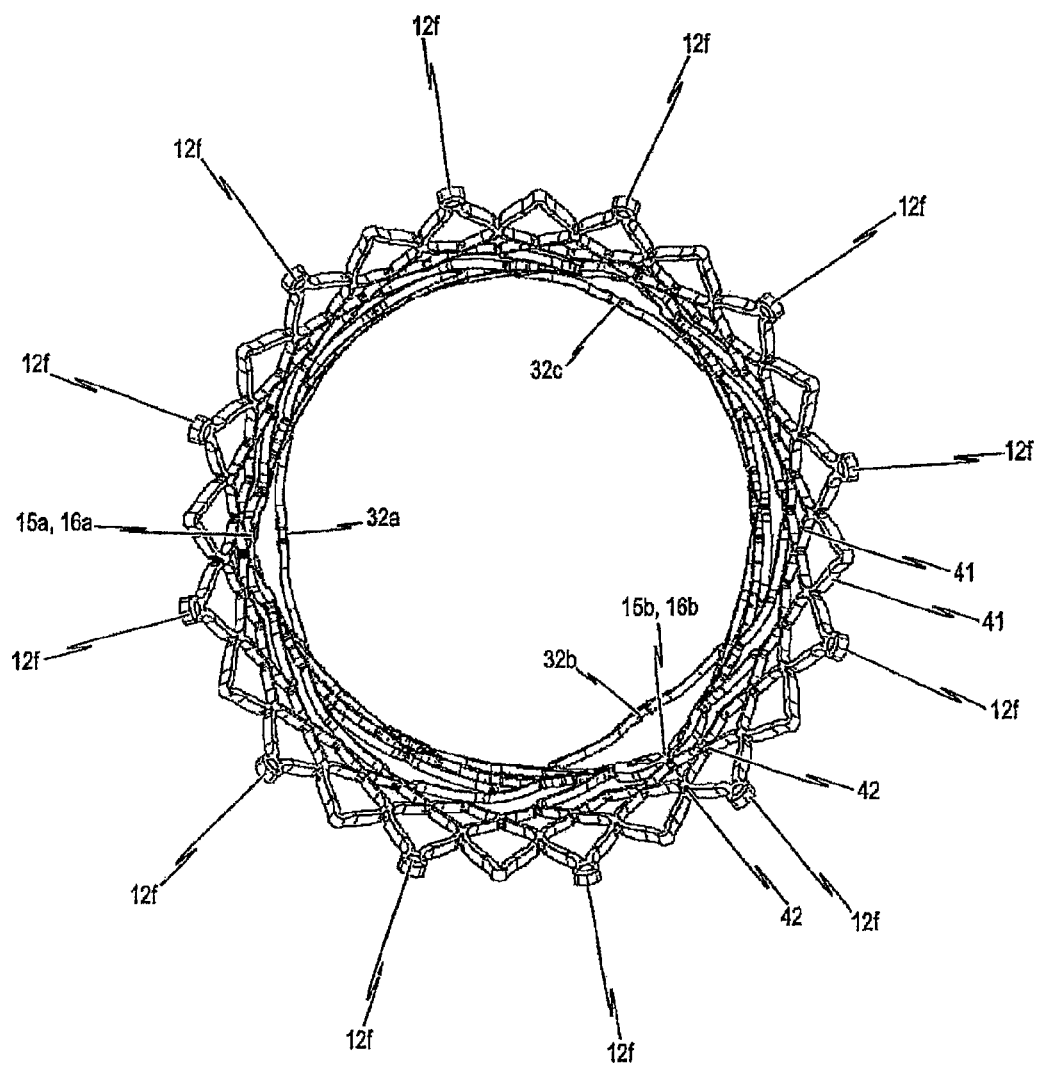
Figure 16F:
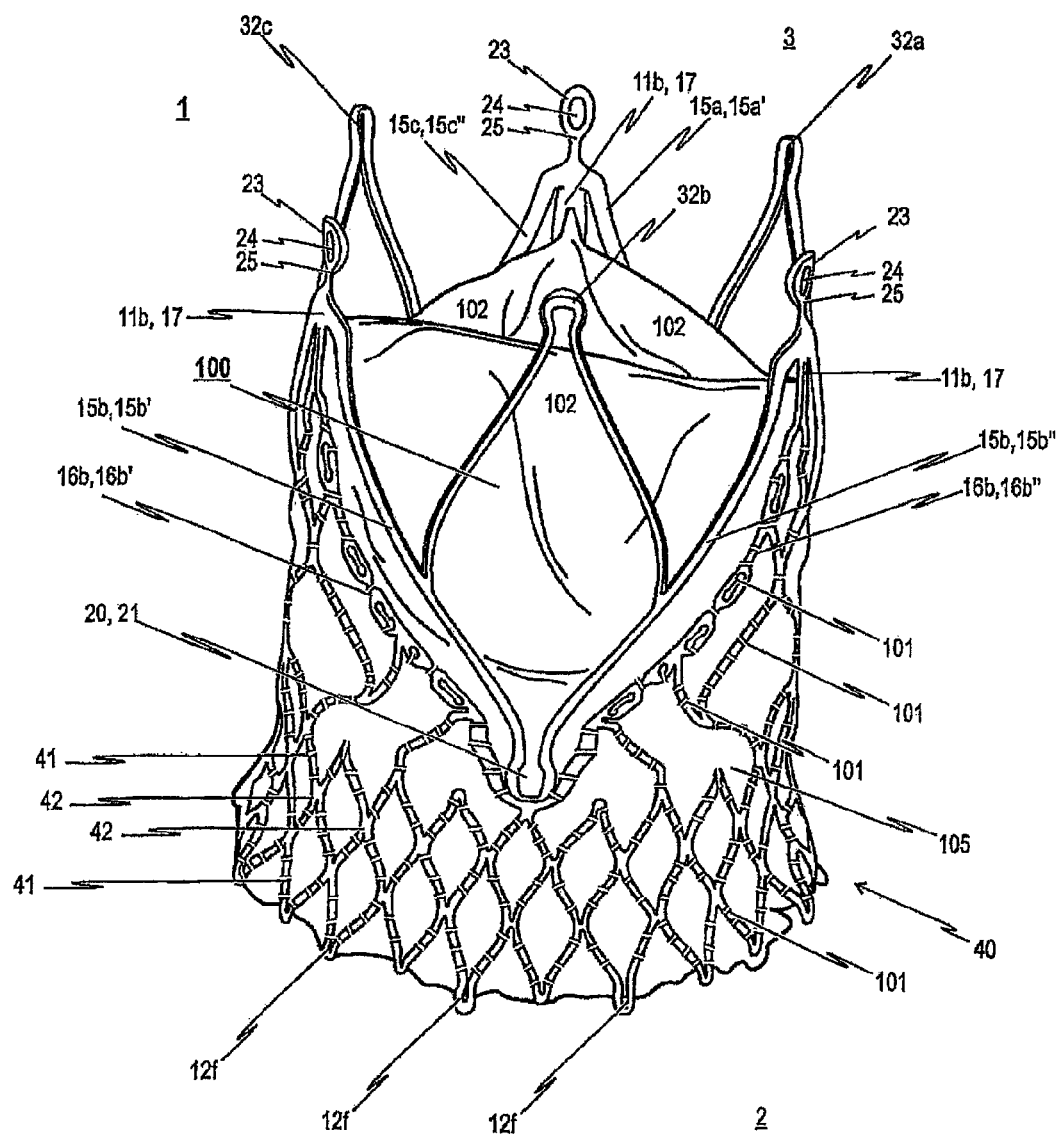
Figure 16G:
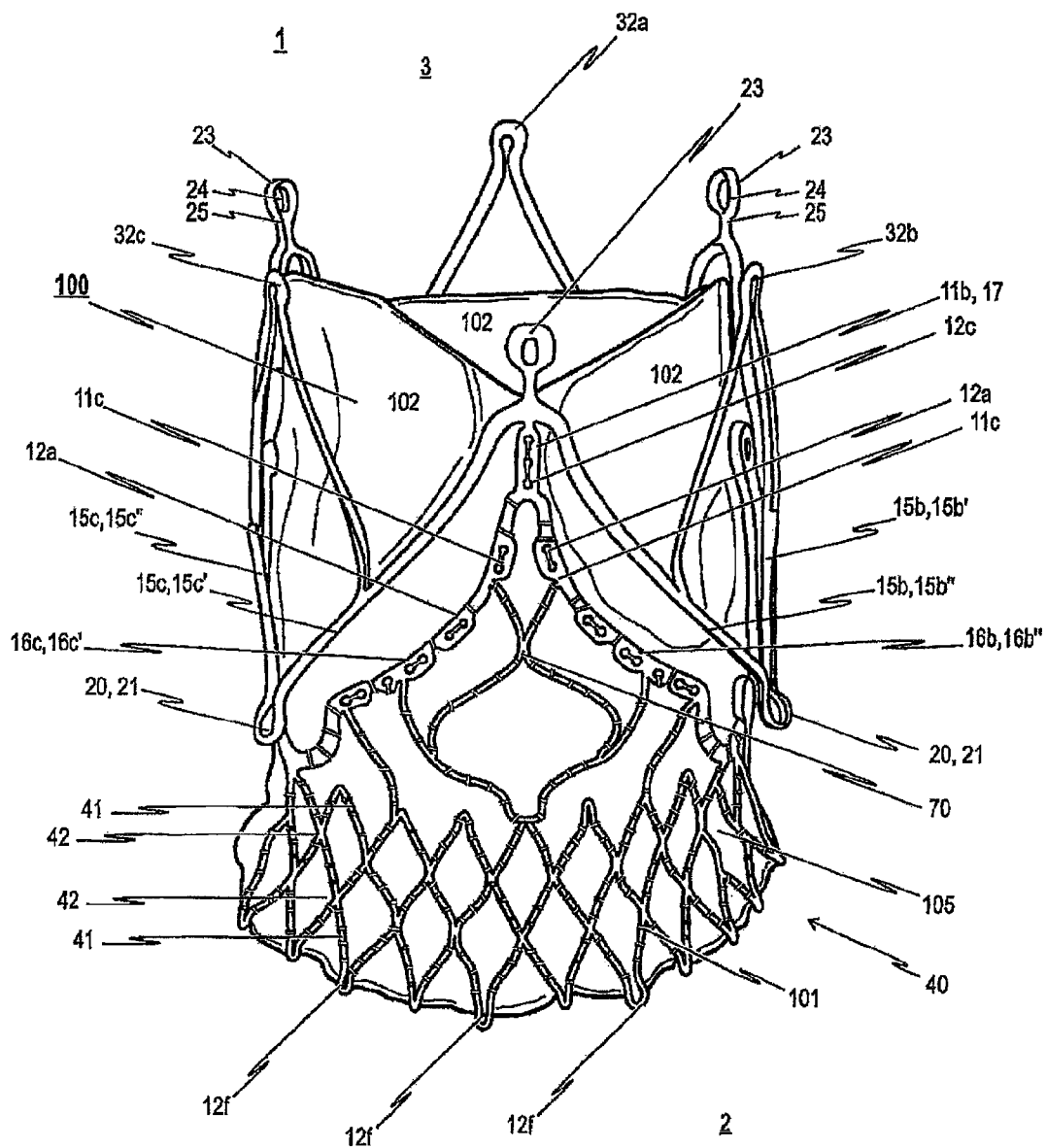
Figure 17A:
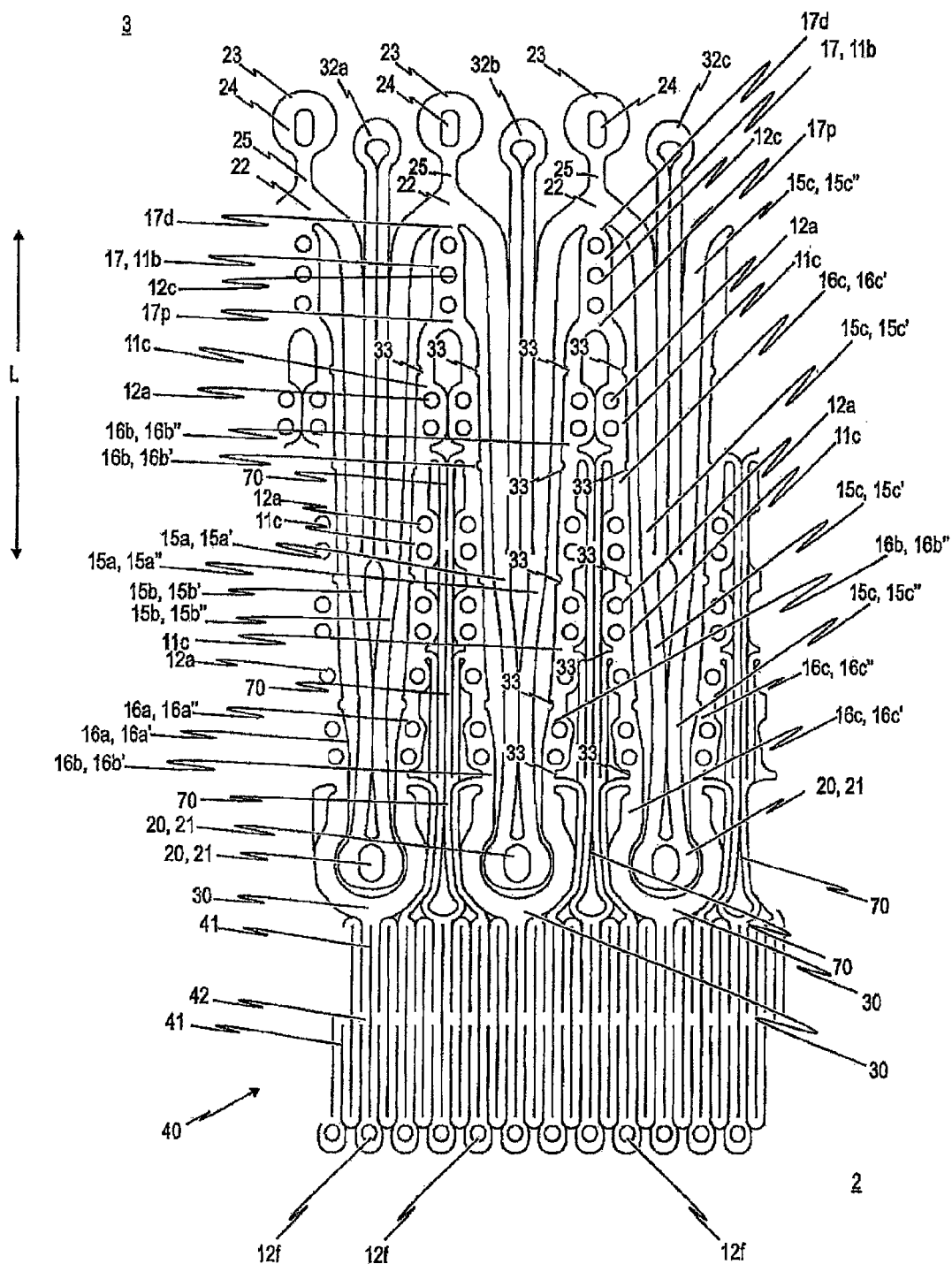
Figure 17B:
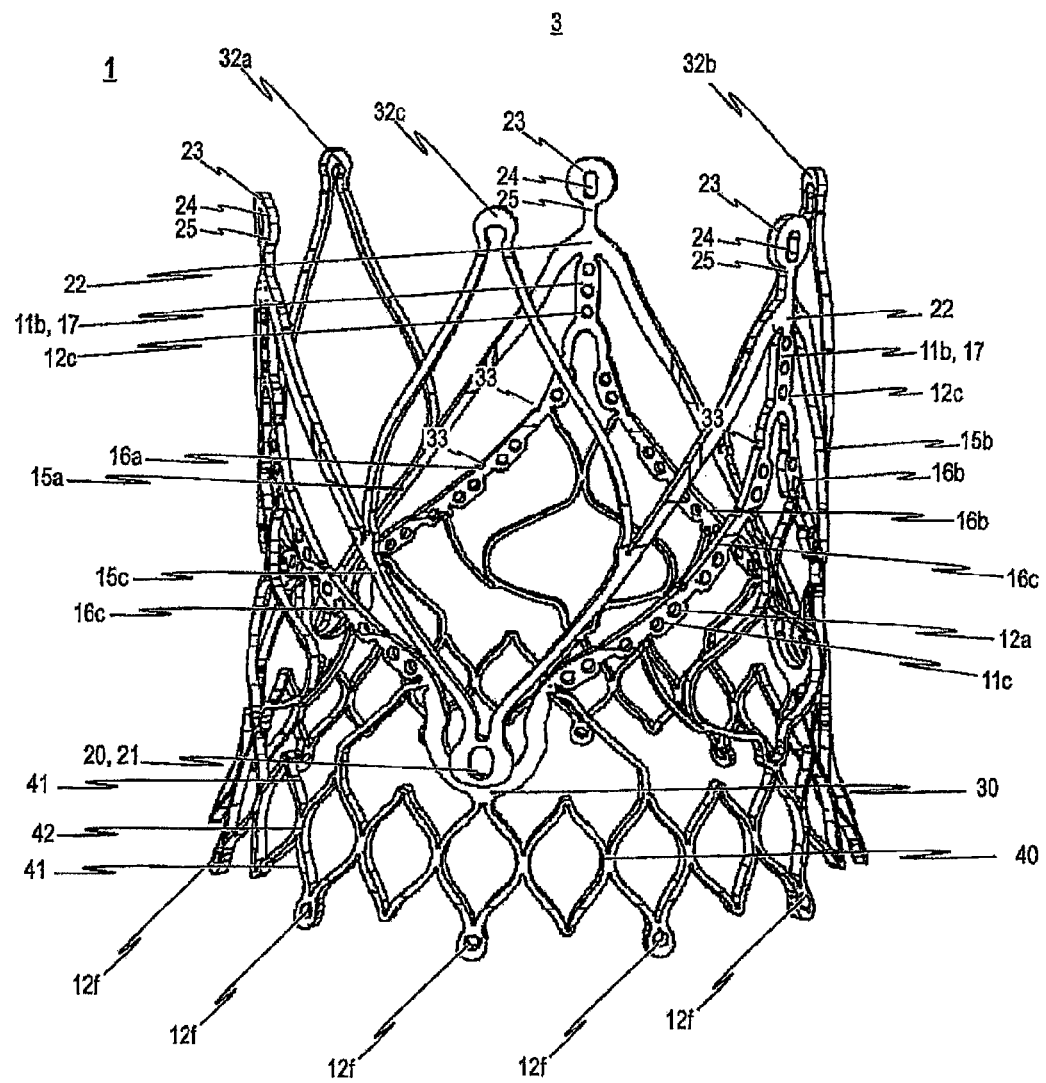
Figure 17C:
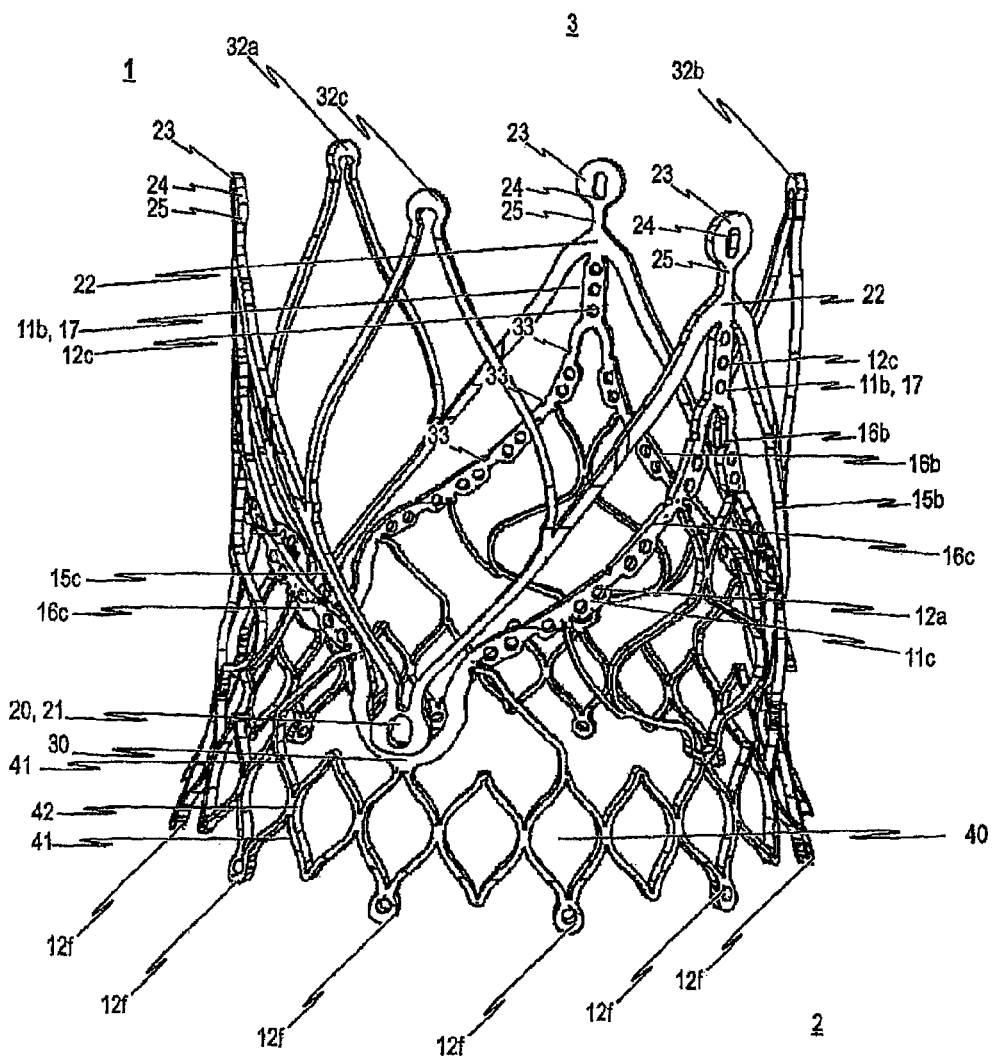
Figure 17D:
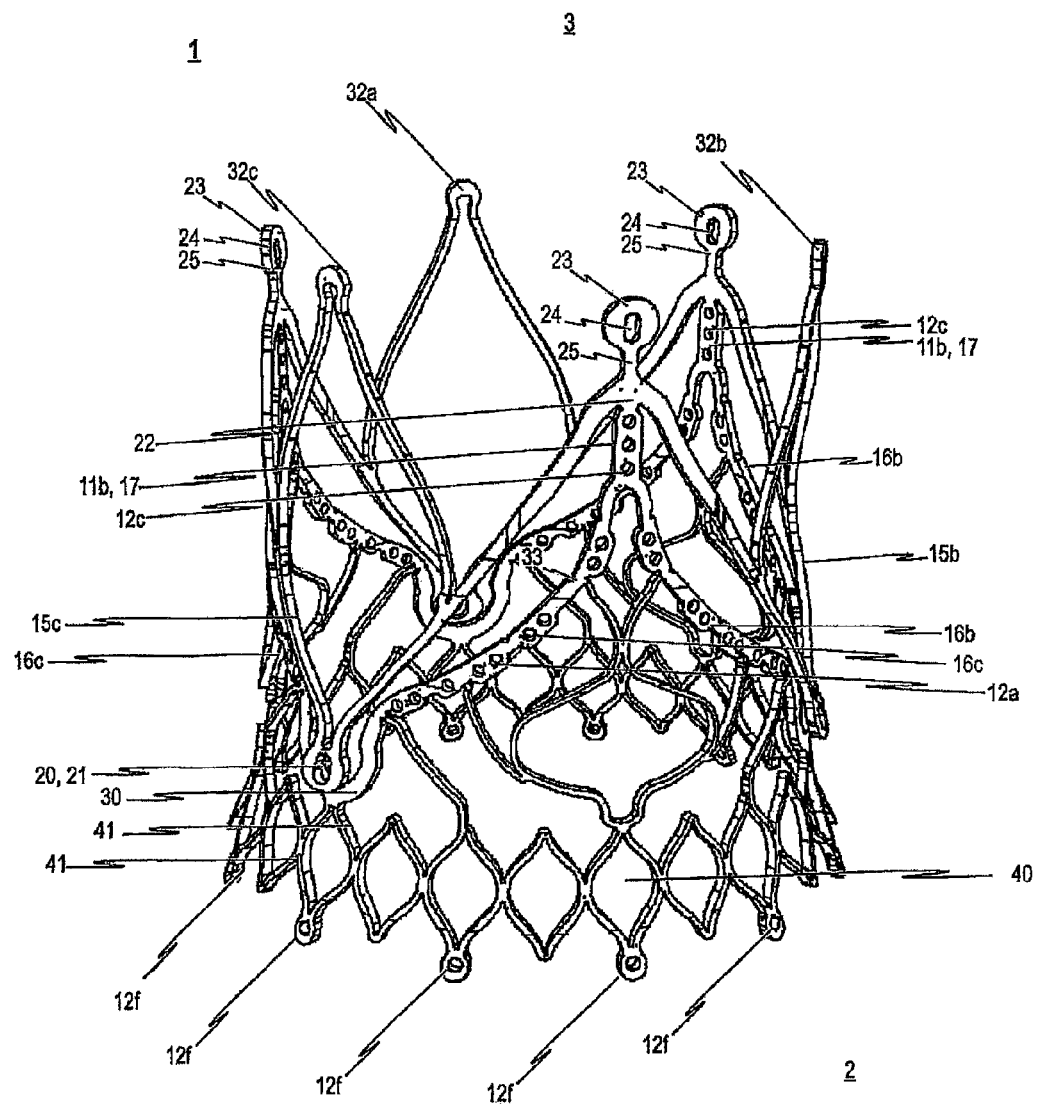
Figure 17E:
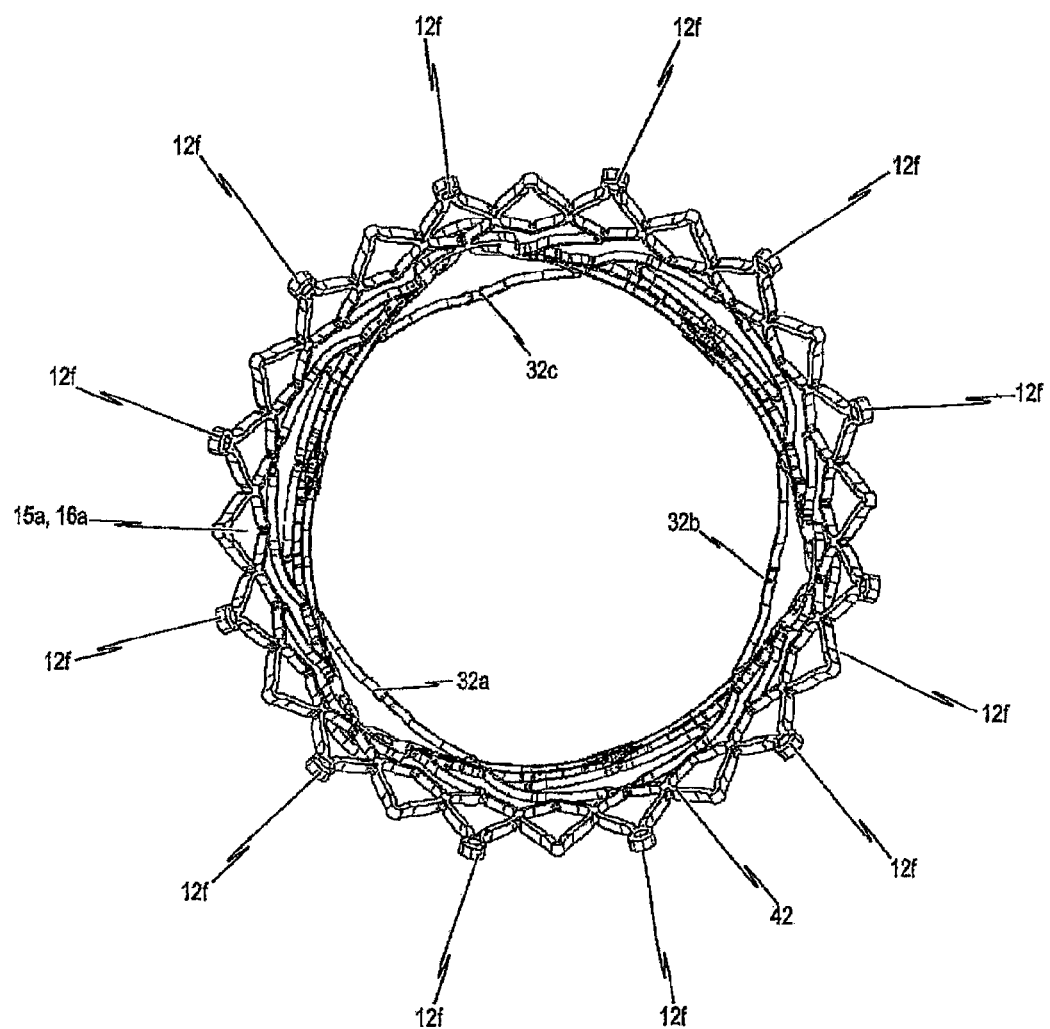
Figure 18C:
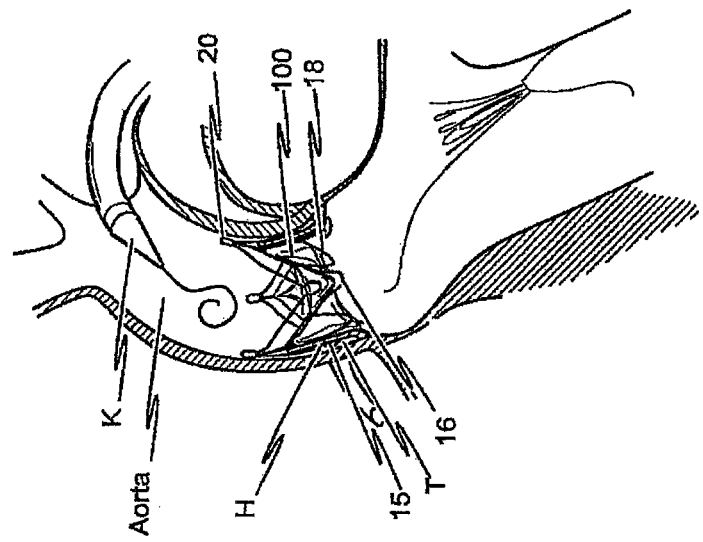
Figure 18B:
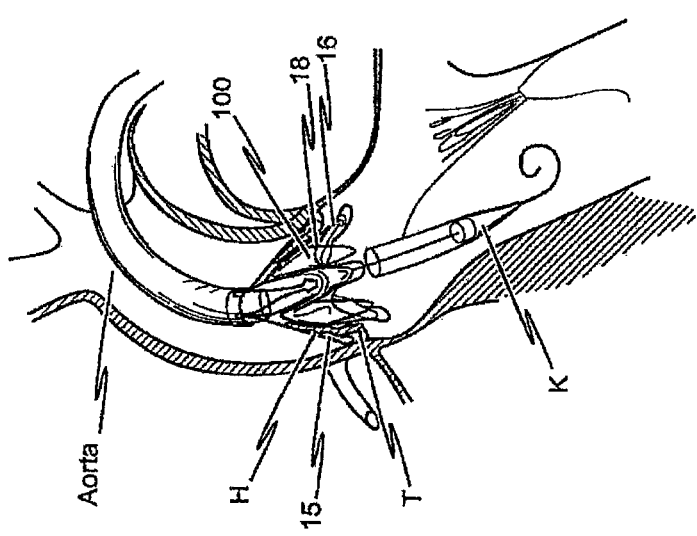
Figure 18A:
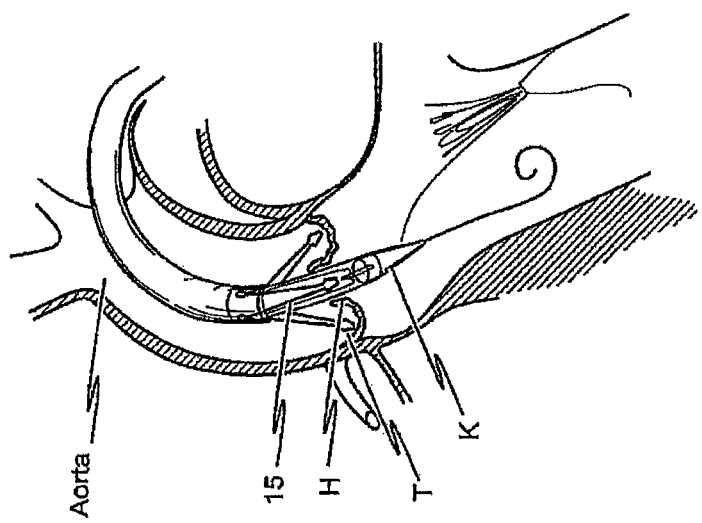
Figure 19A:
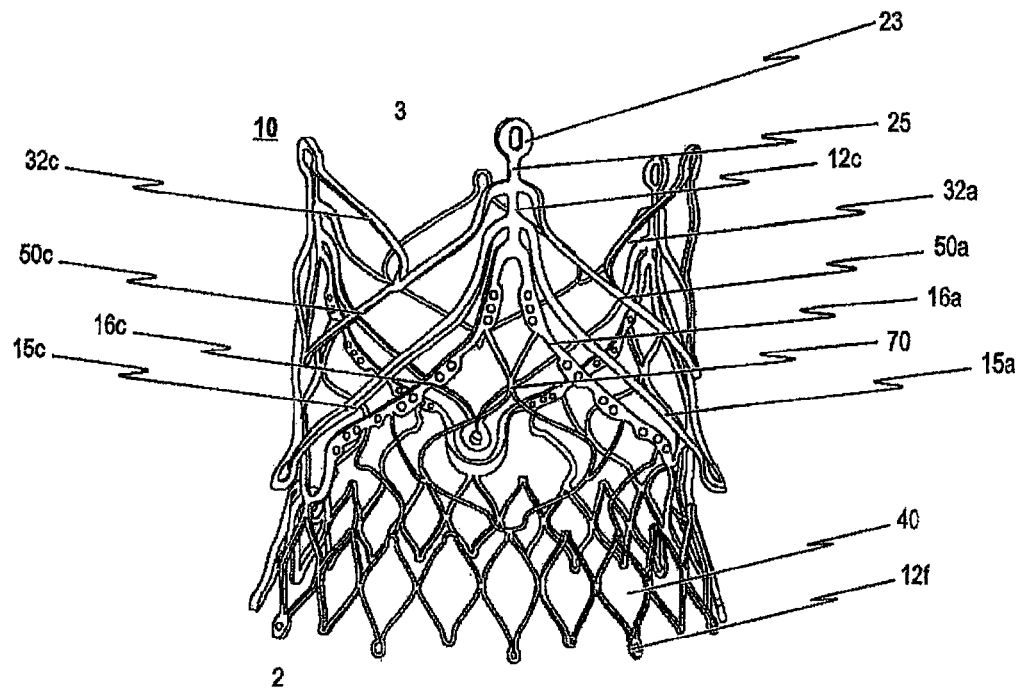
Figure 19B:
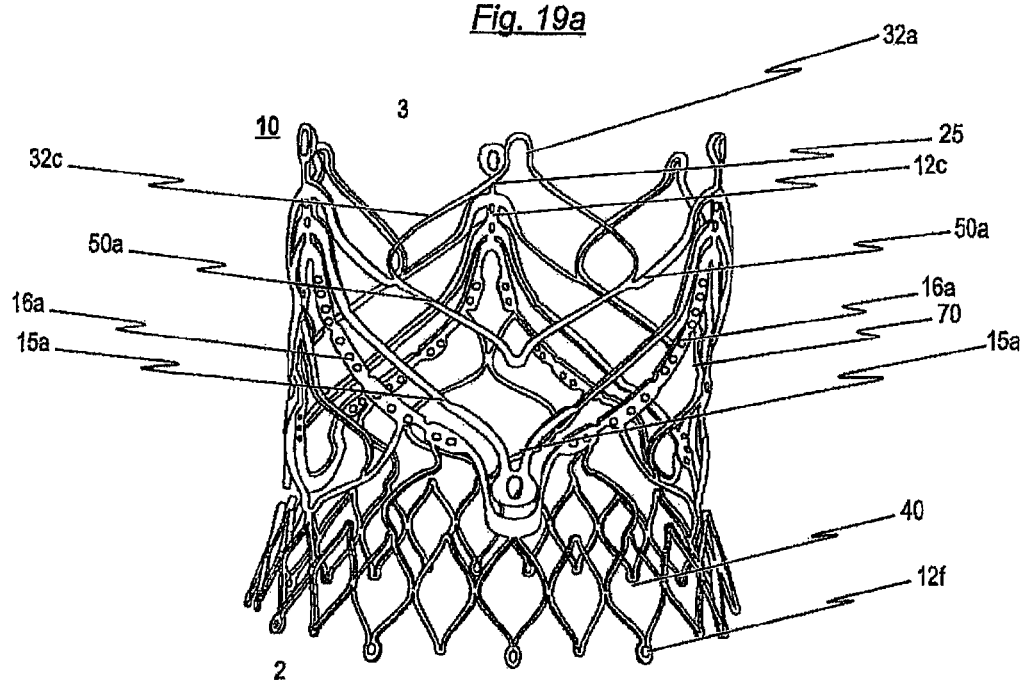
Figure 20A:
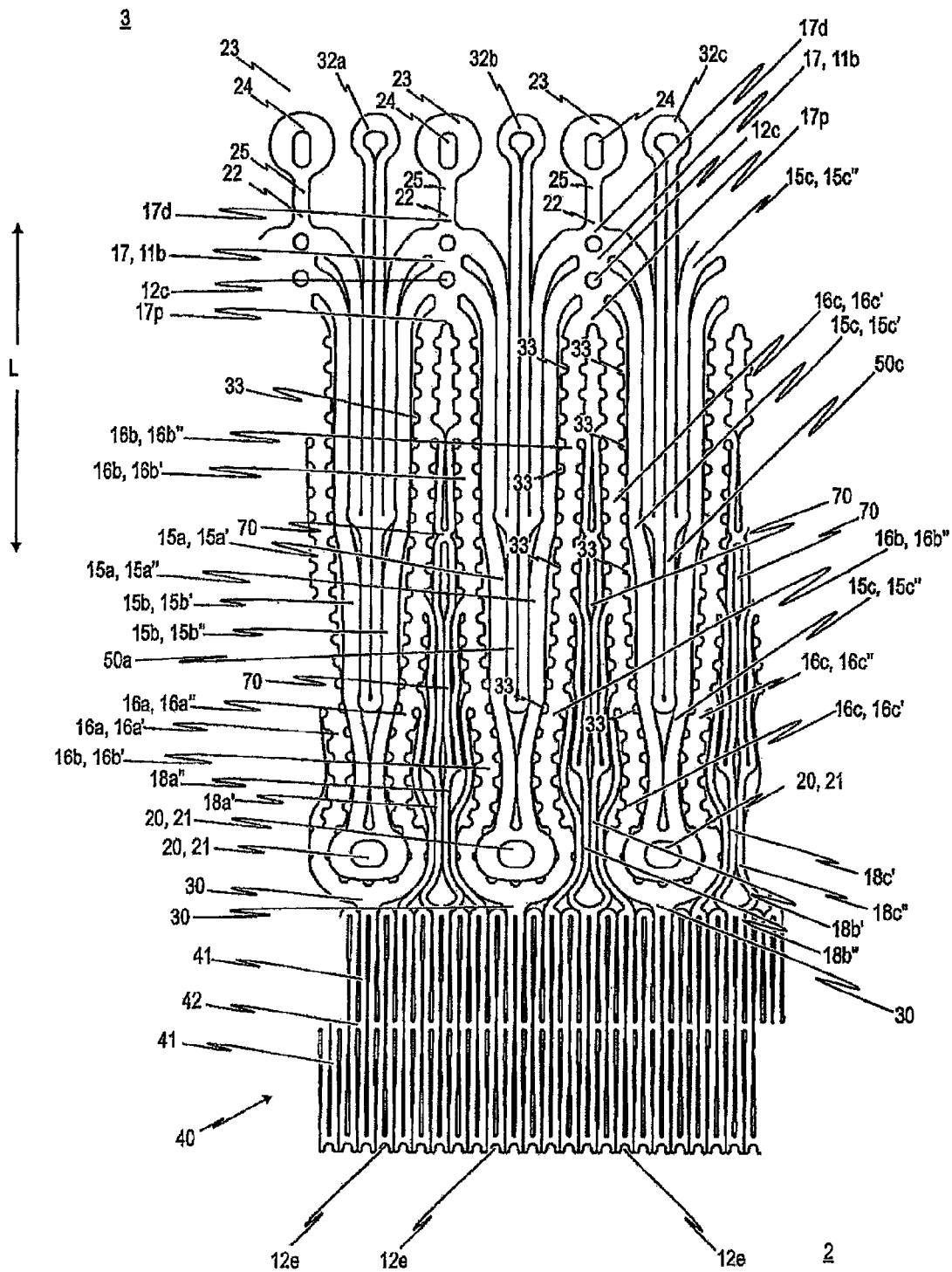
Figure 20B:
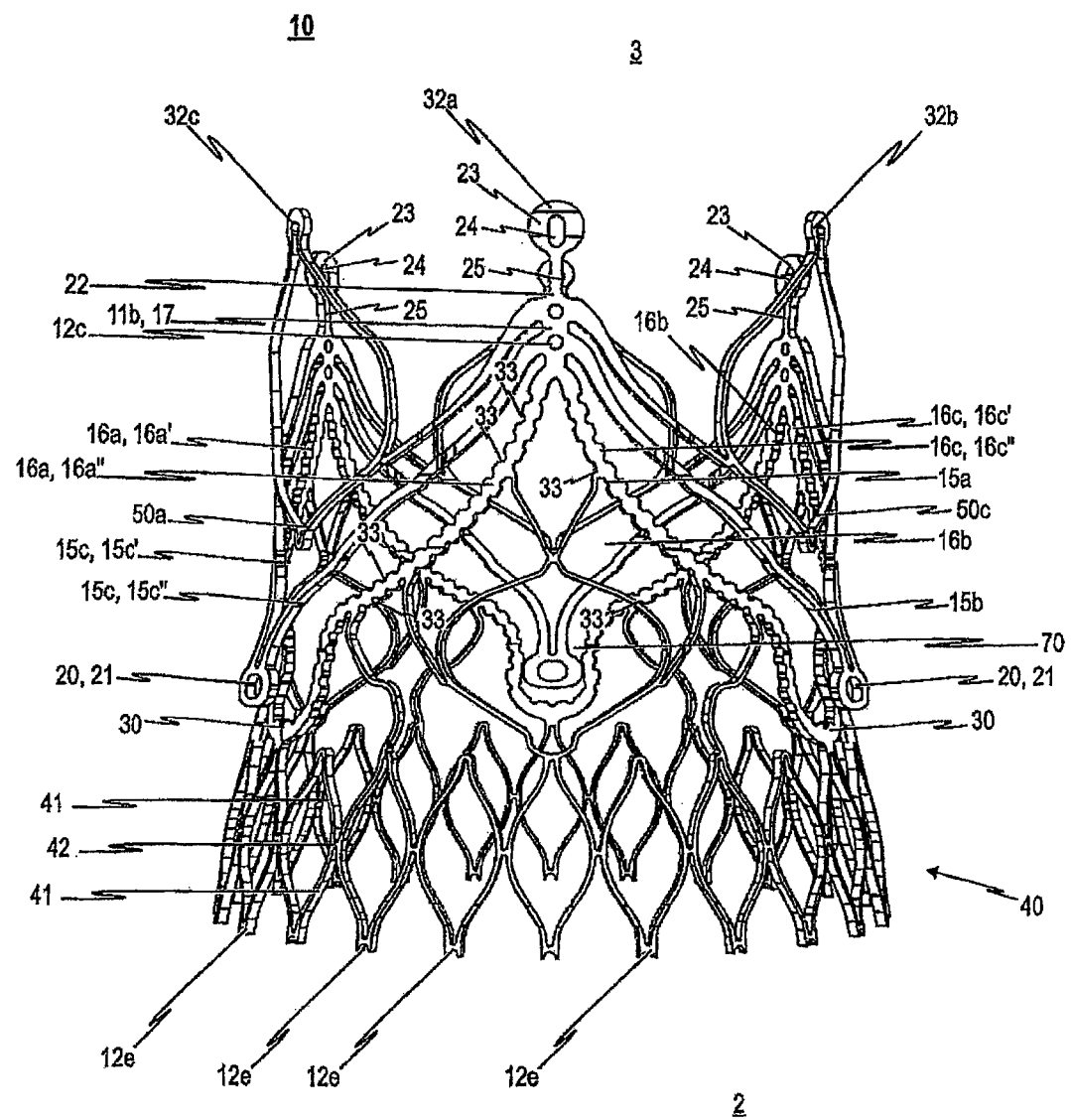
Figure 20C:
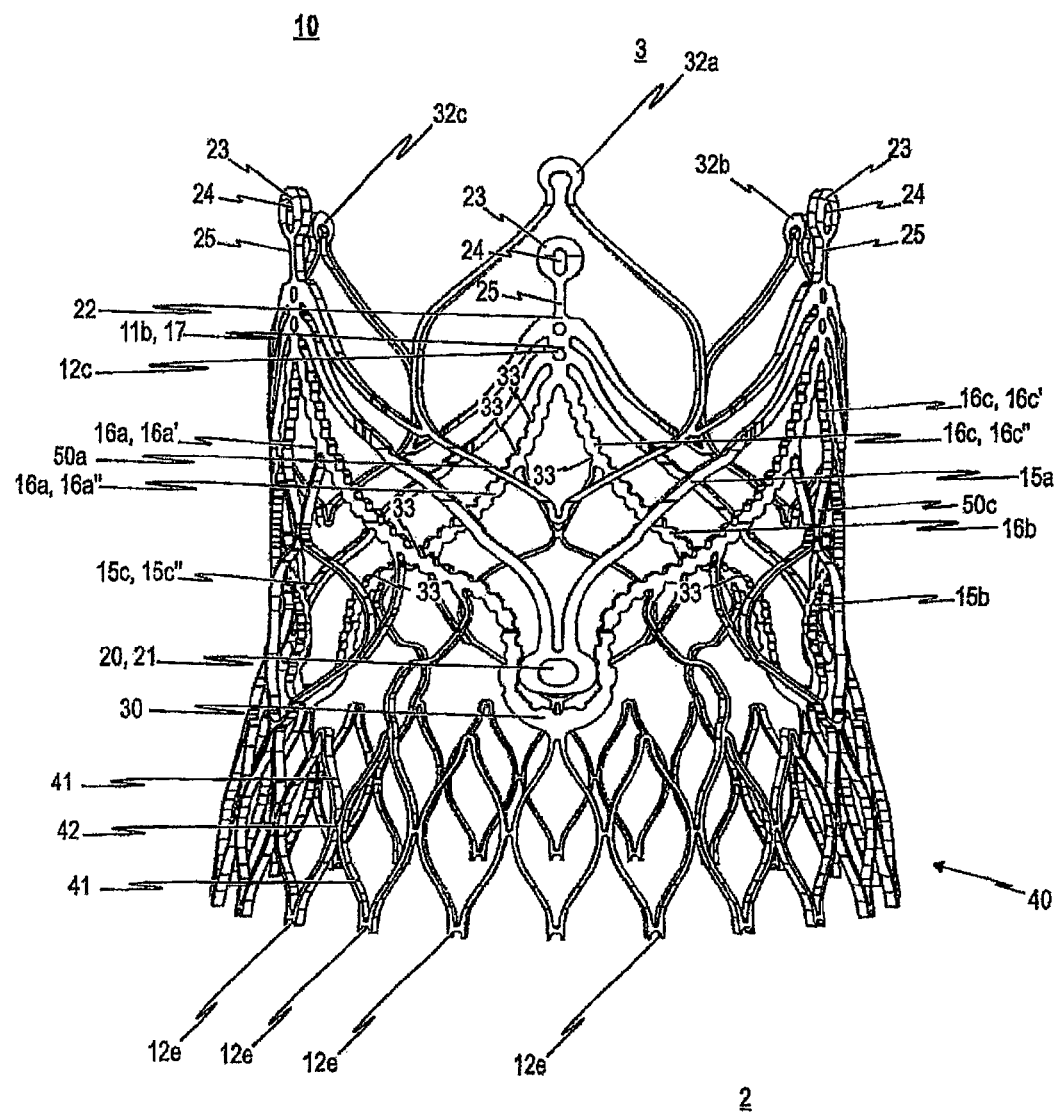
Figure 20D:
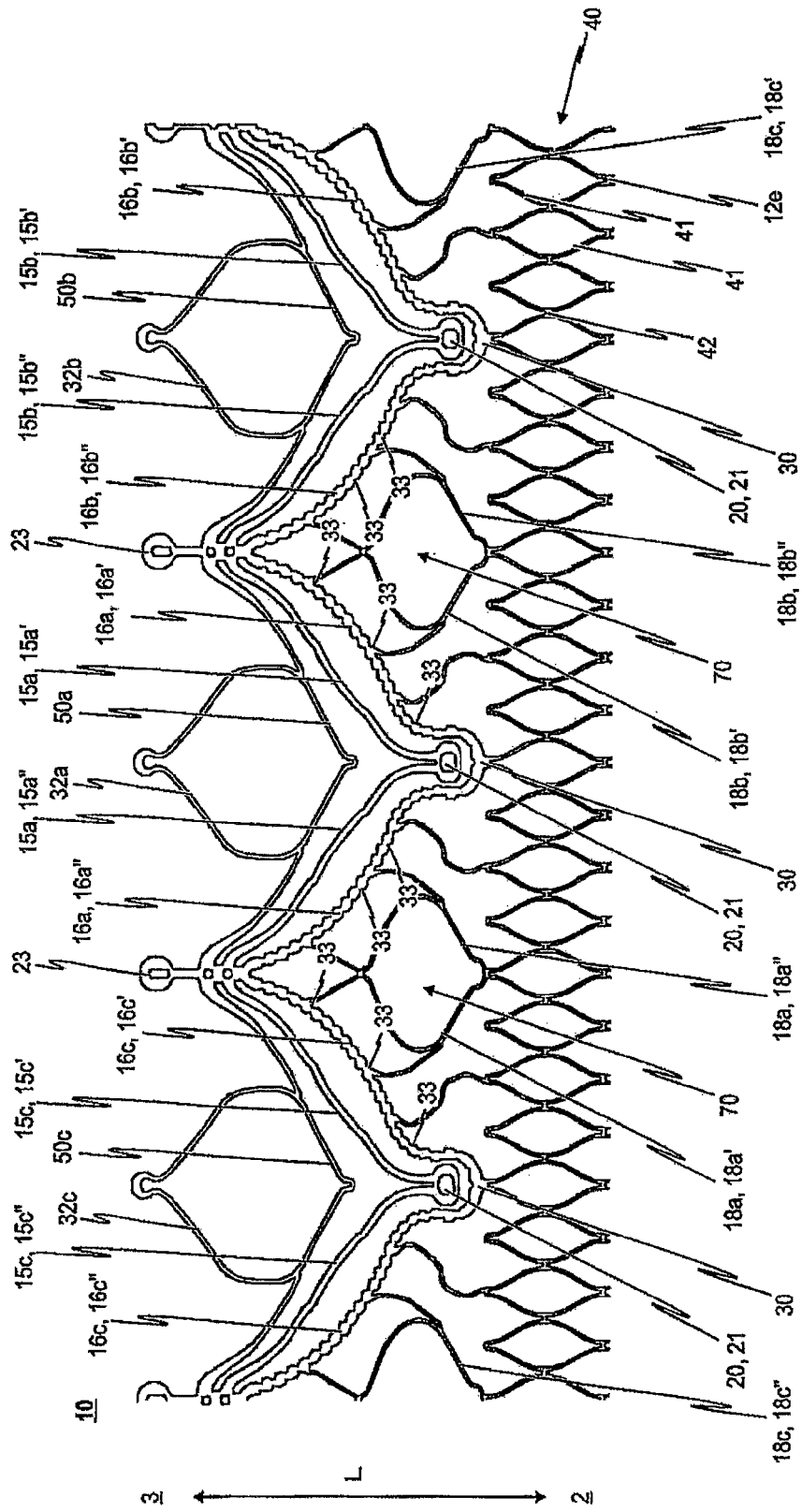
Figure 21:
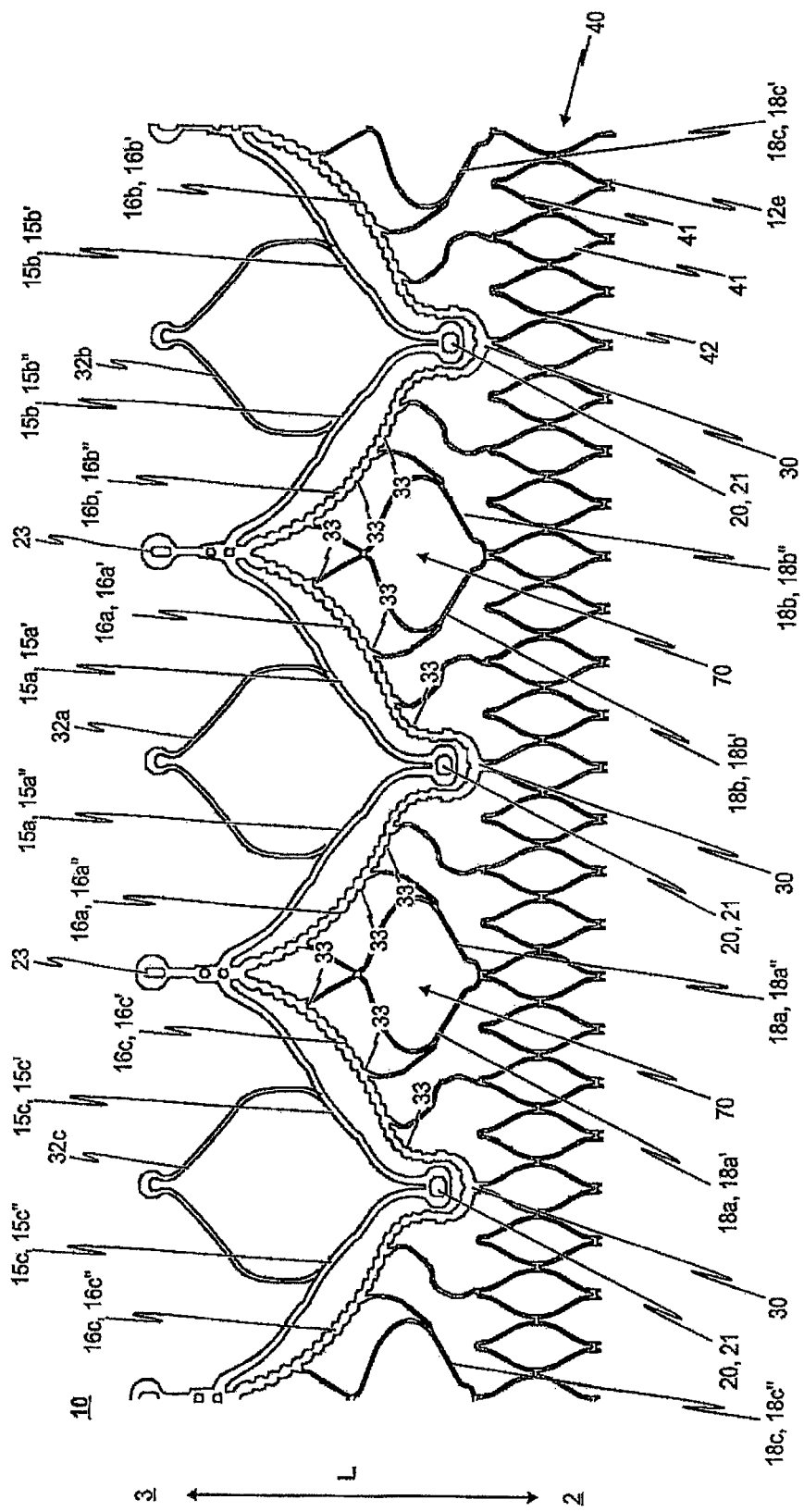
Figure 22:
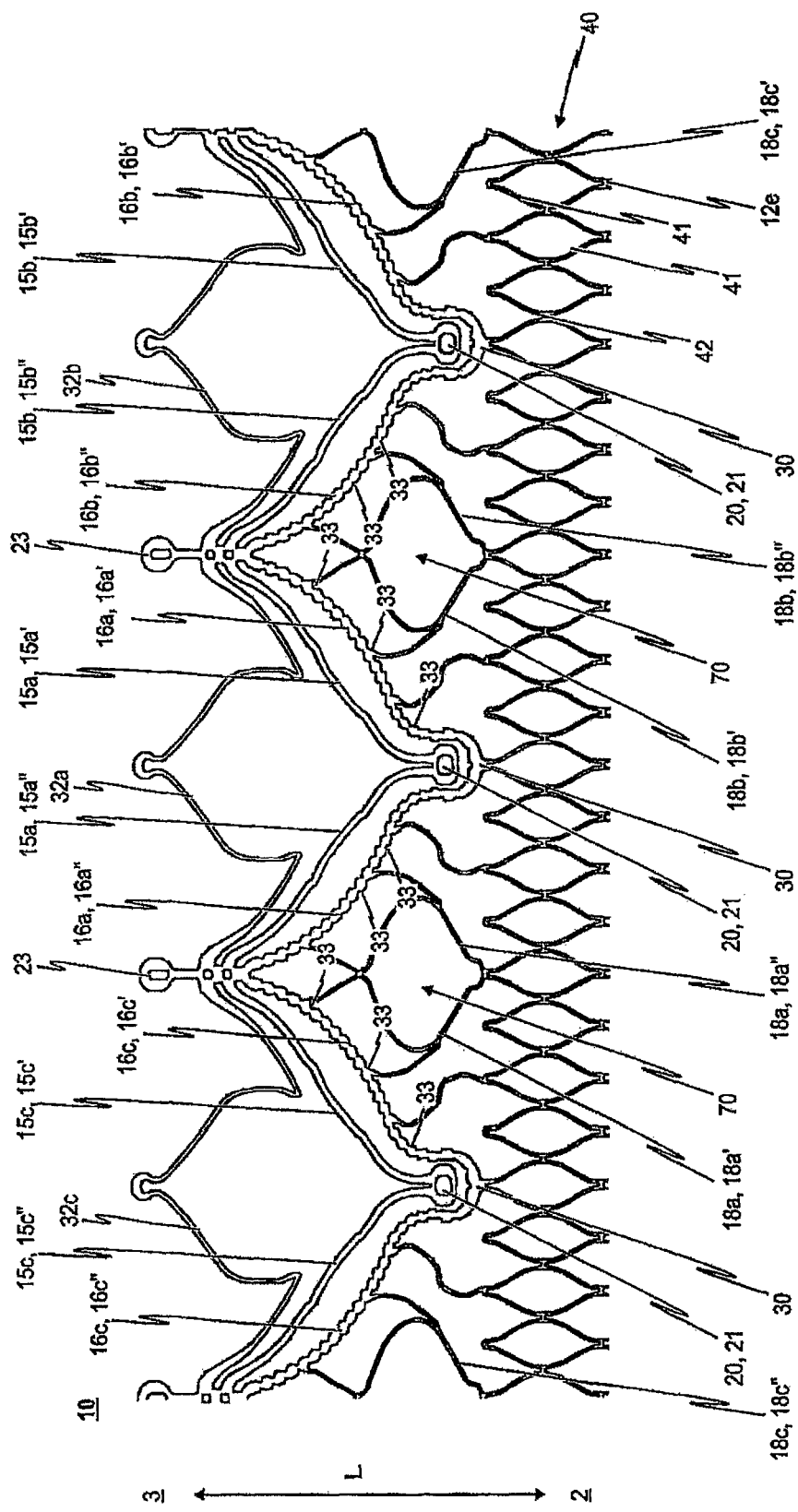

Shown are:

FIG. 1a a side view of a cardiac valve stent capable of supporting and anchoring an endoprosthesis in accordance with a first embodiment of the invention, where the cardiac valve stent is shown in its collapsed state;

FIG. 1b a side view of a cardiac valve stent capable of supporting and anchoring an endoprosthesis in accordance with the first embodiment of the invention, where the cardiac valve stent is shown in its expanded state;

FIG. 1c is a plan view of the lower end of a cardiac valve stent in accordance with the first embodiment of the invention, where the cardiac valve stent is shown in its expanded state;

FIG. 1d a side view of an endoprosthesis for treating a narrowed cardiac valve or a cardiac valve insufficiency, where the endoprosthesis comprises a cardiac valve stent according to the first embodiment of the invention for holding an endoprosthesis;

FIG. 1e a flat roll-out view of a cardiac valve stent according to the first embodiment of the invention;

FIG. 2a a side view of a cardiac valve stent capable of supporting and anchoring an endoprosthesis according to a second embodiment of the invention, where the cardiac valve stent is shown in its collapsed state;

FIG. 2b a first perspective side view of a cardiac valve stent capable of supporting and anchoring an endoprosthesis according to the second embodiment of the invention, whereby the cardiac valve stent is shown in its expanded state;

FIG. 2c a second perspective side view of a cardiac valve stent capable of supporting and anchoring an endoprosthesis according to the second embodiment of the invention, where the cardiac valve stent is shown in its expanded state;

FIG. 2d a perspective side view of an endoprosthesis for treating a narrowed cardiac valve or a cardiac valve insufficiency, where the endoprosthesis comprises a cardiac valve stent according to the second embodiment of the invention for holding an endoprosthesis;

FIG. 2e a flat roll-out view of a cardiac valve stent according to the second embodiment of the invention;

FIG. 3 a flat roll-out view of a cardiac valve stent according to the third embodiment of the invention;

FIG. 4 a flat roll-out view of a cardiac valve stent according to the fourth embodiment of the invention;

FIG. 5a a first perspective side view of a cardiac valve stent capable of supporting and anchoring an endoprosthesis according to the fifth embodiment of the invention, whereby the cardiac valve stent is shown in its expanded state;

FIG. 5b a second perspective side view of a cardiac valve stent capable of supporting and anchoring an endoprosthesis according to the fifth embodiment of the invention, whereby the cardiac valve stent is shown in its expanded state;

FIG. 5c a plan view of the upper end of a cardiac valve stent capable of supporting and anchoring an endoprosthesis according to the fifth embodiment of the invention, whereby the cardiac valve stent is shown in its expanded state;

FIG. 5d a flat roll-out view of a cardiac valve stent according to the fifth embodiment of the invention;

FIG. 6a a first perspective side view of a cardiac valve stent capable of supporting and anchoring an endoprosthesis according to the sixth embodiment of the invention, whereby the cardiac valve stent is shown in its expanded state;

FIG. 6b a second perspective side view of a cardiac valve stent capable of supporting and anchoring an endoprosthesis according to the sixth embodiment of the invention, whereby the cardiac valve stent is shown in its expanded state;

FIG. 6c a third perspective side view of a cardiac valve stent capable of supporting and anchoring an endoprosthesis according to the sixth embodiment of the invention, whereby the cardiac valve stent is shown in its expanded state;

FIG. 6d a flat roll-out view of a cardiac valve stent according to the sixth embodiment of the invention;

FIG. 6e a perspective side view of an endoprosthesis for treating a narrowed cardiac valve or a cardiac valve insufficiency, where the endoprosthesis comprises a cardiac valve stent according to an embodiment of the invention for holding an endoprosthesis, whereby the cardiac valve stent is shown in a partly expanded state;

FIG. 6f a perspective side view of an endoprosthesis for treating a narrowed cardiac valve or a cardiac valve insufficiency, where the endoprosthesis comprises a cardiac valve stent according to the sixth embodiment of the invention for holding an endoprosthesis, whereby the cardiac valve stent is shown in an expanded state;

FIG. 6g a perspective detail view of the head portion of a retaining arch belonging to the cardiac valve stent of the endoprosthesis shown in FIG. 6f;

FIG. 6h a perspective detail view of an additional fastening portion belonging to the cardiac valve stent of the endoprosthesis shown in FIG. 6f;

FIG. 6i a plan view of the lower end of the endoprosthesis shown in FIG. 6f, i.e. a view from the inflow side of the endoprosthesis shown in FIG. 6f;

FIG. 7a a flat roll-out view of a cardiac valve stent according to the seventh embodiment of the invention;

FIG. 7b a first side view of a cardiac valve stent capable of supporting and anchoring an endoprosthesis according to the seventh embodiment of the invention, whereby the cardiac valve stent is shown in its expanded state;

FIG. 7c a second perspective side view of a cardiac valve stent capable of supporting and anchoring an endoprosthesis according to the seventh embodiment of the invention, whereby the cardiac valve stent is shown in its expanded state;

FIG. 8a a flat roll-out view of a cardiac valve stent according to the eighth embodiment of the invention;

FIG. 8b a first perspective side view of a cardiac valve stent capable of supporting and anchoring an endoprosthesis according to the eighth embodiment of the invention, whereby the cardiac valve stent is shown in its expanded state;

FIG. 8c a second perspective side view of a cardiac valve stent capable of supporting and anchoring an endoprosthesis according to the eighth embodiment of the invention, whereby the cardiac valve stent is shown in its expanded state;

FIG. 9a a flat roll-out view of a cardiac valve stent according to the ninth embodiment of the invention;

FIG. 9b a perspective side view of a cardiac valve stent capable of supporting and anchoring an endoprosthesis according to the ninth embodiment of the invention, whereby the cardiac valve stent is shown in its expanded state;

FIG. 10 a flat roll-out view of a cardiac valve stent according to the tenth embodiment of the invention;

FIG. 11 a flat roll-out view of a cardiac valve stent according to the eleventh embodiment of the invention;

FIG. 12 a flat roll-out view of a cardiac valve stent according to the twelfth embodiment of the invention;

FIG. 13a a flat roll-out view of a cardiac valve stent according to the thirteenth embodiment of the invention;

FIG. 13b a first perspective side view of a cardiac valve stent capable of supporting and anchoring an endoprosthesis according to the thirteenth embodiment of the invention, whereby the cardiac valve stent is shown in its expanded state;

FIG. 13c a second perspective side view of a cardiac valve stent capable of supporting and anchoring an endoprosthesis according to the thirteenth embodiment of the invention, whereby the cardiac valve stent is shown in its expanded state;

FIG. 14a a flat roll-out view of a cardiac valve stent according to the fourteenth embodiment of the invention;

FIG. 14b a perspective side view of a cardiac valve stent capable of supporting and anchoring an endoprosthesis according to the fourteenth embodiment of the invention, whereby the cardiac valve stent is shown in its expanded state;

FIG. 15 a flat roll-out view of a cardiac valve stent according to the fifteenth embodiment of the invention;

FIG. 16a a flat roll-out view of a cardiac valve stent according to the sixteenth embodiment of the invention;

FIG. 16b a first perspective side view of a cardiac valve stent capable of supporting and anchoring an endoprosthesis according to the sixteenth embodiment of the invention, whereby the cardiac valve stent is shown in its expanded state;

FIG. 16c a second perspective side view of a cardiac valve stent capable of supporting and anchoring an endoprosthesis according to the sixteenth embodiment of the invention, whereby the cardiac valve stent is shown in its expanded state;

FIG. 16d a third perspective side view of a cardiac valve stent capable of supporting and anchoring an endoprosthesis according to the sixteenth embodiment of the invention, whereby the cardiac valve stent is shown in its expanded state;

FIG. 16e a plan view of the upper end of a cardiac valve stent capable of supporting and anchoring an endoprosthesis according to the sixteenth embodiment of the invention, whereby the cardiac valve stent is shown in its expanded state;

FIG. 16f a first perspective side view of an endoprosthesis for treating a narrowed cardiac valve or a cardiac valve insufficiency, where the endoprosthesis comprises a cardiac valve stent according to the sixteenth embodiment of the invention for holding an endoprosthesis, whereby the cardiac valve stent is shown in an expanded state;

FIG. 16g a second perspective side view of an endoprosthesis for treating a narrowed cardiac valve or a cardiac valve insufficiency, where the endoprosthesis comprises a cardiac valve stent according to the sixteenth embodiment of the invention for holding an endoprosthesis, whereby the cardiac valve stent is shown in an expanded state;

FIG. 17a a flat roll-out view of a cardiac valve stent according to the seventeenth embodiment of the invention;

FIG. 17b a first perspective side view of a cardiac valve stent capable of supporting and anchoring an endoprosthesis according to the seventeenth embodiment of the invention, whereby the cardiac valve stent is shown in its expanded state;

FIG. 17c a second perspective side view of a cardiac valve stent capable of supporting and anchoring an endoprosthesis according to the seventeenth embodiment of the invention, whereby the cardiac valve stent is shown in its expanded state;

FIG. 17d a third perspective side view of a cardiac valve stent capable of supporting and anchoring an endoprosthesis according to the seventeenth embodiment of the invention, whereby the cardiac valve stent is shown in its expanded state;

FIG. 17e a plan view of the upper end of a cardiac valve stent capable of supporting and anchoring an endoprosthesis according to the seventeenth embodiment of the invention, whereby the cardiac valve stent is shown in its expanded state;

FIG. 18a-c a process sequence illustrating a transarterial implantation of an aortic endoprosthesis comprising a cardiac valve stent in accordance with certain embodiments of the invention and a valvular prosthesis affixed to the stent;

FIG. 19a a first perspective side view of a cardiac valve stent capable of supporting and anchoring an endoprosthesis according to the eighteenth embodiment of the invention, whereby the cardiac valve stent is shown in its expanded state;

FIG. 19b a second perspective side view of a cardiac valve stent capable of supporting and anchoring an endoprosthesis according to the eighteenth embodiment of the invention, whereby the cardiac valve stent is shown in its expanded state;

FIG. 20a a flat roll-out view of a cardiac valve stent according to the nineteenth embodiment of the invention, whereby the cardiac valve stent is in its non-expanded state;

FIG. 20b a first perspective side view of a cardiac valve stent capable of supporting and anchoring an endoprosthesis according to the nineteenth embodiment of the invention, whereby the cardiac valve stent is shown in its expanded state;

FIG. 20c a second perspective side view of a cardiac valve stent capable of supporting and anchoring an endoprosthesis according to the nineteenth embodiment of the invention, whereby the cardiac valve stent is shown in its expanded state;

FIG. 20d a flat roll-out view of a cardiac valve stent according to the nineteenth embodiment of the invention, whereby the cardiac valve stent is in its expanded state;

FIG. 21 a flat roll-out view of a cardiac valve stent according to the twentieth embodiment of the invention, whereby the cardiac valve stent is shown in its expanded state; and FIG. 22 a flat roll-out view of a cardiac valve stent according to the twenty-first embodiment of the invention, whereby the cardiac valve stent is shown in its expanded state.

Both the right and left halves of the human heart consist of a ventricle and an atrium. These cavities are separated by the septum of the heart, divided into the atrial septum (septum interatriale) and the ventricular septum (septum interventriculare).

Blood can only flow in one direction through the chambers of the heart due to the cardiac valves situated between the atria and ventricles and in the arteries connected to the ventricles which function like mechanical valves. The superior and inferior vena cava (vena cava superior et inferior) flow into the right atrium. They supply the oxygen-depleted (venous) blood from the systemic circulation to the heart. The tricuspid valve which, like a mechanical valve, prevents a reverse flow of blood into the atrium upon ventricular contraction (systole) is situated between the right atrium and the right ventricle. It comprises three segments, also called leaflets, which are affixed like flaps to the ventricular musculature by ligaments (hence also called the "flap valve"). The two pulmonary arteries depart the right ventricle of the heart via a common trunk (truncus pulmonalis). There is also a valve between the ventricle and the pulmonary trunk, the so-called, pulmonary valve. This type of valve is also called a semilunar valve due to its shape. The pulmonary arteries supply the oxygen-depleted blood to the pulmonary circulation.

Oxygen-rich (arterial) blood then usually flows through four pulmonary veins from the pulmonary circulation to the left atrium. From there, it reaches the left ventricle through a further flap valve, the mitral valve. The outflow is carried by the aorta which, like the pulmonary artery, has a semilunar valve (aortic valve).

During a heart cycle, the atria fill first while the ventricles concurrently disgorge the blood into the arteries. When the ventricular musculature relaxes, the flap valve open due to the drop in pressure in the ventricle and the blood flows in from the atria (auricular systole). This is supported by a contraction of the atria. Ventricular contraction follows: the ventricular musculature contracts, the pressure rises, the flap valves close and the blood can now only flow into the arteries through the now-opened semilunar valves. A reverse blood flow from the arteries during the relaxation phase (diastole) is prevented by the closing of the semilunar valves such that the direction of flow is determined solely by the valves.

The four cardiac valves work like mechanical valves in the heart and prevent a reverse flow of blood in the wrong direction. Each half of the heart has a flap valve (atrioventricular valve) and a semilunar valve. The atrioventricular valves are situated between the atrium and the ventricle and are called the bicuspid/mitral valve and the tricuspid valve. The semilunar valves are situated between the ventricle and the vascular outflow and are called the pulmonary valve and the aortic valve respectively.

A valve defect; i.e. a dysfunction of a cardiac valve's function, can affect any of the four cardiac valves, although the valves on the left side of the heart (aortic and mitral valves) are affected considerably more frequently than those on the right side of the heart (pulmonary and tricuspid valves). Dysfunction can encompass constriction (stenosis), insufficiency or a combination of the two (combined vitium).

In medicine, the term "aortic valve insufficiency", or "aortic insufficiency" for short, refers to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output 40 to 70 ml). This results in characteristically high blood pressure amplitude. This regurgitate blood flow increases the diastolic filling of the left chamber and leads to a volume overload of this section of the heart, a consequence of which is eccentric hypertrophy.

Aortic valve stenosis is a valvular heart disease caused by the incomplete opening of the aortic valve. When the aortic valve becomes stenotic, it causes a pressure gradient between the left ventricle and the aorta. The more constricted the valve, the higher the gradient between the left ventricle and the aorta. For instance, with a mild aortic valve stenosis, the gradient may be 20 mmHg. This means that, at peak systole, while the left ventricle may generate a pressure of 140 mmHg, the pressure that is transmitted to the aorta will only be 120 mm Hg.

In individuals with aortic valve stenosis, the left ventricle has to generate an increased pressure in order to overcome the increased after load caused by the stenotic aortic valve and eject blood out of the left ventricle. The more severe the aortic stenosis, the higher the gradient is between the left ventricular systolic pressures and the aortic systolic pressures. Due to the increased pressures generated by the left ventricle, the myocardium (muscle) of the left ventricle undergoes hypertrophy (increase in muscle mass).

Angina in the setting of aortic valve stenosis is secondary to the left ventricular hypertrophy that is caused by the constant production of increased pressure required to overcome the pressure gradient caused by the aortic valve stenosis. While the myocardium (i.e. heart muscle) of the left ventricle gets thicker, the arteries that supply the muscle do not get significantly longer or bigger, so the muscle may become ischemic (i.e. doesn't receive an adequate blood supply). The ischemia may first be evident during exercise, when the heart muscle requires increased blood supply to compensate for the increased workload. The individual may complain of exertional angina. At this stage, a stress test with imaging may be suggestive of ischemia.

Mitral valve insufficiency (also called mitral insufficiency) is a frequent cardiac valve defect in human medicine and also in at least some animal species. It involves a closing defect or "leakage" of the heart's mitral valve which leads to reverse blood flow from the left ventricle into the left atrium during the ejection phase (systole).

The mitral valve functions like a mechanical valve between the left atrium and the left ventricle of the heart. It opens during the filling phase of the ventricle (diastole) and thus enables the inflow of blood from the atrium. At the beginning of the ejection phase (systole), the sudden increase in pressure in the ventricle leads to the closing of the valve and thus to a "sealing" of the atrium. In so doing, a pressure of only about 8 mmHg prevails in the atrium, while at the same time the systolic pressure of about 120 mmHg in the ventricle forces the blood along its usual path into the main artery (aorta).

In cases of severe mitral insufficiency, however, the regurgitation opening is larger than 40 mm$^2$ and the regurgitation volume greater than 60 ml, which can lead to serious and at times life-threatening changes.

In the acute stage, with a normal size to the left ventricle and the left atrium, there is a considerable increase of the pressure in the atrium and thus also in the pulmonary veins. This can be up to 100 mmHg which, given a normal condition to the pulmonary vessels, leads to immediate pulmonary oedema. The then predominantly reverse blood flow can result in insufficient outflow into the aorta and thus decreased blood flow to all the organs.

To treat a severe narrowed cardiac valve or cardiac valve insufficiency, it is necessary for an endoprosthesis to perform the valve function of the narrowed or diseased cardiac valve. Essential in this respect is that the endoprosthesis is securely positioned and anchored in the implantation site in the heart; i.e. in the plane of the (diseased) cardiac valve to be replaced, so that the endoprosthesis is not displaced or shifted despite the, at times considerable, forces acting on it. Also, an effective seal during systole is important for the mitral valve and during diastole for the aortic valve.

The present invention relates to an expandable stent for an endoprosthesis used in the treatment of a stenosis (narrowing) of a cardiac valve and/or a cardiac valve insufficiency. Furthermore, the present invention relates to a collapsible and expandable prosthesis incorporating a stent that can be delivered to the implant site using a catheter for treatment of a stenosis (narrowing) of a cardiac valve and/or a cardiac valve insufficiency. Although the inventive stent and the valvular prosthesis affixed thereto can be used for replacing any of the four different heart valves, in particular the pulmonary valve and the aortic valve, the application of the invention for treatment of a diseased aortic valve is described in the following only for reasons of simplification.

A cardiac valve stent 10, to which the valvular prosthesis 100 is appropriately affixed, is employed in accordance with at least certain embodiments of the invention to position and anchor said endoprosthesis. A medical device for the treating of a narrowed cardiac valve or a cardiac valve insufficiency consisting of a cardiac valve stent 10 and a valvular prosthesis 100 affixed to the stent 10 will be referred to herein simply as endoprosthesis 1.

FIG. 1*d* shows a side view of such an endoprosthesis 1 for treating a narrowed cardiac valve or a cardiac valve insufficiency, whereby the endoprosthesis 1 comprises a cardiac valve stent 10 to hold a valvular prosthesis 100 in accordance with a first embodiment of the invention. FIG. 2*d* likewise shows a side view of a further endoprosthesis 1 for treating a narrowed cardiac valve or a cardiac valve insufficiency, whereby a cardiac valve stent 10 in accordance with a second embodiment of the invention is employed.

The following description will make reference to the drawings to describe preferred embodiments of the present invention in detail. The cardiac valve stent 10 according to certain embodiments of the invention (hereinafter referred to simply as "stent") exhibits an expandable structure which is able to transform from a first predefinable shape in which the stent 10 is in a collapsed state into a second predefinable shape in which the stent 10 is in an expanded state. FIG. 1*a* shows a side view of a stent 10 according to the first embodiment of the invention, whereby the stent 10 is in its collapsed state. FIG. 2*a* shows the collapsed stent 10 according to a second embodiment of the invention.

In the two embodiments, the stent 10 together with a valvular prosthesis affixed thereon is introduced in a minimally-invasive fashion into the body of a patient in its first shape (cf. FIG. 1*a* and FIG. 2*a*) using an insertion catheter system (not explicitly shown in the drawings). During insertion, a valvular prosthesis 100 affixed to the stent 10 is likewise in a collapsed state. For the sake of clarity, however, both FIGS. 1*a* and 2*a* dispense with a representation of the valvular prosthesis 100 affixed to the stent 10.

Upon reaching the site of implantation in the patient's heart, the stent 10 transforms, through increments, into its expanded shape in which also the valvular prosthesis 100 affixed to the stent 10 also unfolds and expands. The expanded shape of the stent 10 is a permanent shape that has been set by programming. The completely expanded stent 10 according to the first/second embodiment of the invention with the likewise completely unfolded and expanded valvular prosthesis 100 affixed thereto is shown in FIG. 1*d* and FIG. 2*d*. It is important to note that the second shape of the stent 10, i.e. the shape of the stent 10 in its fully expanded but not-implanted state, may differ from the shape of the stent 10 in its fully expanded and implanted state, because, in the implanted state, the shape of the fully expanded stent 10 is at least partly limited by the anatomy at the implantation site.

FIG. 1b and FIG. 1c show the completely expanded stent 10 according to the first embodiment of the invention from different perspectives without the valvular prosthesis 100. FIGS. 2b and 2c show the completely expanded stent 10 according to the second embodiment of the invention, likewise without the valvular prosthesis 100, from different perspectives.

The following will initially make reference to FIGS. 1a to 1e in describing the first embodiment of the stent 10.

The stent 10 according to the first embodiment exhibits a structure integrally cut from a portion of tube, in particular a metal tube. The cutting pattern used to form the design of the stent is depicted in a two-dimensional projection in FIG. 1e.

In detail, the stent 10 has three positioning arches 15a, 15b, 15c which assume the function of self-positioning the stent into the plane of the pulmonary valve (valva trunci pulmonalis) or aortic valve (valva aortae). The positioning arches 15a, 15b, 15c exhibit a rounded head portion 20 which engages in the pockets T of the (diseased) cardiac valve to be treated during positioning of the stent 10 at the site of implantation in the heart (cf. FIG. 18a).

As well as providing a symmetry that matches that of the native valve, the provision of three positioning arches 15a, 15b, 15c also provides rotational accuracy, symmetry and stability. The stent 10 is of course not limited to the use of a total of three positioning arches.

The head portions 20 of the positioning arches 15a, 15b, 15c, respectively pointing towards the lower end 2 of the stent 10, are rounded so that the vascular wall will not be damaged when the positioning arches 15a, 15b, 15c engage in the pockets T of the cardiac valve H to be replaced. To improve movement and position analysis during the implanting of the stent 10 reference markers 21 are provided on or within the head portions 20 of the positioning arches 15a, 15b, 15c. Radio opaque markers or markers which can be activated by infrared or ultrasound lend themselves particularly well hereto.

The positioning arches 15a, 15b, 15c respectively exhibit an essentially U-shaped or V-shaped structure which is closed to the lower end of stent 10. Accordingly, each positioning arch 15a, 15b, 15c has a total of two arms 15a', 15a", 15b', 15b", 15c', 15c" respectively extending from the head portion 20 of the associated positioning arch 15a, 15b, 15c towards the upper end 3 of stent 10. By doing so, each two adjoining arms of two neighbouring positioning arches are connected to one another via a connecting portion 22.

For implanting and explanting the stent 10 together with a valvular prosthesis affixed thereto with a suitable catheter system, the stent 10 comprises catheter retaining means 23 at its upper end 3. The connecting portions 22 are respectively connected to catheter retaining means. 23 via a connecting web 25. The connecting webs 25 will hereinafter be referred to as "second connecting web 25".

The catheter retaining means 23 comprise oval-shaped heads which each comprise a corresponding oval-shaped eyelet 24. The shape of the catheter retaining means 23 complements a crown on the tip of a catheter of a catheter system used to implant/explant stent 10. The crown on the catheter tip has protruding elements that are configured as a negative of the catheter retaining means 23. Alternatively, the protruding elements are shaped to be complementary to the eyelets 24 and are configured as catheter retaining heads.

This realization enables the protruding elements of the crown to form a releasable engagement with the upper area 3 of stent 10 to allow releasable attachment of the stent 10 to the tip of the catheter.

A first connecting web 17 extends essentially in the longitudinal direction L of stent 10 and has an upper end portion 17d and a lower end portion 17p. The upper end portion 17d opens into connecting portion 22 between the two arms 15a', 15a", 15b', 15b", 15c', 15c" of two neighboring positioning arches 15a, 15b, 15c, in addition to the previously-mentioned second connecting web 25. As can be seen in FIG. 1b, the first connecting webs 17 have an essentially inverted Y-shaped configuration and each exhibit a structure that diverges at its lower end portion 17p to give way to the respective arms 16a', 16a", 16b', 16b", 16c', 16c" of two neighboring retaining arches 16a, 16b, 16c.

In between each positioning arch 15 and retaining arch 16 is a fastening arch 19. As is shown particularly clearly in FIG. 1b, the fastening arch extends from the lower end of fastening portion 11 and has a substantially U-shaped or V-shaped structure which is closed to the lower end of stent 10. As is shown in FIG. 1d, the fastening arches serve to support the lower end of valve prosthesis 100. The prosthesis 100 is shaped so that fastening arches 19a, 19b and 19c are located in pockets of the valve material.

This stent design achieves an axially symmetrical structure, whereby each positioning arch 15a, 15b, 15c is allocated one fastening arch 19a, 19b, 19c and one retaining arch 16a, 16b, 16c. The stent 10 of the first embodiment depicted in FIGS. 1a to 1d thus comprises a total of three retaining arches 16a, 16b, 16c which constitutes a retaining segment of stent 10 for accommodating a valvular prosthesis 100 as depicted for example in FIG. 1d.

In the state of the stent 10 shown in FIG. 1a, in which stent 10 is in its first (collapsed) shape, the respective arms 15a', 15a", 15b', 15b", 15c', 15c" of the positioning arches 15a, 15b, 15c directly adjoin the respective arms 19a', 19a", 19b', 19b", 19c', 10c" of the fastening arches 19a, 19b, 19c which, in turn, directly adjoin the respective arms 16a', 16a", 16b', 16b", 16c', 16c" of the associated retaining arches 16a, 16b, 16c.

Reference is made to FIG. 1b, in which the stent 10 pursuant to the first embodiment is shown in its second, expanded shape. It can be particularly recognized from this representation that each positioning arch 15a, 15b, 15c and associated fastening arch 19a, 19b, 19c and retaining arch 16a, 16b, 16c respectively exhibit an essentially U-shaped or V-shaped structure which is closed towards the lower end 2 of the stent 10. Specifically, each positioning arch 15a, 15b, 15c is cut from a material section of a portion of a tube from which the essentially U-shaped or V-shaped structure of the associated fastening arch 19a, 19b, 19c was taken, as can be seen from the cutting pattern depicted in FIG. 1e.

A comparison of FIG. 1a to FIG. 1b shows that, upon the stent 10 expanding; i.e. when the stent 10 transforms from its first shape into its second shape, the stent 10 shortens in the longitudinal direction L while simultaneously enlarging in cross-section. In the expanded state of stent 10, the positioning arches 15a, 15b, 15c are expanded more in the radial direction at the lower end 2 of the stent 10 compared to the upper end 3 of stent 10. Since they protrude more in the radial direction, the positioning arches 15a, 15b, 15c can be deployed into the cardiac valve pockets T of the cardiac valve H to be replaced in a particularly easy manner.

Even when a certain anchoring of the stent 10 together with a valvular prosthesis affixed thereto is achieved at the site of implantation in the heart due to the positioning arches 15a, 15b, 15c already protruding radially from stent 10 in the expanded state of the stent 10, it is noted that the contact force acting on the vascular wall from the positioning arches 15a, 15b, 15c is insufficient to securely anchor the stent 10 at the site of implantation. The previously-mentioned retaining arches 16a, 16b, 16c, which form the lower end 2 of stent 10, are provided for this reason. The retaining arches 16a, 16b, 16c protrude radially from the circumference of the stent 10 in its expanded state such that the retaining arches 16a, 16b, 16c press against the wall of the blood vessel in which the stent is deployed with a radially-acting contact force. In addition, the closed ends of the retaining arches 16a, 16b, 16c flare outwards, protruding radially still further from the circumference of the stent 10. This shape allows the ends of the retaining arches 16a, 16b, 16c to be positioned below the native valve annulus or to be positioned at least on the native valve annulus, thereby providing additional anchoring for the stent 10 together with a valvular prosthesis affixed thereto.

In addition to retaining arches 16a, 16b, 16c, the stent 10 further comprises auxiliary arches 18a, 18b, 18c, which likewise exert a radially-acting contact force against the wall of the blood vessel in the implanted state of stent 10, thereby further improving anchoring of stent 10 and a valvular prosthesis affixed thereto at the site of implantation.

As can be seen from FIG. 1b, stent 10 comprises a total of three essentially U-shaped or V-shaped auxiliary arches 18a, 18b, 18c which are closed towards the lower end 2 of said stent 10. Each auxiliary arch 18a, 18b, 18c connects a first retaining arch 16a, 16b, 16c with a second retaining arch neighboring the first retaining arch.

In a top plan view of the lower end region 2 of the expanded stent 10 (cf. FIG. 1c), the lower end region 2 exhibits a dodecagonal polygonal structure formed from the individual arms 16a', 16a", 16b', 16b", 16c', 16c" of retaining arches 16a, 16b, 16c and the individual arms 18a', 18a", 18b', 18b", 18c', 18c" of the auxiliary arches 18a, 18b, 18c. This stent design particularly provides a total of six arches 16a, 16b, 16c, 18a, 18b, 18c uniformly distributed around the lower end region 2 of stent 10, each of which press against the vascular wall and effectively hold the stent 10 in position in the expanded and implanted state of stent 10 together with a valvular prosthesis affixed thereto.

To recapitulate, providing retaining arches 16a, 16b, 16c on the one hand and auxiliary arches 18a, 18b, 18c on the other results in a radial force being exerted on the vascular wall by the respective lower end portions of these arches. This ensures both a secure seal of a valvular prosthesis 100 affixed to stent 10 relative the vascular wall, as well as a secure anchoring of the stent 10, at the site of implantation in the heart.

In addition to the contact force exerted on the vascular wall by way of the retaining arches 16a, 16b, 16c and auxiliary arches 18a, 18b, 18c, it is conceivable for the upper end region 3 of stent 10 to expand radially 10% to 25% more—in the fully expanded but not implanted state of stent 10—compared to the lower end region 2. This gives the stent 10 a slight concave structure which tapers towards the lower end region 2. However, in its fully expanded and implanted state, the upper end section 3 of the stent 10 may not be expanded radially 10% to 25% more compared to the lower end region 2 because the shape of the stent in its implanted state is limited by the anatomy in the implantation side. However, the upper end section 3 of the stent 10 tends to spread radially somewhat relative to the annular diameter of the constrained lower end section 2 of the stent 10. This ensures secure anchoring of the stent 10 within the vessel by the upper end region 2 of the stent 10 pressing against the vascular wall.

To ensure that minimal longitudinal displacement of a valvular prosthesis affixed to stent 10 can occur relative stent 10, even during the peristaltic movement of the heart and the blood vessel in which stent 10 together with a valvular prosthesis affixed thereto is deployed, the embodiment of the inventive stent 10 depicted in the drawings provides for the stent 10 to comprise a plurality of fastening portions 11 extending in the longitudinal direction L of stent 10, by means of which the tissue component(s) of a valvular prosthesis 100 is affixed to the stent 10. Reference is made to FIG. 1d which shows a side view of an endoprosthesis 1 for treating a narrowed cardiac valve or a cardiac valve insufficiency. The endoprosthesis 1 comprises the stent 10 pursuant the first embodiment of the invention holding a valvular prosthesis 100. The valvular prosthesis 100 comprises at least one leaflet 102 made from a biological or synthetic material.

It will be appreciated that the valvular prosthesis may be made from any suitable material, including biological valves removed from animals such as pigs and horses, man-made biological valves created from connective tissue such as pericardium, tissue grown from cell cultures, and man-made materials and fabrics such as nitinol.

In detail, the first connecting webs 17 of stent 10 connect with connecting portions 22 via their upper ends 17d and with the upper ends 13 of fastening portions 11 via their lower ends 17p. The respective lower ends 14 of the fastening portions which are connected to one and the same connecting web 17 are thereby connected together via an essentially U-shaped or V-shaped auxiliary arch 18a, 18b, 18c which is closed towards the lower end 2 of stent 10.

Specifically, the first embodiment of the inventive stent 10 is shown in FIG. 1d in its expanded state, whereby a valvular prosthesis 100 is fastened to said stent 10 by means of a thread 101 or a thin wire and stretched by the stent 10. It is easily recognized that the widening of the centre area and the lower end region 2 of stent 10 at which the valvular prosthesis 100 is disposed achieves spreading of the endoprosthesis. At the same time, the lower end portions of the retaining arches 16a, 16b, 16c and the auxiliary arches 18a, 18b, 18c exert a radial force on the (not shown in FIG. 1d) vascular wall.

As can be seen from FIG. 1d, a defined plurality of fastening holes 12 are configured in the respective fastening portions 11 of stent 10, and are arranged to be distributed at predefined longitudinal positions along the fastening portions 11. The thread 101 or thin wire with which the tissue component(s) of the valvular prosthesis 100 is attached to stent 10 is guided through each respective fastening hole 12.

Both components constituting the endoprosthesis 1, namely the stent 10 and the valvular prosthesis 100, may be connected together prior to the surgical procedure. The so constructed endoprosthesis 1 can be stored in its expanded shape for a long period of time without structural deterioration in the tissue of the valvular prosthesis 100. The endoprosthesis 1 shall be compressed and brought into its collapsed shape directly prior to the surgical procedure. Then, the endoprosthesis 1 is ready for being inserted into a catheter system which is used for implanting the endoprosthesis 1.

It is conceivable of course that both components constituting the endoprosthesis 1, namely the stent 10 and the valvular prosthesis 100, are not connected together until directly prior to the surgical procedure. Then, the stent 10 shall be stored in its second shape; i.e. in the expanded state, and not brought into its first (collapsed) shape until directly prior the surgical procedure.

It can be noted from FIGS. 1b and 1d that the respective fastening portions 11 are configured in the respective arms 16a', 16a", 16b', 16b", 16c', 16c" of retaining arches 16a, 16b, 16c of stent 10. The size of the fastening holes 12 configured in the fastening portions 11 should be adapted to the thickness of the thread 101 or wire used to fasten the tissue component(s) of the valvular prosthesis 100 to the stent 10.

The cross-sectional shape to the fastening holes 12 may also be adapted to the cross-sectional shape of the thread 101 or wire used to fasten the valvular prosthesis 100. This allows fixing of the valvular prosthesis 100 to the stent 10 at a precise predefined position relative to the stent 10. By providing of a plurality of fastening holes 12 to anchor the valvular prosthesis 100 to the stent 10, precise positioning of the valvular prosthesis on stent 10 is achieved.

Because the fastening holes 12 are adapted to the thickness and/or the cross-sectional shape of the thread 101 or wire used to affix the valvular prosthesis 100 to the stent 10, relative movement between the stent 10 and the valvular prosthesis 100 due to the peristaltic motion of the heart can be effectively prevented when the endoprosthesis 1 is implanted. In the fully expanded and implanted state of the endoprosthesis 1, the valvular prosthesis 100 is thus fastened to the stent 10 with minimal play, based on which friction-induced wear of the thread 101 or wire used to affix the valvular prosthesis is minimized. As shown in the figures the fastening holes 12 have a circular cross-sectional shape.

Although the valve tissue, i.e. the tissue component(s) of the valvular prosthesis 100, shall be securely fastened to the stent 10, it is necessary that the valve tissue must be capable of deforming without damage to allow for the stent lengthening when collapsed.

As already mentioned, the fastening holes 12 configured in the respective fastening portions 11 may be of different diameters, numbers or cross-sectional shapes (oval, square, etc.) according to the diameter of a thread 101 used for affixing the tissue component(s) of the valvular prosthesis 100 to the stent 10, and/or according to the sewing technique utilized for affixing the valvular prosthesis 100 to the stent 10. The diameter, number and/or cross-sectional shape of at least one of the fastening holes 12 may also serve as an indication of the type of the endoprosthesis 1, i.e. the medical device used in the treatment of a narrowing of a cardiac valve and/or a cardiac valve insufficiency. In this respect, the diameter, number and/or cross-sectional shape of the at least one fastening hole 12 may be used for identification to differentiate between different sizes or types of valvular prostheses 100 adapted to be fixed on the stent 10, or may be used for identification to differentiate between different sizes or types of endoprostheses 1, if a valvular prosthesis 100 is already fixed to the stent 10. For example, a small-sized stent 10 having a small-sized valvular prosthesis 100 fixed thereto or a small-sized stent 10 adapted and configured for carrying a small-sized valvular prosthesis 100 could have circular fastening holes 12 whilst a large-sized stent 10 having a large-sized valvular prosthesis 100 fixed thereto or a large-sized stent 10 adapted and configured for carrying a large-sized valvular prosthesis 100 may have triangular fastening holes 12. This allows the surgeon/cardio staff to easily and visually tell different valve sizes, stent types and/or types of the valvular prosthesis apart without the need to measure.

In the first embodiment depicted in FIGS. 1a-e, the fastening portions 11 of the stent 10 (onto which the valvular prosthesis 100 is sewn or sewable) do not change their shape when the stent 10 is compressed, e.g. when the stent 10 is in its first (collapsed) shape shown in FIG. 1a. This phenomenon occurs when standard tube stents are used. Thus the risk of thread wear is minimal.

As described in detail with respect to the sixteenth and seventeenth embodiments of the present invention, however, the retaining arches together with the fastening portions provided in the respective arms of the retaining arches may also be configured such that they do change their shape when the stent 10 is compressed. In detail, according to the sixteenth and seventeenth embodiments of the inventive stent design, the retaining arches are curved in the expanded state of the stent, but relatively straight when the stent is collapsed.

A stent 10 in accordance with a second embodiment is depicted in FIGS. 2a to 2c and is similar in structure and function to the first embodiment of the stent 10 depicted in FIGS. 1a to 1c. The same also holds true for the cutting pattern depicted in FIG. 2e which is, in principle, comparable to the cutting pattern according to FIG. 1e. A detailed description of the common features will therefore not be provided.

A difference to be seen is in the configuration of the catheter retaining means 23 provided at the upper end section 3 of stent 10. In contrast to the first embodiment of the inventive stent 10, heads of an essentially round configuration are used as catheter retaining means 23 in the second embodiment, in each case provided with essentially oval eyelets 24. Due to the round configuration of the heads the risk of producing injury or damage is lowered. Hence, an essentially round configuration of the heads is more atraumatic.

As already indicated, the stent 10 according to certain embodiments of the present invention preferably exhibits a structure integrally cut from a portion of tube, and in particular from a metal tube. A fastening arch 19a, 19b, 19c and a retaining arch 16a, 16b, 16c is allocated to each positioning arch 15a, 15b, 15c, and each retaining arch 16a, 16b, 16c is connected to a neighboring retaining arch by means of an auxiliary arch 18a, 18b, 18c. A fastening portion 11 with a specific number of fastening holes 12 is configured in each arm 16a', 16a", 16b', 16b", 16c', 16c" of retaining arch 16a, 16b, 16c.

FIGS. 1e and 2e each show a flat roll-out view of a stent 10 pursuant the first or second embodiment of the invention. These flat roll-out views respectively correspond to two-dimensional projections of a cutting pattern which can be used in the manufacture of the stent 10 pursuant the first or second embodiment of the invention. This enables a one-piece stent 10 to be cut from a portion of tube, in particular a metal tube. It is evident that, on the one hand, the inventive stent 10 dispenses with fixed-body joints or other similar connective devices between the individual components of stent 10 (positioning arch, retaining arch, auxiliary arch). On the other hand, a stent 10 is provided which exhibits, with minimum longitudinal extension, the functionality of positionability as provided by the positioning arches 15a, 15b, 15c on the one hand and, on the other, the functionality of the defined fastening of a valvular prosthesis 100, as provided by the fastening portions 11 configured in the respective arms 16a', 16a", 16b', 16b", 16c', 16c" of the retaining arch 16a, 16b, 16c.

In addition to its retaining arches 16a, 16b, 16c, the stent 10 further comprises auxiliary arches 18a, 18b, 18c which enable a particularly secure anchoring of stent 10 in the site of implantation in the heart.

A stent 10 according to a third embodiment of the invention also has a one-piece structure cut from a portion of a tube, in particular from a metal tube. The cutting pattern used to form the stent design is shown in a two-dimensional projection in FIG. 3.

The differences between the third embodiment of the stent and the first or second embodiments can be seen by referring to the two-dimensional cutting pattern shown in FIG. 3. As is also the case in the first or second embodiment, the third embodiment of the stent 10 has a total of three positioning arches 15a, 15b, 15c, which undertake the function of automatic positioning of the cardiac valve stent in the plane of the pulmonary valve or the aortic valve.

The stent 10 is made from Nitinol and positioning arches 15a, 15b, 15c are programmed during manufacture, by a suitable heat treatment of the positioning arches 15a, 15b, 15c, so that, in the stent's expanded state, i.e. when the permanent shape has been assumed after exceeding the switching temperature, the positioning arches not only spread apart in a radial direction, as illustrated in FIGS. 1b, 1d and 2b, 2d, but simultaneously curve in a slightly convex manner in the direction of the stent 10. This measure makes it possible for the head portions 20 of the positioning arches 15a, 15b, 15c to lie parallel with the longitudinal axis L of the expanded stent 10 in an ideal manner. As a result, during the Implantation of the cardiac valve stent 10, the head portions 20 of the positioning arches 15a, 15b, 15c can be inserted particularly easily into the pockets T of the native heart valve H (see FIG. 18a). In particular, this minimizes damage to surrounding tissue when the positioning arches 15a, 15b, 15c are inserted into the pockets T of the native heart valve H. The shape also allows the positioning arches 15a, 15b, 15c to exert an additional clipping force on the native valve leaflets by pinching the native leaflet at the bottom of each arch.

In addition, the convex curvature of the positioning arches 15a, 15b, 15c enables an especially secure support of the stent 10 at the implantation site since the positioning arches 15a, 15b, 15c are better adapted to the anatomy of the pockets T of the native heart valves H and their surroundings.

As in a stent 10 according to the first and second embodiment (see for example FIGS. 1b, 1c, 1d and 2b, 2c, 2d), a stent 10 of the third embodiment, has catheter retaining means 23 with eyelets 24. As with previously described embodiments, a suitable catheter system can be releasably coupled to the catheter retaining means 23 to facilitate a minimally-invasive, transvascular implantation and explantation of the stent 10.

As with the stent 10 of the first or second embodiment, the retaining arches 16a, 16b, 16c and auxiliary arches 18a, 18b, 18c serve to secure radial fixing of the stent 10 at the implantation site and for stretching a valvular prosthesis fastened to the stent by way of fastening arches 19a, 19b, 19c. No further discussion is needed to explain that the retaining arches 16a, 16b, 16c and the auxiliary arches 18a, 18b, 18c of this embodiment of the stent also function to seal an implanted valvular prosthesis. Similarly, the retaining arches 16a, 16b, 16c and positioning arches 15a, 15b, 15c clamp the native heart valve H like a paperclip and consequently contribute to the secure anchoring of the stent 10 at the implantation site in the heart.

Stent 10 according to the third embodiment differs from the first and second embodiments in that the respective arms 16a', 16a", 16b', 16b", 16c', 16c" of each retaining arch 16a, 16b, 16c extend from the fastening portion 11 to the lower end 2 of the cardiac valve stent and are connected together by means of a connecting portion 30. The connecting portion 30 has a different shape when compared with the U-shaped or V-shaped connecting portions 30 in the embodiments according to FIGS. 1b, 1c, 1d and 2b, 2c, 2d. In particular, the connecting portion 20 has a waist just above the corresponding connecting portion 30' of the fastening arch. The waists in the retaining and fastening arches accommodate an enlarged head 31 at the lower end of each auxiliary arch 18a, 18b, 18c.

Looking at FIG. 3 in detail, each connecting portion 30 which connects the two arms 16a', 16a", 16b', 16b", 16c', 16c" of a retaining arch 16a, 16b, 16c has almost an O-shaped configuration. This shape offers more space for fastening a valvular prosthesis 100 to the stent 10 and also effectively counteracts the occurrence of load peaks which can occur in the implanted state of the endoprosthesis during the transmission of loads between the valvular prosthesis and the stent.

The alternative shape of the connecting portion 30 further increases the effective contact area between the lower end of the retaining arch 16a, 16b, 16c and the vessel wall, when the stent is positioned at the implantation site in its expanded state. Because of this, an improved seal can be obtained between the stent with the valvular prosthesis attached to it and the vessel wall. Furthermore, the radial forces acting in the expanded state of the stent, which are transmitted via the retaining arches 16a, 16b, 16c to the vessel wall, are distributed over a discrete contact area, thereby counteracting the occurrence of load peaks. The risk of damage from the retaining arches 16a, 16b, 16c to the vessel wall is also reduced.

Each connecting portion 30' which connects the two arms 19a', 19a", 19b', 19b", 19c', 19c" of a fastening arch 19a, 19b, 19c has a more angular shape that assists with anchoring of a valvular prosthesis 100 to the stent 10.

The alternative shapes of the closed ends of the retaining and fastening arches (16, 19), accommodates the enlarged heads 31 of shortened auxiliary arches 18a, 18b, 18c. The enlarged head 31 enables the auxiliary arches to be used to support the valve material 100, as well as providing additional radial force. The heads 31 include fastening holes 12 for additional attachment of the prosthetic valve 100 which further stabilizes the prosthetic valve 100 attached to the stent. The additional fastening holes 12 also reduce the likelihood of miss-aligning the valve 100 within the stent 10 and minimize any longitudinal movement of the valve 100 once the endoprosthesis 1 has been implanted. In addition and as already discussed in relation to the retaining arches 16a, 16b, 16c, an enlarged contact area is provided with the widened head portions 31, which improves the anchorage of the stent 10 at the implantation site while minimizing the risk of damage to the vessel wall.

As can be seen from the cutting pattern of FIG. 3, the upper arm portions of the respective retaining arches 16a, 16b, 16c are connected to the lower region 14 of the associated fastening portion 11, while the upper arm portions of the auxiliary arches 18a, 18b, 18c are connected to the central region of the associated fastening portion 11. In this way, it is possible to form secure connections between the arms 16a', 16a", 16b', 16b", 16c', 16c" of the retaining arches 16a, 16b, 16c, and between the arms 18a', 18a", 18b', 18*b*", 18*c*', 18*c*" of the auxiliary arches 18*a*, 18*b*, 18*c* and the fastening portion 11 without having to enlarge the overall size of the stent 10.

A yet further difference between the stent of the third embodiment and the stents of the first and second embodiments is the inclusion of notches 26. As shown in FIG. 3, the notches 26 are located at the lower end of the fastening portion 11 and are formed in the arms of the auxiliary arches 18*a*, 18*b*, 18*c* and the retaining arches 16*a*, 16*b*, 16*c*. To ensure the strength of the stent is maintained, the notches are shaped in the arms rather than being cut out of the arms. The notches 26 function as additional guides and anchoring points for suture thread or wire.

To accommodate the notches 26, the auxiliary arches 18*a*, 18*b*, 18*c* extend from the fastening portion 11 mid-way along the length of the fastening portion 11, rather than from the lower end of the fastening portion 11. This provides each auxiliary arch 18*a*, 18*b*, 18*c* with sufficient flexibility that would otherwise be lacking from a shorter auxiliary arch.

FIG. 4 shows flat roll-out view of a stent 10 according to a fourth embodiment of the invention, the flat roll-out view depicted in FIG. 4 corresponding to the two-dimensional projection of a cutting pattern suitable for the manufacture of a stent 10 according to a fourth embodiment of the invention.

The fourth embodiment of the stent 10 is similar to the third embodiment. However, the stent of the fourth embodiment includes additional fastening holes 12*a* provided for fastening a valvular prosthesis. Specifically, the additional fastening holes 12*a* are at the lower end 17*p* of the first connecting webs 17. The additional fastening holes 12*a* are configured as eyelets on the first connecting webs 17 between the fastening portion 11 and the connecting portion 22. It is of course conceivable that the additional fastening holes 12*a* are not configured as eyelets but are directly formed in the first connecting webs. The additional fastening holes 12*a* enable the upper region of a valvular prosthesis to be additionally secured to the stent 10.

The size of the additional fastening holes 12*a* may be adapted to the thickness of particular thread or wire used to fasten the valvular prosthesis to the stent 10. The cross-sectional shape of the additional fastening holes 12*a* may also be adapted to the cross-sectional shape of the thread or wire used for fastening the valvular prosthesis. Due to the presence of a number of additional fastening holes 12*a* for fixing the valvular prosthesis to the cardiac valve stent, the fastening position of the valvular prosthesis to the cardiac valve stent can be precisely defined.

As an alternative to fastening holes 12*a*, the same region of the stent 10 may be provided with one or more additional notches. These notches perform the same function as the fastening holes 12*a* and assist with additional anchoring of a prosthetic valve within the stent 100.

A stent 10 according to the fifth embodiment of the invention is shown in FIGS. 5*a*-*c* with the stent 10 in its expanded state. FIGS. 5*a* and 5*b* show side views of the stent 10, while FIG. 5*c* shows a plan view on the upper end 3 of the stent 10. FIG. 5*d* shows a flat roll-out view of a stent according to the fifth embodiment of the invention, which corresponds to a two-dimensional projection of a cutting pattern suitable for the manufacture of a stent according to the fifth embodiment of the invention, the stent being cut integrally from a portion of tube, in particular a metal tube.

The stent 10 according to the fifth embodiment is comparable in structural and functional respect to the stent of the third embodiment. In particular, the stent 10 of the fifth embodiment similarly has a total of three positioning arches 15*a*, 15*b*, 15*c*, which again undertake the function of automatic positioning of the stent 10 in the plane of the valve of the pulmonary valve or the aortic valve. As in other embodiments of the stent 10, the positioning arches 15*a*, 15*b*, 15*c* have a radiused head portion 20, which engages in the pockets of the native heart valve H being treated during positioning of the stent 10 at the implantation site in the heart (see FIG. 18*a*).

A total of three retaining arches 16*a*, 16*b*, 16*c* and three fastening arches 19*a*, 19*b*, 19*c* are also provided.

The fifth embodiment stent 10 differs from the stent of the third embodiment in that further notches 26*a* are provided in addition to the fastening holes 12 in the fastening portion 11. As can be seen in FIG. 5*d*, a series of notches 26*a* are provided which serve as additional anchoring means for the tissue component(s) of the valvular prosthesis 100 and guides for the suture thread or wire. These additional notches 26*a* also minimize movement of the suture thread or wire thereby reducing wear on the thread or wire by rubbing on the first connecting web 17 when the endoprosthesis 1 is implanted. The additional notches 26*a* also ensure that the upper region of a valvular prosthesis can be fastened firmly to the cardiac valve stent 10 allowing minimal movement of the prosthesis thereby further minimizing the likelihood of wear induced by friction on the suture thread or wire.

It is conceivable of course that the additional notches 26*a* are adapted to the thickness of the suture thread or wire. In particular, the additional notches 26*a* may be radiused to minimize damage to the suture thread or wire.

The fifth embodiment of the stent 10 also includes radial arches 32*a*, 32*b*, 32*c* extending from the positioning arches 15*a*, 15*b*, 15*c* towards the upper end 3 of the stent 10. As is shown most clearly in FIGS. 5*a* and 5*b*, the stent 10 has three radial arches 32*a*, 32*b*, 32*c*, with each arch 32*a*, 32*b*, 32*c* located between the two arms 15*a*, 15*a*', 15*b*, 15*b*', 15*c*, 15*c*' of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

As can be seen in particular in the cutting pattern shown in FIG. 5*d*, each arm 32', 32" of a radial arch 32 merges at about the mid-point of the length of the stent 10 into an arm 15*a*', 15*a*", 15*b*', 15*b*", 15*c*', 15*c*" of an opposing positioning arch 15*a*, 15*b*, 15*c*.

The two arms 32', 32" of each radial arch 32*a*, 32*b*, 32*c* are connected together at the upper end 3 of the stent 10 by means of a radiused connecting portion or head. This head is not only radiused but also widens at the tip so that the head abuts against the interior wall of the vessel over as large a contact area as possible when the stent 10 is in its expanded and implanted state.

The heads of each radial arch 32*a*, 32*b*, 32*c* also serve as additional means by which the stent 10 may be retained in a catheter before and during implantation and/or to recapture the stent after implantation.

FIG. 5*c* shows a perspective plan view from the upper end 3 of the stent 10 and illustrates that the radial arches 32*a*, 32*b*, 32*c* are programmed so that they extend in a radial direction outside the circumference of the stent 10 when the stent 10 is in its expanded state. In this way an increased contact force can be applied to the vessel wall by the upper end region of the stent 10. This, in turn, allows an increased security in the fixing of the stent 10 in situ, thereby reducing the likelihood of migration of the stent. Therefore, in its expanded state, in addition to the clamping effect of the positioning arches, the stent 10 of the fifth embodiment is secured in place on implantation via radial forces exerted by the retaining arches 16*a*, 16*b*, 16*c*, the auxiliary arches 18*a*, 18*b*, 18*c* and the radial arches 32*a*, 32*b*, 32*c*, all of which project outwards in a radial direction from the circumference of the stent 10.

It can be seen from the cutting pattern shown in FIG. 5*d* that the radial arches 32*a*, 32*b*, 32*c* do not project in the longitudinal direction L of the stent 10 beyond the plane in which the catheter retaining means 23 or the fastening means with fastening eyelets 24 are situated. This ensures that the catheter retaining means 23 can co-operate with corresponding means within a suitable implantation catheter without interference from the heads of the radial arches 32*a*, 32*b*, 32*c*. Indeed, as explained above, the heads themselves can be used as additional catheter retaining means or additional means to effect explanation of the stent 10.

In principle, the stent 10 may have more than three radial arches 32 in order to increase the radial contact force further. It is also possible to provide barb elements on all or some of the radial arches 32*a*, 32*b*, 32*c*, for example, to allow a still better anchoring of the stent 10 at the implantation site.

A stent 10 according to a sixth embodiment of the invention is shown in FIGS. 6*a-d* and FIGS. 6*f-i*. FIGS. 6*a-c* show various side views the stent 10 in its expanded state while a flat roll-out view of a stent according to the sixth embodiment is shown in FIG. 6*d*, said roll-out view corresponds to a two-dimensional projection of a cutting pattern suitable for the manufacture of the stent according to the sixth embodiment.

FIG. 6*e* shows a side view of an endoprosthesis for treating a narrowed cardiac valve or a cardiac valve insufficiency, where the endoprosthesis comprises a cardiac valve stent which is similar to the sixth embodiment of the invention for holding a valvular prosthesis. In detail, FIG. 6*e* shows a valvular prosthesis 100 attached to a stent 10 as an example on how to fix a valvular prosthesis 100 to a stent 10. This example is applicable to the stent embodiments described herein.

FIG. 6*f* show a side view of an endoprosthesis for treating a narrowed cardiac valve or a cardiac valve insufficiency, where the endoprosthesis comprises the cardiac valve stent according to the sixth embodiment of the invention for holding a valvular prosthesis.

FIGS. 6*g* and 6*h* show various perspective detail views of the endoprosthesis shown in FIG. 6*f*. FIG. 6*i* shows a plan view of the lower end of the endoprosthesis shown in FIG. 6*f*.

As in the embodiments previously described, the stent 10 of the sixth embodiment is again configured as a one-piece structure cut from a portion of tube, in particular from a metal tube, the cutting pattern being shown as a two-dimensional projection in FIG. 6*d*.

The sixth embodiment of the stent 10 is in principle similar in structure and function with respect to the fifth embodiment. To avoid repetition, reference is therefore made to the above description of the fifth embodiment. In particular, essentially U-shaped or V-shaped radial arches 32*a*, 32*b*, 32*c* are likewise provided to increase the radially acting contact force in the upper region of the stent 10.

The sixth embodiment differs from the fifth embodiment in that fixing bridges 27 with additional fastening portions 11*a* are provided for additional fastening of the tissue component(s) of the valvular prosthesis. The presence of fixing bridges 27 with additional fastening portions 11*a* is a particular advantage when a valve constructed from a sheet of biological material, such as pericardium, is used as a valvular prosthesis, i.e. a valvular prosthesis which is made up of several pieces of material. When pericardial valves are used, care must be taken to ensure that the pericardial material can be securely attached to the stent 10. For this reason, the stent 10 according to the sixth embodiment has a total of three fixing bridges 27 each comprising additional fastening portions 11*a*. Each fixing bridge 27 is attached to one of the first connecting webs 17 and extends in the direction of the lower end 2 of the stent 10.

The additional fastening portions 11*a* provided on the fixing bridges 27 have yet more fastening holes 12*b* and/or other fastening means, for example notches 26*b*, to anchor a thread or a thin wire which is used to fastened the pericardial material or the valvular prosthesis to the stent 10 allowing minimal, preferably no, movement of the valvular prosthesis. It is of course conceivable to provide fastening holes or fastening eyelets, the diameter of which is adapted to the thickness of the thread or wire used for fastening the valvular prosthesis. In general, the fastening holes 12*b* or notches 26*b* should be radiused to minimize wear of the thread or the wire induced by friction so far as is possible.

Reference is made to FIGS. 6*e* and 6*f* which show side views of an endoprosthesis 1 for treating a narrowed cardiac valve or a cardiac valve insufficiency. In the embodiment depicted in FIG. 6*f*, the stent 10 corresponds to a stent pursuant the sixth embodiment of the invention for holding a valvular prosthesis 100. The description of how the valvular prosthesis 100 is fixed to the stent 10 with respect to the sixth embodiment is also applicable to a stent 10 according to the other embodiments described herein.

The valvular prosthesis 100 comprises at least one leaflet 102 (see FIG. 6*i*) made from a biological or synthetic material. In particular, FIG. 6*e* shows a side view of a endoprosthesis 1, whereby the cardiac stent 10 is shown in a partially expanded state. FIG. 6*f* shows a side view of a endoprosthesis 1, whereby the cardiac stent 10 is shown in a fully expanded state. FIGS. 6*g-i* show various perspective detail views of the endoprosthesis 1 depicted in FIG. 6*f*. In detail, FIG. 6*g* is a perspective detail view of the head portion 30 of a retaining arch 16*a* and FIG. 6*h* is a perspective detail view of an additional fastening portion 11*a*. FIG. 6*i* is a plan view of the lower end 2 of the endoprosthesis 1 shown in FIG. 6*f*.

To ensure that minimal longitudinal displacement of the valvular prosthesis 100 affixed to stent 10 can occur relative stent 10, even during the peristaltic movement of the heart and the blood vessel in which stent 10 is deployed, the stent 10 according to the sixth embodiment of the invention comprises a plurality of fastening portions 11 extending in the longitudinal direction L of stent 10. In addition, the stent 100 according to the sixth embodiment is provided with additional fastening portions 11*a*, each of which is attached to one of the first connecting webs 17 and extends in the direction of the lower end 2 of the stent 10. By means of both the fastening portions 11 and the additional fastening portions 11*a* the tissue component(s) of the valvular prosthesis 100 is affixed to the stent 10.

In detail, the tissue component(s) of the valvular prosthesis 100 is fastened to the stent 10 by means of a thread 101 or a thin wire which is guided through each respective fastening hole 12, 12*b* of the fastening portions 11 and the additional fastening portions 11*a*, respectively. This allows fixing of the valvular prosthesis 100 to the stent 10 at a precise predefined position relative to the stent 10. By providing of a plurality of fastening holes 12 to anchor the valvular prosthesis 100 to the stent 10, precise positioning of the valvular prosthesis 100 on stent 10 is achieved.

Reference is made to FIG. 6*e* which shows an endoprosthesis 1 with a stent 10 which is a variant of the stent according to the sixth embodiment of the invention. The stent 10 shown in FIG. 6e is not yet fully expanded. An endoprosthesis 1 with a fully-expanded stent 10 according to the sixth embodiment of the invention is shown in FIG. 6f.

The stent 10 according to the present invention is—as will be described in detail below with reference to the illustrations of FIGS. 18a-c—advanced in the collapsed state in minimally-invasive fashion via an insertion catheter system either from the apex cordis (i.e. transapical) or through the femoral artery and the aortic arch (i.e. transfemoral) to the site of implantation at the heart. During the insertion procedure, the stent 10 with the valvular prosthesis 100 affixed thereto is accommodated in the tip K of the catheter system in the collapsed state (cf. FIG. 18a). Upon reaching the site of implantation at the heart, the stent 10 with the valvular prosthesis 100 affixed thereto is sequentially released by the selective manipulating of parts of the proximal side K of the delivery portion of the catheter system.

It is important to note that the insertion procedure shown in FIGS. 18a-c is an insertion procedure by which an endoprosthesis 1 is inserted through the femoral artery and the aortic arch (i.e. transfemoral) to the site of implantation at the heart. However, the invention is not limited to the specific delivery access described with reference to FIGS. 18a-c. Rather, for implanting the endoprosthesis 1 various approaches may be used, for example a transapical approach for treating the aortic valve by which the endoprosthesis is brought to the site of implantation at the heart from the apex cordis (i.e. a transapical approach).

In detail, during a first release step, the proximal side K of the delivery portion of the insertion catheter system is manipulated such that the positioning arches 15a-c of stent 10 are released while the remaining parts of the stent 10, in particular the retaining arches 16a, 16b, 16c, the auxiliary arches 18a-c and the radial arches 32a-c are still in their collapsed state (cf. FIG. 18a). The positioning arches 15a-c released during the first release step expand and spread radially outward. The expanded positioning arches 15a-c can then be inserted into the pockets T of the patient's native cardiac valve H by suitably moving the proximal side K of the delivery portion of the catheter system (cf. FIG. 18a).

In the second release step which follows, the proximal side K of the delivery portion of the insertion catheter system is manipulated such that the arches forming the lower end 2 of the stent 10 (auxiliary arches 18a-c and retaining arches 16a, 16b, 16c) are released while the upper end 3 of the stent 10 is however still firmly affixed to the proximal side K of the delivery portion of the catheter system and is not released (cf. FIG. 18b).

The positioning arches 15a-c disposed on stent 10 and also the retaining arches 16a, 16b, 16c may be curved in convex and arched fashion in the lower direction; i.e. toward the lower end 2 of stent 10, whereby such a rounded form may reduce injuries to the artery as well as facilitate the unfolding during the self-expansion. Such a design may enable an easier insertion of the positioning arches 15a-c into the pockets of the native cardiac valve without correspondingly injuring the neighboring tissue or blood vessels.

In FIG. 6e, the endoprosthesis 1 exhibiting the stent 10 in accordance with one embodiment of the invention with a valvular prosthesis 100 affixed to said stent 10 is shown in a state after the second release step in which only the upper end 3 with the catheter retaining means 23 is firmly connected to the tip K of the insertion catheter system while the remaining portions of the stent 10 have already been released and radially expanded. It can be seen from the FIG. 6e illustration that due to the self-expansion of the retaining arches 16a, 16b, 16c and the auxiliary arches 18a-c, the valvular prosthesis 100 affixed thereto has already expanded (at least partly).

As shown in FIG. 6e, the upper end section 3 of stent 10 is still accommodated in a sleeve-like portion P within a delivery portion of a catheter system (not explicitly shown in FIG. 6e). This remains the case until the unfolding and positioning of the valvular prosthesis 100 has taken place to the extent that it can be checked for functionality.

If the functional test shows that the valvular prosthesis 100 satisfactorily functions, the sleeve-like portion P can be pulled back distally so that also the upper end section 3 of stent 10 with the catheter retaining means 23 is fully released (cf. FIG. 18c).

It can further be seen from the FIG. 6e illustration how the valvular prosthesis 100 can be affixed to the stent 10 by means of threads 101. A pericardial valvular prosthesis 100 is used in the embodiment depicted which is sewn to fastening holes 12b of a fixing bridge 27 extending between two neighboring retaining arches 16a, 16b. See FIG. 6c and FIG. 6f. The valvular prosthesis 100 may be virtually tubular with a substantially circular cross-section. At the lower end 2 of the stent 10, the valvular prosthesis 100 exhibits a bead 105. This bead 105, which is annular in the plan view of endoprosthesis 1, is formed by turning the lower end of the valvular prosthesis 100 inside out by rolling it over on itself. As shown in FIG. 6e, the annular bead 105 is overedged by thread 101. The annular bead 105 may be of a different configuration.

The annular bead 105 at the lower end of the valvular prosthesis 100 may provide a secure anchoring of the peripheral area of the valvular prosthesis 100 to the blood vessel in the implanted state of the endoprosthesis 1, even given the peristaltic motion, and thus may provide a secure seal relative the vascular wall.

The annular bead 105 at the lower end of the valvular prosthesis 100 may also provide good contact and more uniform structure at the lower end section 2 of the stent 10 to more evenly distribute the radial forces needed to anchor the endoprosthesis 1 in its implanted state. In this regard, sealing and preventing leakage after implantation of the endoprosthesis 1 can be achieved. Over time, tissue growth will further secure the endoprosthesis 1 to prevent any movement relative to the blood vessel in the implanted state of the endoprosthesis 1 or leakage. When implanting the endoprosthesis 1 in a native blood vessel any leakage between the peripheral area of the annular bead 105 and the vascular wall is sealed by a good contact and radial pressure between the endoprosthesis 1 and the diseased native valve annulus. Accordingly, the bead-shaped area 105 provides a secure seal, particularly also during the filling phase of the heart cycle (diastole).

FIG. 6i likewise shows a plan view of the lower end 2 of the endoprosthesis 1 depicted for example in FIG. 6f, i.e. a view from the inflow side of the endoprosthesis shown in FIG. 6f, whereby the stent 10 for the endoprosthesis 1 is shown in its fully-expanded state.

As shown in FIG. 6i, the leaflets 102 of the valvular prosthesis 100 are in a semi-closed position, as is the case in the beginning of the diastole of the heart.

As shown in FIGS. 6f and 6g in detail, the fixing bridges 27 with the additional fastening portions 11a also have notches 26b to anchor the thread or thin wire which is used to fasten the pericardial material or the tissue component(s) of the valvular prosthesis 100 to the stent 10 allowing minimal, preferably no, movement of the valvular prosthesis. Further, the auxiliary arches 18*a-c* are used as fastening means for anchoring the valvular prosthesis 100 to the stent 10.

It can also be noted from FIGS. 6*f* and 6*g* that lower part of the valvular prosthesis 100 is turned inside out such as to form a circumferential flap in which the respective head portions 30' of the fastening arches 19*a-c* and the respective head portions 31 of the auxiliary arches 18*a-c* engage. The valvular prosthesis 100 is thus fastened to the stent 10 with minimal play such that relative movement between the stent 10 and the valvular prosthesis 100 due to the peristaltic motion of the heart can be effectively prevented when the endoprosthesis 1 is implanted.

A seventh embodiment of the inventive stent 10 will be described in the following with reference to FIGS. 7*a-c*. Here, FIGS. 7*b* and 7*c* each show side views of the fully-expanded stent 10 according to the seventh embodiment.

Except for the lower end section, the stent 10 according to the seventh embodiment essentially corresponds to the stent according to the sixth embodiment of the present invention described above with reference to FIGS. 6*a-d* and FIGS. 6*f-i*.

Hence, the stent 10 according to the seventh embodiment has also a total of three positioning arches 15*a*, 15*b*, 15*c*, which again undertake the function of automatic positioning of the stent 10 in the plane of the valve of the pulmonary valve or the aortic valve. As in other embodiments of the stent 10, the positioning arches 15*a*, 15*b*, 15*c* have a radiused head portion 20, which engages in the pockets of the native heart valve H being treated during positioning of the stent 10 at the implantation site in the heart (see FIG. 18*a*).

A total of three retaining arches 16*a*, 16*b*, 16*c* is also provided. Contrary to the stent design of the sixth embodiment, however, in the stent design according to the seventh embodiment, the two arms 16*a*', 16*a*", 16*b*', 16*b*", 16*c*', 16*c*" of each retaining arch 16*a*, 16*b*, 16*c* are not connected to each other via a connecting portion which has almost an O-shaped configuration. Rather, in the seventh embodiment, the lower end section of each arm of the retaining arches 16*a*, 16*b*, 16*c* merges into an annular collar 40, which will be described in more detail below.

As in the sixth embodiment of the present invention, the stent design according to the seventh embodiment is also provided with fixing bridges 27 with additional fastening portions 11*a* for additional fastening of the tissue component (s) of a valvular prosthesis or parts of a valvular prosthesis. Each fixing bridge 27 is attached to one of the first connecting webs 17 and extends in the direction of the lower end 2 of the stent 10. The additional fastening portions 11*a* provided on the fixing bridges 27 have yet more fastening holes 12*b* and notches 26*b* to anchor a thread or a thin wire which is used to fastened the pericardial material or the tissue component(s) of the valvular prosthesis to the stent 10 allowing minimal, preferably no, movement of the valvular prosthesis. It is of course conceivable to provide fastening holes or fastening eyelets, the diameter of which is adapted to the thickness of the thread or wire used for fastening the tissue component(s) of the valvular prosthesis.

The seventh embodiment of the stent 10 also includes radial arches 32*a*, 32*b*, 32*c* extending from the positioning arches 15*a*, 15*b*, 15*c* towards the upper end 3 of the stent 10. As is shown most clearly in FIGS. 7*b* and 7*c*, the stent 10 has three radial arches 32*a*, 32*b*, 32*c*, with each arch 32*a*, 32*b*, 32*c* located between the two arms 15*a*, 15*a*', 15*b*, 15*b*', 15*c*, 15*c*' of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

Since in the implanted state of the endoprosthesis 1, substantial forces act on the valvular prosthesis 100 during the filling phase of the heart cycle (diastole), which are transmitted to the stent affixed with the valvular prosthesis 100, the secure anchoring of the stent 10 with the valvular prosthesis 100 affixed thereto at the site of implantation may of distinct importance. The seventh to eleventh embodiments of the stent 10 described in the following incorporate further measures which can be provided additionally to the above-described embodiments of retaining arches, auxiliary arches and radial arches which may more securely anchor of stent 10, endoprosthesis 1 respectively, at the site of implantation and which may prevent a positional displacement of endoprosthesis 1.

In detail, at least one annular collar 40, which forms the lower end 2 of the stent 10, is provided in accordance with the seventh embodiment as an additional anchoring measure for the stent 10 depicted in FIGS. 7*b-c*.

FIG. 7*a* shows a flat roll-out view of another cardiac valve stent according to the seventh embodiment of the invention. The roll-out view depicted in FIG. 7*a* corresponds to a two-dimensional projection of a cutting pattern which my be used in the production of a cardiac valve stent according to the seventh embodiment in order to enable a cardiac valve stent according to the seventh embodiment to be integrally cut from a section of tube, in particular a metal tube.

Apart from the connection of the annular collar 40 to the stent body, the stent design depicted in FIG. 7*a* corresponds to the design of the stents 10 shown in FIGS. 7*b-c*. In detail, according to the stent design depicted in the roll-out view of FIG. 7*a*, in the modification of the seventh embodiment, the stent is provided with fastening arches 19*a*, 19*b*, 19*c* and retaining arches 16*a*, 16*b*, 16*c*. As shown in the flat roll-out view according to FIG. 7*a*, a fastening arch 19*a*, 19*b*, 19*c* and a retaining arch 16*a*, 16*b*, 16*c* is allocated to each positioning arch 15*a*, 15*b*, 15*c*, and each retaining arch 16*a*, 16*b*, 16*c* is connected to a neighboring retaining arch by means of an auxiliary arch 18*a*, 18*b*, 18*c*. A fastening portion with a specific number of fastening holes 12 is configured in each arm 16*a*', 16*a*", 16*b*', 16*b*", 16*c*', 16*c*" of retaining arch 16*a*, 16*b*, 16*c*.

Contrary to the stent design of, for example, the sixth embodiment, however, in the stent design depicted in FIG. 7*a*, neither the two arms 16*a*', 16*a*", 16*b*', 16*b*", 16*c*', 16*c*" of each retaining arch 16*a*, 16*b*, 16*c* nor the two arms 19*a*', 19*a*", 19*b*', 19*b*", 19*c*', 19*c*" of each fastening arch 19*a*, 19*b*, 19*c* are respectively connected to each other via a connecting portion which has almost an O-shaped configuration. Rather, in the stent design depicted in FIG. 7*a*, the lower end section of each arm of the retaining arches 16*a*, 16*b*, 16*c* on the one hand and the lower end section of each arm of the fastening arches 19*a*, 19*b*, 19*c* on the other hand respectively merges into an annular collar 40 having an identical configuration compared with the annular collar of the stent design depicted in FIGS. 7*b-c*.

Contrary to the stent design depicted in FIG. 7*a*, the stent 10 shown in FIGS. 7*b-c* is provided with an annular collar 40 which is merely connected to each or a part of the lower end sections of the respective retaining arms 16*a*', 16*a*", 16*b*', 16*b*", 16*c*', 16*c*" of retaining arches 16*a*, 16*b*, 16*c* since the stent 10 shown in FIGS. 7*b-c* is not provided with fastening arches as the stent design depicted in FIG. 7*a*. On the other hand, however, the stent design depicted in FIG. 7*a* is provided with an annular collar 40 which is connected to each or a part of the lower end sections of the respective retaining arms 16a', 16a", 16b', 16b", 16c', 16c" of retaining arches 16a, 16b, 16c as well as to each or a part of the lower end sections of the respective arms 19a', 19a", 19b', 19b", 19c', 19c" of the fastening arches 19a-c.

In general, however, the stent 10 of the seventh embodiment an annular collar 40 wherein the annular collar 40 may also be connected to each or a part of the lower end sections of the respective arms 18a', 18a", 18b', 18b", 18c', 18c" of the auxiliary arches 18a, 18b, 18c, as can be seen in particular from the flat roll-out view pursuant to FIG. 7a or the side view pursuant to FIG. 7b or the perspective view pursuant to FIG. 7c.

The annular collar 40 exhibits a plurality of supporting webs 41 which run parallel to the longitudinal axis of the stent 10 in the non-expanded state of said stent 10 and are inter-connected by transversal webs 42 (cf. FIG. 7a). In the expanded state of stent 10, the supporting webs 41 and the transversal webs 42 form a rhomboidal or serpentine-like annular collar 40 which abuts against the vascular wall in the implanted state of endoprosthesis 1, stent 10 respectively. FIGS. 7b and 7c show the annular collar 40 in the expanded state.

The annular collar 40 serves as a supporting body through which the radial forces developing due to the self-expansion are transmitted to the vascular wall. Since a relatively large contact area of the stent 10 interacts with the vascular wall, and because of the rhomboidal or serpentine structure to the annular collar 40, there may be a decreased risk of injury to the artery or the tissue despite the increased radial forces.

Accordingly, not only the rigidity of the stent 10 can be increased after its self-expansion by the providing of the annular collar 40, but also the anchorage of the stent 10 in the implanted state can be improved or strengthened. Additionally, the annular cross-sectional shape to annular collar 40 increases the seal between the vascular wall and the endoprosthesis 1.

Such an annular collar 40 is advantageously configured as a self-expandable supporting structure which advantageously effects an even further improved anchoring of the stent 10 at the site of implantation due to its radially-outward-acting contact pressure and its design such that a displacing of the stent 10 with the valvular prosthesis 100 can be further prevented.

An eighth embodiment of the inventive stent 10 is shown in FIGS. 8a-c. In detail, FIG. 8b and FIG. 8c each show a stent 10 of the eighth embodiment in a side view, whereby the stent 10 is fully expanded. FIG. 8a shows a flat roll-out view of a cardiac valve stent according to the eighth embodiment of the invention, said roll-out view depicted in FIG. 8a corresponding to a two-dimensional projection of a cutting pattern applicable to manufacturing a cardiac valve stent according to the eighth embodiment to cut the cardiac valve stent integrally from a portion of a tube, in particular a metal tube.

Except for the upper end section, the stent 10 according to the eighth embodiment essentially corresponds to the stent according to the fifth embodiment of the present invention described above with reference to FIGS. 5a-d.

Hence, the stent 10 of the eighth embodiment similarly has a total of three positioning arches 15a, 15b, 15c, which again undertake the function of automatic positioning of the stent 10 in the plane of the valve of the pulmonary valve or the aortic valve. As in other embodiments of the stent 10, the positioning arches 15a, 15b, 15c have a radiused head portion 20, which engages in the pockets of the native heart valve H being treated during positioning of the stent 10 at the implantation site in the heart (see FIG. 18a).

A total of three retaining arches 16a, 16b, 16c and three fastening arches 19a, 19b, 19c are also provided.

Furthermore, in the eighth embodiment stent 10, further notches 26a are provided in addition to the fastening holes 12 in the fastening portion 11 which serve as additional anchoring means for the tissue component(s) of the valvular prosthesis 100 and guides for the suture thread or wire. These additional notches 26a also minimize movement of the suture thread or wire thereby reducing wear on the thread or wire by rubbing on the first connecting web 17 when the endoprosthesis 1 is implanted. The additional notches 26a also ensure that the upper region of a valvular prosthesis can be fastened firmly to the cardiac valve stent 10 allowing minimal movement of the prosthesis thereby further minimizing the likelihood of wear induced by friction on the suture thread or wire.

A total of three retaining arches 16a, 16b, 16c and three fastening arches 19a, 19b, 19c are also provided.

In contrast to the seventh embodiment (cf. FIG. 7a-c), however, the lower end 2 of the stent 10 remains unchanged in the eighth embodiment while an upper annular collar 40' is formed at the upper end 3 of the stent 10. As FIGS. 8b and 8c show, the annular collar 40' is constructed of supporting webs 41 and transversal webs 42 and forms a rhombic supporting structure in the expanded state.

To be seen from the illustration of the cutting pattern according to FIG. 8a is that the upper annular collar 40' utilized in the eighth embodiment is connected to the upper head portions of radial arches 32a, 32b, 32c. On the other hand, the upper annular collar 40' is connected to the second connecting web 25 such that it is disposed at a distance from the plane in which the catheter retaining means 23 are positioned in the expanded state (cf. FIGS. 8b, 8c). Specifically, the annular collar 40' in the eighth embodiment is situated between the plane in which the catheter retaining means 23 lies and the plane in which the connecting portion 22 of the two arms of neighboring positioning arches 15a-c lies. To this end, the connecting web 25 is—compared to the connecting web in the fifth embodiment—configured to be somewhat longer.

Since the upper annular collar 40' utilized in the eighth embodiment is comparable to the lower annular collar 40 utilized in the seventh embodiment in terms of functioning. In particular, the upper annular collar 40' provides good anchoring to prevent migration of the endoprosthesis in its implanted state and a uniform distribution of these radial forces.

The following will reference FIGS. 9a and 9b in describing a ninth embodiment of the stent 10 according to the invention. FIG. 9b thereby shows a perspective view of a stent 10 according to the ninth embodiment in the expanded state. FIG. 9a shows a flat roll-out view of a cardiac valve stent according to the ninth embodiment of the invention. The roll-out view depicted in FIG. 9a corresponds to a two-dimensional projection of a cutting pattern applicable to manufacturing a cardiac valve stent according to the ninth embodiment in order to cut the cardiac valve stent integrally from a portion of a tube, in particular a metal tube.

Since an upper annular collar 40' is likewise formed at the upper end 3 of the stent 10, the stent 10 in accordance with the ninth embodiment is similar to the previously-described stent according to FIGS. 8a-c (eighth embodiment). In contrast to the eighth embodiment, the upper annular collar 40' in the ninth embodiment is configured to be longer in the longitudinal direction of the stent 10. Specifically, a comparison of FIG. 9b and FIG. 8b shows that in the ninth embodiment, two rhombic annular bodies lying atop one another are employed as the annular collar 40'. This may increase the radial contact force that the stent 10 exerts from its upper end 3. A correspondingly elongated connecting web 25 is again utilized in the embodiment according to FIGS. 9a-b.

FIG. 10 shows a flat roll-out view of a cardiac valve stent 10 in accordance with a tenth embodiment of the invention, said roll-out view also being a two-dimensional projection of a cutting pattern which can be used to cut a cardiac valve stent 10 in accordance with a tenth embodiment as one integral piece from a portion of a tube, in particular a metal tube.

As also with the eighth embodiment described above with reference to FIGS. 8a-b and the ninth embodiment described above with reference to FIGS. 9a-b, the tenth embodiment of the inventive stent 10 essentially corresponds to the embodiment described with reference to FIGS. 5a-d.

In contrast, for example, to the eighth embodiment (cf. FIG. 8a-c), however, the upper end 3 of the stent 10 remains unchanged in the tenth embodiment while a lower annular collar 40 is formed at the lower end 2 of the stent 10. As FIG. 10 shows, the annular (lower) collar 40 is also constructed of supporting webs 41 and transversal webs 42 and forms a rhombic supporting structure in the expanded state.

To be seen from the illustration of the cutting pattern according to FIG. 10 is that the lower annular collar 40 utilized in the tenth embodiment is connected to the lower head portions of retaining arches 16a, 16b, 16c, of fastening arches 19a, 19b, 19c, and of auxiliary arches 18a, 18b, 18c. On the other hand, the lower annular collar 40 is connected to the retaining arches 16a, 16b, 16c, of fastening arches 19a, 19b, 19c, and of auxiliary arches 18a, 18b, 18c such that it is disposed at a distance from the plane in which the catheter retaining means 23 is positioned in the expanded state.

Since the lower annular collar 40 utilized in the tenth embodiment is comparable to the lower annular collar 40 utilized in the seventh embodiment in terms of functioning, and is not further described for clarification purposes.

FIG. 11 shows a flat roll-out view of a cardiac valve stent 10 in accordance with a eleventh embodiment of the invention.

Except for the upper and lower end section, the stent 10 according to the eleventh embodiment is similar to the stent 10 according to the fifth embodiment of the present invention described above with reference to FIGS. 5a-d.

Hence, the stent 10 according to the eleventh embodiment has also a total of three positioning arches 15a, 15b, 15c, which again undertake the function of automatic positioning of the stent 10 in the plane of the valve of the pulmonary valve or the aortic valve. As in other embodiments of the stent 10, the positioning arches 15a, 15b, 15c have a radiused head portion 20, which engages in the pockets of the native heart valve H being treated during positioning of the stent 10 at the implantation site in the heart (see FIG. 18a).

A total of three retaining arches 16a, 16b, 16c and three fastening arches 19a, 19b, 19c are also provided.

The eleventh embodiment of the stent 10 also includes radial arches 32a, 32b, 32c extending from the positioning arches 15a, 15b, 15c towards the upper end 3 of the stent 10. As is shown in FIG. 11, the stent 10 has three radial arches 32a, 32b, 32c, with each arch 32a, 32b, 32c located between the two arms 15a, 15a', 15b, 15b', 15c, 15' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

The eleventh embodiment of the stent (cf. FIG. 11) differs from the fifth embodiment of the present invention described above with reference to FIGS. 5a-d in that two annular collars 40, 40', which forms the lower and upper ends 2, 2' of the stent 10, are provided in accordance with the eleventh embodiment as an additional anchoring measure for the stent 10. As in the seventh embodiment described above with reference to FIGS. 7a-c, the lower annular collar 40 is connected to the lower end sections of the respective retaining arms 16a', 16a", 16b', 16b", 16c', 16c" of retaining arches 16a, 16b, 16c and the lower end sections of the respective arms 19a', 19a", 19b', 19b", 19c', 19c" of the fastening arches 19a-c, as can be seen in particular from the cutting pattern pursuant FIG. 11. On the other hand, the upper annual collar 40' utilized in the eleventh embodiment is connected to the upper head portions of radial arches 32a, 32b, 32c. In detail, the annual collar 40' in the eleventh embodiment is situated between the plane in which the catheter retaining means 23 lies and the plane in which the connecting portion 22 of the two arms of neighboring positioning arches 15a-c lies.

As already described with respect to the seventh to tenth embodiment of the present invention, the upper and lower annular collars 40, 40' exhibits a plurality of supporting webs 41 which run parallel to the longitudinal axis of the stent 10 in the non-expanded state of said stent 10 and are interconnected by transversal webs 42 (cf. FIG. 11). Again, in the expanded state of stent 10, the supporting webs 41 and the transversal webs 42 form a rhomboidal or serpentine-like annular collars 40, 40' which abuts against the vascular wall in the implanted state of endoprosthesis 1, stent 10 respectively.

A comparison of FIG. 11 with the cutting patterns according to FIGS. 8a and 9a shows that the stent 10 in accordance with the eleventh embodiment of the invention basically proceeds from the stent 10 according to the eighth embodiment (cf. FIGS. 8a-c), whereby for the purpose of improved anchoring, an additional (lower) annular collar 40 is formed at the lower end 2 of the stent 10. This additional lower annular collar corresponds substantially to the lower annular collar employed in the seventh embodiment (cf. FIGS. 7a-c). To avoid repetition, reference is made to the foregoing remarks with respect to the seventh and eighth embodiments.

Naturally, the annular collar 40 or 40' can in principle also be arranged in a plane in which the valvular prosthesis is situated. It is furthermore not imperative for the annular collar 40 to be connected to all the end sections of the retaining arches 16a, 16b, 16c or the auxiliary fastening arches 19a-c respectively. Nor does the upper annular collar 40' necessarily have to be connected to all the end sections of the radial arches 32.

FIG. 12 shows a flat roll-out view of a cardiac valve stent in accordance with a twelfth embodiment of the invention. The roll-out view depicted in FIG. 12 could also be used as a cutting pattern for manufacturing a stent according to the twelfth embodiment. A side view or a perspective view of a stent according to the twelfth embodiment is not shown in the drawings.

Elements in FIG. 12 that are generally similar to previously described elements have the same reference numbers compared with the reference numbers in FIGS. 1 to 11 previously used for the similar elements.

In principle, the stent according to the twelfth embodiment is similar to the stent of the fifth embodiment already described with reference to FIGS. 5a-d. To avoid repetition, reference is therefore made to the above description of the fifth embodiment.

Briefly summarized, the stent of the twelfth embodiment similarly has a total of three positioning arches 15a, 15b, 15c, which again undertake the function of automatic positioning of the stent in the plane of the pulmonary valve or the aortic valve. As in other embodiments of the stent, the positioning arches 15a, 15b, 15c have a radiused head portion 20, which engages in the pockets of the native heart valve H being treated during positioning of the stent at the implantation site in the heart (see FIG. 18a).

Also, the stent of the twelfth embodiment is provided with a total of three retaining arches 16a, 16b, 16c. According to the cutting pattern depicted in FIG. 12, however, in the stent design according to the twelfth embodiment, fastening arches may be omitted. It is, of course, possible to provide the stent structure of the twelfth embodiment with such fastening arches as described in connection with, for example, the stent of the fifth embodiment.

In addition, essentially U-shaped or V-shaped radial arches 32a, 32b, 32c are likewise provided to increase the radially acting contact force in the upper region 3 of the stent. The radial arches 32a, 32b, 32c of the stent according to the twelfth embodiment extend from the positioning arches 15a, 15b, 15c towards the upper end 3 of the stent. According to the cutting pattern depicted in FIG. 12, the stent of the twelfth embodiment has three radial arches 32a, 32b, 32c, with each arch 32a, 32b, 32c located between the two arms 15a, 15a', 15b, 15b', 15c, 15c' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c. Each arm 32', 32" of a radial arch 32 merges at about the mid-point of the length of the stent into an arm 15a', 15a", 15b', 15b", 15c', 15c" of an opposing positioning arch 15a, 15b, 15c.

The two arms 32', 32" of each radial arch 32a, 32b, 32c are connected together at the upper end 3 of the stent by means of a radiused connecting portion or head. This head is not only radiused but also widens at the tip so that the head abuts against the interior wall of the vessel over as large a contact area as possible when the stent of the twelfth embodiment is in its expanded and implanted state.

The heads of each radial arch 32a, 32b, 32c also serve as additional means by which the stent of the twelfth embodiment may be retained in a catheter before and during implantation and/or to recapture the stent after implantation.

In addition to retaining arches 16a, 16b, 16c, the stent of the twelfth embodiment further comprises auxiliary arches 18a, 18b, 18c, which likewise exert a radially-acting contact force against the wall of the blood vessel in the implanted state of stent, thereby further improving anchoring of stent at the site of implantation.

To recapitulate, providing retaining arches 16a, 16b, 16c on the one hand and auxiliary arches 18a, 18b, 18c on the other hand results in a radial force being exerted on the vascular wall by the respective lower end portions of these arches. This provides both a secure seal of a valvular prosthesis affixed to the stent relative the vascular wall, as well as a secure anchoring of the stent, at the site of implantation in the heart.

As can be seen from the cutting pattern according to FIG. 12, the stent of the twelfth embodiment comprises a total of three essentially U-shaped or V-shaped auxiliary arches 18a, 18b, 18c which are closed towards the lower end 2 of the stent. Each auxiliary arch 18a, 18b, 18c connects a first retaining arch 16a, 16b, 16c with a second retaining arch neighboring the first retaining arch.

Although not explicitly illustrated in the cutting pattern according to FIG. 12, the radial arches 32a, 32b, 32c are preferably programmed so that they extend in a radial direction outside the circumference of the stent when the stent of the twelfth embodiment is in its expanded state. In this way, an increased contact force can be applied to the vessel wall by the upper end region of the stent when the stent of the twelfth embodiment is in its expanded and implanted state. This, in turn, may provide an increased security in the fixing of the stent in situ, thereby reducing the likelihood of migration of the stent. Therefore, in its expanded and implanted state, in addition to the clamping effect of the positioning arches, the stent of the twelfth embodiment is secured in place on implantation via radial forces exerted by the retaining arches 16a, 16b, 16c, the auxiliary arches 18a, 18b, 18c and the radial arches 32a, 32b, 32c, all of which project outwards in a radial direction from the circumference of the stent.

It can be seen from the cutting pattern shown in FIG. 12 that the radial arches 32a, 32b, 32c do not project in the longitudinal direction L of the stent beyond the plane in which the catheter retaining means 23 or the fastening means with fastening eyelets 24 are situated. This ensures that the catheter retaining means 23 can co-operate with corresponding means within a suitable implantation catheter without interference from the heads of the radial arches 32a, 32b, 32c. Indeed, as explained above, the heads themselves can be used as additional catheter retaining means or additional means to effect explanation of the stent of the twelfth embodiment.

As in the fifth embodiment, the stent according to the twelfth embodiment may have more than three radial arches 32 in order to increase the radial contact force further. It is also possible to provide barb elements on all or some of the radial arches 32a, 32b, 32c, for example, to anchor the stent at the implantation site.

As already indicated, the stent according to the twelfth embodiment exhibits a structure integrally cut from a portion of tube, and in particular from a metal tube. As in other stent embodiments of the present invention, in the stent according to the twelfth embodiment, a retaining arch 16a, 16b, 16c is allocated to each positioning arch 15a, 15b, 15c, and each retaining arch 16a, 16b, 16c is connected to a neighboring retaining arch by means of an auxiliary arch 18a, 18b, 18c. Also, at least one fastening portion 11 with a specific number of fastening holes 12 is configured in each arm 16a', 16a", 16b', 16b", 16c', 16c" of retaining arch 16a, 16b, 16c.

The stent of the twelfth embodiment differs, in particular, from the stent of the fifth embodiment in that the stent according to the twelfth embodiment is not provided with additional notches denoted, for example, in FIGS. 5a-d with reference number "26a". Rather, instead of additional notches, the stent according to the twelfth embodiment comprises first and second additional fastening portions 11a, 11b for additional fastening of the tissue component(s) of a valvular prosthesis or parts of a valvular prosthesis.

In detail, first additional fastening portions 11a are provided for additional fastening of the tissue component(s) of the valvular prosthesis or parts of a valvular prosthesis. These first additional fastening portions 11a are provided with auxiliary fastening holes 12b and/or other fastening means, for example notches, to anchor a thread or a thin wire which is used to fastened the pericardial material or the tissue component(s) of the valvular prosthesis to the stent allowing minimal, preferably no, movement of the valvular prosthesis. The first additional fastening portions 11*a* are arranged between the first and second arms 16*a*", 16*b*'; 16*b*", 16*c*'; 16*c*", 16*a*' of two neighboring retaining arches 16*a*, 16*b*, 16*c* and extend from the respective lower ends 17*d* of the first connecting webs 17 in the direction of the lower end 3 of the stent, the first connecting webs 17 being provided with the already mentioned second additional fastening portions 11*b*.

In addition to the first additional fastening portions 11*a*, the stent according to the twelfth embodiment further comprises second additional fastening portions 11*b*. In detail, each first connecting web 17 of the stent according to the twelfth embodiment is provided with at least one second additional fastening portion 11*b*, said at least one second additional fastening portion 11*b* being a portion which comprises additional auxiliary fastening holes 12*c* and/or other fastening means. The at least one second additional fastening portion 11*b* extends essentially in the longitudinal direction L of stent according to the twelfth embodiment.

A comparison of the cutting pattern depicted in FIG. 12 with the cutting pattern depicted, for example, in FIG. 5*d*, shows that each of the first connecting webs 17 of the stent according to the twelfth embodiment is provided with one second additional fastening portion 11*b*. In this regard, the stent according to the twelfth embodiment is provided with second additional fastening portions 11*b*, the upper end portions thereof open into connecting portion 22 between the two arms 15*a*', 15*a*", 15*b*', 15*b*", 15*c*', 15*c*" of two neighboring positioning arches 15*a*, 15*b*, 15*c*.

On the other hand, in the stent design according to the twelfth embodiment, the first connecting webs 17 with the second additional fastening portions 11*b* each exhibit a structure that diverges at the respective lower end portions of the first connecting webs 17 to give way to the respective arms 16*a*', 16*a*", 16*b*', 16*b*", 16*c*', 16*c*" of two neighboring retaining arches 16*a*, 16*b*, 16*c*.

In detail, the first connecting webs 17 with the second additional fastening portions 11*b* connect with connecting portions 22 via their upper ends 17*d* and with the upper ends of the first additional fastening portions 11*a* on the one hand as well as with the upper ends of the respective arms 16*a*', 16*a*", 16*b*', 16*b*", 16*c*', 16*c*" of the retaining arches 16*a*, 16*b*, 16*c* via their lower ends 17*p*.

The additional auxiliary fastening holes 12*c* and/or other fastening means of the second additional fastening portions 11*b* serve for anchoring a thread or a thin wire which is used to fastened the pericardial material or the tissue component (s) of the valvular prosthesis to the stent allowing minimal, preferably no, movement of the valvular prosthesis.

With regard to the first and second additional fastening portions 11*a*, 1ib of the stent according to the twelfth embodiment, it is of course conceivable to provide fastening holes 12*b*, 12*c* or fastening eyelets, the diameter of which is adapted to the thickness of the thread or wire used for fastening the tissue components) of the valvular prosthesis. Preferably, the fastening holes 12*b*, 12*c* or fastening eyelets should be radiused to minimize wear of the thread or the wire induced by friction so far as is possible.

The presence of first and second additional fastening portions 11*a*, 11*b* with auxiliary and additional auxiliary fastening holes 12*b*, 12*c* is a particular advantage when a valve constructed from a sheet of biological material, such as pericardium, is used as an endoprosthesis, including a valvular prosthesis which is made up of several pieces of material.

When pericardial valves are used, care must be taken to ensure that the pericardial material can be securely attached to the stent. For this reason, the stent according to the twelfth embodiment has a total of three first additional fastening portions 11*a* each comprising auxiliary fastening holes 12*b*, as well as a total of three second additional fastening portions lib each comprising additional auxiliary fastening holes 12*c*.

Apart from the above described difference, the stent of the twelfth embodiment differs particularly from the stent of the fifth embodiment in that the stent according to the twelfth embodiment is provided with at least one so-called "leaflet guard arch".

In detail, according to the cutting pattern depicted in FIG. 12, the stent of the twelfth embodiment is provided with a total of three leaflet guard arches 50*a*, 50*b*, 50*c*, each comprising two leaflet guard arms. It can be seen from the cutting pattern shown in FIG. 12 that, in the structure of the stent according to the twelfth embodiment, a leaflet guard arch 50*a*, 50*b*, 50*c* is provided in between each positioning arch 15*a*, 15*b*, 15*c*. Hence, in the stent according to the twelfth embodiment, a leaflet guard arch 50*a*, 50*b*, 50*c* is allocated to each positioning arch 15*a*, 15*b*, 15*c*.

Each leaflet guard arch 50*a*, 50*b*, 50*c* has a substantially U-shaped or V-shaped structure which is closed to the lower end 2 of stent. In particular, each leaflet guard arch 50*a*, 50*b*, 50*c* has a shape that is roughly similar to the shape of the positioning arch 15*a*, 15*b*, 15*c* in between the corresponding leaflet guard arch 50*a*, 50*b*, 50*c* is arranged. Furthermore, each leaflet guard arch 50*a*, 50*b*, 50*c* extends in the same direction as the positioning arch 15*a*, 15*b*, 15*c*.

In the stent design of the twelfth embodiment, each arm of a leaflet guard arch 50*a*, 50*b*, 50*c* merges at about the mid-point of the length of an arm of a radial arch 32*a*, 32*b*, 32*c* into the arm of an opposing radial arch 32*a*, 32*b*, 32*c*. It can be seen from the cutting pattern shown in FIG. 12 that, according to the stent design of the twelfth embodiment, the leaflet guard arches 50*a*, 50*b*, 50*c* do not project in the longitudinal direction L of the stent approximately beyond the plane in which the lower end portion of the at least one fastening portion 11 configured in each arm 16*a*', 16*a*", 16*b*', 16*b*", 16*c*', 16*c*" of retaining arch 16*a*, 16*b*, 16*c* are situated. The leaflet guard arches 50*a*, 50*b*, 50*c* may extend lower than the lower end of the fastening portion 11 so long as the positioning arches 15*a*, 15*b*, 15*c* can deploy during the expansion of the stent 10 and that the leaflet guard arches 50*a*, 50*b*, 50*c* do not interfere during deployment.

In this regard, during the insertion procedure, the stent with a valvular prosthesis affixed thereto can be sequentially released upon reaching the site of implantation at the heart wherein, during a first release step, the proximal side K of the delivery portion of the insertion catheter system is manipulated such that the positioning arches 15*a-c* of stent are released while the remaining parts of the stent, in particular the leaflet guard arches 50*a*, 50*b*, 50*c*, the retaining arches 16*a*, 16*b*, 16*c*, the auxiliary arches 18*a-c* and the radial arches 32*a-c* are still in their collapsed state (cf. FIG. 18*a*). The positioning arches 15*a-c* released during the first release step expand and spread radially outward. The expanded positioning arches 15*a-c* can then be inserted into the pockets T of the patient's native cardiac valve H by suitably moving the proximal side K of the delivery portion of the catheter system (cf. FIG. 18*a*).

In the second release step which follows, the proximal side K of the delivery portion of the insertion catheter system is manipulated such that the leaflet guard arches 50*a*, 50*b*, 50*c* are released while the remaining parts of the stent, in particular the retaining arches 16a, 16b, 16c, the auxiliary arches 18a-c and the radial arches 32a-c are still in their collapsed state. The leaflet guard arches 50a, 50b, 50c released during the second release step expand and spread radially outward. The expanded leaflet guard arches 50a, 50b, 50c push the diseased leaflets, i.e. the leaflets of the native (diseased) cardiac valve, to the neighboring tissue or blood vessel.

In the third release step which follows, the proximal side K of the delivery portion of the insertion catheter system is manipulated such that the arches forming the lower end 2 of the stent (auxiliary arches 18a-c and retaining arches 16a, 16b, 16c) are released while the upper end 3 of the stent is however still firmly affixed to the proximal side K of the delivery portion by using a sleeve-like portion and is not released (cf. FIG. 18b). Also, the radial arches 32a-c are still in their compressed state.

If a functional test shows that the valvular prosthesis 100 affixed to the stent satisfactorily functions, the sleeve-like portion at the proximal side K of the catheter system can be distally pushed further in the direction to the lower end section of the stent 10 in order to release the radial arches 32a, 32b and 32c.

Then, also the upper end section 3 of the stent 10 with the catheter retaining means 23 is fully released, as shown in FIG. 18c. This can be obtained by distally pushing the sleeve-like portion at the delivery portion of the catheter system further in the direction to the lower end section 3 of the stent 10.

The positioning arches 15a-c disposed on the stent and also the retaining arches 16a, 16b, 16c may be curved in convex and arched fashion in the direction to the lower end section of the stent; i.e. toward the lower end 2 of the stent, whereby such a rounded form may reduce injuries to the artery as well as facilitate the unfolding during the self-expansion. Such a design may enable an easier insertion of the positioning arches 15a-c into the pockets of the native cardiac valve without correspondingly injuring the neighboring tissue or blood vessels.

Although not explicitly illustrated in the cutting pattern according to FIG. 12, the leaflet guard arches 50a, 50b, 50c are preferably programmed so that they extend in a radial direction outside the circumference of the stent when the stent of the twelfth embodiment is in its expanded state. In this way, an increased contact force can be applied to the leaflets of the native (diseased) cardiac valve when the stent of the twelfth embodiment is in its expanded and implanted state. This, in turn, allows an increased security in the fixing of the stent in situ.

When the stent is in its expanded and implanted state, the leaflet guard arches 50a, 50b, 50c actively keep the diseased leaflets, i.e. the leaflets of the native cardiac valve, from impinging the leaflet tissue of the valvular prosthesis attached to the stent, when the positioning arches 15a, 15b, 15c are placed outside, the native leaflets. In addition, the leaflet guard arches 50a, 50b, 50c may also provide additional anchoring and securing against migration. This feature is unique compared to the cage known from the prior art stent designs which are not provided with positioning arches to push the diseased leaflets out of the way.

In addition to the above described features, the stent design according to the twelfth embodiment further differs from the stent design of, for example, the fifth embodiment in that the stent according to the twelfth embodiment is provided with additional arches. In the expanded state of the stent, each of these additional arches (hereinafter "extra arches") has a substantially U-shaped or V-shaped structure which is closed to the lower end 2 of stent. In particular, each extra arch extends in the same direction as the retaining arch 16a, 16b, 16c and the auxiliary arch 18a, 18b, 18c and positioned therebetween.

In detail, according to the cutting pattern depicted in FIG. 12, the stent of the twelfth embodiment is provided with a total of six extra arches 60a-f, each comprising two arms. These extra arches 60a-f exert a radially-acting contact force against the wall of the blood vessel in the implanted state of stent, thereby further improving anchoring of the stent at the site of implantation.

Providing retaining arches 16a, 16b, 16c and auxiliary arches 18a, 18b, 18c on the one hand and extra arches 60a-f on the other hand may provide a radial force being exerted on the vascular wall by the respective lower end portions of these arches. This provides both a secure seal of a valvular prosthesis affixed to stent relative the vascular wall, as well as a secure anchoring of the stent, at the site of implantation in the heart.

As can be seen from the cutting pattern according to FIG. 12, the stent of the twelfth embodiment comprises a total of three essentially U-shaped or V-shaped extra arches 60a-f which are closed towards the lower end 2 of the stent. Each extra arch connects a retaining arch 16a, 16b, 16c with an auxiliary arch 18a, 18b, 18c neighboring the retaining arch 16a, 16b, 16c. Hence, in the stent according to the twelfth embodiment, one extra arch is allocated to each retaining arch 16a, 16b, 16c and each auxiliary arch 18a, 18b, 18c.

This stent design particularly provides a total of twelve arches (retaining arches 16a, 16b, 16c, auxiliary arches 18a, 18b, 18c and extra arches 60a-f) substantially uniformly distributed around the lower end region 2 of stent, each of which press against the vascular wall and effectively hold the stent in position in the expanded and implanted state of stent. Hence, in a top plan view of the lower end region 2 of the expanded stent (not explicitly shown), the lower end region 2 of the stent exhibits a polygonal structure having a plurality of vertices formed from the individual arms 16a', 16a", 16b', 16b", 16c', 16c" of the retaining arches 16a, 16b, 16c, the individual arms 18a', 18a", 18b', 18b", 18c', 18c" of the auxiliary arches 18a, 18b, 18c, as well as from the individual arms of the extra arches 60a, 60b, 60c, 60d, 60e, 60f. In this regard, the stent according to the twelfth embodiment has a lower end section 2 with a continuous design that may provide a substantially uniform radial force to help secure the stent in its implanted stage and resist migration. Such a radial force may also help to minimize the risk of leakage.

On the other hand, the extra arches 60a-f of the stent according to the twelfth embodiment may not increase the overall length of the stent. Hence, although this stent design may provide uniform radial force, the risk of contacting with the nerve bundles and heart block if the lower end portion of the stent is below the annulus at the location where the nerve bundles enter, may be reduced.

A stent 10 according to a thirteenth embodiment of the invention is shown in FIGS. 13b and 13c. In detail, FIGS. 13b and 13c show various side views the stent 10 in its expanded state while a flat roll-out view of a stent 10 according to the thirteenth embodiment is shown in FIG. 13a. The roll-out view depicted in FIG. 13a corresponds to a two-dimensional projection of a cutting pattern suitable for the manufacture of a stent according to the thirteenth embodiment. Elements in FIGS. 13a-c that are generally similar to previously described elements have the same reference numbers.

As in the embodiments previously described, the stent 10 of the thirteenth embodiment is configured as a one-piece structure cut from a portion of tube, in particular from a metal tube, the cutting pattern being shown as a two-dimensional projection in FIG. 13*a*.

The thirteenth embodiment of the stent 10 is similar in structure and function with respect to the previously described twelfth embodiment. To avoid repetition, reference is therefore made to the above description of the twelfth embodiment.

Hence, the stent 10 according to the thirteenth embodiment is provided with corresponding retaining arches 16*a*, 16*b*, 16*c*. One retaining arch 16*a*, 16*b*, 16*c* is allocated to each positioning arch 15*a*, 15*b*, 15*c*, wherein each retaining arch 16*a*, 16*b*, 16*c* is connected to a neighboring retaining arch by means of an auxiliary arch 18*a*, 18*b*, 18*c*. Also, according to the thirteenth embodiment of the stent 10, at least one fastening portion 11 with a number of fastening holes 12 is configured in each arm 16*a'*, 16*a"*, 16*b'*, 16*b"*, 16*c'*, 16*c"* of the retaining arches 16*a*, 16*b*, 16*c*.

In addition to the at least one fastening portion 11, the stent 10 according to the thirteenth embodiment also comprises first and second additional fastening portions 11*a*, 11*b* for additional fastening of a valvular prosthesis or parts of a valvular prosthesis. In this regard, the stent 10 has a configuration with an enhanced number of fastening portions 11, 11*a*, 11*b* to attach the material of a valvular prosthesis.

As in the twelfth embodiment, the stent 10 depicted in FIG. 13*b* or 13*c* is also provided with a total of three leaflet guard arches 50*a*, 50*b*, 50*c*, each of said leaflet guard arches 50*a*, 50*b*, 50*c* comprising two leaflet guard arms. It can be seen from the cutting pattern shown in FIG. 13*a* that, a leaflet guard arch 50*a*, 50*b*, 50*c* is provided in between each positioning arch 15*a*, 15*b*, 15*c*. Hence, in the stent design according to the thirteenth embodiment, one leaflet guard arch 50*a*, 50*b*, 50*c* is allocated to each positioning arch 15*a*, 15*b*, 15*c*.

As shown in FIG. 13*b* or 13*c*, each arm of a leaflet guard arch 50*a*, 50*b*, 50*c* merges at about the mid-point of the length of an arm of a radial arch 32*a*, 32*b*, 32*c* into the arm of an opposing radial arch 32*a*, 32*b*, 32*c*. Again, as in the stent design according to the twelfth embodiment, the leaflet guard arches 50*a*, 50*b*, 50*c* of the stent 10 according to the thirteenth embodiment project in the longitudinal direction L of the stent approximately to the plane in which the lower end portion of the at least one fastening portion 11 configured in each arm 16*a'*, 16*a"*, 16*b'*, 16*b"*, 16*c'*, 16*c"* of retaining arch 16*a*, 16*b*, 16*c* is placed. In this regard, during the insertion procedure, the stent 10 of the thirteenth embodiment can be sequentially released as already described in connection with the stent design of the twelfth embodiment.

As previously mentioned, the respective arms of the leaflet guard arches 50*a*, 50*b*, 50*c* merge at about the mid-point of the length of an arm of a radial arch 32*a*, 32*b*, 32*c* into the arm of an opposing radial arch 32*a*, 32*b*, 32*c*. Contrary to the twelfth embodiment, however, in the stent design of the thirteenth embodiment, the arms 32*a'*, 32*a"*, 32*b'*, 32*b"*, 32*c'*, 32*c"* of the radial arches 32*a*, 32*b*, 32*c* do not merge into an arm 15*a'*, 15*a"*, 15*b'*, 15*b"*, 15*c'*, 15*c"* of an opposing positioning arch 15*a*, 15*b*, 15*c*. According to the stent design of the thirteenth embodiment, the respective arms 32*a'*, 32*a"*, 32*b'*, 32*b"*, 32*c'*, 32*c"* of the radial arches 32*a*, 32*b*, 32*c* are not directly connected with the arms 15*a'*, 15*a"*, 15*b'*, 15*b"*, 15*c'*, 15*c"* of an opposing positioning arch 15*a*, 15*b*, 15*c*.

Rather, the leaflet guard arms of the stent design according to the thirteenth embodiment are directly connected with one of the second connecting webs 25, i.e. with one of the webs which connect the connecting portions 22 of the stent 10 with the catheter retaining means 23. As already mentioned above, the connecting portions 22 of the stent 10 is used for connecting each two adjoining arms 15*b"*, 15*c'*; 15*c"*, 15*a'*; 15*a"*, 15*b'* of two neighboring positioning arches 15*b*, 15*c*, 15*a*. In this regard, the deployment of the positioning arches 15*a*, 15*b*, 15*c* is enhanced without releasing the leaflet guard arches 50*a*, 50*b*, 50*c* until the positioning arches 15*a*, 15*b*, 15*c* are placed behind the diseased leaflets in the valve pockets.

As can be seen in particular from the two-dimensional cutting pattern according to FIG. 13*a*, the stent design of the thirteenth embodiment is also provided with a total of six extra arches 60*a-f*, each of which having a substantially U-shaped or V-shaped structure which is closed to the lower end 2 of the stent 10. In particular, each extra arch 60*a-f* extends in the same direction as the retaining arch 16*a*, 16*b*, 16*c* and the auxiliary arch 18*a*, 18*b*, 18*c*, between which the corresponding extra arch 60*a-f* is provided.

Referring to FIG. 13*b* or FIG. 13*c*, the stent design of the thirteenth embodiment provides a total of twelve arches (retaining arches 16*a*, 16*b*, 16*c*, auxiliary arches 18*a*, 18*b*, 18*c* and extra arches 60*a-f*) uniformly distributed around the lower end region 2 of stent 10. In the expanded and implanted stage of the stent 10, this specific structure of the lower end section 2 shall press against the vascular wall to hold the stent 10 in position.

As in the stent design according to the twelfth embodiment, the lower end region 2 of the stent 10 of the thirteenth embodiment also exhibits a polygonal structure having eighteen vertices formed from the individual arms 16*a'*, 16*a"*, 16*b'*, 16*b"*, 16*c'*, 16*c"* of retaining arches 16*a*, 16*b*, 16*c*, the individual arms 18*a'*, 18*a"*, 18*b'*, 18*b"*, 18*c'*, 18*c"* of the auxiliary arches 18*a*, 18*b*, 18*c*, as well as the individual arms of the extra arches 60*a-f*. In this regard, the stent 10 of the thirteenth embodiment has a lower end section 2 with a continuous design which may provide substantially uniform radial force to help secure the stent 10 in its implanted stage and may help resist migration. Such a uniform radial force may also help minimize the risk of blood leakage in the expanded and implanted stage of the stent 10 and a valvular prosthesis affixed thereto.

The stent 10 according to the thirteenth embodiment also differs from the stent of the twelfth embodiment in that additional fastening portions are provided at the lower end 2 of the stent 10. In detail, according to FIG. 13*b* or FIG. 13*c*, the stent 10 of the thirteenth embodiment is provided with three essentially U-shaped or V-shaped auxiliary arches 18*a*, 18*b*, 18*c*, each of said auxiliary arches 18*a*, 18*b*, 18*c* being provided at its lower end section with an additional fastening portion provided in the head portion 31 of the respective auxiliary arches 18*a*-18*c*.

As can be seen from FIG. 13*a*, a defined plurality of fastening holes 12*d* are configured in the respective fastening portions provided in the respective head portions 31 of the auxiliary arches 18*a*, 18*b*, 18*c*. Furthermore, in the stent design of the thirteenth embodiment, the respective arms 16*a'*, 16*a"*, 16*b'*, 16*b"*, 16*c'*, 16*c"* of each retaining arch 16*a*, 16*b*, 16*c* extend from the fastening portion 11 to the lower end 2 of the cardiac valve stent 10 and are connected together by means of a connecting portion 30, wherein this connection portion 30 is also provided with fastening holes 12*e*.

In this regard, the auxiliary arches 18a, 18b, 18c with the fastening holes 12d on the one hand and the connection portions 30 with the fastening holes 12e on the other hand provide for additional fastening holes 12d, 12e at the lower end section 2 of the stent 10, wherein these additional fastening holes 12d, 12e are arranged to be equally distributed around the continuous design of the lower end section 2 of the stent 10. A thread 101 or a thin wire with which a valvular prosthesis 100 is attached to stent 10 may be guided through each of the respective fastening holes 12d, 12e.

Hence, the additional fastening holes 12d, 12e are provided at the lower end section 2 of the stent 10 for additional fastening of a valvular prosthesis or parts of a valvular prosthesis. The presence of additional fastening holes 12d, 12e at the lower end section 2 of the stent 10 may provide additional structure to attach the valve skirt of the valvular prosthesis and minimize leakage. In addition, the additional fastening holes 12d, 12e at the lower end section 2 of the stent 10 may help keep the skirt of the valvular prosthesis from moving when the valve is collapsed into a catheter for implanting the stent with the valvular prosthesis affixed thereto.

FIG. 14b shows a side view of a stent 10 according to the fourteenth embodiment of the invention, whereby the stent 10 is in its completely expanded state. The stent 10 according to the fourteenth embodiment exhibits a structure integrally out from a portion of a tube, in particular a metal tube. The cutting pattern used to form the design of the stent 10 according to the fourteenth embodiment is depicted in a two-dimensional projection in FIG. 14a.

Again, elements in FIGS. 14a and 14b that are generally similar to previously described elements have the same reference numbers.

Except for the structure of the lower end section 2, the stent 10 according to the fourteenth embodiment is substantially similar to the stent according to the thirteenth embodiment of the present invention described above with reference to FIGS. 13a and 13b.

Hence, the stent 10 according to the fourteenth embodiment has also a total of three positioning arches 15a, 15b, 15c, which again undertake the function of automatic positioning of the stent 10. As in other embodiments of the stent 10, each of the positioning arches 15a, 15b, 15c has a radiused head portion 20, which engages in the pockets of the native heart valve H being treated during positioning of the stent 10 at the implantation site in the heart (see FIG. 18a).

The fourteenth embodiment of the stent 10 also includes radial arches 32a, 32b, 32c. As is shown most clearly in FIG. 14b, the stent 10 has three radial arches 32a, 32b, 32c, with each arch 32a, 32b, 32c located between the two arms 15a, 15a', 15b, 15b', 15c, 15c' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

As in the thirteenth embodiment, in the stent design of the fourteenth embodiment, the respective arms 32a', 32a", 32b', 32b", 32c', 32c" of the radial arches 32a, 32b, 32c are not directly connected with the arms 15a', 15a", 15b', 15b", 15c', 15c" of an opposing positioning arch 15a, 15b, 15c. Rather, the respective arms 32a', 32a", 32b', 32b", 32c', 32c" of the radial arches 32a, 32b, 32c are directly connected to leaflet guard arms which in turn are directly connected with one of the second connecting webs 25, i.e. with one of the webs which connect the connecting portions 22 of the stent 10 with the catheter retaining means 23. In this regard, the deployment of the positioning arches 15a, 15b, 15c is enhanced without releasing the leaflet guard arches 50a, 50b, 50c until the positioning arches 15a, 15b, 15c are placed behind the diseased leaflets in the valve pockets.

A total of three retaining arches 16a, 16b, 16c is also provided. One retaining arch 16a, 16b, 16c is allocated to each positioning arch 15a, 15b, 15c. Also, according to the fourteenth embodiment of the inventive stent 10, at least one fastening portion 11 with a number of fastening holes 12 is configured in each arm 16a', 16a", 16b', 16b", 16c', 16c" of the retaining arches 16a, 16b, 16c.

In addition to the at least one fastening portion 11, the stent 10 according to the fourteenth embodiment also comprises first and second additional fastening portions 11a, 11b for additional fastening of the tissue component(s) of the valvular prosthesis or parts of a valvular prosthesis. In this regard, the stent 10 has a configuration with an enhanced number of fastening portions 11, 11a, 11b to attach the material of a valvular prosthesis.

As in the twelfth or thirteenth embodiment, the stent 10 depicted in FIG. 14b is also provided with a total of three leaflet guard arches 50a, 50b, 50c, each of said leaflet guard arches 50a, 50b, 50c comprising two leaflet guard arms. As shown in the cutting pattern depicted in FIG. 14a, a leaflet guard arch 50a, 50b, 50c is provided in between each positioning arch 15a, 15b, 15c, i.e. one leaflet guard arch 50a, 50b, 50c is allocated to each positioning arch 15a, 15b, 15c.

The respective arms of the leaflet guard arches 50a, 50b, 50c merges at about the mid-point of the length to the arm of an opposing radial arch 32a, 32b, 32c. As in the thirteenth embodiment, the arms 32a', 32a", 32b', 32b", 32c', 32c" of the radial arches 32a, 32b, 32c do not merge into an arm 15a', 15a", 15b', 15b", 15c', 15c" of an opposing positioning arch 15a, 15b, 15c, because the respective arms 32a', 32a", 32b', 32b", 32c', 32c" of the radial arches 32a, 32b, 32c are not directly connected with the arms 15a', 15a", 15b', 15b", 15c', 15c" of an opposing positioning arch 15a, 15b, 15c. Rather, the leaflet guard arms of the stent design according to the fourteenth embodiment are directly connected with one of the second connecting webs 25, i.e. with one of the webs which connect the connecting portions 22 of the stent 10 with the catheter retaining means 23. As already mentioned above, the connecting portions 22 of the stent 10 is used for connecting each two adjoining arms 15b", 15c'; 15c", 15a'; 15a", 15b' of two neighboring positioning arches 15b, 15c, 15a.

The stent 10 depicted in FIG. 14b is not provided with extra arches at its lower end section 2. Rather, similar to the stent design according to the seventh embodiment (cf. FIGS. 7a-c), the stent 10 of the fourteenth embodiment comprises at least one annular collar 40, which forms the lower end section 2 of the stent 10. This at least one collar 40 serves as an additional anchoring measure for the stent 10 depicted in FIG. 14b.

The at least one annular collar 40 may be connected to each or a part of the lower end sections of the respective arms 16a', 16a", 16b', 16b", 16c', 16c" of the retaining arches 16a, 16b, 16c, as can be seen in particular from the cutting pattern pursuant to FIG. 14a.

The at least one annular collar 40 exhibits a plurality of supporting webs 41 which run parallel to the longitudinal axis of the stent 10 in the non-expanded state of said stent 10 and are inter-connected by transversal webs 42 (cf. FIG. 14a). In the expanded state of stent 10, the supporting webs 41 and the transversal webs 42 form a rhomboidal or serpentine-like annular collar 40 which abuts against the vascular wall in the implanted state of the stent 10. FIG. 14*b* shows the annular collar 40 in the expanded state.

The annular collar 40 serves as a supporting body through which the radial forces developing due to the self-expansion are transmitted to the vascular wall. Since a relatively large contact area of the stent 10 interacts with the vascular wall, and because of the rhomboidal or serpentine structure to the annular collar 40, there may be a decreased risk of injury to the artery or the tissue despite the increased radial forces.

It is important to note that a certain amount of radial force is needed to prevent migration of the implanted endoprosthesis 1. Hence, a more uniform structure of the lower end section of the stent provides a more uniform distribution of the radial pressure provided by the stent in its fully expanded state. In this regard, the radial pressure provided by the stent in its fully expanded state is distributed and there are reduced high contact pressures for the same overall radial force.

Accordingly, not only the rigidity of the stent 10 can be increased after its self-expansion by the providing of the annular collar 40, but also the anchorage of the stent 10 in the implanted state can be improved or strengthened. Additionally, the annular cross-sectional shape to annular collar 40 increases the seal between the vascular wall and the stent having a vascular prosthesis affixed thereto.

Such an annular collar 40 is advantageously configured as a self-expandable supporting structure which advantageously effects an even further improved anchoring of the stent 10 at the site of implantation due to its radially-outward-acting contact pressure and its design such that a displacing of the stent 10 with a valvular prosthesis affixed thereto can be further prevented.

The stent 10 depicted in FIG. 14*b* is not provided with auxiliary arches at the lower end section of the stent body. Rather, instead of auxiliary arches, the stent 10 according to the fourteenth embodiment comprises a structure of lattice cells 70 formed by a plurality of struts in the area between the arms of two neighbouring (adjacent) retaining arches 16*a*, 16*b*, 16*c*, thereby providing for an additional support of the commissures of a heart valve prosthesis attached to the stent 10.

In addition, this structure of the lattice cells 70 formed by a plurality of struts in the area between the adjacent arms of two neighbouring retaining arches 16*a*, 16*b*, 16*c* may provide uniform stent structure which may minimize blood leakage in the implanted stage of the stent 10 having a heart valve prosthesis attached thereto.

Hence, according to the stent design of the fourteenth embodiment, the lower end section of the annular collar 40 is provided at the lower end section of the stent body and connected with the stent body via the retaining arches 16*a*, 16*b*, 16*c* on the one hand and the previously described structure of the lattice cells 70 on the other hand.

Although not shown in FIG. 14*b*, however, the stent 10 of the fourteenth embodiment may of course also comprise auxiliary arches similar to the stent design previously described with reference to the embodiments depicted in FIGS. 7*b* and 7*c*.

It is important to note, however, that the stent 10 depicted in FIG. 14*b* comprises a several number of eyelets 12*f* uniformly distributed around the lower end section of the annular collar 40. These eyelets 12*f* can be used for fixing a heart valve prosthesis (not shown in FIG. 14*b*) to the stent 10, which may reduce the risk of an axial displacement of the heart valve prosthesis 100 relative to the stent 10.

FIG. 15 shows a flat roll-out view of a cardiac valve stent of still another embodiment (fifteenth embodiment). The roll-out view depicted in FIG. 15 corresponds to a two-dimensional projection of a cutting pattern which can be used to cut a cardiac valve stent of the fifteenth embodiment in accordance with the invention as one integral piece from a portion of a tube, in particular a metal tube. A side view or a perspective view of a stent according to the fifteenth embodiment is not shown in the drawings.

Again, elements in FIG. 15 that are generally similar to previously described elements have the same reference numbers compared with the reference numbers previously used for the similar elements.

The stent according to the fifteenth embodiment essentially corresponds to the stent of the fourteenth embodiment previously described with reference to FIGS. 14*a* and 14*b*. To avoid repetition, reference is therefore made to the above description of the fourteenth embodiment.

In the two-dimensional projection of a cutting pattern according to FIG. 15, the corresponding cutting lines for cutting out respective leaflet guard arches have been omitted for clarity reasons only. Hence, although the cutting pattern according to FIG. 15 is—for the sake of clarity only—not provided with corresponding cutting lines, a stent which has been cut in accordance with the design of the fifteenth embodiment may also provided with corresponding leaflet guard arches. In particular, it is advantageous when the stent according to the fifteenth embodiment is provided with a total of three leaflet guard arches, each of said three leaflet guard arches being constituted by two leaflet guard arms. As the previously discussed stent designs according to the twelfth, thirteenth and fourteenth embodiments, a stent of the fifteenth embodiment shall have a structure with a total of three leaflet guard arches, wherein one of said three leaflet guard arches is allocated to each positioning arch 15*a*, 15*b*, 15*c* and provided in between each positioning arch 15*a*, 15*b*, 15*c*.

Furthermore, in the stent design of the fifteenth embodiment each of the leaflet guard arches shall preferably have a substantially U-shaped or V-shaped structure which is closed to the lower end 2 of stent. In particular, each leaflet guard arch shall have a shape that is roughly similar to the shape of the positioning arch 15*a*, 15*b*, 15*c* in between the corresponding leaflet guard arch is arranged. Furthermore, each leaflet guard arch shall extend in the same direction as the positioning arch 15*a*, 15*b*, 15*c* in between the corresponding leaflet guard arch is provided.

The stent design according to the fifteenth embodiment of the invention is also provided with an annular collar 40 which is arranged at the lower end section of the stent body. As in the stent design according to the fourteenth embodiment, this at least one collar 40 serves as an additional anchoring measure for a stent cut from a portion of a tube by using the cutting pattern depicted in FIG. 15.

According to the cutting pattern depicted in FIG. 15, the at least one annular collar 40 is connected to the head portions 30 provided at the lower end sections of the respective arms 16*a'*, 16*a"*, 16*b'*, 16*b"*, 16*c'*, 16*c"* of the retaining arches 16*a*, 16*b*, 16*c*. As can be seen from the cutting pattern pursuant to FIG. 15, the at least one annular collar 40 exhibits a plurality of supporting webs 41 which run parallel to the longitudinal axis L of the stent in the non-expanded state of said stent and are inter-connected by transversal webs 42. As in the stent design according to the fourteenth embodiment, in the expanded state of the stent, the supporting webs 41 and the transversal webs 42 will form a rhomboidal or serpentine-like annular collar 40 which abuts against the vascular wall in the implanted state of the stent.

The technical effects which can be obtained by the at least one collar 40 provided at the lower end section 2 of the stent have already been described in connection with the stent of the fourteenth embodiment of the invention. Hence, in order to avoid repetitions, reference is made to the previously discussed aspects.

The stent design according to the fifteenth embodiment differs from the stent design according to the fourteenth embodiment in that at the lower end section of every second supporting web 41 of the annular collar 40 an eyelet 12f as an additional fastening means is provided. In this regard, the eyelets 12f are more uniformly distributed around the lower end section of the annular collar 40, thereby providing a more uniform fixation of a heart valve prosthesis to the stent. Hence, the risk of an axial displacement of the heart valve prosthesis relative to the stent may be further reduced.

As in the stent design according to the previously described fourteenth embodiment, the stent design of the fifteenth embodiment is further provided with a structure of lattice cells 70 formed by a plurality of struts in the area between the arms of two neighbouring (adjacent) retaining arches 16a, 16b, 16c. As depicted in the cutting pattern of FIG. 15, the struts which are forming the structure of lattice cells 70 are respectively connected to the arms of the retaining arches 16a, 16b, 16c. In this regard, an additional support of the commissures of a heart valve prosthesis attached to the stent is provided.

The stent design of the fifteenth embodiment differs from the previously described stent designs in that the stent according to the fifteenth embodiment is not provided with first additional fastening portions are arranged between the first and second arms 16a'', 16b'; 16b'', 16c'; 16c'', 16a' of two neighboring retaining arches 16a, 16b, 16c and extend from the respective lower ends 17d of the first connecting webs 17 in the direction of the lower end 3 of the stent.

Rather, according to the stent design of the fifteenth embodiment, the respective arms 16a', 16a'', 16b', 16b'', 16c', 16c'' of the retaining arches 16a, 16b, 16c are provided with a number of additional fastening portions 11c, each having a number of additional fastening holes 12a provided for fastening the tissue component(s) of a valvular prosthesis. Specifically, the additional fastening portions 11c are separated from each other and distributed over the length of each arm 16a', 16a'', 16b', 16b'', 16c', 16c'' of the retaining arches 16a, 16b, 16c. The additional fastening holes 12a are directly formed in the additional fastening portions 11c. It is of course conceivable that the additional fastening holes 12a are not formed in the arms 16a', 16a'', 16b', 16b'', 16c', 16c'' of the retaining arches 16a, 16b, 16c but are configured as eyelets. The additional fastening holes 12a enable the upper region of a valvular prosthesis to be additionally secured to the stent.

The size of the additional fastening holes 12a may be adapted to the thickness of particular thread or wire used to fasten the valvular prosthesis to the stent. The cross-sectional shape of the additional fastening holes 12a may also be adapted to the cross-sectional shape of the thread or wire used for fastening the valvular prosthesis. Due to the presence of a number of additional fastening holes 12a for fixing the valvular prosthesis to the cardiac valve stent, the fastening position of the valvular prosthesis to the cardiac valve stent can be precisely defined.

As an alternative to fastening holes 12a, the same region of the stent 10 may be provided with one or more additional notches. These notches perform a similar function as the fastening holes 12a and assist with additional anchoring of a prosthetic valve within the stent.

A stent 10 according to a sixteenth embodiment of the invention is shown in FIGS. 16b to 16g. In particular, FIG. 16b is a first perspective side view of a cardiac valve stent according to the sixteenth embodiment of the invention, whereby the cardiac valve stent 10 is shown in its expanded state. Second and third side views of the cardiac valve stent 10 in its expanded state are shown in FIGS. 16c and 16d.

On the other hand, FIG. 16e shows a plan view of the upper end of the cardiac valve stent 10 according to the sixteenth embodiment of the invention in its expanded state.

A flat roll-out view of a stent according to the sixteenth embodiment is shown in FIG. 16a.

FIG. 16f shows a side view of an endoprosthesis for treating a narrowed cardiac valve or a cardiac valve insufficiency, where the endoprosthesis comprises a cardiac valve stent which is similar to the fifteenth embodiment of the invention for holding a valvular prosthesis. In detail, FIG. 16f shows a valvular prosthesis 100 attached to a stent 10 as an example on how to fix a valvular prosthesis 100 to a stent 10. This example is similarly applicable to the other stent embodiments described herein.

FIG. 16g shows a side view of an endoprosthesis for treating a narrowed cardiac valve or a cardiac valve insufficiency, where the endoprosthesis comprises the cardiac valve stent according to the sixteenth embodiment of the invention for holding a valvular prosthesis.

As in the embodiments previously described, the stent 10 of the sixteenth embodiment is again configured as a one-piece structure cut from a portion of tube, in particular from a metal tube, the cutting pattern being shown as a two-dimensional projection in FIG. 16a.

Also, the stent design according to the sixteenth embodiment of the invention is also provided with an annular collar 40 which is arranged at the lower end section of the stent body. As in the stent design according to the fourteenth or fifteenth embodiment, this at least one collar 40 serves as an additional anchoring measure for a stent cut from a portion of a tube by using the cutting pattern depicted in FIG. 15.

The sixteenth embodiment of the stent 10 is similar in structure and function with respect to the fifteenth embodiment. To avoid repetition, reference is therefore made to the above description of the fifteenth embodiment. In particular, essentially U-shaped or V-shaped radial arches 32a, 32b, 32c are likewise provided to increase the radially acting contact force in the upper region of the stent 10.

In addition, the stent 10 according to the sixteenth embodiment is provided with corresponding retaining arches 16a, 16b, 16c. One retaining arch 16a, 16b, 16c is allocated to one of the positioning arches 15a, 15b, 15c. Also, according to the sixteenth embodiment of the inventive stent 10, a number of additional fastening portions 11c with a number of additional fastening holes 12a is configured in each arm 16a', 16a'', 16b', 16b'', 16c', 16c'' of the retaining arches 16a, 16b, 16c.

In addition to the additional fastening portions 11c, the stent 10 according to the sixteenth embodiment also comprises second additional fastening portions 11b for additional fastening of the tissue component(s) of a valvular prosthesis or parts of a valvular prosthesis. As already discussed with respect to the twelfth embodiment, each first connecting web 17 of the stent is provided with at least one second additional fastening portion 11b, said at least one second additional fastening portion 11b being a portion which comprises additional auxiliary fastening holes 12c and/or other fastening means. The at least one second additional fastening portion 11b extends essentially in the longitudinal direction L of stent according to the twelfth embodiment.

In this regard, the stent 10 according to the sixteenth embodiment has a configuration with a number of fastening portions 11, 11b to attach the material of a valvular prosthesis.

As in the thirteenth embodiment of the invention, the stent 10 depicted in FIGS. 16b-g may also be provided with leaflet guard arches, wherein one leaflet guard arch may be provided in between each positioning arch 15a, 15b, 15c. Hence, although for reasons of clarity not explicitly shown in FIGS. 16b-g, in the stent design according to the sixteenth embodiment, one leaflet guard arch may be allocated to each positioning arch 15a, 15b, 15c as previously discussed with reference to the twelfth, thirteenth or fourteenth embodiment.

As already mentioned, the structure of the sixteenth embodiment is quite similar to the structure of the previously described fifteenth embodiment. However, the sent design depicted in FIGS. 16b-g differs from the fifteenth embodiment particularly with respect to the specific structure of the respective arms 16a', 16a", 16b', 16b", 16c', 16c" of the retaining arches 16a, 16b, 16c.

In detail, according to the stent design of the sixteenth embodiment, in the expanded state of the stent 10, the respective arms 16a', 16a", 16b', 16b", 16c', 16c" of the retaining arches 16a, 16b, 16c are formed similar to how a surgical placed tissue valve might be constructed. Furthermore, the respective arms 16a', 16a", 16b', 16b", 16c', 16c" of the retaining arches 16a, 16b, 16c are provided with a number of additional fastening portions 11c, each having a number of additional fastening holes 12a or eyelets provided for fastening the tissue component(s) of a valvular prosthesis. These additional fastening holes 12a or eyelets provide for good attachment points of the leaflet and skirt of a heart valve prosthesis attached to the stent 10.

Hence, according to the stent design of the sixteenth embodiment, in the expanded state of the stent 10, the respective arms 16a', 16a", 16b', 16b", 16c', 16c" of the retaining arches 16a, 16b, 16c have a shape that substantially matches the leaflets of a heart valve prosthesis attached to the stent 10. This specific design of the respective arms 16a', 16a", 16b', 16b", 16c', 16c" of the retaining arches 16a, 16b, 16c is unique for catheter delivered valves and has valve durability advantages. The so formed arms 16a', 16a", 16b', 16b", 16c', 16c" of the retaining arches 16a, 16b, 16c serve for supporting the skirt and edge of the leaflets of a heart valve prosthesis attached to the stent 10 across the gap behind the positioning arches 15a-c. As depicted, for example, in FIGS. 16b-d, the respective arms 16a', 16a", 16b', 16b", 16c', 16c" of the retaining arches 16a, 16b, 16c follow the shape of the leaflets of a valvular prosthesis (not shown in FIGS. 16b-d) affixed to the stent 10 in its expanded state. Furthermore, the respective arms 16a', 16a", 16b', 16b", 16c', 16c" of the retaining arches 16a, 16b, 16c are designed to have a minimized unsupported gap from one arm to the other arm of a retaining arch 16a, 16b, 16c at the location behind the positioning arches 15a-c.

In detail and as depicted in the cutting pattern shown in FIG. 16a, the respective arms 16a', 16a", 16b', 16b", 16c', 16c" of the retaining arches 16a, 16b, 16c are provided with a plurality of bending edges 33. These bending edges 33 divide each arm 16a', 16a", 16b', 16b", 16c', 16c" into a plurality of arm segments. The arm segments of a arm 16a', 16a", 16b', 16b", 16c', 16c" of the retaining arches 16a, 16b, 16c are interconnected thereby constituting a retaining arch arm which describes an essentially straight line in the not-expanded state of the stent 10. In this regard, reference is also made to the cutting pattern depicted in FIG. 16a which shows the uncurved configuration of the respective arms 16a', 16a", 16b', 16b", 16c', 16c" of the retaining arches 16a, 16b, 16c.

When manufacturing the stent 10, the stent structure and in particular the structure of the retaining arches 16a, 16b, 16c is programmed such that the respective arms 16a', 16a", 16b', 16b", 16c', 16c" of the retaining arches 16a, 16b, 16c have a curved shape in the expanded state of the stent 10. The shape of the respective arms 16a', 16a", 16b', 16b", 16c', 16c" of the retaining arches 16a, 16b, 16c is such defined that the arms follow the shape of the leaflets 102 of a valvular prosthesis 100 to be affixed to the stent 10 (cf. FIGS. 16f and 16g).

Hence, the respective arms 16a', 16a", 16b', 16b", 16c', 16c" of the retaining arches 16a, 16b, 16c of the stent 10, onto which the valvular prosthesis 100 is sewn or sewable, will change their shape when the stent 10 expands, wherein the retaining arches 16a, 16b, 16c are curved in the expanded state of the stent 10, but relatively straight when the stent 10 is collapsed.

As can be seen, for example, in FIGS. 16b-d, the curvature of the respective arms 16a', 16a", 16b', 16b", 16c', 16c" of the retaining arches 16a, 16b, 16c is achieved by segmenting the arms 16a', 16a", 16b', 16b", 16c', 16c". In detail, the arms 16a', 16a", 16b', 16b", 16c', 16c" are segmented by providing a plurality of bending edges 33. In the expanded state of the stent 10, two neighboring arm segments are angled relative to each other, wherein the bending point of these two neighboring arm segments is defined by the bending edge. 33 which is provided in between the both neighboring arm segments. Hence, the greater the number of bending edges 33 provided in an arm 16a', 16a", 16b', 16b", 16c', 16c" of a retaining arch 16a, 16b, 16c, the greater the number of arm segments which may extend in different directions in the expanded state of the stent 10. In this respect, the shape of the respective arms 16a', 16a", 16b', 16b", 16c', 16c" of the retaining arches 16a, 16b, 16c can be precisely adapted to the shape of the leaflets of the valvular prosthesis to be affixed to the stent 10.

Reference is made to FIGS. 16f and 16g which show side views of an endoprosthesis 1 for treating a narrowed cardiac valve or a cardiac valve insufficiency. In the embodiment depicted in FIGS. 16f and 16g, the stent 10 corresponds to a stent pursuant the sixteenth embodiment of the invention for holding a valvular prosthesis 100. The description of how the valvular prosthesis 100 is fixed to the stent 10 with respect to the sixteenth embodiment is also applicable to a stent 10 according to the other embodiments described herein.

The valvular prosthesis 100 comprises at least one leaflet 102 (see FIG. 16f or 16g) made from a biological or synthetic material. In particular, FIGS. 16f and 16g respectively show a side view of the endoprosthesis 1, whereby the cardiac stent 10 is shown in a fully expanded state.

To reduce longitudinal displacement of the valvular prosthesis 100 affixed to stent 10 relative to the stent 10, even during the peristaltic movement of the heart and the blood vessel in which stent 10 is deployed, the stent 10 according to the sixteenth embodiment of the invention comprises a plurality of fastening portions 11 extending in the longitudinal direction L of stent 10. In addition, the stent 100 according to the sixteenth embodiment is provided with additional fastening portions 11b, 11c. By means of both, the fastening portions 11 and the additional fastening portions 11b, 11c the tissue component(s) of the valvular prosthesis 100 is affixed to the stent 10.

In detail, the valvular prosthesis 100 is fastened to the stent 10 by means of a thread 101 or a thin wire which is guided through fastening holes 12, 12a of the fastening portions 11 and the additional fastening portions 11b, 11c, respectively. This allows fixing of the tissue component(s) of the valvular prosthesis 100 to the stent 10 at a predefined position relative to the stent 10.

It can further be seen from the FIG. 16f or FIG. 16g illustration how the valvular prosthesis 100 can be affixed to the stent 10 by means of threads 101. A pericardial valvular prosthesis 100 is used in the embodiment depicted which is sewn to fastening holes 12f, 12c provided in the fastening portions 11c of the retaining arches 16a, 16b, 16c on the one hand and in the fastening portions 11b on the other hand. The valvular prosthesis 100 may be tubular with a substantially circular cross-section. At the lower end 2 of the stent 10, the valvular prosthesis 100 exhibits a bead 105. This bead 105, which is annular in the plan view of endoprosthesis 1, is formed by turning the lower end of the valvular prosthesis 100 inside out by rolling it over on itself and defines the inflow edge of the endoprosthesis 1.

The annular bead 105 at the lower end of the valvular prosthesis 100 may provide anchoring of the peripheral area of the valvular prosthesis 100 to the blood vessel in the implanted state of the endoprosthesis 1, even given the peristaltic motion, and thus may provide a seal relative the vascular wall. Due to the annular collar 40 provided at the lower end section 2 of the stent 10, the annular bead 105 at the lower end of the valvular prosthesis 100 has a round shape adapted to the anatomy in the implantation side. In this regard, the contact surface between the lower end section 2 of the endoprosthesis 1 in its expanded and implanted state and the wall of the blood vessel, into which the endoprosthesis 1 is inserted, may be enhanced, thereby improving sealing between the endoprosthesis 1 and the wall of the blood vessel.

The annular bead 105 may achieve a seal of the valvular prosthesis 100 at the vascular wall despite the basic triangular structure to the stent 10 in a plan view of the expanded endoprosthesis 1. When implanting the endoprosthesis 1 in a native blood vessel any leakage between the peripheral area of the annular bead 105 and the vascular wall may be sealed by naturally-occurring accretion, in particular calcification. Accordingly, the bead-shaped area 105 provides a seal, particularly also during the filling phase of the heart cycle (diastole).

The material for the valvular prosthesis 100 and, in particular the material for the leaflets 102 of the valvular prosthesis 100 can be made from synthetics, animal valves or other animal tissues such as pericardium. The animal tissues can be from a number of types of animals. Preferably, the leaflet tissue of the valvular prosthesis 100 is from either bovine or porcine pericardium, but other animals can also be considered, for example equine, kangaroo, etc.

Animal pericardium is the preferred material for optimum valve design and the ability to collapse into a catheter system having a small diameter. Although bovine is preferred, the thickness is generally thicker than porcine and it has been discovered that there may be substantial swelling of the tissue (35%) during fixation. This swelling may make bovine more difficult to collapse for small catheter size deployment.

As depicted in FIG. 16e, the stent 10 according to the sixteenth embodiment comprises a continuous design of its lower end section 2. Due to this continuous design, in the implanted and expanded state of the stent 10, via the lower end section 2 of the stent 10 an uniform radial force is applied to the wall of the blood vessel into which the stent 10 is deployed. In this regard, an endoprosthesis 1 constituted by a stent 10 according to the sixteenth embodiment and a valvular prosthesis 100 affixed to the stent 10 is further secured against migration in the implanted state of the endoprosthesis 1.

In addition, an improved sealing between the endoprosthesis 1 and the wall of the blood vessel may be achieved when an uniform radial force is applied from the lower end section 2 of the stent 10 to the wall of the blood vessel.

In order to further improve securing of the position of an implanted and expanded endoprosthesis 1 and preventing antegrade migration, the stent 10 according to the sixteenth embodiment is provided with a flared or tapered section with a radius shape at its lower end section 2. In detail and as depicted in FIGS. 16b-e, in the expanded state of the stent 10, the lower end section of the annular collar 40 constitutes the flared or tapered section of the stent 10.

The stent 10 depicted in FIGS. 16b-e has at its lower end section 2 a flared or tapered section with a radius shape; however, it is also conceivable that the flared or tapered section is not uniformly around the circumference of the stent 10. For example, the stent 10 may have a flare only near the locations of the positioning arches 15a-c, wherein no flare is provided near the commissure regions, i.e. the regions in between the two arms 15a', 15a", 15b', 15b", 15c', 15c" of two neighboring positioning arches 15a, 15b, 15c.

Although not shown in the drawings, it is particularly preferred for the stent 10 according to any embodiments of the invention that the stent 10 has a scalloped inflow edge design at its lower end section 2 when the stent 10 is in its expanded state. Hence, the inflow edge of the stent 10 does not lie entirely in a plane perpendicular to the longitudinal direction L of the stent 10. Rather, the edge of the stent on its inflow side may have a scalloped shape. In addition, the scalloped inflow edge may also be flared or tapered around its entire circumference or only at selected locations. For example, one embodiment may include a flare at the inflow edge only near the locations of the positioning arches that transition to a non-flared straight cylindrical shape in the area between two neighboring positioning arches. In particular, the location of the respective flares and the respective straight cylindrical shape may be determined by the location of the arms of the respective retaining arches to which the tissue component(s) of the valvular prosthesis is attached.

A stent 10 having such a scalloped inflow edge design reduces the length of the stent 10 having an inflow edge which lies in a plane perpendicular to the longitudinal direction L of the stent 10 in areas that have critical structures such as those containing nerve bundles. However, the scallop shape generally follows the native valve annulus and does not compromise the ability of the valve to seal against leakage The invention is not limited to a stent which is provided with a scalloped inflow edge design. Rather, it is conceivable that the stent 10 according to the invention is provided with an inflow edge having a non-continuous flare design or a tapered flare design with an inflow edge that lies in a plane perpendicular to the longitudinal direction L of the stent 10 or a design which is provided with flares non-continuously distributed around the inflow edge or with flares having a tapered configuration for inflow edge of a stent 10 that does not lie entirely in a plane perpendicular to the longitudinal direction L of the stent 10.

A stent 10 according to a seventeenth embodiment of the invention is shown in FIGS. 17b to 17e. In particular, FIG. 17b is a first perspective side view of a cardiac valve stent according to the seventeenth embodiment of the invention, whereby the cardiac valve stent 10 is shown in its expanded state. Second and third side views of the cardiac valve stent 10 in its expanded state are shown in FIGS. 17c and 17d.

On the other hand, FIG. 17e shows a plan view of the upper end of the cardiac valve stent 10 according to the seventeenth embodiment of the invention in its expanded state.

A flat roll-out view of a stent 10 according to the seventeenth embodiment is shown in FIG. 17a.

The seventeenth embodiment of the stent 10 is similar in structure and function with respect to the sixteenth embodiment. However, the sent design depicted in FIGS. 16b-e differs from the sixteenth embodiment particularly with respect to the specific structure of the annular collar 40. In detail, the seventeenth embodiment is provided with an annular collar 40 which is shortened in its length by having only one row of cells instead of two in the annular collar.

The above described embodiments of the inventive stent have a specific structure that can provide some flexing during diastole to relieve and better distribute leaflet stresses in order to avoid high stress concentrations at the attachment points at which the valvular prosthesis 100 is connected to the stent 10. For offering flexibility to the leaflets 102 of a heart valve prosthesis 100 attached to the stent 10 and for enhancing the durability of the prosthesis 100 affixed to the stent 10, the stent 10 preferably has not a continuous cage around the circumference at the top of the new valve commissures, i.e. the commissures of a valvular prosthesis 100 affixed to the stent 10. In this regard, there is some inherent flexibility of the stent commissures.

In particular, the stents 10 described herein, which are not provided with an upper collar 40' at the upper end section 3 of the stent 10, offer valve commissure flexibility advantages over other cage valve designs. Surgical biological prosthetic valves are designed with stents that provide some flexibility at the upper end section of the valve commissures to reduce stress concentrations in the valve leaflets that enhances the longevity (i.e. valve durability) of the prosthesis and to improve leaflet coaptation.

It is preferred that the stent diameter at the base, i.e. the diameter at the lower end section 2 of the stent 10, should be able to accommodate a range of annulus diameters around the target diameter. Within this range the forces applied due to the stiffness should be adequate to prevent migration, but not too great to cause annular rupture. At the top of the commissures, it is desirable that the stent not vary in diameter significantly to minimize the impact to the valve coaptation or opening performance even when the annulus diameter is not exactly at the target diameter.

In addition, the overall stent height should be minimized to shorten the delivery section of the catheter. This is important because the portion of the delivery catheter system containing the endoprosthesis 1 is generally stiff relative to the rest of the catheter system. In case of a transfemoral approach, it is an advantage to have greater flexibility in the catheter system to follow the curves of the patient anatomy (e.g. the ascending aorta).

As already discussed in connection with the sixteenth embodiment, a more continuous base design may provide uniform radial force to secure the valve against migration. Uniform radial force may also minimize leakage in the implanted stage. Preferably, the base of the stent 10 is flared with a radius shape or a slight taper to a larger diameter as shown, for example, in FIG. 17b. In this respect, this stent design may further improve securing the valve position and preventing antegrade migration.

As depicted in FIG. 17e, the stent 10 according to the seventeenth embodiment comprises a continuous design of its lower end section 2. Due to this continuous design, in the implanted and expanded state of the stent 10, via the lower end section 2 of the stent 10 an uniform radial force is applied to the wall of the blood vessel into which the stent 10 is deployed. Furthermore, the stent 10 depicted in FIGS. 17b-e has at its lower end section 2 a flared or tapered section with a radius shape; however, it is also conceivable that the flared or tapered section is not uniformly around the circumference of the stent 10.

If the implanted and expanded stent together with a valvular prosthesis affixed thereto cannot extend too far below the annulus of the heart there may be the risk that the implanted endoprosthesis consisting of the stent one the one hand and the valvular prosthesis on the other hand contacts the nerve bundles and heart block. The nerve bundles may enter at a location approximately 6 to 10 mm below the annulus of the heart.

In this regard, it may be preferred to reduce the total height of the stent and thus the total height of the endoprosthesis to be implanted into the body of the patient. As in the seventeenth embodiment depicted in FIGS. 17a-e, this can be achieved by having one row of cells in the annular collar 40 instead of two rows of cells as, for example, in the stent design of the fourteenth embodiment (cf. 14a-b).

On the other hand, also a scalloped inflow edge design is conceivable. Hence, the stent 10 may have a scalloped inflow edge design at its lower end section 2 when the stent 10 is in its expanded state. With such a design, the inflow edge of the stent 10 does not lie in a plane perpendicular to the longitudinal direction L of the stent 10. Rather, the edge of the stent on its inflow side may have a scalloped shape with flares near the locations of the positioning arches and indentations in the area between two neighboring positioning arches. In particular, the shape and location of the respective flares and the respective indentations may be determined by the arms of the respective retaining arches to which the tissue component(s) of the valvular prosthesis is attached.

The stent 10 is preferably made from a shape memory material. The state of stent 10 shown in FIG. 1a or FIG. 2a, in which the stent 10 is in its first shape and thus in its collapsed state, is the so-called "temporary" shape of the stent structure made from a shape memory material. When an external stimulus acts on the stent structure according to FIG. 1a or FIG. 2a, the shape memory effect is activated. Thus, the predefined permanent shape saved during the manufacture of the stent 10 as pursuant, for example, FIG. 1b or FIG. 2b, is restored provided that no encapsulating forces, i.e. radially inward acting forces, act on the stent to keep the stent in its collapsed state.

Said external stimulus is preferably a specifiable switching temperature whereby, to activate the shape memory effect and thus regenerate the saved permanent shape of the stent 10, the stent material is warmed to a higher temperature than the switching temperature. By selecting a suitable chemical composition of the material used for stent 10, a specific switching temperature can be predefined. In the preferred embodiment of the solution described herein, the switching temperature ranges from between about 20° C. and the body temperature of the patient.

The surface of the stent 10 should be smooth and edges should be rounded to maximize fatigue, biocompatibility and minimize damage to attached tissue and sutures or damage to native tissue. Hence, it is preferred that the surface of the stent 10 is polished, for example electropolished. Polishing of the stent surface can be performed before or after the programming process during which the shape of the desired (expanded) stent structure is fixed.

When implanting the stent 10, it is conceivable for the stent 10 to be cooled during the insertion procedure. Once the stent 10 has been guided to its desired site of implantation, i.e. to the native cardiac valve H (cf. FIG. 18a), preferably using a suitable insertion catheter system, the cooling can be stopped. The stent 10 is then allowed to warm up to the patient's body temperature (37° C.) and the shape memory effect of the stent material is thus activated. Due to the self-expanding property of stent 10 having been triggered, radial forces are generated which act on the individual components of the stent, in particular on the positioning arches 15a, 15b, 15c, the retaining arches 16a, 16b, 16c and the auxiliary arches 18a, 18b, 18c of the stent 10.

The stent 10 described herein, as well as the insertion catheter system used to implant the stent, are preferably configured so that the stent 10 with the valvular prosthesis 100 affixed thereto can be introduced transarterially into the body of the patient. In one example, the stent 10 is accommodated in the tip of the catheter of the insertion catheter system, the catheter tip being introduced into the body via, for example, puncture of the A. femoris communis (inguinal artery). A suitable catheter system is described in WO2006/076890 and PCT/EP2008/003803, the details of which are incorporated herein by reference.

Alternatively, the stent 10 according to certain embodiments of the invention is also suited for transapical implantation, in which—coming from the apex of the heart—the catheter tip of the insertion catheter system is advanced to the aortic valve through, for example, the left ventricle. With a catheter tip modified accordingly, an analogous implantation of the stent 10 with the valvular prosthesis 100 is thus possible. A suitable catheter system is described in PCT/EP2008/003803, the details of which are incorporated herein by reference Regardless of whether the stent 10 is delivered to the site of implantation via a transarterial or transapical approach, the tip of the catheter of the insertion catheter system is preferably advanced to the implantation site using angiographic (angiography) and echocardiographic (ultrasound) control. The actual implantation of stent 10 with the attached valvular prosthesis 100 then follows.

FIGS. 18a to 18c schematically show the process sequence to illustrate transarterial implantation of an endoprosthesis 1 comprising a stent 10 in accordance with certain embodiments of the invention. As shown, the implantation of the stent 10 with the valvular prosthesis 100 attached thereto ensues such that the individual components of the stent 10 accommodated in a delivery portion of a catheter system are successively released by appropriately manipulating the delivery portion of an insertion catheter system.

The catheter system used to implant the stent 10 described herein is ideally configured such that a liquid cooling agent can be fed through a hollow interior of the catheter system to the delivery portion of the catheter system. The liquid cooling agent, for example in the form of a saline solution, maintains the stent 10 accommodated in the delivery portion of the catheter system at a temperature below the switching temperature while the proximal side K of the delivery portion of the catheter system is being advanced to the site of implantation. This is of particular advantage when a shape memory material is provided as the material of the stent 10.

This is because the stent 10 transforms from a temporary shape into a permanent shape upon the influence of an external stimulus. The temporary shape is the first shape of stent 10 (in collapsed state, when the stent 10 is accommodated in the delivery portion of the catheter system) and the "permanent shape" is the second shape of stent 10 (the expanded state of the stent 10).

It is to be noted that the "permanent shape" of the expanded stent 10 conforms to the native shape of its environment. This allows for variations in the shape of the environment at the site of implantation which will vary from patient to patient. This property of stent 10, related to the "permanent shape" of the expanded stent 10 automatically adapting completely to the native shape of its environment, will thus always ensure that the valvular prosthesis 100 is optimally implanted.

The difference between the fully expanded permanent shape of the stent 10 and the constrained shape of the stent 10 in its implanted stage depends from the environment at the side of implantation and determines the radial pressures applied by the stent 10 to the vessel wall for preventing migration and for assuring good sealing. The fully expanded shape of the stent 10 is designed to provide the appropriate radial pressures for the target patient anatomy size.

Because a shape memory material such as Nitinol, i.e. an equiatomic alloy of nickel and titanium, can be used for the stent 10 described herein, a particularly gentle implantation procedure is achievable when implanting the stent 10 with the valvular prosthesis 100 affixed thereto. Nitinol as material for the stent 10 is preferred because of its good biocompatibility.

The stent 10 accommodated in the delivery portion of the catheter system can be cooled by flushing the insertion catheter system with a suitable cooling agent while the delivery portion of the catheter system is being advanced to keep the temperature of the stent material below the critical transition temperature. Once the delivery portion of the catheter system with the cooled stent 10 has been advanced to the site of implantation, cooling of the stent 10 should be stopped, as a consequence of which the stent 10 warms up to the body temperature (37° C.) of the patient and the shape memory effect of the stent material is thus activated.

Once the self-expanding property of the individual components of stent 10 have been activated, radial forces are generated which act on the individual components of stent 10, in particular on the positioning arches 15a, 15b, 15c, the retaining arches 16a, 16b, 16c, the leaflet guard arches 50a, 50b, 50c and the auxiliary arches 18a, 18b, 18c of stent 10. Since the respective components of stent 10 are still situated in the delivery portion of the catheter system, the radial forces developing upon the critical switching temperature being exceeded and acting on the individual components of the stent 10 are still compensated by the wall of the delivery portion of the catheter system, so that—despite the activation of the shape memory effect—the stent 10 is forcibly kept in its first (collapsed) shape.

Upon the subsequent manipulation of the delivery portion of the catheter system—by the appropriate incremental release of the stent 10—the individual components of stent 10, are then discharged from the delivery portion of the catheter system.

For example, as FIG. 18a shows, the positioning arches 15a, 15b, 15c of stent 10 spread out radially due to the acting radial forces. The expanded positioning arches 15a, 15b, 15c can then be positioned into the pockets T of the native cardiac valve H.

Thereafter—as depicted in FIG. 18b—the remaining components of stent 10 are sequentially released from the delivery portion of the catheter system. The released remaining components of stent 10, in particular the auxiliary arches 18a, 18b, 18c and the retaining arches 16a, 16b, 16c with the valvular prosthesis 100, then spread out radially and the valvular prosthesis 100 attached to the fastening portions 11 unfolds like an umbrella.

The radial forces acting on both the retaining arches 16a, 16b, 16c and the auxiliary, arches 18a, 18b, 18c of the stent 10 as well as the radial forces acting on the upper end region 3 of stent 10, result in the stent 10 being pressed radially against the vascular wall (cf. FIG. 18c). This effects a secure anchoring of stent 10 with the expanded valvular prosthesis 100 at the site of implantation on the one hand and, on the other, a reliable seal of the valvular prosthesis 100 at the lower end 2 of stent 10.

The delivery portion of the insertion catheter system is then manipulated further to release the eyelets 24 of the stent 10, thereby allowing the upper end region 3 of the stent 10 to expand. In so doing, the leaflets of the native cardiac valve H are clamped between respective positioning and retaining arches and the valvular prosthesis 100 disposed on the lower end 2 of stent 10 can spread open.

After the successful implantation of the stent 10 and valvular prosthesis 100, the catheter is then removed from the body of the patient.

The stent 10 is not limited to being made from shape memory material which self-expands from its first (collapsed) shape into its second (expanded) shape in response to an external stimulus. Rather, it is also categorically conceivable for the stent 10 to be expanded using a conventional balloon system.

It will be appreciated that the solution described herein is also not limited to the specific embodiments as described with reference to the attached drawings. Rather, the invention encompasses combinations of the individual features exemplified in the embodiments described.

In particular, the stent 10 may not be provided with radial arches 32a-c. Rather, the base configuration of the stent 10 may only comprise a plurality of positioning arches 15a-c and a plurality of retaining arches 16a, 16b, 16c.

A eighteenth embodiment of the stent 10 according to the present invention is described in the following with reference to FIGS. 19a-b. In detail, FIG. 19a shows a first perspective side view of a cardiac valve stent capable of supporting and anchoring an endoprosthesis according to the eighteenth embodiment of the invention, whereby the cardiac valve stent is shown in its expanded state, and FIG. 19b shows a second perspective side view of a cardiac valve stent capable of supporting and anchoring an endoprosthesis according to the eighteenth embodiment of the invention, whereby the cardiac valve stent is shown in its expanded state.

Hence, the stent 10 according to the eighteenth embodiment comprises a plurality of positioning arches 15a, 15b, 15c configured to be positioned within a plurality of pockets T of the patient's native heart valve H and positioned on a first side of a plurality of native heart valve leaflets, and a plurality of retaining arches 16a, 16b, 16c configured to be positioned on a second side of the plurality of native heart valve leaflets opposite the first side, wherein furthermore a plurality of leaflet guard arches 50a, 50b, 50c are provided, each interspaced between the two arms 15a', 15a", 15b', 15b", 15c', 15c" of one of the plurality of positioning arches 15a, 15b, 15c. In addition, the respective arms 16a', 16a", 16b', 16b", 16c', 16c" of the retaining arches 16a, 16b, 16c are preferably provided with a plurality of bending edges 33 in order to divide each arm 16a', 16a", 16b', 16b", 16c', 16c" into a plurality of arm segments, wherein the structure of the stent 10 is programmed such that the respective arms 16a', 16a", 16b', 16b", 16c', 16c" of the retaining arches 16a, 16b, 16c have a curved shape at least in the expanded state of the stent 10. In particular, the shape of the respective arms 16a', 16a", 16b', 16b", 16c', 16c" of the retaining arches 16a, 16b, 16c shall be such defined that the arms follow the shape of the leaflets 102 of a valvular prosthesis 100 to be affixed to the stent 10 (cf. FIGS. 16f and 16g).

In addition, the stent 10 according to the eighteenth embodiment may further include at least one auxiliary arch 18a, 18b, 18c interspaced between two adjacent retaining arches 16a, 16b, 16c, wherein the at least one auxiliary arch 18a, 18b, 18c includes a first arm 18a', 18b', 18c' connected at a first end thereof to a first retaining arch 16a, 16b, 16c and a second arm 18a", 18b", 18c" connected at a first end thereof to a second retaining arch 16a, 16b, 16c, and wherein the first and second arms 18a', 18a", 18b', 18b", 18c', 18c" of the at least one auxiliary arch 18a, 18b, 18c each include respective second ends connected to one another at a joint that includes at least one fastening hole configured to receive a suture.

In addition or instead of the at least one auxiliary arch 18a, 18b, 18c, the stent according to the eighteenth embodiment of the invention may further comprise at least one radial arch 32a, 32b, 32c substantially circumferentially aligned with at least one of the plurality of positioning arches 15a, 15b, 15c.

Furthermore, the stent 10 according to the eighteenth embodiment of the invention may also be provided with a plurality of extra arches 60a, 60b, 60c, each of said plurality of extra arches 60a, 60b, 60c being interspaced between a first retaining arch 16a, 16b, 16c and an adjacent second retaining arch 16a, 16b, 16c.

Also, at least one annular collar 40, 40' may be provided at the lower end section 2 and/or at the upper end section 3 of the stent 10 according to the eighteenth embodiment of the invention.

Moreover, with respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

In addition, a liner or sheath, typically a fabric, polymeric or pericardial sheet, membrane, or the like, may be provided over at least a portion of the exterior of the stent 10 to cover all or most of the surface of the outside of the stent 10, extending from a location near the lower end section of the stent to a location near the upper end section of the stent. The liner may be attached to the stent 10 at at least one end, as well as at a plurality of locations between said ends thereby forming an exterior coverage. Such exterior coverage provides a circumferential seal against the inner wall of the blood vessel lumen in order to inhibit leakage of blood flow between the stent 10 and the luminal wall thereby and to prevent a blood flow bypassing the endoprosthesis 1.

For example, the liner may be stitched or otherwise secured to the stent 10 along a plurality of circumferentially spaced-apart axial lines. Such attachment permits the liner to fold along a plurality of axial fold lines when the stent 10 is radially compressed. The liner will further be able to open and conform to the luminal wall of the tubular frame as the frame expands. Alternatively, the liner may heat welded, or ultrasonically welded to the stent 10. In an exemplary embodiment where the stent 10 is provided with a plurality of independent fastening portions 11, 11a, the liner may be secured at these fastening portions 11, 11a. In a second exemplary embodiment where a plurality of independent arches (positioning arches 15a, 15b, 15c, retaining arches 16a, 16b, 16c, auxiliary arches 18a, 18b, 18c and/or fastening arches 19, 19a, 19b, 19c) are provided, the liner is secured to these arches preferably along axial lines. The liner will preferably be circumferentially sealed against the stent 10 at at least one end.

By covering at least a part of the outside surface of the stent 10 with the liner or sheath, thrombogenicity of the endoprosthesis 1 resulting from exposed stent elements is greatly reduced or eliminated. Such reduction of thrombogenicity is achieved while maintaining the benefits of having a stent structure which is used for spreading up a valvular prosthesis 100 and for anchoring the valvular prosthesis 100 in place.

As already mentioned, the stent 10 can be compressed from a relaxed, large diameter configuration to a small diameter configuration to facilitate introduction. It is necessary, of course, that the outer liner remain attached to the stent 10 both in its radially compressed configuration and in its expanded, relaxed configuration.

The liner is composed of pericardial material or conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as Dacron® yarn (Dupont, Wilmington, Del.).

A nineteenth embodiment of the stent 10 according to the present invention is described in the following with reference to FIGS. 20a to 20d.

In detail, FIG. 20a shows a flat roll-out view of a cardiac valve stent 10 pursuant the nineteenth embodiment of the invention, whereby the stent 10 is in its non-expanded state. This flat roll-out view corresponds to a two-dimensional projection of a cutting pattern which can be used in the manufacture of the stent 10 pursuant the nineteenth embodiment of the invention. This enables a one-piece stent 10 to be cut from a portion of tube, in particular a metal tube. It is evident that, on the one hand, the inventive stent 10 dispenses with fixed-body joints or other similar connective devices between the individual components of stent 10 (positioning arch, retaining arch, auxiliary arch). On the other hand, a stent 10 is provided which exhibits, with minimum longitudinal extension, the functionality of positionability as provided by the positioning arches 15a, 15b, 15c on the one hand and, on the other hand, the functionality of the defined fastening of a valvular prosthesis, as provided by the fastening portions 11 configured in the respective arms 16a', 16a", 16b', 16b", 16c', 16c" of the retaining arch 16a, 16b, 16c. Moreover, the defined fastening of a valvular prosthesis is achieved by additional fastening means which comprise a several number of notches 12e uniformly distributed around the lower end section of an annular collar 40 which is arranged at the lower end section of the stent body.

FIG. 20b shows a first perspective side view of a cardiac valve stent 10 capable of supporting and anchoring an endoprosthesis according to the nineteenth embodiment of the invention, whereby the cardiac valve stent 10 is shown in its expanded state, and FIG. 20c shows a second perspective side view of a cardiac valve stent capable of supporting and anchoring an endoprosthesis according to the nineteenth embodiment of the invention, whereby the cardiac valve stent is also shown in its expanded state.

FIG. 20d shows a flat roll-out view of a cardiac valve stent 10 according to the nineteenth embodiment of the invention. Contrary to the flat roll-out view depicted in FIG. 20a, however, the flat roll-out view according to FIG. 20d shows the cardiac valve stent 10 is in its expanded state.

Thus, it appears that the stent 10 according to the nineteenth embodiment comprises a plurality of positioning arches 15a, 15b, 15c and a plurality of retaining arches 16a, 16b, 16c. Each of the plurality of positioning arches 15a, 15b, 15c is configured to be positioned within a plurality of pockets T of the patient's native heart valve H and positioned on a first side of a plurality of native heart valve leaflets (see FIGS. 18a to 18c). On the other hand, each of the plurality of retaining arches 16a, 16b, 16c is configured to be positioned on a second side of the plurality of native heart valve leaflets opposite the first side (see also FIGS. 18a-c).

Furthermore, a plurality of leaflet guard arches 50a, 50b, 50c are provided, each interspaced between the two arms 15a', 15a", 15b', 15b", 15c', 15c" of one of the plurality of positioning arches 15a, 15b, 15c. In addition, the respective arms 16a', 16a", 16b', 16b", 16c', 16c" of the retaining arches 16a, 16b, 16c are preferably provided with a plurality of bending edges 33 in order to divide each arm 16a', 16a", 16b', 16b", 16c', 16c" into a plurality of arm segments, wherein the structure of the stent 10 is programmed such that the respective arms 16a', 16a", 16b', 16b", 16c', 16c" of the retaining arches 16a, 16b, 16c have a curved shape at least in the expanded state of the stent 10. In particular, the shape of the respective arms 16a', 16a", 16b', 16b", 16c', 16c" of the retaining arches 16a, 16b, 16c shall be such defined that the arms follow the shape of the leaflets 102 of a valvular prosthesis 100 to be affixed to the stent 10.

In detail and as depicted in the flat roll-out view shown in FIG. 20a, the respective arms 16a', 16a", 16b', 16b", 16c', 16c" of the retaining arches 16a, 16b, 16c are provided with a plurality of bending edges 33. These bending edges 33 may be uniformly distributed along the length of each retaining arch arm 16a', 16a", 16b', 16b", 16c', 16c" thereby dividing each arm 16a', 16a", 16b', 16b", 16c', 16c" into a plurality of arm segments. The arm segments of a corresponding retaining arch arm 16a', 16a", 16b', 16b", 16c', 16c" are interconnected thereby constituting a retaining arch arm which describes an essentially straight line in the not-expanded state of the stent 10. In this regard, reference is made to the flat roll-out view depicted in FIG. 20a which shows the uncurved configuration of the respective arms 16a', 16a", 16b', 16b", 16c', 16c" of the retaining arches 16a, 16b, 16c.

When manufacturing the stent 10, the stent structure and in particular the structure of the retaining arches 16a, 16b, 16c is programmed such that the respective retaining arch arms 16a', 16a", 16b', 16b", 16c', 16c" have a curved shape in the expanded state of the stent 10. The shape of the respective retaining arch arms 16a', 16a", 16b', 16b", 16c', 16c" is such defined that the arms follow the shape of the leaflets of a valvular prosthesis 100 to be affixed to the stent 10 (cf. FIG. 20d).

Hence, the respective retaining arch arms 16a', 16a", 16b', 16b", 16c', 16c", onto which the valvular prosthesis 100 is sewn or sewable, will change their shape when the stent 10 expands, wherein the retaining arches 16a, 16b, 16c are curved in the expanded state of the stent 10, but relatively straight when the stent 10 is collapsed.

As can be seen, for example, in FIG. 20d, the curvature of the respective retaining arch arms 16a', 16a", 16b', 16b", 16c', 16c" is achieved by segmenting the arms 16a', 16a", 16b', 16b'', 16c', 16c''. In detail, the arms 16a', 16a'', 16b', 16b'', 16c', 16c'' are segmented by providing a plurality of bending edges 33. In the expanded state of the stent 10, two neighboring arm segments are angled relative to each other, wherein the bending point of these two neighboring arm segments is defined by the bending edge 33 which is provided in between the both neighboring arm segments. Hence, the greater the number of bending edges 33 provided in an arm 16a', 16a'', 16b', 16b'', 16c', 16c'' of a retaining arch 16a, 16b, 16c, the greater the number of arm segments which may extend in different directions in the expanded state of the stent 10. In this respect, the shape of the respective retaining arch arms 16a', 16a'', 16b', 16b'', 16c', 16c'' can be precisely adapted to the shape of the leaflets of the valvular prosthesis to be affixed to the stent 10.

According to the stent design of the nineteenth embodiment, the respective arms 16a', 16a'', 16b', 16b'', 16c', 16c'' of the retaining arches 16a, 16b, 16c are not provided with fastening holes 12a, as it is the case, for example, in the eighteenth or seventeenth embodiment. Rather, in the nineteenth embodiment, the bending edges 33 provided in the retaining arch arms 16a', 16a'', 16b', 16b'', 16c', 16c'' are not only used for defining a bending point of two neighboring arm segments, but also as fastening notches which can be used for fixing a heart valve prosthesis to the stent 10.

A comparison with, for example, the flat roll-out view pursuant to FIG. 17a (seventeenth embodiment) illustrates directly that the respective retaining arch arms 16a', 16a'', 16b', 16b'', 16c', 16c'' of the stent design according to the nineteenth embodiment is at least partly much more thinner compared with the respective retaining arch arms of the seventeenth embodiment which are provided with fastening portions having fastening holes 12a. By reducing the thickness of the retaining arch arms 16a', 16a'', 16b', 16b'', 16c', 16c'', the bendability of the arms is increased which allows a more precise adaptation of the shape of the respective retaining arch arms 16a', 16a'', 16b', 16b'', 16c', 16c'' to the shape of the leaflets of the valvular prosthesis to be affixed to the stent 10.

Moreover, by using the bending edges 33 provided in the retaining arch arms 16a', 16a'', 16b', 16b'', 16c', 16c'' as fastening notches for fixing a heart valve prosthesis to the stent 10, a greater number of attachment points compared with the number of fastening holes 12a can be generated. In this regard, high stress concentrations at each single attachment point can be effectively avoided.

In addition, in the nineteenth embodiment, the attachment points (bending edges 33) to be used for fixing a heart valve prosthesis to the retaining arch arms 16a', 16a'', 16b', 16b'', 16c', 16c'' of the stent 10 are more uniformly distributed along the respective retaining arch arms 16a', 16a'', 16b', 16b'', 16c', 16c'', thereby providing a more uniform fixation of a heart valve prosthesis to the stent. Hence, the risk of an axial displacement of the heart valve prosthesis relative to the stent may be further reduced. Each individual bending edge 30 provided in the respective retaining arch arms 16a', 16a'', 16b', 16b'', 16c', 16c'' thereby serves to guide a thread or thin wire with which the tissue component(s) of the valvular prosthesis is affixed or sewn to the corresponding retaining arch arm 16a', 16a'', 16b', 16b'', 16c', 16c'' of the stent 10. In detail, the means (thread or thin wire) provided for fastening the tissue component(s) of the valvular prosthesis to the respective retaining arch arms 16a', 16a'', 16b', 16b'', 16c', 16c'' is guided by way of the bending edge 33 acting as fastening notch so that a longitudinal displacement of the valvular prosthesis relative to the stent 10 is substantially minimized. This also allows exact positioning of the valvular prosthesis relative the stent 10.

In addition, the stent 10 according to the nineteenth embodiment may further include at least one auxiliary arch 18a, 18b, 18c interspaced between two adjacent retaining arches 16a, 16b, 16c, wherein the at least one auxiliary arch 18a, 18b, 18c includes a first arm 18a', 18b', 18c' connected at a first end thereof to a first retaining arch 16a, 16b, 16c and a second arm 18a'', 18b'', 18c'' connected at a first end thereof to a second retaining arch 16a, 16b, 16c, and wherein the first and second arms 18a', 18a'', 18b', 18b'', 18c', 18c'' of the at least one auxiliary arch 18a, 18b, 18c each include respective second ends connected to an annular collar 40 which is arranged at the lower end section of the stent body. As in the previously described stent design ($14^{th}$ to $18^{th}$ embodiment), this at least one collar 40 serves as an additional anchoring measure for a stent cut from a portion of a tube by using the cutting pattern depicted in FIG. 20a.

In detail, the respective first and second arms 18a', 18a'', 18b', 18b'', 18c', 18c'' of the at least one auxiliary arch 18a, 18b, 18c are part of a strut or web structure which is provided between the first and second arms 18a', 18a'', 18b', 18b'', 18c', 18c'' of two adjacent auxiliary arches 18a, 18b, 18c in order to support a valvular prosthesis 100 to be affixed to the stent 10 (see, for example, FIGS. 16f and 16g). As can be seen, for example, from FIG. 20d the strut or web structure may be composed by a plurality of struts or strut-like members which are interconnected such as to form a reinforcement structure. Each strut or strut-like element of the reinforcement structure serves as reinforcement member in order to increase the strength or resistance to deformation of the area between the first and second arms 18a', 18a'', 18b', 18b'', 18c', 18c'' of two adjacent auxiliary arches 18a, 18b, 18c. The reinforcement structure thereby provides mechanical reinforcement to the stent 10. Moreover, the reinforcement members of the reinforcement structure between the first and second arms 18a', 18a'', 18b', 18b'', 18c', 18c'' of two adjacent auxiliary arches 18a, 18b, 18c provides for an additional support of the commissures of a heart valve prosthesis attached to the stent 10.

The terms "strength" or "resistance to deformation" as used herein may be used to denote any of a number of different properties associated with the reinforcement members. For example, the terms may be used to refer to properties of the material from which the reinforcement members are made, such as the yield strength, the modulus of elasticity, the modulus of rigidity, or the elongation percentage. Similarly, the terms may be used to refer to the hardness of the reinforcement members. Hardness may be characterized as the "durometer" of the material, in reference to the apparatus used to measure the hardness of the material. The terms may also be used to denote geometric characteristics of the reinforcement members, such as the thickness of the reinforcement members. The terms "strength" or "resistance to deformation" may also be used to characterize any combination of the above properties as well as additional properties and/or characteristics.

The strength or resistance to deformation of the area between the first and second arms 18a', 18a'', 18b', 18b'', 18c', 18c'' of two adjacent auxiliary arches 18a, 18b, 18c can be increased in any number of ways. As can be seen from FIG. 20d, the strength or resistance to deformation of the area between the first and second arms 18a', 18a'', 18b', 18b'', 18c', 18c'' of two adjacent auxiliary arches 18a, 18b, 18c can be increased, for example, by providing a reinforcement structure formed by at least one, and preferably by a plurality of reinforcement elements (e.g. struts or strut-like members) which are interconnected to each other.

It is also conceivable that a reinforcement web is provided in order to increase the strength or resistance to deformation of the area between the first and second arms 18a', 18a", 18b', 18b", 18c', 18c" of two adjacent auxiliary arches 18a, 18b, 18c. This reinforcement web may also be composed by a plurality of reinforcement elements (e.g. struts or strut-like members) which are interconnected to each other thereby forming a rhomboidal pattern.

The strength or resistance to deformation of the area between the first and second arms 18a', 18a", 18b', 18b", 18c', 18c" of two adjacent auxiliary arches 18a, 18b, 18c can be increased, for example, by increasing the thickness of the reinforcement members, by eliminating stress concentration risers in the design of the stent 10, or by changing other aspects of the geometry of the reinforcement members. The strength can also be increased by changing the material properties of the stent 10 and/or the reinforcement members. For example, the reinforcement members can be made from a number of different materials, preferably shape memory materials, each having a different level of hardness. In this regard, it is conceivable to vary the stoichiometric composition of the material used for forming the stent and the reinforcement members such as to adapt the material properties of the stent 10 and/or the reinforcement members to the specific needs of each stent application. It is also conceivable to use different materials, for example nitinol and a shape-memory polymer, for forming the stent and the reinforcement members. In this manner, the selection of the reinforcement members can be tailored to the specific needs of each stent application. For example, in regions where a high external force is expected, reinforcement members having a high hardness may be preferred. The strength may also be increased by combining material properties with geometric changes.

As can be seen from FIG. 20d, the stent 10 according to the nineteenth embodiment is provided with a reinforcement structure which is constituted by a plurality of lattice cells 70 formed by a plurality of struts in the area between the arms 16a', 16a", 16b', 16b", 16c', 16c" of two neighbouring (adjacent) retaining arches 16a, 16b, 16c, thereby providing for an additional support of the commissures of a heart valve prosthesis attached to the stent 10.

In addition, this structure of the lattice cells 70 formed by a plurality of struts in the area between the adjacent arms of two neighbouring retaining arches 16a, 16b, 16c may provide uniform stent structure which may minimize blood leakage in the implanted stage of the stent 10 having a heart valve prosthesis attached thereto.

The upper end sections of the respective struts which are forming the structure of the lattice cells 70 are connected to the respective arms of the retaining arches 16a, 16b, 16c. Preferably, the upper end sections of the struts comprise a widened diameter in order to strengthen the connection between the upper end sections of the struts and the arms of the retaining arches 16a, 16b, 16c.

The already mentioned annular collar 40, which is provided at the lower end section of the stent body, is connected with the stent body via the retaining arches 16a, 16b, 16c on the one hand and the second ends of the respective arms 18a', 18a", 18b', 18b", 18c', 18c" of the at least one auxiliary arch 18a, 18b, 18c on the other hand, wherein these arms 18a', 18a", 18b', 18b", 18c', 18c" of the at least one auxiliary arch 18a, 18b, 18c are part of the structure of the lattice cells 70. In particular, the stent 10 according to the nineteenth embodiment of the invention is provided with an annular collar 40 which is shortened in its length by having only a single row of cells.

As can be seen from the flat roll-out view pursuant to FIG. 20a, the annular collar 40 at the lower end section of the stent body exhibits a plurality of supporting webs 41 which run parallel to the longitudinal axis L of the stent 10 in the non-expanded state of the stent 10 and are inter-connected by transversal webs 42. As can be seen from the two-dimensional roll-out view pursuant to FIG. 20c, however, in the expanded state of the stent 10, the supporting webs 41 and the transversal webs 42 forms a rhomboidal or serpentine-like annular collar 40 which abuts against the vascular wall in the implanted state of the stent 10.

In order to further improve securing of the position of an implanted and expanded endoprosthesis 1 and preventing antegrade migration, the stent 10 according to the nineteenth embodiment is provided with a flared or tapered section with a radius shape at its lower end section 2. In detail and as depicted in FIGS. 20b and 20c, in the expanded state of the stent 10, the lower end section of the annular collar 40 constitutes the flared or tapered section of the stent 10.

The stent 10 depicted in FIGS. 20b and 20c has at its lower end section 2 a flared or tapered section with a radius shape; however, it is also conceivable that the flared or tapered section is not uniformly around the circumference of the stent 10. For example, the stent 10 may have a flare only near the locations of the positioning arches 15a, 15b, 15c, wherein no flare is provided near the commissure regions, i.e. the regions in between the two arms 15a', 15a", 15b', 15b", 15c', 15c" of two neighboring positioning arches 15a, 15b, 15c.

As depicted in FIGS. 20b and 20c, the stent 10 according to the nineteenth embodiment comprises a continuous design of its lower end section 2. Due to this continuous design, in the implanted and expanded state of the stent 10, via the lower end section 2 of the stent 10 an uniform radial force is applied to the wall of the blood vessel into which the stent 10 is deployed.

If the implanted and expanded stent together with a valvular prosthesis affixed thereto extend too far below the annulus of the heart there may be the risk that the implanted endoprosthesis consisting of the stent one the one hand and the valvular prosthesis on the other hand contacts the nerve bundles and heart block. The nerve bundles may enter at a location approximately 6 to 10 mm below the annulus of the heart.

In order to avoid that the lower end section 2 of the implanted stent 10 may touch the atrioventricular node, the stent 10 pursuant to the nineteenth embodiment is provided with an annular collar 40 which is shortened in its length by having only a single row of cells. In this regard, the total height of the stent 10 and thus the total height of the endoprosthesis 1 to be implanted into the body of the patient are reduced.

Moreover, in the programming process during which the shape of the desired (expanded) stent structure is fixed, the supporting webs 41 of the annular collar 40 may be programmed so that—when the stent 10 of the nineteenth embodiment is in its expanded state—only the upper section of the annular collar 40 extends in a radial direction outside the circumference of the stent 10, whereas the lower end section of the annular collar 40 bended relative to the upper section of the annular collar 40 in the radial direction inside the circumference of the stent 10. The lower end section of the annular collar 40 may be bended such that it extends, for example, approximately parallel to the longitudinal direction L of the stent 10. In this way, an increased contact force (radial force) is applied by the upper section of the annular collar 40 to the wall of the blood vessel into which the stent 10 is deployed, whereas the risk is reduced that the lower end section of the annular collar 40 can tough the atrioventricular node.

It is important to note, that the stent 10 according to the nineteenth embodiment comprises a several number of notches 12*e* uniformly distributed around the lower end section of the annular collar 40. These notches 12*e* can be used for fixing a heart valve prosthesis (not shown in FIGS. 20*b* and 20*c*) to the stent 10, which may reduce the risk of an axial displacement of the heart valve prosthesis 100 relative to the stent 10. Since a plurality of notches 12*e* are used as additional fastening means it is possible to utilize the lower end sections of every supporting web 41 of the annular collar 40 for additionally fastening a heart valve prosthesis to the stent 10. This appears directly from the flat roll-out view pursuant to FIG. 20*a*.

A comparison with, for example, the flat roll-out view pursuant to FIG. 17*a* (seventeenth embodiment) illustrates directly that the provision of eyelets 12*f* at the lower end sections of every supporting web 41 of the annular collar 40 requires much more material for each eyelet 12*f* compared with the amount of material which is necessary for forming respective notches 12*e*. Since it is conceivable for the stent 10 to exhibit a structure integrally cut from a portion of tube, in particular from a metal tube, which incorporates all structural components of the stent 10, in particular the positioning arches 15*a*, 15*b*, 15*c*, the retaining arches 16*a*, 16*b*, 16*c* and the annular collar 40 with defined additional fastening means at the lower end thereof, an elaborate cutting pattern for forming the design of the stent 10 from the original tube portion is important. In particular, it must be taken into account that the structure of the stent 10 with all structural stent components must be cut from the limited lateral area of the original tube portion.

Hence, by providing notches 12*e* instead of eyelets 12*f* as additional fastening means at the lower end section of the annular collar 40, a greater number of notches 12*e* compared with the number of eyelets 12*f* can be generated. In detail, according to the nineteenth embodiment, the lower end sections of every supporting web 41 of the annular collar 40 is provided with a corresponding notch 12*e* acting as additional fastening means. In contrast, in the seventeenth and eighteenth embodiments only the lower end sections of every second supporting web 41 of the annular collar 40 can be provided with a corresponding eyelet 12*f* acting as additional fastening means.

In this regard, the stent design according to the nineteenth embodiment differs from the stent design, for example, according to the eighteenth embodiment in that at the lower end section of every supporting web 41 of the annular collar 40 an additional fastening means is provided. This is due to the fact that, in the nineteenth embodiment of the stent 10, notches 12*e* are used as additional fastening means.

Hence, in the nineteenth embodiment, the additional fastening means to be used for fixing a heart valve prosthesis to the stent 10 are more uniformly distributed around the lower end section of the annular collar 40, thereby providing a more uniform fixation of a heart valve prosthesis to the stent. Hence, the risk of an axial displacement of the heart valve prosthesis relative to the stent may be further reduced. Each individual notch 12*e* provided at the lower end section of the annular collar 40 thereby serves to guide a thread or thin wire with which the tissue component(s) of the valvular prosthesis is affixed or sewn to the lower end section of the annular collar 40 of the stent 10. In detail, the means (thread or thin wire) provided for fastening the tissue component(s) of the valvular prosthesis to the lower end section of the annular collar 40 is guided by way of the notches 12*e* so that a longitudinal displacement of the valvular prosthesis relative to the stent 10 is substantially minimized. This also allows exact positioning of the valvular prosthesis relative the stent 10.

Moreover, by using corresponding notches 12*e* for the secure and defined fixing of the tissue component(s) of the valvular prosthesis to the lower end section of the annular collar 40 of the stent 10, the means (threads or thin wires) used to fasten the tissue component(s) to the stent 10 are effectively prevented from being squeezed and thus degraded when the stent 10 with the valvular prosthesis affixed thereto, i.e. the endoprosthesis 1, is compressed and brought into its collapsed shape such as to be ready for being inserted into a catheter system which is used for implanting the endoprosthesis 1. In this regard, the risk of structural deterioration in the threads or thin wires used to fasten the tissue component(s) of the valvular prosthesis 100 to the stent 10 is reduced.

The cross-sectional shape to the notches 12*e* may be adapted to the cross-sectional shape of the thread or thin wire used to fasten the tissue component(s) of the valvular prosthesis 100. This allows fixing of the tissue component(s) of the valvular prosthesis 100 to the stent 10 at a precise predefined position relative to the stent 10. Because the fastening holes 12 are adapted to the thickness and/or the cross-sectional shape of the thread or thin wire used to affix the valvular prosthesis 100 to the stent 10, relative movement between the stent 10 and the tissue component(s) of the valvular prosthesis 100 due to the peristaltic motion of the heart can be effectively prevented when the endoprosthesis 1 is implanted. In the fully expanded and implanted state of the endoprosthesis 1, the tissue component(s) of the valvular prosthesis 100 is/are thus fastened to the stent 10 with minimal play, based on which friction-induced wear of the thread or thin wire used to affix the valvular prosthesis is minimized. As shown in, for example, in FIG. 20*a*, the notches 12*e* have a semi-circular cross-sectional shape.

As can be seen, in particular from FIGS. 20*b* to 20*d*, the stent 10 according to the nineteenth embodiment of the invention may further comprise at least one radial arch 32*a*, 32*b*, 32*c* which enables a particularly secure anchoring of the stent 10 in the site of implantation in the heart and which is substantially circumferentially aligned with at least one of the plurality of positioning arches 15*a*, 15*b*, 15*c*. In addition to its radial arches 32*a*, 32*b*, 32*c*, the stent 10 is further provided with a total of three leaflet guard arches 50*a*, 50*b*, 50*c*, each comprising two leaflet guard arms. It can be seen from the flat roll-out view shown in FIG. 20*a* that, in the structure of the stent according to the nineteenth embodiment, a leaflet guard arch 50*a*, 50*b*, 50*c* is provided in between each positioning arch 15*a*, 15*b*, 15*c*. Hence, in the stent according to the twelfth embodiment, a leaflet guard arch 50*a*, 50*b*, 50*c* is allocated to each positioning arch 15*a*, 15*b*, 15*c*.

Referring to the flat roll-out view shown in FIG. 20*a*, the radial arches 32*a*, 32*b*, 32*c* of the stent 10 according to the nineteenth embodiment extend from the leaflet guard arches 50*a*, 50*b*, 50*c* towards the upper end 3 of the stent 10. As is shown most clearly in FIG. 20*a*, the stent 10 has three radial arches 32*a*, 32*b*, 32*c*, with each arch 32*a*, 32*b*, 32*c* located between the two arms of each leaflet guard arch 50*a*, 50*b*, 50*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

On the other hand, each leaflet guard arch 50*a*, 50*b*, 50*c* has a substantially U-shaped or V-shaped structure which is closed to the lower end 2 of stent. Again, each leaflet guard arch 50*a*, 50*b*, 50*c* has a shape that is roughly similar to the shape of the positioning arch 15*a*, 15*b*, 15*c* in between the corresponding leaflet guard arch 50*a*, 50*b*, 50*c* is arranged. Furthermore, each leaflet guard arch 50*a*, 50*b*, 50*c* extends in the same direction as the positioning arch 15*a*, 15*b*, 15*c*.

In the stent design of the nineteenth embodiment, each arm of a leaflet guard arch 50*a*, 50*b*, 50*c* merges at about the mid-point of the length of an arm of a radial arch 32*a*, 32*b*, 32*c* into the arm of an opposing radial arch 32*a*, 32*b*, 32*c*. According to the stent design of the nineteenth embodiment, the leaflet guard arches 50*a*, 50*b*, 50*c* project in the longitudinal direction L of the stent and have a reduced length such that the positioning arches 15*a*, 15*b*, 15*c* can deploy during the expansion of the stent 10 and the leaflet guard arches 50*a*, 50*b*, 50*c* do not interfere during deployment.

The positioning arches 15*a*, 15*b*, 15*c* disposed on the stent 10 and also the retaining arches 16*a*, 16*b*, 16*c* may be curved in convex and arched fashion in the direction to the lower end section of the stent; i.e. toward the lower end 2 of the stent, whereby such a rounded form may reduce injuries to the artery as well as facilitate the unfolding during the self-expansion. Such a design may enable an easier insertion of the positioning arches 15*a*, 15*b*, 15*c* into the pockets T of the native cardiac valve without correspondingly injuring the neighboring tissue or blood vessels (cf. FIGS. 18*a* to 18*c*).

Although not explicitly illustrated in the flat roll-out view according to FIG. 20*a*, in the programming process during which the shape of the desired (expanded) stent structure is fixed, the leaflet guard arches 50*a*, 50*b*, 50*c* are preferably programmed so that they extend in a radial direction outside the circumference of the stent 10 when the stent 10 of the nineteenth embodiment is in its expanded state. In this way, an increased contact force can be applied to the leaflets H of the native (diseased) cardiac valve when the stent of the nineteenth embodiment is in its expanded and implanted state. This, in turn, allows an increased security in the fixing of the stent in situ.

When the stent is in its expanded and implanted state, the leaflet guard arches 50*a*, 50*b*, 50*c* actively keep the diseased leaflets H, i.e. the leaflets of the native cardiac valve, from impinging the leaflet tissue of the valvular prosthesis 100 attached to the stent 10, when the positioning arches 15*a*, 15*b*, 15*c* are placed outside the native leaflets. In addition, the leaflet guard arches 50*a*, 50*b*, 50*c* may also provide additional anchoring and securing against migration. This feature may be unique compared to the cage known from the prior art stent designs which are not provided with positioning arches to push the diseased leaflets out of the way.

As can be seen from the roll-out view depicted in FIG. 20*a*, according to the stent design of the nineteenth embodiment, the two arms 32', 32" of each radial arch 32*a*, 32*b*, 32*c* are connected together at the upper end 3 of the stent 10 by means of a radiused connecting portion or head. This head is not only radiused but also widens at the tip so that the head abuts against the interior wall of the vessel over as large a contact area as possible when the stent 10 is in its expanded and implanted state. The heads of each radial arch 32*a*, 32*b*, 32*c* may also serve as additional means by which the stent 10 may be retained in a catheter before and during implantation and/or to recapture the stent after implantation.

In the programming process during which the shape of the desired (expanded) stent structure is fixed, the radial arches 32*a*, 32*b*, 32*c* are programmed so that they extend in a radial direction outside the circumference of the stent 10 when the stent 10 is in its expanded state. In this way an increased contact force can be applied to the vessel wall by the upper end region of the stent 10. This, in turn, allows an increased security in the fixing of the stent 10 in situ, thereby reducing the likelihood of migration of the stent 10. Therefore, in its expanded state, in addition to the clamping effect of the positioning arches 15*a*, 15*b*, 15*c* and in addition to the additional anchoring obtainable by the leaflet guard arches 50*a*, 50*b*, 50*c*, the stent 10 of the nineteenth embodiment is secured in place on implantation via radial forces exerted by the retaining arches 16*a*, 16*b*, 16*c*, the auxiliary arches 18*a*, 18*b*, 18*c*, the radial arches 32*a*, 32*b*, 32*c*, and the annular collar 40, all of which project outwards in a radial direction from the circumference of the stent 10.

It can be seen from the flat roll-out view shown in FIG. 20*a* that the radial arches 32*a*, 32*b*, 32*c* do not project in the longitudinal direction L of the stent 10 beyond the plane in which the catheter retaining means 23 or the fastening means with fastening eyelets 24 are situated. This may ensure that the catheter retaining means 23 can co-operate with corresponding means within a suitable implantation catheter without interference from the heads of the radial arches 32*a*, 32*b*, 32*c*. Indeed, as explained above, the heads themselves can be used as additional catheter retaining means or additional means to effect explanation of the stent 10.

In principle, the stent 10 may have more than three radial arches 32 in order to increase the radial contact force further. It is also possible to provide barb elements on all or some of the radial arches 32*a*, 32*b*, 32*c*, for example, to allow a still better anchoring of the stent 10 at the implantation site.

Moreover, with respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

In addition, a liner or sheath, typically a fabric, polymeric or pericardial sheet, membrane, or the like, may be provided over at least a portion of the exterior of the stent 10 to cover all or most of the surface of the outside of the stent 10, extending from a location near the lower end section of the stent to a location near the upper end section of the stent. The liner may be attached to the stent 10 at at least one end, as well as at a plurality of locations between said ends thereby forming an exterior coverage. Such exterior coverage provides a circumferential seal against the inner wall of the blood vessel lumen in order to inhibit leakage of blood flow between the stent 10 and the luminal wall thereby and to prevent a blood flow bypassing the endoprosthesis 1.

For example, the liner may be stitched or otherwise secured to the stent 10 along a plurality of circumferentially spaced-apart axial lines. Such attachment permits the liner to fold along a plurality of axial fold lines when the stent 10 is radially compressed. The liner will further be able to open and conform to the luminal wall of the tubular frame as the frame expands. Alternatively, the liner may heat welded, or ultrasonically welded to the stent 10. The liner may be secured to the plurality of independent arches (positioning arches 15*a*, 15*b*, 15*c*, retaining arches 16*a*, 16*b*, 16*c*, auxiliary arches 18*a*, 18*b*, 18*c*, leaflet guard arches 50*a*, 50*b*, 50*c*) preferably along axial lines. In addition, the liner may be secured to the annular collar 40 provided at the lower end section 2 of the stent 10. The liner will preferably be circumferentially sealed against the stent 10 at at least one end.

By covering at least a part of the outside surface of the stent 10 with the liner or sheath, thrombogenicity of the endoprosthesis 1 resulting from exposed stent elements is greatly reduced or eliminated. Such reduction of thrombogenicity is achieved while maintaining the benefits of having a stent structure which is used for spreading up a valvular prosthesis 100 and for anchoring the valvular prosthesis 100 in place.

As already mentioned, the stent 10 can be compressed from a relaxed, large diameter configuration to a small diameter configuration to facilitate introduction. It is necessary, of course, that the outer liner remain attached to the stent 10 both in its radially compressed configuration and in its expanded, relaxed configuration.

The liner is composed of pericardial material or conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as Dacron® yarn (Dupont, Wilmington, Del.).

A twentieth embodiment of the stent 10 according to the present invention is described in the following with reference to FIG. 21 which is a flat roll-out view of this embodiment, whereby the cardiac valve stent 10 is shown in its expanded state.

The twentieth embodiment of the stent 10 is similar in structure and function with respect to the nineteenth embodiment. To avoid repetition, reference is therefore made to the above description of the nineteenth embodiment. In particular, the lower end section of the stent 10 is constituted by an annular collar 40 which is likewise provided with notches 12e acting as additional fastening means.

In addition, the stent 10 according to the twentieth embodiment is provided with retaining arches 16a, 16b, 16c whose arms 16a', 16a", 16b', 16b", 16c', 16c" are segmented by a plurality of bending edges 33 which are not only used for defining a bending point of two neighboring arm segments, but also as fastening notches which can be used for fixing a heart valve prosthesis to the stent 10.

The twentieth embodiment of the stent 10 also includes radial arches 32a, 32b, 32c extending from the positioning arches 15a, 15b, 15c towards the upper end 3 of the stent 10. As is shown in the FIG. 21, the stent 10 has three radial arches 32a, 32b, 32c, with each arch 32a, 32b, 32c located between the two arms 15a, 15a', 15b, 15b', 15c, 15c' of each positioning arch 15a, 15b, 15c. Each radial arch 32a, 32b, 32c has a shape that is roughly inverse to each positioning arch 15a, 15b, 15c and extends in the opposite direction to each one of the positioning arches 15a, 15b, 15c.

Contrary to the stent design of the nineteenth embodiment, however, the stent design of the twentieth embodiment is not provided with leaflet guard arches 50a, 50b, 50c. Furthermore, each arm of a radial arch 32a, 32b, 32c merges at about the mid-point of the length of the stent 10 into an arm 15a', 15a", 15b', 15b", 15c', 15c" of an opposing positioning arch 15a, 15b, 15c.

A twenty-first embodiment of the stent 10 according to the present invention is described in the following with reference to FIG. 22. In detail, FIG. 22 is a flat roll-out view of the twenty-first embodiment, whereby the cardiac valve stent 10 is shown in its expanded state.

From a comparison of FIG. 22 with FIG. 20d it is derivable that the twenty-first embodiment of the stent 10 is similar in structure and function with respect to the nineteenth embodiment. To avoid repetition, reference is therefore made to the above description of the nineteenth embodiment.

The twenty-first embodiment of the stent 10 only differs from the nineteenth embodiment in that the respective lower end sections of the leaflet guard arches 50a, 50b, 50c are removed. In particular, the lower end sections of the leaflet guard arches 50a, 50b, 50c between the points where each arm of a radial arch 32a, 32b, 32c merges is removed.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A device configured for implantation at a heart valve, the device comprising:
an expandable stent comprising:
a first stent segment extending along a first length portion of the stent, the first stent segment configured to be positioned and radially expanded against a vascular wall of a native aortic valve site, the first stent segment comprising a plurality of closed cell structures defining a circumference of the stent along the first length portion, the plurality of closed cell structures having a uniform density around the circumference; and
a second stent segment disposed along a second length portion of the stent, the second stent segment comprising a first plurality of interconnected strut members having a first strut density and a second plurality of interconnected strut members having a second strut density, the first and second plurality of interconnected strut members being disposed in alternating regions around a circumference of the stent, the first strut density being higher than the second strut density,
wherein, in an implanted position of the stent at the heart valve, regions of the alternating regions having the first strut density are configured to be aligned with respective commissures of the heart valve and regions of the alternating regions having the second strut density are configured to be aligned with respective cusps of the heart valve.

2. The device of claim 1, further comprising:
a valve prosthesis comprising a plurality of prosthetic valve leaflets attached to the expandable stent;
wherein:
the regions of the alternating regions of the second stent segment having the first strut density are located on an inflow side of the valve prosthesis, and
the regions of the alternating regions of the second stent segment having the second strut density are located on an outflow side of the valve prosthesis.

3. The device of claim 1, wherein the first stent segment includes an inflow end of the stent when the stent is in an implanted position at the heart valve.

4. The device of claim 3, wherein the inflow end of the stent is configured to expand radially more than an oppositely disposed, outflow end of the stent.

5. The device of claim 4, wherein the inflow end of the stent is configured to expand to a diameter ranging from about 22 mm to about 33 mm.

6. The device of claim 4, wherein the stent has a concave outer surface tapering toward the outflow end of the stent.

7. The device of claim 3, wherein, in an expanded configuration of the stent, the first stent segment is more rigid than the second stent segment.

8. The device of claim 3, wherein, in an implanted position of the stent at the heart valve:
the first stent segment is configured to provide a first outward radial force against a vascular wall,
the second stent segment is configured to provide a second outward radial force against a vascular wall, and
the first outward radial force is greater than the second outward radial force.

9. The device of claim 8, wherein, in the implanted position of the stent at the heart valve, the uniform density of the plurality of closed cell structures of the first stent segment is configured to uniformly distribute the first outward radial force along the vascular wall.

10. The device of claim 1, wherein the first stent segment comprises a plurality of axially stacked rows of closed cell structures.

11. The device of claim 1, wherein the regions of the alternating regions having the first strut density are configured to minimize blood leakage when the stent is in an implanted position at the heart valve.

12. The device of claim 1, wherein the regions of the alternating regions having the second strut density each comprise:
a positioning arch extending along the second length portion of the stent, the positioning arch terminating in an apex facing in a direction toward the first length portion of the stent; and
a retaining arch circumferentially aligned with and substantially enclosing the positioning arch.

13. The device of claim 12, wherein the apex of each positioning arch terminates at an axial location along the stent where the second stent segment meets the first stent segment.

14. The device of claim 12, wherein end sections of the strut members forming the regions of the alternating regions having the first strut density are connected to respective arms of the retaining arches.

15. The device of claim 14, wherein the end sections have a larger diameter than the rest of the strut members forming the regions of the alternating regions having the first strut density.

16. The device of claim 1, wherein the alternating regions of the second stent segment comprise three regions having the first strut density and three regions having the second strut density.

* * * * *